US008759318B2

(12) United States Patent
Chamberlain et al.

(10) Patent No.: US 8,759,318 B2
(45) Date of Patent: Jun. 24, 2014

(54) PHOSPHORAMIDATE DERIVATIVES OF GUANOSINE NUCLEOSIDE COMPOUNDS FOR TREATMENT OF VIRAL INFECTIONS

(75) Inventors: Stanley Chamberlain, Alpharetta, GA (US); Jeff Hutchins, Alpharetta, GA (US); Karolina Madela, Cardiff (GB); Christopher McGuigan, Cardiff (GB); John Vernachio, Alpharetta, GA (US); Mohamed Aljarah, Cardiff (GB); Arnaud Gilles, Cardiff (GB)

(73) Assignees: Inhibitex, Inc., Alpharetta, GA (US); University College Cardiff Consultants Limited, Cardiff (GB)

( * ) Notice: Subject to any disclaimer, the term of this patent is extended or adjusted under 35 U.S.C. 154(b) by 241 days.

(21) Appl. No.: 13/143,098

(22) PCT Filed: Jan. 11, 2010

(86) PCT No.: PCT/US2010/020632
§ 371 (c)(1),
(2), (4) Date: Nov. 8, 2011

(87) PCT Pub. No.: WO2010/081082
PCT Pub. Date: Jul. 15, 2010

(65) Prior Publication Data
US 2012/0052046 A1 Mar. 1, 2012

Related U.S. Application Data

(60) Provisional application No. 61/143,527, filed on Jan. 9, 2009, provisional application No. 61/185,426, filed on Jun. 9, 2009.

(51) Int. Cl.
*A01N 43/04* (2006.01)
*A61K 31/70* (2006.01)

(52) U.S. Cl.
USPC .............. 514/48; 514/43; 514/45; 536/26.72; 536/27.1; 536/27.13

(58) Field of Classification Search
None
See application file for complete search history.

(56) References Cited

U.S. PATENT DOCUMENTS

| 6,812,219 | B2 | 11/2004 | LaColla et al. |
| 6,914,054 | B2 | 7/2005 | Sommadossi et al. |
| 7,112,600 | B1 | 9/2006 | Hashimoto et al. |
| 7,157,441 | B2 * | 1/2007 | Sommadossi et al. .......... 514/47 |
| 7,321,029 | B2 | 1/2008 | Gryaznov et al. |
| 7,662,809 | B2 | 2/2010 | Ercolani et al. |
| 7,795,250 | B2 | 9/2010 | Colarusso et al. |
| 7,803,944 | B2 | 9/2010 | Beaulieu et al. |
| 2003/0050229 | A1 | 3/2003 | Sommadossi et al. |
| 2003/0138797 | A1 | 7/2003 | Iyer et al. |
| 2004/0167096 | A1 | 8/2004 | Cheng et al. |
| 2007/0037770 | A1 | 2/2007 | Gryaznov et al. |
| 2007/0265222 | A1 | 11/2007 | MacCoss et al. |
| 2008/0286230 | A1 | 11/2008 | Sommadossi et al. |
| 2009/0215715 | A1 | 8/2009 | McGuigan et al. |
| 2011/0124592 | A1 | 5/2011 | McGuigan et al. |

FOREIGN PATENT DOCUMENTS

| WO | WO-02/04425 | 1/2002 |
| WO | WO-03/007945 | 1/2003 |
| WO | WO 2004/003000 | 1/2004 |
| WO | WO-2004/058792 | 7/2004 |
| WO | WO-2005/080399 | 9/2005 |
| WO | WO-2006/121820 | 11/2006 |
| WO | WO 2006/121820 A1 * | 11/2006 ............. A61K 31/70 |

OTHER PUBLICATIONS

Ford, Jr. et al, "Lipophile, Acid-Stable, Adenosine Deaminase-Activated Anti-HIV Prodrugs for Central Nervous System Delivery. 2. 6-Halo and 6-Alkoxy Prodrugs of 2'—Fluoro-2', 3'-dideoxyinosine", 1995, pp. 1189-1195, vol. 38, No. 7, Journal of Medical Chemistry.
Kisor et al, "Pharmacokinetics of Nelarabine and 9-Beta-D-Arabinofuranosyl Guanine in Pediatric and Adult Patients During a Phase I Study of Nelarabine for the Treatment of Refractory Hematologioc Malignancies", Mar. 2000, pp. 995-1003, vol. 18, No. 5., Journal of Clinical Oncology.
Knaggs et al, "A QSAR Study Investigating the Effect of L-Alanine Ester Variation on the Anti-HIV Activity of Some Phosphoramidate Derivatives of d4T", 2000, pp. 2075-2078, vol. 10, Bioorganic & Medicinal Chemistry Letters.
Lambe et al, "2-Amino-6-methoxypurine Arabinoside: An Agent for T-Cell Malignancies", Aug. 1, 1995, pp. 3352-3356, vol. 55, Cancer Research.
Perrone et al, "First Example of Phosphoramidate Approach Applied to a 4'-Substituted Purine Nucleoside (4'-Azidoadenosine): Conversion of an Inactive Nucleoside to a Submicromolar Compound versus Hepatitis C Virus", 2007, pp. 5463-5470, vol. 50, No. 22, Journal of Medical Chemistry.
McGuigan et al, "Application of Phosphoramidate ProTide Technology Significantly Improves Antiviral Potency of Carbocyclic Adenosine Derivatives", 2006, pp. 7215-7226, vol. 49, J. Med. Chem.
McGuigan et al, "Application of Phosphoramidate Pronucleotide Technology to Abacavir Leads to a Significant Enhancement of Antiviral Potency", 2005, pp. 3504-3515, vol. 48, J. Med. Chem.
Cahard et al, "Aryloxy Phosphoramidate Triesters as Pro-Tides", 2004, pp. 371-382, vol. 4, Mini-Reviews in Medicinal Chemistry.
Supplementary European Search Report dated Apr. 22, 2013 in corresponding EP Application No. 10 72 9622.
Office Action dated Jun. 7, 2013 in corresponding CN Application No. 201080011524.0.
Gunic et al, "6-Hydrazinopurine 2'-methyl ribonucleosides and their 5'-monophosphate prodrugs as potent hepatitis C virus inhibitors", Apr. 3, 2007, vol. 17, No. 9, pp. 2456-2458, BioOrganic & Medicinal Chemistry Letters, Pergamon, Elsevier Science, GB.

(Continued)

*Primary Examiner* — Patrick Lewis
(74) *Attorney, Agent, or Firm* — B. Aaron Schulman; Stites & Harbison, PLLC.

(57) ABSTRACT

Phosphoramidate compounds derived from guanine bases having enhanced therapeutic potency are provided, and these compounds in particular have enhanced potency with respect to treatment of viral infections, such as hepatitis C virus. Pharmaceutical compositions, methods of preparing the compounds, and methods of using the compounds and compositions to treat viral infections are also provided.

78 Claims, 3 Drawing Sheets

(56) References Cited

OTHER PUBLICATIONS

McGuigan et al, "The phosphoramidate ProTide approach greatly enhances the activity of beta-2'-C-methylguanosine against hepatitis C virus", Aug. 1, 2009, vol. 19, No. 15, pp. 4316-4320, BioOrganic & Medicinal Chemistry Letters, Pergamon, Elsevier Science, GB.

McGuigan et al, "Phosphoramidate ProTides of 2'-C-Methylguanosine as Highly Potent Inhibitors of Hepatitis C Virus. Study of Their in Vitro and in Vivo Properties", Jul. 8, 2010, vol. 53, No. 13, pp. 4949-4957, Journal of Medicinal Chemistry.

McGuigan et al, "Design, synthesis and evaluation of a novel double pro-drug: INX-08189. A new clinical candidate for hepatitis C virus", Aug. 15, 2010, vol. 20, No. 16, pp. 4850-4854, BioOrganic & Medicinal Chemistry Letters, Pergamon, Elsevier Science, GB.

Office Action dated Feb. 4, 2014 in corresponding Chinese Patent Application No. 2011-545488.

\* cited by examiner

PHOSPHORAMIDATE DERIVATIVES OF GUANOSINE NUCLEOSIDE COMPOUNDS FOR TREATMENT OF VIRAL INFECTIONS

CROSS-REFERENCE TO RELATED APPLICATIONS

The present application claims the benefit of U.S. provisional application Ser. No. 61/185,426, filed Jun. 6, 2009, and U.S. provisional application Ser. No. 61/143,527 filed Jan. 9, 2009, both of said applications incorporated herein by reference.

FIELD OF THE INVENTION

This application relates to novel nucleoside phosphoramidates and their use as agents for treating viral diseases. Such compounds are inhibitors of RNA-dependant RNA viral replication and specifically, inhibitors of HCV NS5B polymerase. As inhibitors of HCV replication, such compounds are useful for treatment of hepatitis C infection in mammals.

BACKGROUND OF THE INVENTION

HCV is a member of the Flaviviridae family of RNA viruses that affect animals and humans. The genome is a single 9.6-kilobase strand of RNA, and consists of one open reading frame that encodes for a polyprotein of approximately 3000 amino acids flanked by untranslated regions at both 5' and 3' ends (5'-and 3'-UTR). The polyprotein serves as the precursor to at least 10 separate viral proteins critical for replication and assembly of progeny viral particles.

Hepatitis C Virus (HCV) infection is a major health problem that leads to chronic liver disease, such as cirrhosis and hepatocellular carcinoma, in a substantial number of infected individuals, estimated to be 2-15% of the world population. There are an estimated 4.5 million infected people in the United States alone, according to the U.S. Center for Disease control. According to the World Health Organization, there are more than 200 million infected individuals worldwide, with at least 3 to 4 million people being infected each year. Once infected, about 20% of people clear the virus, but the remainder can harbor HCV for the rest of their lives.

Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring At present, the standard treatment for chronic HCV is interferon alpha (IFN-alpha) in combination with ribavirin, which requires at least six (6) months of treatment. However, treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha and ribavirin. By now, standard therapy of chronic hepatitis C has been changed to the combination of pegylated IFN-alpha plus ribavirin. However, a number of patients still have significant side effects, primarily related to ribavirin.

Ribavirin causes significant hemolysis in 10-20% of patients treated at currently recommended doses, and the drug is both teratogenic and embryotoxic. Even with recent improvements, a substantial fraction of patients do not respond with a sustained reduction in viral load and there is a clear need for more effective antiviral therapy of HCV infection.

A number of other approaches are being pursued to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. Among the viral targets, the NS3/4A protease/helicase and the NS5B RNA-dependent RNA polymerase are considered the most promising viral targets for new drugs.

A number of patents disclose and claim inventions relating to CV NS5B inhibitors. For example, WO 2006/046039, WO 2006/046030 and WO 2006/029912, incorporated by reference herein, relate to tetracyclic indole compounds and pharmaceutically acceptable salts thereof, for the treatment or prevention of infection by hepatitis C virus. WO 2005/080399, incorporated by reference herein, relates to fused heterotetracyclic compounds, pharmaceutically acceptable salts thereof; and their use in aiding to remedy hepatitis C infection as potent (HCV) polymerase inhibitors. WO 2003007945, incorporated by reference herein, relates to HCV NS5B inhibitors. Further, WO 2003010140, incorporated by reference herein, relates to specific inhibitors of RNA dependent RNA polymerases, particularly viral polymerases within the Flaviviridae family, more particularly to HCV polymerase. WO 200204425, incorporated by reference herein, relates to specific inhibitors of RNA dependent RNA polymerases, particularly viral polymerases within the Flaviviridae family, and more particularly the NS5B polymerase of HCV. WO 200147883, incorporated by reference herein, relates to specific fused-ring compounds or the like or pharmaceutically acceptable salts thereof. Such compounds and salts exhibit an anti-HCV (hepatitis C virus) activity by virtue of their inhibitory activity against HCV polymerase, thus being useful as therapeutic or preventive agents for hepatitis C.

However, in view of the worldwide epidemic level of HCV and other members of the Flaviviridae family of viruses, and further in view of the limited treatment options, there is a strong need for new effective drugs for treating infections cause by these viruses.

SUMMARY OF THE INVENTION

This invention is directed to novel compounds that are useful in the treatment of viral infections in mammals mediated, at least in part, by a virus in the Flaviviridae family of viruses. According to some embodiments, the present invention provides for novel compounds of formula (I) having the structure:

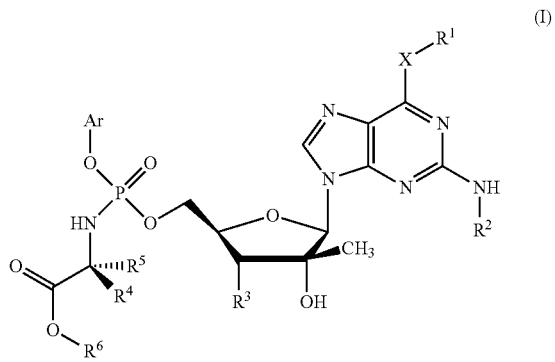

(I)

wherein Ar is selected from
phenyl,
naphthyl,

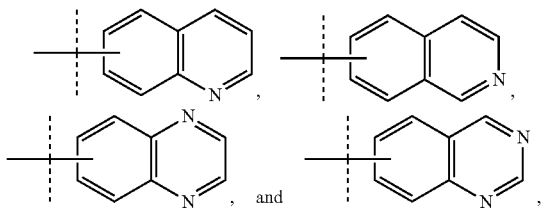

any of which are optionally substituted with
   $C_1$-$C_6$alkyl,
   $C_1$-$C_6$alkoxy,
   di($C_1$-$C_6$)alkylamino or
   $C_1$-$C_6$alkylcarboxy($C_1$-$C_6$)alkyl-;
X is selected from S, NH and O;
$R^1$ is selected from
   $C_1$-$C_6$ alkyl,
   benzyl,
   substituted benzyl; and
   aryl($C_0$-$C_6$)alkyl- wherein the aryl is optionally substituted by
      halo,
      $C_1$-$C_6$alkoxy, and
      $C_1$-$C_6$alkyl;
$R^2$ is selected from
   hydrogen,
   phenyl,
   aryl, and
   aryl($C_0$-$C_6$)alkyl- wherein the aryl is optionally substituted by
      halo,
      $C_1$-$C_6$alkoxy, and
      $C_1$-$C_6$alkyl;
$R^3$ is selected from H and OH;
$R^4$ and $R^5$ are independently selected from
   hydrogen,
   $C_1$-$C_6$alkyl optionally substituted with alkylthio,
   benzyl optionally substituted with one or more
      halo,
      $C_1$-$C_6$alkyl, or
      $C_1$-$C_6$alkoxy,
   phenyl optionally substituted with one or more
      halo,
      $C_1$-$C_6$alkyl, or
      $C_1$-$C_6$alkoxy;
$R^6$ is selected from
   $C_1$-$C_{10}$alkyl,
   $C_3$-$C_8$cycloalkyl,
   $C_3$-$C_8$cycloalkyl-alkyl-,
   phenyl($C_1$-$C_6$)alkyl- optionally substituted with
      $C_1$-$C_6$alkyl,
      $C_1$-$C_6$alkoxy, and
      halo,
   indanyl and
   heterocycloalkyl;
and pharmaceutically acceptable salts thereof.

According to other embodiments, the present invention extends to a pharmaceutical composition comprising one or more compounds of formula I and a pharmaceutically acceptable carrier, excipient or diluent. The pharmaceutically acceptable carrier, excipient or diluent may be pure sterile water, phosphate buffered saline or an aqueous glucose, solution. In addition, the compounds as reflected in formula I will include polymorphs thereof.

Also provided are methods for treating a viral infection in a mammal mediated at least in part by a virus in the Flaviviridae family wherein an instant method comprises administering to a mammal that has been diagnosed with said viral infection a pharmaceutical composition comprising compounds of formula I.

Also provided are methods for treating a viral infection in a human or animal patient that is mediated at least in part by a virus in the Flaviviridae family wherein an instant method comprises administering to a human or animal patient in need thereof an effective amount of a pharmaceutical composition comprising compounds of formula I.

In one embodiment, the virus is hepatitis C virus (or HCV). The present methods further extend to combination treatment comprising administration of a therapeutically effective amount of one or more agents active against hepatitis C virus. Such active agents against hepatitis C virus may include interferon-alpha or pegylated interferon-alpha alone or in combination with ribavirin or levovirin.

Additional compounds in accordance with the invention are provided as set forth below, and it is contemplated that these additional compounds will also be useful in methods of treating a Flavivirus family infection, including infections caused by HCV. Methods, pharmaceutical compositions and combinations such as those referred to herein for formula I are also contemplated with regard to the additional compounds as set forth herein.

BRIEF DESCRIPTION OF THE DRAWING FIGURES

DETAILED DESCRIPTION OF THE INVENTION

Figure 1:
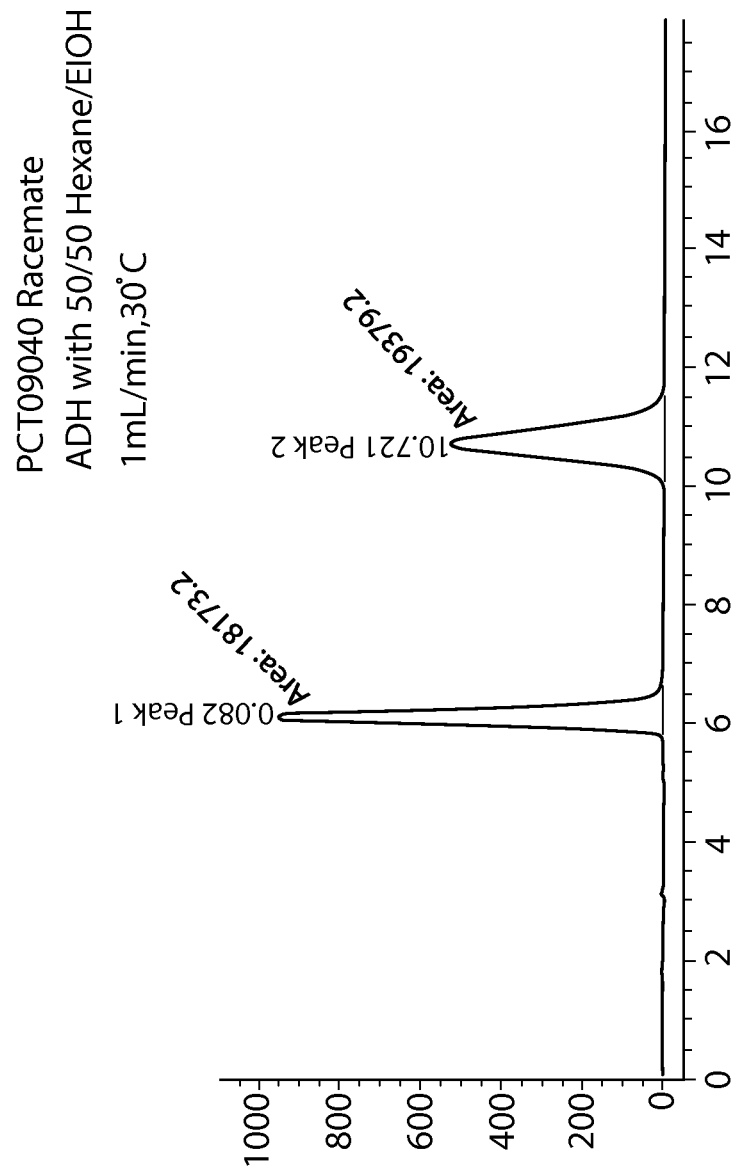
FIG. 1 is a graph showing the separation of diastereomers by chiral chromatography.

The present invention relates to chemical compounds, their preparation and their use in the treatment of viral infections particularly in mammals. Particularly, although not exclusively, the present invention relates to chemical compounds useful as anti-hepatitis C virus (HCV) agents.

Specifically, the present invention describes certain nucleoside aryl phosphoramidates, their synthesis, and their use as precursors to inhibitors of RNA-dependent RNA viral polymerase, particularly their use as precursors to inhibitors of hepatitis C virus (HCV) NS5-B polymerase, as precursors to inhibitors of HCV replication, and for the treatment of hepatitis C infection.

It is an object of the present invention to provide novel chemical compounds useful for treatment of viral infections in mammals, specifically for treatment of hepatitis C infection in mammals.

According to an embodiment of the present invention there is provided a compound of formula (I):

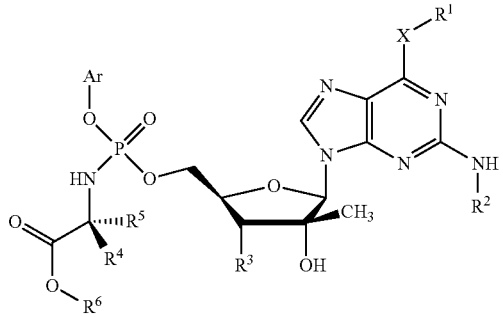 (I)

wherein Ar is selected from
phenyl,
naphthyl,

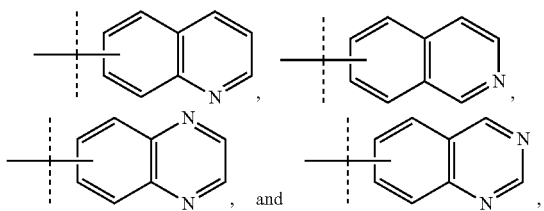

any of which are optionally substituted with
 $C_1$-$C_6$alkyl,
 $C_1$-$C_6$alkoxy,
 di($C_1$-$C_6$)alkylamino or
 $C_1$-$C_6$alkylcarboxy($C_1$-$C_6$)alkyl-;
X is selected from S, NH and O;
$R^1$ is selected from
 $C_1$-$C_6$ alkyl,
 benzyl,
 substituted benzyl; and
 aryl($C_0$-$C_6$)alkyl- wherein the aryl is optionally substituted by
  halo,
  $C_1$-$C_6$alkoxy, and
  $C_1$-$C_6$alkyl;
$R^2$ is selected from
 hydrogen,
 phenyl,
 aryl, and
 aryl($C_0$-$C_6$)alkyl- wherein the aryl is optionally substituted by
  halo,
  $C_1$-$C_6$alkoxy, and
  $C_1$-$C_6$alkyl;
$R^3$ is selected from H and OH;
$R^4$ and $R^5$ are independently selected from
 hydrogen,
 $C_1$-$C_6$alkyl optionally substituted with alkylthio,
 benzyl optionally substituted with one or more
  halo,
  $C_1$-$C_6$alkyl, or
  $C_1$-$C_6$alkoxy,
 phenyl optionally substituted with one or more
  halo,
  $C_1$-$C_6$alkyl, or
  $C_1$-$C_6$alkoxy;
$R^6$ is selected from
 $C_1$-$C_{10}$alkyl,
 $C_3$-$C_8$cycloalkyl,
 $C_3$-$C_8$cycloalkyl-alkyl-,
 phenyl($C_1$-$C_6$)alkyl- optionally substituted with
  $C_1$-$C_6$alkyl,
  $C_1$-$C_6$alkoxy, and
  halo,
 indanyl and
 heterocycloalkyl;
and the pharmaceutically acceptable salts thereof.

According to second embodiment of the present invention there is provided a compound of formula (I) above
wherein Ar is selected from
 naphthyl,

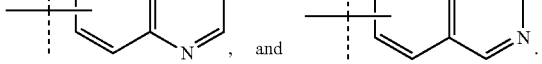

any of which are optionally substituted with
 $C_1$-$C_6$alkyl,
 $C_1$-$C_6$alkoxy,
 di($C_1$-$C_6$)alkylamino or
 $C_1$-$C_6$alkylcarboxy($C_1$-$C_6$)alkyl-;
X is selected from S, NH and O;
$R^1$ is selected from
 $C_1$-$C_6$ alkyl,
 benzyl,
 substituted benzyl; and
 aryl($C_0$-$C_6$)alkyl- wherein the aryl is optionally substituted by
  halo,
  $C_1$-$C_6$alkoxy, and
  $C_1$-$C_6$alkyl;
$R^2$ is selected from
 hydrogen,
 phenyl,
 aryl, and
 aryl($C_0$-$C_6$)alkyl- wherein the aryl is optionally substituted by
  halo,
  $C_1$-$C_6$alkoxy, and
  $C_1$-$C_6$alkyl;
$R^3$ is selected from H and OH;
$R^4$ and $R^5$ are independently selected from
 hydrogen,
 $C_1$-$C_6$alkyl optionally substituted with alkylthio,
 benzyl optionally substituted with one or more
  halo,
  $C_1$-$C_6$alkyl, or
  $C_1$-$C_6$alkoxy,
 phenyl optionally substituted with one or more
  halo,
  $C_1$-$C_6$alkyl, or
  $C_1$-$C_6$alkoxy;
$R^6$ is selected from
 $C_1$-$C_{10}$alkyl,
 $C_3$-$C_8$cycloalkyl,
 $C_3$-$C_8$cycloalkyl-alkyl-,
 phenyl($C_1$-$C_6$)alkyl- optionally substituted with
  $C_1$-$C_6$alkyl,
  $C_1$-$C_6$alkoxy, and
  halo,
 indanyl and
 heterocycloalkyl;
and the pharmaceutically acceptable salts thereof.

According to a third embodiment of the present invention there is provided a compound of formula (I)
wherein Ar is selected from
phenyl,
naphthyl,

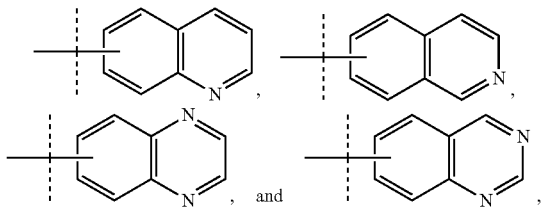

any of which are optionally substituted with
$C_1$-$C_6$alkyl,
$C_1$-$C_6$alkoxy,
di($C_1$-$C_6$)alkylamino or
$C_1$-$C_6$alkylcarboxy($C_1$-$C_6$)alkyl-;
X is O;
$R^1$ is selected from
$C_1$-$C_6$ alkyl,
benzyl,
substituted benzyl; and
aryl($C_0$-$C_6$)alkyl- wherein the aryl is optionally substituted by
halo,
$C_1$-$C_6$alkoxy, and
$C_1$-$C_6$alkyl;
$R^2$ is selected from
hydrogen,
phenyl,
aryl, and
aryl($C_0$-$C_6$)alkyl- wherein the aryl is optionally substituted by
halo,
$C_1$-$C_6$alkoxy, and
$C_1$-$C_6$alkyl;
$R^3$ is selected from H and OH;
$R^4$ and $R^5$ are independently selected from
hydrogen,
$C_1$-$C_6$alkyl optionally substituted with alkylthio,
benzyl optionally substituted with one or more
halo,
$C_1$-$C_6$alkyl, or
$C_1$-$C_6$alkoxy,
phenyl optionally substituted with one or more
halo,
$C_1$-$C_6$alkyl, or
$C_1$-$C_6$alkoxy;
$R^6$ is selected from
$C_1$-$C_{10}$alkyl,
$C_3$-$C_8$cycloalkyl,
$C_3$-$C_8$cycloalkyl-alkyl-,
phenyl($C_1$-$C_6$)alkyl- optionally substituted with
$C_1$-$C_6$alkyl,
$C_1$-$C_6$alkoxy, and
halo,
indanyl and
heterocycloalkyl;
and the pharmaceutically acceptable salts thereof.
According to a fourth embodiment of the present invention there is provided a compound of formula (I)
wherein Ar is selected from
phenyl,
naphthyl,

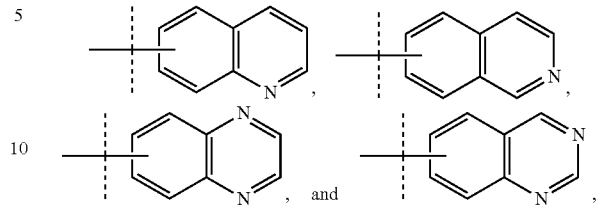

any of which are optionally substituted with
$C_1$-$C_6$alkyl,
$C_1$-$C_6$alkoxy,
di($C_1$-$C_6$)alkylamino or
$C_1$-$C_6$alkylcarboxy($C_1$-$C_6$)alkyl-;
X is selected from S, NH and O;
$R^1$ is selected from $C_1$-$C_6$ alkyl,
$R^2$ is selected from
hydrogen,
phenyl,
aryl, and
aryl($C_0$-$C_6$)alkyl- wherein the aryl is optionally substituted by
halo,
$C_1$-$C_6$alkoxy, and
$C_1$-$C_6$alkyl;
$R^3$ is selected from H and OH;
$R^4$ and $R^5$ are independently selected from
hydrogen,
$C_1$-$C_6$alkyl optionally substituted with alkylthio,
benzyl optionally substituted with one or more
halo,
$C_1$-$C_6$alkyl, or
$C_1$-$C_6$alkoxy,
phenyl optionally substituted with one or more
halo,
$C_1$-$C_6$alkyl, or
$C_1$-$C_6$alkoxy;
$R^6$ is selected from
$C_1$-$C_{10}$alkyl,
$C_3$-$C_8$cycloalkyl,
$C_3$-$C_8$cycloalkyl-alkyl-,
phenyl($C_1$-$C_6$)alkyl- optionally substituted with
$C_1$-$C_6$alkyl,
$C_1$-$C_6$alkoxy, and
halo,
indanyl and
heterocycloalkyl;
and the pharmaceutically acceptable salts and polymorphs thereof.
According to a fifth embodiment of the present invention there is provided a compound of formula (I)
wherein Ar is selected from
phenyl,
naphthyl,

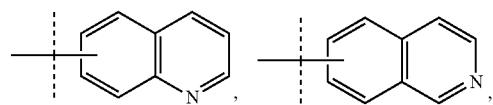

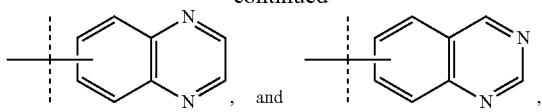

any of which are optionally substituted with
$C_1$-$C_6$alkyl,
$C_1$-$C_6$alkoxy,
di($C_1$-$C_6$)alkylamino or
$C_1$-$C_6$alkylcarboxy($C_1$-$C_6$)alkyl-;
X is selected from S, NH and O;
$R^1$ is selected from
$C_1$-$C_6$ alkyl,
benzyl,
substituted benzyl; and
aryl($C_0$-$C_6$)alkyl- wherein the aryl is optionally substituted by
halo,
$C_1$-$C_6$alkoxy, and
$C_1$-$C_6$alkyl;
$R^2$ is hydrogen,
$R^3$ is selected from H and OH;
$R^4$ and $R^5$ are independently selected from
hydrogen,
$C_1$-$C_6$alkyl optionally substituted with alkylthio,
benzyl optionally substituted with one or more
halo,
$C_1$-$C_6$alkyl, or
$C_1$-$C_6$alkoxy,
phenyl optionally substituted with one or more
halo,
$C_1$-$C_6$alkyl, or
$C_1$-$C_6$alkoxy;
$R^6$ is selected from
$C_1$-$C_{10}$alkyl,
$C_3$-$C_8$cycloalkyl,
$C_3$-$C_8$cycloalkyl-alkyl-,
phenyl($C_1$-$C_6$)alkyl- optionally substituted with
$C_1$-$C_6$alkyl,
$C_1$-$C_6$alkoxy, and
halo,
indanyl and
heterocycloalkyl;
and the pharmaceutically acceptable salts thereof.

According to sixth embodiment of the present invention there is provided a compound of formula (I)
wherein Ar is selected from
phenyl,
naphthyl,

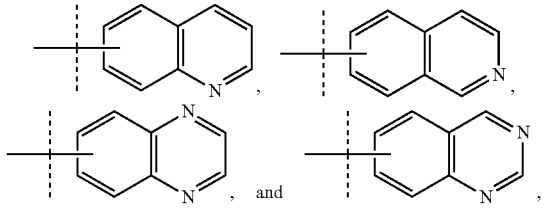

any of which are optionally substituted with
$C_1$-$C_6$alkyl,
$C_1$-$C_6$alkoxy,
di($C_1$-$C_6$)alkylamino or
$C_1$-$C_6$alkylcarboxy($C_1$-$C_6$)alkyl-;
X is selected from S, NH and O;
$R^1$ is selected from
$C_1$-$C_6$ alkyl,
benzyl,
substituted benzyl; and
aryl($C_0$-$C_6$)alkyl- wherein the aryl is optionally substituted by
halo,
$C_1$-$C_6$alkoxy, and
$C_1$-$C_6$alkyl;
$R^2$ is selected from
hydrogen,
phenyl,
aryl, and
aryl($C_0$-$C_6$)alkyl- wherein the aryl is optionally substituted by
halo,
$C_1$-$C_6$alkoxy, and
$C_1$-$C_6$alkyl;
$R^3$ is OH;
$R^4$ and $R^5$ are independently selected from
hydrogen,
$C_1$-$C_6$alkyl optionally substituted with alkylthio,
benzyl optionally substituted with one or more
halo,
$C_1$-$C_6$alkyl, or
$C_1$-$C_6$alkoxy,
phenyl optionally substituted with one or more
halo,
$C_1$-$C_6$alkyl, or
$C_1$-$C_6$alkoxy;
$R^6$ is selected from
$C_1$-$C_{10}$alkyl,
$C_3$-$C_8$cycloalkyl,
$C_3$-$C_8$cycloalkyl-alkyl-,
phenyl($C_1$-$C_6$)alkyl- optionally substituted with
$C_1$-$C_6$alkyl,
$C_1$-$C_6$alkoxy, and
halo,
indanyl and
heterocycloalkyl;
and pharmaceutically acceptable salts thereof.

According to seventh embodiment of the present invention there is provided a compound of formula (I)
wherein Ar is selected from
phenyl,
naphthyl,

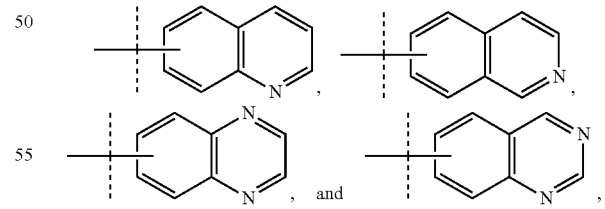

any of which are optionally substituted with
$C_1$-$C_6$alkyl,
$C_1$-$C_6$alkoxy,
di($C_1$-$C_6$)alkylamino or
$C_1$-$C_6$alkylcarboxy($C_1$-$C_6$)alkyl-;
X is selected from S, NH and O;
$R^1$ is selected from
$C_1$-$C_6$ alkyl,
benzyl, substituted benzyl; and
aryl($C_0$-$C_6$)alkyl- wherein the aryl is optionally substituted by
halo,
$C_1$-$C_6$alkoxy, and
$C_1$-$C_6$alkyl;
$R^2$ is selected from
hydrogen,
phenyl,
aryl, and
aryl($C_0$-$C_6$)alkyl- wherein the aryl is optionally substituted by
halo,
$C_1$-$C_6$alkoxy, and
$C_1$-$C_6$alkyl;
$R^3$ is selected from H and OH;
$R^4$ and $R^5$ are independently selected from
hydrogen,
$C_1$-$C_6$alkyl optionally substituted with alkylthio, and
phenyl optionally substituted with one or more
halo,
$C_1$-$C_6$alkyl, or
$C_1$-$C_6$alkoxy;
$R^6$ is selected from
$C_1$-$C_{10}$alkyl,
$C_3$-$C_8$cycloalkyl,
$C_3$-$C_8$cycloalkyl-alkyl-,
phenyl($C_1$-$C_6$)alkyl- optionally substituted with
$C_1$-$C_6$alkyl,
$C_1$-$C_6$alkoxy, and
halo,
indanyl and
heterocycloalkyl;
and the pharmaceutically acceptable salts.

According to eighth embodiment of the present invention there is provided a compound of formula (I)
wherein Ar is selected from
phenyl,
naphthyl,

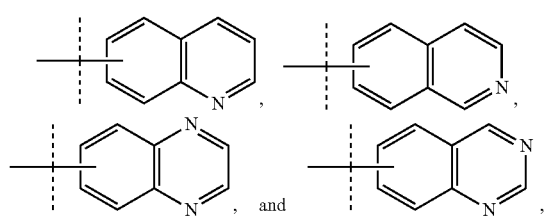
, and any of which are optionally substituted with
$C_1$-$C_6$alkyl,
$C_1$-$C_6$alkoxy,
di($C_1$-$C_6$)alkylamino or
$C_1$-$C_6$alkylcarboxy($C_1$-$C_6$)alkyl-;
X is selected from S, NH and O;
$R^1$ is selected from
$C_1$-$C_6$ alkyl,
benzyl,
substituted benzyl; and
aryl($C_0$-$C_6$)alkyl- wherein the aryl is optionally substituted by
halo,
$C_1$-$C_6$alkoxy, and
$C_1$-$C_6$alkyl;
$R^2$ is selected from
hydrogen,
phenyl,
aryl, and
aryl($C_0$-$C_6$)alkyl- wherein the aryl is optionally substituted by
halo,
$C_1$-$C_6$alkoxy, and
$C_1$-$C_6$alkyl;
$R^3$ is selected from H and OH;
$R^4$ is selected from
$C_1$-$C_6$alkyl optionally substituted with alkylthio, and
phenyl optionally substituted with one or more
halo,
$C_1$-$C_6$alkyl, or
$C_1$-$C_6$alkoxy;
$R^5$ is hydrogen;
$R^6$ is selected from
$C_1$-$C_{10}$alkyl,
$C_3$-$C_8$cycloalkyl,
$C_3$-$C_8$cycloalkyl-alkyl-,
phenyl($C_1$-$C_6$)alkyl- optionally substituted with
$C_1$-$C_6$alkyl,
$C_1$-$C_6$alkoxy, and
halo,
indanyl and
heterocycloalkyl;
and the pharmaceutically acceptable salts thereof.

According to ninth embodiment of the present invention there is provided a compound of formula (I)
wherein Ar is selected from
phenyl,
naphthyl,

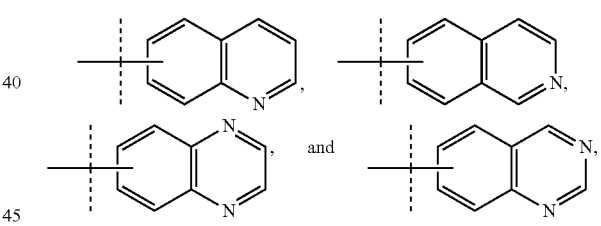
, and any of which are optionally substituted with
$C_1$-$C_6$alkyl,
$C_1$-$C_6$alkoxy,
di($C_1$-$C_6$)alkylamino or
$C_1$-$C_6$alkylcarboxy($C_1$-$C_6$)alkyl-;
X is selected from S, NH and O;
$R^1$ is selected from
$C_1$-$C_6$ alkyl,
benzyl,
substituted benzyl; and
aryl($C_0$-$C_6$)alkyl- wherein the aryl is optionally substituted by
halo,
$C_1$-$C_6$alkoxy, and
$C_1$-$C_6$alkyl;
$R^2$ is selected from
hydrogen,
phenyl,
aryl, and-aryl($C_0$-$C_6$)alkyl- wherein the aryl is optionally substituted by
  halo,
  $C_1$-$C_6$alkoxy, and
  $C_1$-$C_6$alkyl;
$R^3$ is selected from H and OH;
$R^4$ and $R^5$ are independently selected from
  hydrogen,
  $C_1$-$C_6$alkyl optionally substituted with alkylthio,
  benzyl optionally substituted with one or more
    halo,
    $C_1$-$C_6$alkyl, or
    $C_1$-$C_6$alkoxy,
  phenyl optionally substituted with one or more
    halo,
    $C_1$-$C_6$alkyl, or
    $C_1$-$C_6$alkoxy;
$R^6$ is selected from
  $C_1$-$C_{10}$alkyl,
  phenyl($C_1$-$C_6$)alkyl- optionally substituted with halo, and
  heterocycloalkyl;
and the pharmaceutically acceptable salts thereof.

In each case, the above compounds are provided along with their polymorphs and phosphorus diastereomers.

In accordance with the present invention there are provided the following specific embodiments of the above compounds:

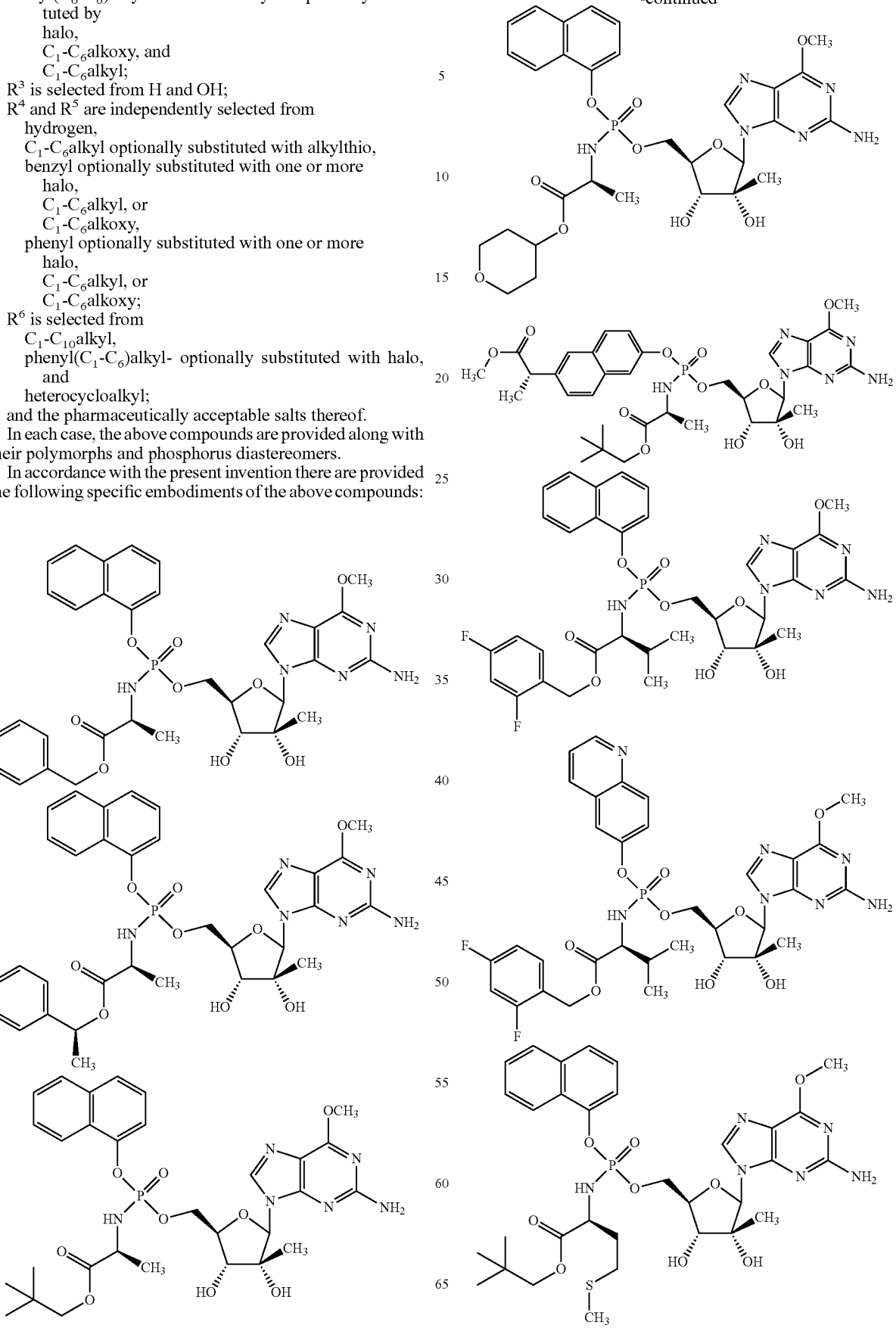

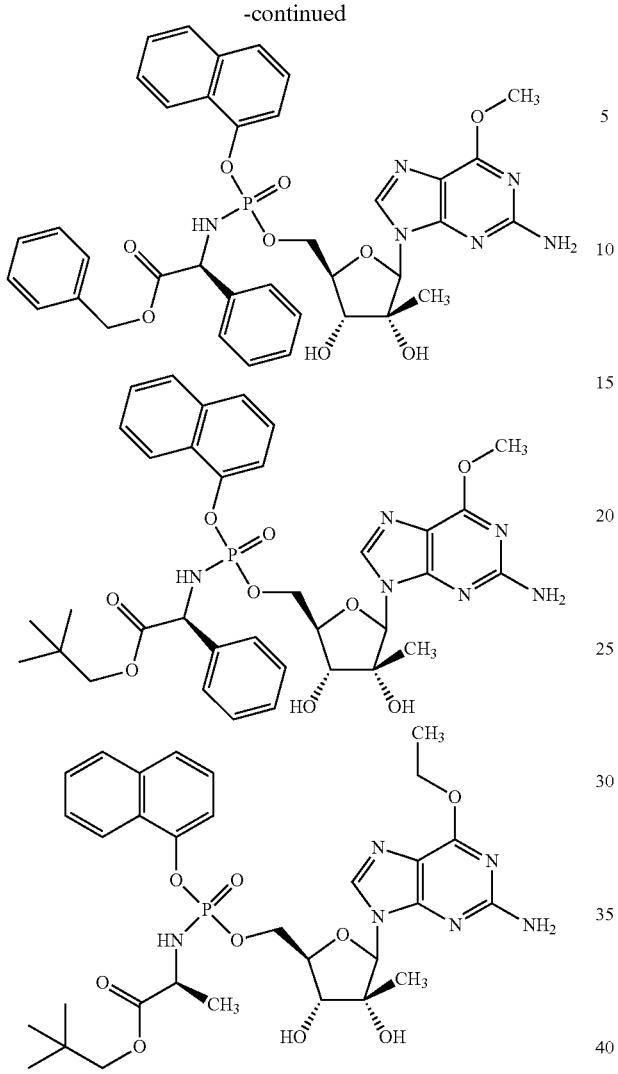

In accordance with the present invention there are provided the following specific embodiments of the above compounds:

Benzyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)propanoate;

1(S)-Phenylethyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate;

2,2-Dimethylpropyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate;

(2S)-Tetrahydro-2H-pyran-4-yl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

(2S)-Methyl 2-(6-(((((2R,-3R,4R)-5-(2-amino-6-methoxy-9H-purin-9-yl)-3,4-dihydroxy-4-methyltetrahydrofuran-2-yl)methoxy)((S)-1-(neopentyloxy)-1-oxopropan-2-ylamino)phosphoryloxy)naphthalen-2-yl)propanoate;

2,4-Difluorobenzyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)-3-methylbutanoate;

(2S)-2,4-Difluorobenzyl 2-(((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)-3-methylbutanoate;

(2S)-Neopentyl 2-((((((2R,3R,4R)-5-(2-amino-6-methoxy-9H-purin-9-yl)-3,4-dihydroxy-4-methyltetrahydrofuran-2-yl)methoxy) (naphthalen-1-yloxy)phosphorylamino)-4-(methylthio)butanoate;

(2S)-Benzyl 2-((((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-Neopentyl 2-((((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

2,2-Dimethylpropyl 2(S)-((((2R,3R,4R,5R)-5-(2-amino-6-ethoxy-9H-purin-9-yl)-3,4-dihydroxy-4-methyltetrahydrofuran-2-yl)methoxy(naphthalene-1-yloxy) phosphorylamino)propanoate;

1(S)-Phenylethyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate;

2,2-Dimethylpropyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate;

Benzyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)propanoate;

(2S)-2,4-Difluorobenzyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy) phosphorylamino)propanoate;

1(S)-Phenylethyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate;

(2S)-2,3-Dihydro-1H-inden-2-yl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

(2S)-Propyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino) propanoate;

(2S)-3,3-Dimethylbutyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy) phosphorylamino)propanoate;

(2S)-Isobutyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

2,2-Dimethylpropyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate;

(S)-P 2,2-Dimethylpropyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate;

(R)-P 2,2-Dimethylpropyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate;

(2S)-Isopropyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

(2S)-Cyclopentyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

(2S)-Cyclohexyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

(2S)-Tetrahydro-2H-pyran-4-yl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

(2S)-2,4-difluorobenzyl 2-((((2R,3R,4R)-5-(2-amino-6-methoxy-9H-purin-9-yl)-3,4-dihydroxy-4-methyltetrahydrofuran-2-yl)methoxy)(6-((S)-1-methoxy-1-oxopropan-2-yl)naphthalen-2-yloxy)phosphorylamino)propanoate;

(2S)-methyl 2-(6-((((2R,-3R,4R)-5-(2-amino-6-methoxy-9H-purin-9-yl)-3,4-dihydroxy-4-methyltetrahydrofuran-2-yl)methoxy)((S)-1-(neopentyloxy)-1-oxopropan-2-ylamino)phosphoryloxy)naphthalen-2-yl)propanoate;

(2S)-methyl 2-(6-((((2R,-3R,4R)-5-(2-amino-6-methoxy-9H-purin-9-yl)-3,4-dihydroxy-4-methyltetrahydrofuran-2-yl)methoxy)((S)-1-oxo-1-(tetrahydro-2H-pyran-4-yloxy)propan-2-ylamino)phosphoryloxy)naphthalen-2-yl)propanoate;

(2S)-2,4-difluorobenzyl 2-((((2R,-3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)propanoate;

(2S)-neopentyl 2-((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)propanoate;

(2S)-tetrahydro-2H-pyran-4-yl 2-((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)propanoate;

(2S)-neopentyl 2-((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)propanoate;

(2S)-tetrahydro-2H-pyran-4-yl 2-((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)propanoate;

(2S)-neopentyl 2-((((2R,3R,4R)-5-(2-amino-6-methoxy-9H-purin-9-yl)-3,4-dihydroxy-4-methyltetrahydrofuran-2-yl)methoxy)(phenoxy)phosphorylamino) propanoate;

(2S)-Neopentyl 2-((((2R,3R,4R)-5-(2-amino-6-methoxy-9H-purin-9-yl)-3,4-dihydroxy-4-methyltetrahydrofuran-2-yl)methoxy) (6-((S)-1-methoxy-1-oxopropan-2-yl)naphthalen-2-yloxy)phosphorylamino)-3-methylbutanoate;

(2S)-2,4-Difluorobenzyl 2-((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)-3-methylbutanoate;

(2S)-Neopentyl 2-((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)-3-methylbutanoate;

(2S)-2,4-Difluorobenzyl 2-((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)-3-methylbutanoate;

(2S)-Neopentyl 2-((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)-3-methylbutanoate;

(2S)-Neopentyl 2-((((2R,3R,4R)-5-(2-amino-6-methoxy-9H-purin-9-yl)-3,4-dihydroxy-4-methyltetrahydrofuran-2-yl)methoxy)(quinolin-8-yloxy)phosphorylamino)-3-methylbutanoate;

(2S)-Neopentyl 2-(((((2R,3R,4R))-5-(2-amino-6-methoxy-9H-purin-9-yl)-3,4-dihydroxy-4-methyltetrahydrofuran-2-yl)methoxy)(2-methylnaphthalen-1-yloxy) phosphorylamino)-3-methylbutanoate;

(2S)-Neopentyl 2-(((((2R,3R,4R)-5-(2-amino-6-methoxy-9H-purin-9-yl)-3,4-dihydroxy-4-methyltetrahydrofuran-2-yl)methoxy)(3-tert-butylnaphthalen-1-yloxy)phosphorylamino)-3-methylbutanoate;

(2S)-Neopentyl 2-(((((2R,3R,4R)-5-(2-amino-6-methoxy-9H-purin-9-yl)-3,4-dihydroxy-4-methyltetrahydrofuran-2-yl)methoxy)(3,7-di-tert-butylnaphthalen-1-yloxy)phosphorylamino)-3-methylbutanoate;

Benzyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)-3-methylbutanoate;

2,4-Difluorobenzyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)-3-methylbutanoate;

(2S)-((S)-1-Phenylethyl) 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy) phosphorylamino)-3-methylbutanoate;

(2S)-((S)-1-(4-Bromophenyl)ethyl) 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-((S)-1-(2-Bromophenyl)ethyl) 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-Methyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-Neopentyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-Cyclopropylmethyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy) phosphorylamino)-3-methylbutanoate;

(2S)-Cyclobutyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate;

Cyclopentyl 2(S)-(((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)-3-methylbutanoate;

Cyclohexyl 2(S)-(((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)-3-methylbutanoate;

(2S)-Tetrahydro-2H-pyran-4-yl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-benzyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-methyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-propyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-neopentyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-cyclohexyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-benzyl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate;

(2S)-2,4-difluorobenzyl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate;

(2S)-((S)-1-phenylethyl) 2-((((2R,-3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate;

2,2-dimethylpropyl 2 (S)-(((((2R,3R,4R,5R)-5-(2-amino-6-ethoxy-9H-purin-9-yl)-3,4-dihydroxy-4-methyltetrahydrofuran-2-yl)methoxy(naphthalene-1-yloxy)phosphorylamino)propanoate;

(2S)-isopropyl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate;

(2S)-tetrahydro-2H-pyran-4-yl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate;

(2S)-neopentyl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-neopentyl 2-(((((2R,3R,4R)-5-(2-amino-6-(methylamino)-9H-purin-9-yl)-3,4-dihydroxy-4-methyltetrahydrofuran-2-yl)methoxy)(naphthalen-1-yloxy)phosphorylamino)propanoate;

(2S)-((S)-1-phenylethyl) 2-((((2R,3R,4R)-5-(2-amino-6-(methylamino)-9H-purin-9-yl)-3,4-dihydroxy-4-methyltetrahydrofuran-2-yl)methoxy)(naphthalen-1-yloxy)phosphorylamino)propanoate;

(2S)-neopentyl 2-((((2R,3R,4R,5R)-5-(2-amino-6-(methylamino)-9H-purin-9-yl)-3,4-dihydroxy-4-methyltetrahydrofuran-2-yl)methoxy)(quinolin-6-yloxy)phosphorylamino)propanoate;

2,2-Dimethylpropyl 2(S)-(((((2R,3R,4R,5R)-5-(2-amino-6-benzylamino-9H-purin-9-yl)-3,4-dihydroxy-4-methyltetrahydrofuran-2-yl)methoxy(naphthalene-1-yloxy)phosphorylamino)propionate;

(2S)-neopentyl 2-((((2R,3R,4R)-5-(2-amino-6-(phenethylamino)-9H-purin-9-yl)-3,4-dihydroxy-4-methyltetrahydrofuran-2-yl)methoxy)(naphthalen-1-yloxy)phosphorylamino)propanoate;

(2S)-((S)-1-phenylethyl) 2-((((2R,3R,4R)-5-(2-amino-6-(methylthio)-9H-purin-9-yl)-3,4-dihydroxy-4-methyltetrahydrofuran-2-yl)methoxy)(naphthalen-1-yloxy)phosphorylamino)propanoate;

(2S)-neopentyl 2-((((2R,3R,4R)-5-(2-amino-6-(methylthio)-9H-purin-9-yl)-3,4-dihydroxy-4-methyltetrahydrofuran-2-yl)methoxy)(naphthalen-1-yloxy)phosphorylamino)propanoate;

(2S)-neopentyl 2-((((2R,3R,4R,5R)-5-(2-amino-6-(methylthio)-9H-purin-9-yl)-3,4-dihydroxy-4-methyltetrahydrofuran-2-yl)methoxy)(quinolin-6-yloxy)phosphorylamino)propanoate;

(2S)-benzyl 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate;

(2S)-((S)-1-phenylethyl) 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate;

(2S)-neopentyl 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate;

(2S)-cyclohexyl 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate;

benzyl (2S)-benzyl 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)-3-methylbutanoate; and (2S)-neopentyl 2-((((2R,3R,4R,5R)-5-(2-(4-fluorobenzylamino)-6-methoxy-9H-purin-9-yl)-3,4-dihydroxy-4-methyltetrahydrofuran-2-yl)methoxy) (naphthalen-1-yloxy)phosphorylamino)propanoate;

Once again, in each case with regard to the foregoing specific compounds, it is contemplated that the invention will include polymorphs and phosphorus diastereomers thereof.

In yet another embodiment of the present invention, there are provided the following additional compounds that are contemplated as being useful in the methods of treatment in accordance with the invention as set forth herein:

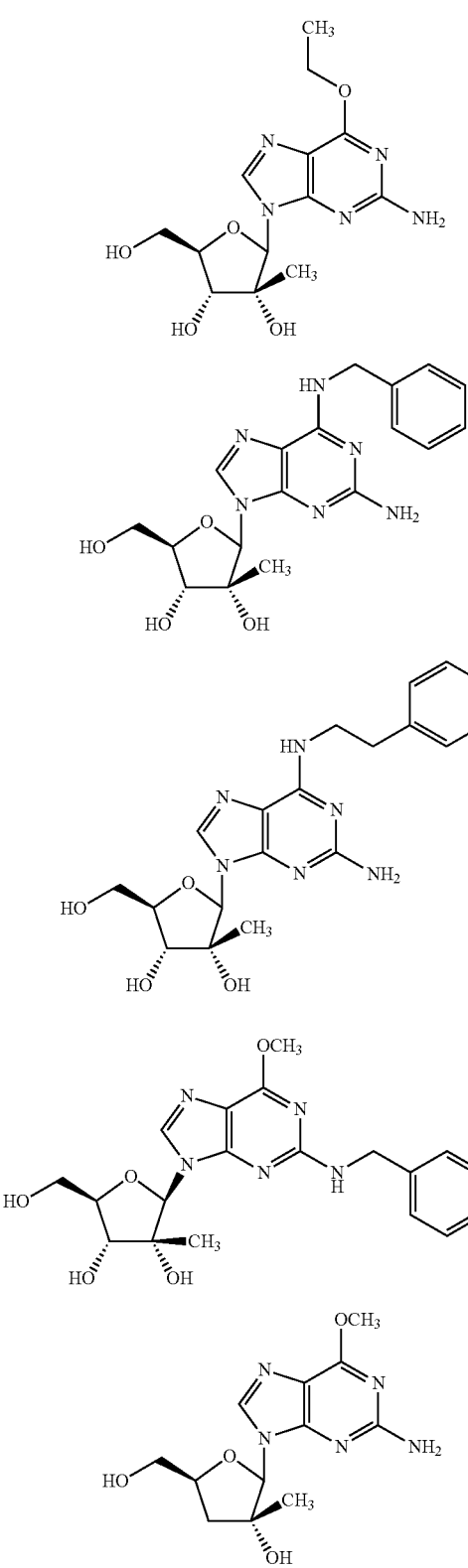

and pharmaceutically acceptable salts thereof.

The compounds of formulae II-VI above, are also considered novel compounds with antiviral activity in accordance with the invention, and thus are useful in the antiviral methods of the invention, and are also useful as intermediates in the preparation of compounds of formula (I) as described above. These compounds also include polymorphs and diastereomers thereof, and can be made into pharmaceutical compositions in the same manner set forth herein.

In further embodiments of the present invention, additional compounds are provided as follows:

A compound of formula (XL) below is also provided as an antiviral compound in accordance with the invention which has the structure:

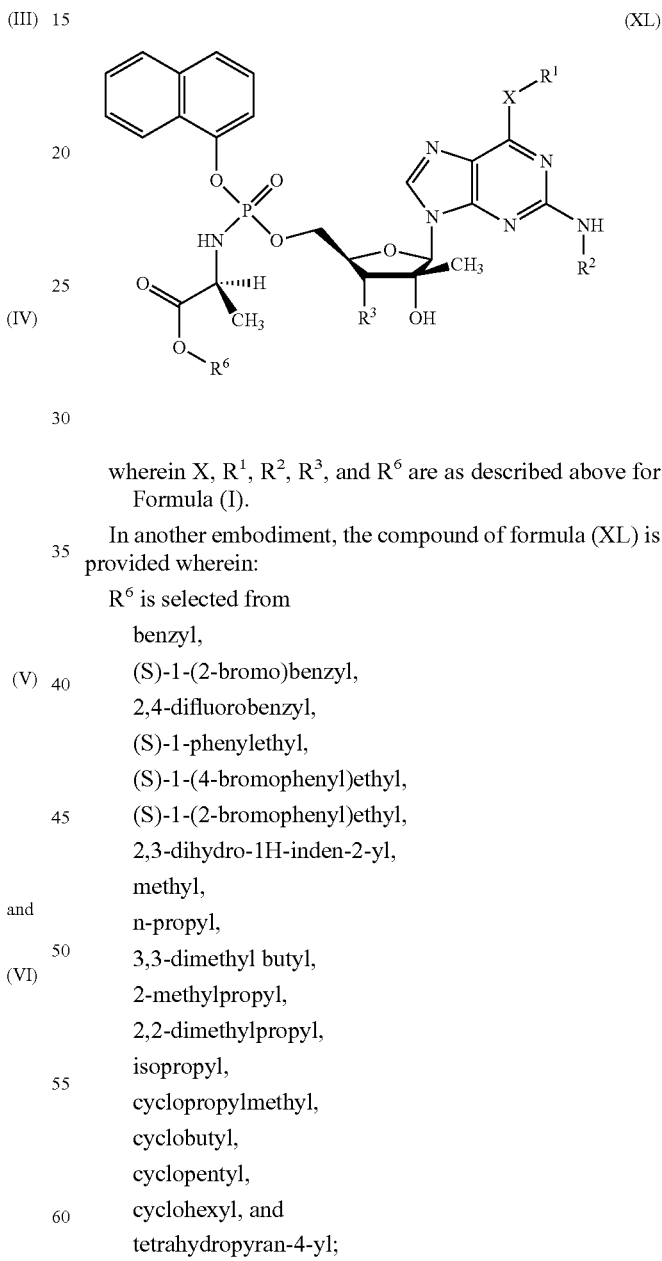

wherein X, $R^1$, $R^2$, $R^3$, and $R^6$ are as described above for Formula (I).

In another embodiment, the compound of formula (XL) is provided wherein:

$R^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl,
2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl;
and
X, $R^1$, $R^2$, and $R^3$ are as described for Formula (I).

A compound of formula (XLI) below is also provided as an antiviral compound in accordance with the invention which has the structure:

(XLI)

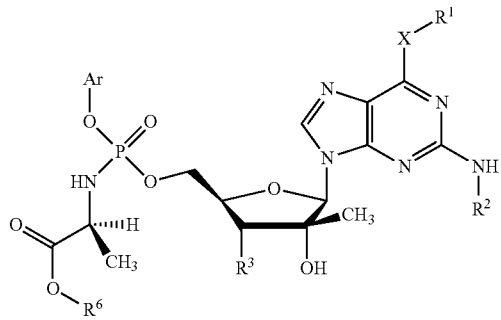

wherein Ar, X, R¹, R², R³, and R⁶ are as described above for Formula (I).

In another embodiment, the compound of formula (XLI) is provided wherein:
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl,
2-naphthyl,
quinolin-5-yl,
quinolin-6-yl,
quinolin-8-yl, and
phenyl;
and
X, R¹, R², R³ and R⁶ are as described above for Formula (I).

In addition, another compound of formula (XLI) is provided wherein
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl,
quinolin-8-yl, and
phenyl;
R⁶ is selected from
benzyl,
(S)-1-(2-bromo)-benzyl,
2,4-difluorobenzyl,
(S)-1-phenylethyl,
(S)-1-(4-bromophenyl)ethyl,
(S)-1-(2-bromophenyl)ethyl,
2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl;
and
X, R¹, R², and R³ are as described above for Formula (I).

A compound of formula (XLII) below is also provided as an antiviral compound in accordance with the invention which has the structure:

(XLII)

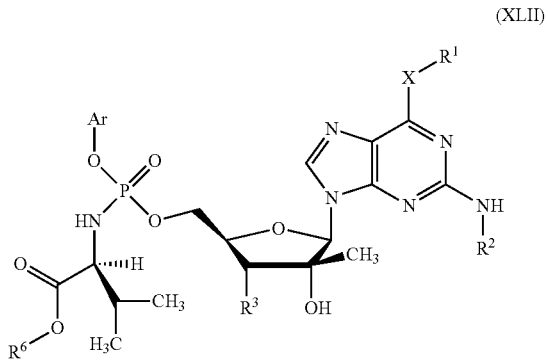

wherein Ar, X, R¹, R², R³, and R⁶ are as described above for Formula (I).

In another embodiment, the compound of formula (XLII) is provided wherein:
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl,
quinolin-8-yl, and
phenyl;
R⁶ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
-isopropyl,
cyclopropylmethyl,
cyclobutyl,
cyclopentyl,
cyclohexyl, and
tetrahydropyran-4-yl;
and
X, R¹, R², and R³ are as described above for Formula (I).

In addition, another compound of formula (XLII) is provided wherein:
Ar is 1-naphthyl; and
X, R¹, R², R³ and R⁶ are as described above for Formula (I).

In addition, another compound of formula (XLII) is provided wherein:
Ar is 1-naphthyl;
R⁶ is selected from
benzyl,
(S)-1-(2-bromo)benzyl,
2,4-difluorobenzyl,
(S)-1-phenylethyl,
(S)-1-(4-bromophenyl)ethyl, (S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl;
and
X, $R^1$, $R^2$, and $R^3$ are as described above for Formula (I).

A compound of formula (XLIII) below is also provided as an antiviral compound in accordance with the invention which has the structure:

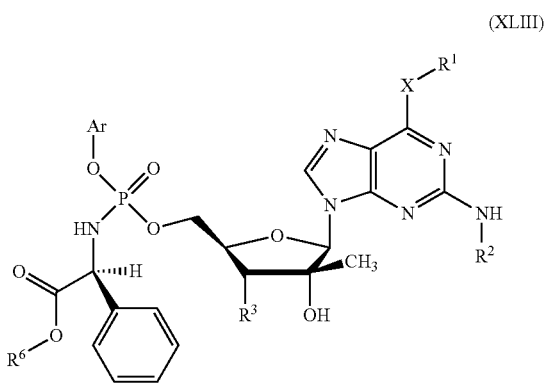

(XLIII)

wherein Ar, X, $R^1$, $R^2$, $R^3$, and $R^6$ are as described above for Formula (I).

In another embodiment, the compound of formula (XLIII) is provided wherein:
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl,
quinolin-8-yl, and
phenyl;
$R^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
-isopropyl,
cyclopropylmethyl,
cyclobutyl,
cyclopentyl,
cyclohexyl, and
tetrahydropyran-4-yl;
and
X, $R^1$, $R^2$, and $R^3$ are as described above for Formula (I).

In addition, another compound of formula (XLIII) is provided wherein:
Ar is 1-naphthyl; and
X, $R^1$, $R^2$, $R^3$ and $R^6$ are as described above for Formula (I).

In addition, another compound of formula (XLIII) is provided wherein:
Ar is 1-naphthyl;
$R^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
-isopropyl,
cyclopropylmethyl,
cyclobutyl,
cyclopentyl,
cyclohexyl, and
tetrahydropyran-4-yl;
and
X, $R^1$, $R^2$, and $R^3$ are as described above for Formula (I).

A compound of formula (XLIV) below is also provided as an antiviral compound in accordance with the invention which has the structure:

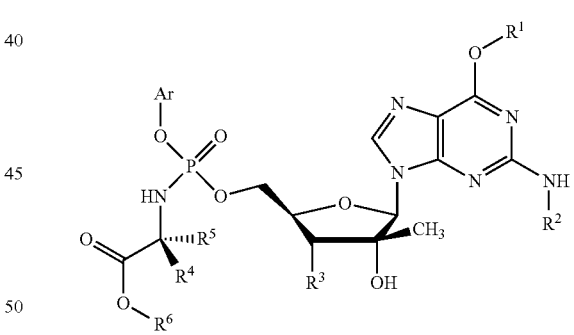

(XLIV)

wherein Ar, and $R^1$-$R^6$ are as described above for Formula (I).

In another embodiment, the compound of formula (XLIV) is provided wherein:
$R^4$ and $R^5$ are independently selected from
hydrogen,
methyl,
isopropyl,
2-thiomethylethyl,
2-methylpropyl,
1-methylpropyl, and
phenyl;
and
Ar, $R^1$, $R^2$, $R^3$, and $R^6$ are as described above for Formula (I).

In addition, another compound of formula (XLIV) is provided wherein:
R¹ is ethyl;
and
Ar, R²-R⁶ are as described above for Formula (I).

In addition, another compound of formula (XLIV) is provided wherein:
R¹ is ethyl;
Ar is selected from
  (S)-2-(3-methoxybut-3-oxo-2-yl)naphthalen-6-yl,
  2-methylnaphthalen-1-yl,
  3-tert-butylnaphthalen-1-yl,
  3,7-di-tert-butylnaphthalen-1-yl,
  1-naphthyl, 2-naphthyl,
  quinolin-5-yl, quinolin-6-yl,
  quinolin-8-yl, and
  phenyl;
R⁴ and R⁵ are independently selected from
  hydrogen,
  methyl,
  isopropyl,
  2-thiomethylethyl,
  2-methylpropyl,
  1-methylpropyl, and
  phenyl;
R⁶ is selected from
  benzyl,
  (S)-1-(2-bromo)benzyl,
  2,4-difluorobenzyl,
  (S)-1-phenylethyl,
  (S)-1-(4-bromophenyl)ethyl,
  (S)-1-(2-bromophenyl)ethyl, 2,3-dihydro-1H-inden-2-yl,
  methyl,
  n-propyl,
  3,3-dimethyl butyl,
  2-methylpropyl,
  2,2-dimethylpropyl,
  isopropyl,
  cyclopropylmethyl,
  cyclobutyl,
  cyclopentyl,
  cyclohexyl, and
  tetrahydropyran-4-yl;
and
R² and R³ are as described above for Formula (I).

A compound of formula (XLV) below is also provided as an antiviral compound in accordance with the invention which has the structure:

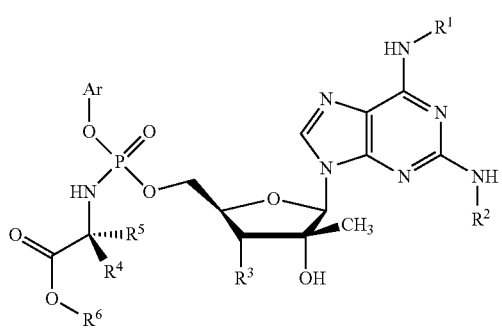

(XLV)

wherein Ar, and R¹-R⁶ are as described above for Formula (I).

In another embodiment, the compound of formula (XLV) is provided wherein:
Ar is selected from
  (S)-2-(3-methoxybut-3-oxo-2-yl)naphthalen-6-yl,
  2-methylnaphthalen-1-yl,
  3-tert-butylnaphthalen-1-yl,
  3,7-di-tert-butylnaphthalen-1-yl,
  1-naphthyl, 2-naphthyl,
  quinolin-5-yl, quinolin-6-yl,
  quinolin-8-yl, and
  phenyl;
R⁴ and R⁵ are independently selected from
  hydrogen,
  methyl,
  isopropyl,
  2-thiomethylethyl,
  2-methylpropyl,
  1-methylpropyl, and
  phenyl;
R⁶ is selected from
  benzyl,
  (S)-1-(2bromo benzyl,
  2,4-difluorobenzyl,
  (S)-1-phenylethyl,
  (S)-1-(4-bromophenyl)ethyl,
  (S)-1-(2-bromophenyl)ethyl, 2,3-dihydro-1H-inden-2-yl,
  methyl,
  n-propyl,
  3,3-dimethyl butyl,
  2-methylpropyl,
  2,2-dimethylpropyl,
  isopropyl,
  cyclopropylmethyl,
  cyclobutyl,
  cyclopentyl,
  cyclohexyl, and
  tetrahydropyran-4-yl;
and
R¹, R² and R³ are as described above for Formula (I).

A compound of formula (XLVI) below is also provided as an antiviral compound in accordance with the invention which has the structure:

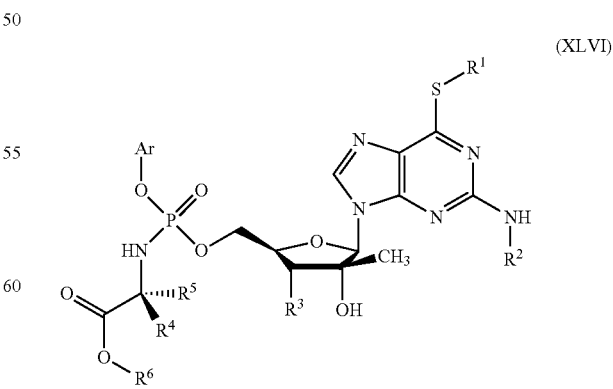

(XLVI)

wherein Ar, and R¹-R⁶ are as described above for Formula (I).

In another embodiment, the compound of formula (XLVI) is provided wherein:
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl,
quinolin-8-yl, and
phenyl;
$R^4$ and $R^5$ are independently selected from
hydrogen,
methyl,
isopropyl,
2-thiomethylethyl,
2-methylpropyl,
1-methylpropyl, and
phenyl;
$R^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl;
and
$R^1$, $R^2$ and $R^3$ are as described above for Formula (I).

A compound of formula (XLVII) below is also provided as an antiviral compound in accordance with the invention which has the structure:

(XLVII)

wherein Ar, X, and $R^1$, $R^2$, $R^4$, $R^5$ and $R^6$ are as described above for Formula (I).

In another embodiment, the compound of formula (XLVII) is provided wherein:
$R^4$ and $R^5$ are independently selected from
hydrogen,
methyl,
isopropyl,
2-thiomethylethyl,
2-methylpropyl,
1-methylpropyl, and
phenyl;
and
Ar, $R^1$, $R^2$, $R^3$, and $R^6$ are as described above for Formula (I).

In addition, another compound of formula (XLVII) is provided wherein
X is O;
and
Ar, $R^1$, $R^2$, $R^4$, $R^5$ and $R^6$ are as described above for Formula (I).

In addition, another compound of formula (XLVII) is provided wherein
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl,
quinolin-8-yl, and
phenyl;
$R^1$ is methyl;
$R^4$ and $R^5$ are independently selected from
hydrogen,
methyl,
isopropyl,
2-thiomethylethyl,
2-methylpropyl,
1-methylpropyl, and
phenyl;
$R^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl;
and
X and $R^2$ are as described above for formula (I).

In addition, another compound of formula (XLVII) is provided wherein
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl,
quinolin-8-yl, and
phenyl;
X is O;

$R^4$ and $R^5$ are independently selected from
hydrogen,
methyl,
isopropyl,
2-thiomethylethyl,
2-methylpropyl,
1-methylpropyl, and
phenyl;
$R^6$ is selected from
benzyl,
(S)-1-(2-bromo) benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl;
and
$R_1$ and $R^2$ are as described above for formula (I).
In addition, another compound of formula (XLVII) is provided wherein
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl,
quinolin-8-yl, and
phenyl;
X is O;
$R^1$ is methyl;
$R^4$ and $R^5$ are independently selected from
hydrogen,
methyl,
isopropyl,
2-thiomethylethyl,
2-methylpropyl,
1-methylpropyl, and
phenyl;
$R^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl;
and
$R^2$ is as described above for formula (I).

A compound of formula (XLVIII) below is also provided as an antiviral compound in accordance with the invention which has the structure:

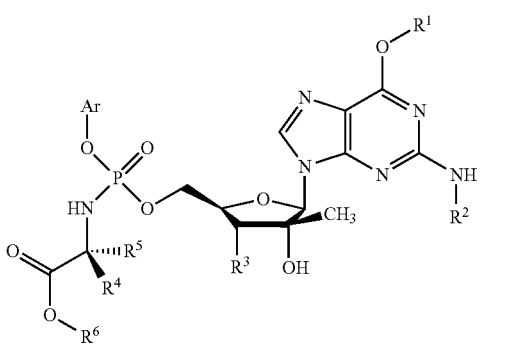

(XLVIII)

wherein $R^2$ is other than H;
and
Ar, $R^1$, $R^3 R^4$, $R^5$ and $R^6$ are as described above for Formula (I).
In addition, the compound of formula (XLVIII) may also be provided wherein:
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl,
quinolin-8-yl, and
phenyl;
$R^1$ is methyl;
$R^2$ is other than H;
$R^4$ and $R^5$ are independently selected from
hydrogen,
methyl,
isopropyl,
2-thiomethylethyl,
2-methylpropyl,
1-methylpropyl, and
phenyl;
$R^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl, cyclohexyl, and
tetrahydropyran-4-yl;
and
R³ is as described above for formula (I).

Once again, in each case with regard to the foregoing compounds, it is contemplated that the invention will include polymorphs and phosphorus diastereomers thereof. In addition, the above compounds will be useful in pharmaceutical compositions as set forth above, and these compounds and compositions will be useful in the antiviral methods of treatment as discussed herein.

In yet another embodiment in accordance with the invention, the above compounds according to formula (I) above can include different diastereomers around phosphorous, as set forth in the following example:

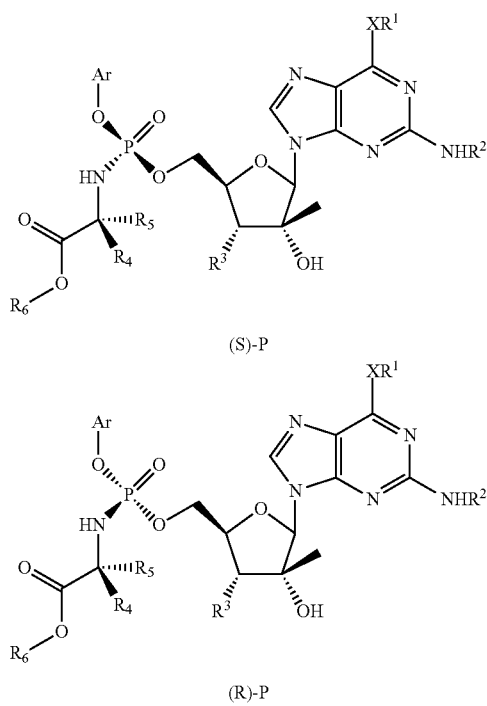

In yet another embodiment in accordance with the invention, compounds can also be obtained which include a mixture of the two phosphorous diastereomers set forth above in any proportion from 1:99 to 99:1, e.g. 10:90, 25:75, 40:60, 50:50, 60:40. 75:25, 90:10, etc. In the above example, the mixtures will include a desired percentage of the (S)-P form and the remaining percentage of the (R)-P form.

According to other embodiments of the present invention there is provided a compound of formulas (I-VI) above for use in a method of treatment of a viral infection of the family Flaviviridae, for example in the treatment of hepatitis C virus. According to other embodiments of the present invention there is provided a pharmaceutical composition comprising a compound of formulas I-VI in combination with a pharmaceutically acceptable carrier, diluent or excipient.

Compounds according to the present invention have surprisingly been found to have enhanced anti-viral activity. In particular, compounds according to the present invention have been found to have enhanced potency with respect to hepatitis C virus. Further, compounds according to the present invention have surprisingly been found to have enhanced stability in rodent plasma. In particular, compounds according to the present invention have been found to have stabilities of greater than 4 hours in mouse plasma.

Definitions

As used herein, the term "alkyl" refers to a straight or branched saturated monovalent cyclic or acyclic hydrocarbon radical, having the number of carbon atoms as indicated (or where not indicated, an acyclic alkyl group preferably has 1-20, more preferably 1-6, more preferably 1-4 carbon atoms and a cyclic alkyl group preferably has 3-20, preferably 3-10, more preferably 3-7 carbon atoms), optionally substituted with one, two, three or more substituents independently selected from the group set out above. By way of non-limiting examples, suitable alkyl groups include methyl, ethyl, propyl, butyl, pentyl, hexyl, octyl, nonyl, isopropyl, 2-butyl, cyclopropyl, cyclohexyl, cyclopentyl and dodecyl. The term "$C_3$-$C_8$cycloalkyl" refers to cyclic alkyl group comprising from about 3 to about 8 C atoms. The term "$C_3$-$C_8$cycloalkylalkyl" refers to an acyclic alkyl group substituted by a cyclic alkyl group comprising from about 3 to about 8 C atoms.

As used herein, the term "alkenyl" refers to a straight or branched unsaturated monovalent acyclic or cyclic hydrocarbon radical having one or more C=C double bonds and having the number of carbon atoms as indicated (or where not indicated, an acyclic alkenyl group preferably has 2-20, more preferably 2-6, more preferably 2-4 carbon atoms and a cyclic alkenyl group preferably has 4-20, more preferably 4-6 carbon atoms), optionally substituted with one, two, three or more substituents independently selected from the group set out above. By way of non-limiting examples, suitable alkenyl groups include vinyl, propenyl, butenyl, pentenyl and hexenyl.

As used herein, the term "alkynyl" refers to a straight or branched unsaturated monovalent acyclic or cyclic hydrocarbon radical having one or more triple C/C bonds and having the number of carbon atoms as indicated (or where not indicated, an acyclic alkynyl group preferably has 2-20, more preferably 2-6, more preferably 2-4 carbon atoms and a cyclic alkynyl group preferably has 7-20, more preferably 8-20 carbon atoms), optionally substituted with one, two, three or more substituents independently selected from the group set out above.

As use herein, the term "alkoxy" or the term "alkyloxy" refers to the group alkyl-O—, where alkyl is as defined above and where the alkyl moiety may optionally be substituted by one, two, three or more substituents as set out above for alkyl. By way of non-limiting examples, suitable alkoxy groups include methoxy, ethoxy, n-propoxy, iso-propoxy, n-butoxy, tert-butoxy, sec-butoxy, n-pentoxy, n-hexoxy and 1,2-dimethylbutoxy. The term "cycloalkyloxy" refers to the group cyclicalkyl-O—, where cyclicalkyl is as defined above and where the cyclicalkyl moiety may be optionally substituted by one, two, three or more substituents as set out above for alkyl.

As used herein, the term "alkylthio" refers the group alkyl-S—, where alkyl is as defined above and where the alkyl moiety may optionally be substituted by one, two, three or more substituents as set out above for alkyl. By way of non-limiting examples, suitable alkylthio groups include methylthio, ethylthio, n-propylthio, iso-propylthio, n-butylthio, tert-butylthio, sec-butylthio, n-pentylthio, n-hexoxy and 1,2-dimethylbutylthio.

As used herein, the term "aryloxy" refers to the group aryl-O—, where aryl is as defined below and where the aryl moiety may optionally be substituted by one, two, three or more substituents as set out above with respect to the group Ar.

As used herein, the term "alkoxyalkyl" refers to an alkyl group having an alkoxy substituent. Binding is through the alkyl group. The alkyl moiety and the alkoxy moiety are as defined herein with respect to the definitions of alkyl and alkoxy, respectively. The alkoxy and alkyl moieties may each be substituted by one, two, three or more substituents as set out above with regard to the definition of alkyl.

As used herein, the term "alkylthioalkyl" refers to an alkyl group having an alkylthio substituent. Binding is through the alkyl group. The alkyl moiety and the alkylthio moiety are as defined herein with respect to the definitions of alkyl and alkylthio, respectively. The alkylthio and alkyl moieties may each be substituted by one, two, three or more substituents as set out above with regard to the definition of alkyl.

As used herein, the term "alkoxyaryl" refers to an aryl group having an alkoxy substituent. Binding is through the aryl group. The alkoxy moiety and the aryl moiety are as defined herein with respect to the definitions of alkoxy and aryl, respectively. The alkoxy and aryl moieties may each be substituted by one, two, three or more substituents, as defined herein with regard to the definitions of alkoxy and aryl, respectively.

As used herein, the term "cycloalkylaryl" refers to an aryl group having a cyclic alkyl substituent. Binding is through the aryl group. The cycloalkyl moiety and the aryl moiety are as defined herein with respect to the definitions of cycloalkyl and aryl, respectively.

As used herein, the term "aryl($C_1$-$C_6$)alkyl-" refers to a $C_1$-$C_6$ alkyl group substituted at any carbon by an aryl group. Binding is through the alkyl group. The aryl moiety and the alkyl moiety are as defined herein with respect to the definitions of aryl and alkyl. The aryl group may be substituted. By way of non-limiting examples, suitable aryl($C_1$-$C_6$)alkyl- groups include benzyl, 1-phenylethyl, 3-phenylpropyl, 4-chlorobenzyl, 4-fluorobenzyl, 2,4-difluorobenzyl, and the like.

As used herein, the term "alkylcarboxy($C_1$-$C_6$)alkyl-" refers to a $C_1$-$C_6$ alkyl group substituted at any carbon by an alkylcarboxy [alkyl-C(=O)O—] group. The alkyl moiety is as defined hereinabove. By way of non-limiting examples, suitable alkylcarboxy($C_1$-$C_6$)alkyl- groups include acetoxymethyl [$CH_3C$(=O)O—$CH_2$—], propanoyloxyethyl [$CH_3CH_2C$(=O)O—$CH_2CH_2$—], neo-pentoyloxypropyl [$(CH_3)_3CCH_2C$(=O)O—$CH_2\,CH_2\,CH_2$—] and the like.

A cycloalkyl moiety and the aryl moiety may each be optionally substituted by one, two, three or more substituents as set out herein with regard to the definitions of alkyl and aryl, respectively.

As used herein the term "aryl" refers to a monovalent unsaturated aromatic carbocyclic radical having one, two, three, four, five or six rings, preferably one, two or three rings, which may be fused or bicyclic. An aryl group may optionally be substituted by one, two, three or more substituents as set out above with respect to optional substituents that may be present on the group Ar. Preferred aryl groups are: an aromatic monocyclic ring containing 6 carbon atoms; an aromatic bicyclic or fused ring system containing 7, 8, 9 or 10 carbon atoms; or an aromatic tricyclic ring system containing 10, 11, 12, 13 or 14 carbon atoms. Non-limiting examples of aryl include phenyl and naphthyl. These compounds may include substituent groups, preferably those substituent groups independently selected from hydroxy (—OH), acyl (R'—C(=O)), acyloxy (R'—C(O)—O—), nitro (—$NO_2$), amino (—$NH_2$), carboxyl (—COOH), cyano (—CN), $C_1$-$C_6$monoalkylamino, $C_1$-$C_6$dialkylamino, thiol, chloro, bromo, fluoro, iodo, $SO_3H$, —SH, —SR', wherein R' is independently selected from halo, $C_1$-$C_6$alkoxy, and $C_1$-$C_6$alkyl.

As used herein, the term "heterocycloalkyl" refers to a saturated or partially unsaturated heterocyclic ring system having one, two, three, four, five or six rings, preferably one, two or three rings, which may be fused or bicyclic, and having contained within the ring or rings at least one member selected from the group consisting of N, O and S. The prefix "$C_5$-$C_{20}$" or "$C_5$-$C_{10}$" used before heterocycloalkyl means, respectively, a five to twenty or a five to ten-membered ring system at least one of which members is selected from the group consisting of N, O and S. Preferred heterocycloalkyl systems are: a monocyclic ring system having five members of which at least one member is a N, O or S atom and which optionally contains one additional O atom or one, two or three additional N atoms; a monocyclic ring having six members of which one, two or three members are a N or O atom; a bicyclic ring system having nine members of which at least one member is a N, O or S atom and which optionally contains one, two or three additional N atoms; or a bicyclic ring system having ten members of which one, two or three members are a N atom. By way of non-limiting examples, suitable heterocycloalkyl groups include tetrahydrofuranyl, tetrahydropyranyl, pyrrolidinyl, morpholinyl, tetrahydrothiopyranyl, thiomorpholinyl, and piperidinyl When a radical is drawn as a structure, e.g.,

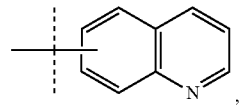

As used herein, the term "indanyl" refers to the fused bicyclic radical of structure,

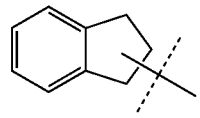

wherein the point of attachment of the radical to the rest of the molecule is on any available non-aromatic carbon atom.

Available carbon atoms and/or heteroatoms of the "heterocycloalkyl" ring systems described above may be substituted on the ring with one or more heteroatoms. Where the ring(s) is substituted with one or more heteroatoms, heteroatom substituents are selected from oxygen, nitrogen, sulphur and halogen (F, Cl, Br and I). Where the ring(s) is substituted with one or more heteroatoms, preferably there are 1, 2, 3 or 4 heteroatom substituents selected from the group consisting of oxygen, nitrogen and/or halogen. Preferred substituent groups are independently selected from hydroxy, acyl, acyloxy, nitro, amino, $SO_3H$, SH, SR', wherein R' is independently selected from the same groups as R; carboxyl, cyano, ($C_1$-$C_6$)alkylamino, ($C_1$-$C_6$)dialkylamino, thiol, chloro, bromo, fluoro and iodo.

Furthermore, the compounds of this invention contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The compounds of this invention may contain one or more asymmetric centers, depending upon the location and nature of the various substituents desired. Asymmetric carbon atoms or phosphorous atoms may be present in the (R) or (S) configuration or (R,S) configuration. In certain instances, asymmetry may also be present due to restricted rotation about a given bond, for example, the central bond adjoining two substituted aromatic rings of the specified compounds. Substituents on a ring may also be present in either cis or trans form, and a substituent on a double bond may be present in either Z or E form. It is intended that all such configurations (including enantiomers and diastereomers) are included within the scope of the present invention. Preferred compounds are those with the absolute configuration of the compound of this invention which produces the more desirable biological activity. Separated, pure or partially purified isomers or racemic mixtures of the compounds of this invention are also included within the scope of the present invention. Such compounds can be prepared or isolated as pure stereoisomers, i.e., as individual enantiomers or diastereomers, or as stereoisomer-enriched mixtures. All such stereoisomers (and enriched mixtures) are included within the scope of this invention. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like, also well-known in the art and exemplified the experimental examples below.

The term "pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "pharmaceutically acceptable partial salts" in included in the term "pharmaceutically acceptable salts" and refers to compounds having a substituent capable of having more than one group form a salt but less than the maximum amount of such groups actually form a salt. For example, a diphospho group can form a plurality of salts and, if only partially ionized, the resulting group is sometimes referred to herein as a partial salt. It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl- (substituted aryl)-substituted aryl. Similarly, it is understood that the above definitions are not intended to include impermissible substitution patterns (e.g., methyl substituted with 5 fluoro groups or a hydroxyl group pendent to a carbon atom of an ethenylic or acetylenic unsaturation). Such impermissible substitution patterns are well known to the skilled artisan.

The term "polymorphs" refers to any polymorphic forms that can exist in the compounds of formula (I), as recognized by one of ordinary skill in the art. As known in the art, polymorphism is an ability of a compound to crystallize as more than one distinct crystalline or "polymorphic" species. A "polymorph" is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989). Specifically, the compounds of this invention may be prepared by various methods known in the art of organic chemistry in general and nucleoside and nucleotide analogue synthesis in particular. General reviews of the preparation of nucleoside and nucleotide analogues include 1) Michelson A. M., "*The Chemistry of Nucleosides and Nucleotides*," Academic Press, New York, 1963; 2) Goodman L., "*Basic Principles in Nucleic Acid Chemistry*," Academic Press, New York, 1974, vol. 1, Ch. 2; and 3) "*Synthetic Procedures in Nucleic Acid Chemistry*," Eds. Zorbach W. & Tipson R., Wiley, New York, 1973, vol. 1 & 2.

Strategies available for synthesis of compounds of this invention are illustrated in the synthetic schemes below. For example, Reaction Scheme 1 illustrates a general method of preparation of the compounds of formula (Ia) [(formula (I) where $R^3$ is OH.]

Reaction Scheme 1 ($R^3$ = OH)

Step 1:

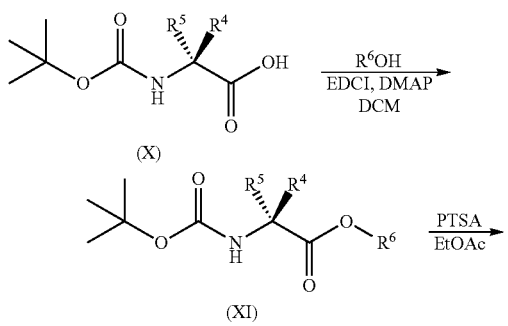

Step 2:

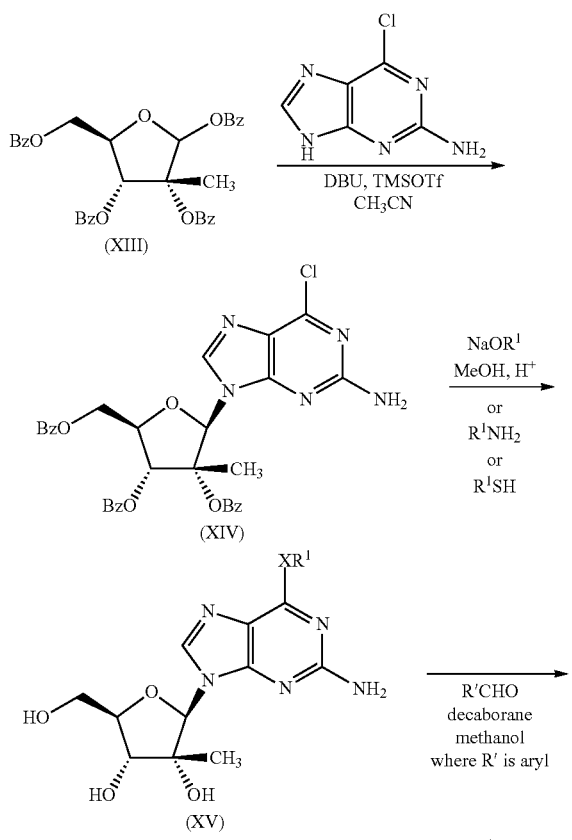

Step 3:

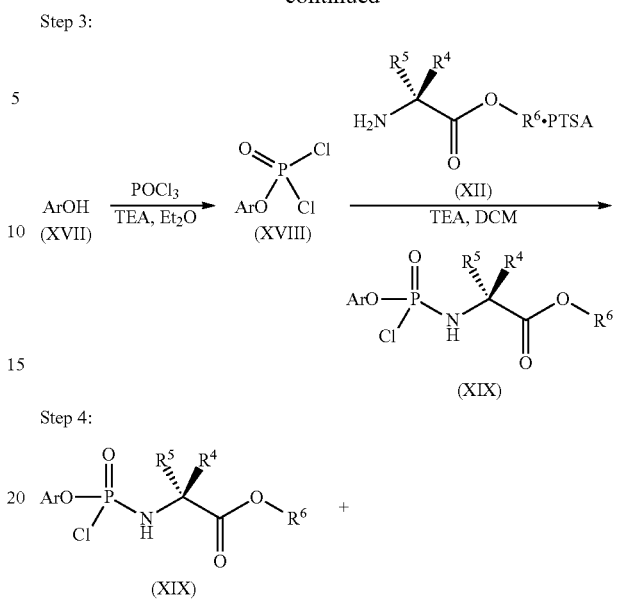

Step 4:

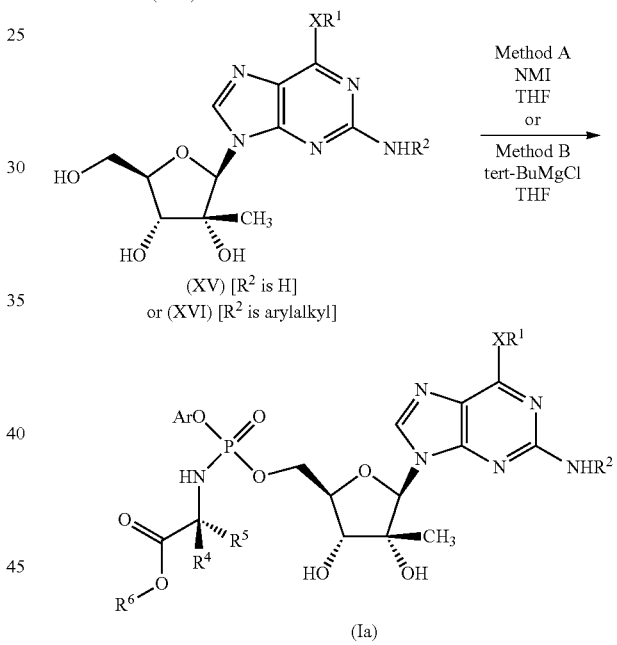

In this scheme, a protected amino acid of general formula (X) is esterified with an alcohol of formula $R^6OH$, facilitated by addition of such reagents as EDCI and DMAP, and carried out in an inert solvent such as dichloromethane, to produce the compound of formula (XI). Alternatively, many other commonly used ester forming reagents such as DCC/DMAP, trifluoroacetic anhydride, N,N'-carbonyldiimidazole and $PPh_3/CCl_4$ can be used. Removal of the BOC protecting group from compound (XI) and conversion to a salt of formula (XII) is carried out by its reaction with an organic acid such as PTSA in a suitable solvent such as ethyl acetate. Alternatively the BOC group can be removed with other acids such as trifluoroacetic acid and hydrochloric acid (HCl) which provide the corresponding TFA or HCl salts.

In Step 2, the protected sugar derivative of formula (XIII) is allowed to react with the 2-amino-6-chloropurine, using a non-nucleophilic base such as DBU, and a Lewis acid such as TMS triflate in a polar solvent such as acetonitrile, to produce the compound of formula (XIV). This reaction can be done at 0° C. to 100° C., but most preferably at 60° C. Alternatively, other nucleoside coupling reagents such as BSA/SnCl$_4$, or HMDS/TMSOTf can be used either with or with prior persilylation. Alternatively other know nucleoside coupling reagents, as described in the Handbook of Nucleoside Synthesis by Helmut Vorbruggen and Carmen Ruh-Pohlenz (John Wiley & Sons, Copyright 2001 by Organic Reactions) can be used. The nucleoside coupling reaction can be carried out in other polar or non-polar aprotic solvents such as, but not limited to, dichloroethane, toluene, o-, m-, or p-xylene or DCM. Displacement of the chlorine attached to the purine portion of the molecule by an oxygen nucleophile is carried out using an alkoxide ($R^1O-$) using the parent alcohol ($R^1OH$) as solvent, to produce the formula (XV) intermediate where X is O. Compounds of formula (XV), where X is NH, are similarly prepared by reaction of (XIV) with a nitrogen nucleophile of formula $R^1NH_2$. These reactions can be done with the $R^1NH_2$ as the solvent, or with $R^1NH_2$ as a reagent in a solvent such as, but not limited to ethanol, isopropanol, THF, acetonitrile, or DMF. Compounds of formula (XV), where X is S, are similarly prepared by reaction of (XIV) with a sulfur nucleophile of formula $R^1SH$. These reactions can be done with the $R^1SH$ as the solvent, or with $R^1SH$ as a reagent in a solvent such as, but not limited to ethanol, isopropanol, THF, acetonitrile, or DMF.

Conversion to the formula (XVI) compound is carried out by reductive amination in which an arylaldehyde, optionally substituted by halo on the aryl portion, is allowed to react with the formula (XV) compound in the presence of a selective reducing agent such as decaborane in a protic solvent such as methanol. This reaction can be run at 0° C. to 100° C. and most optimally at −25° C. Alternatively, other reducing agents can be used such as sodium cyano borohydride or sodium boro hydride, or other reductive amination reagents as described in "Comprehensive Organic Synthesis" Eds. B. M. Trost and I. Fleming, Pergamon, Oxford (1991), Vol 8, Part 1.2 p 25.

In Step 3, the aryl chloroamidate of formula (XIX) is prepared by reaction of the hydroxylated aryl compound of formula (XVII) with phosphorous oxychloride in the presence of a non-nucleophilic base such as triethylamine, to provide the intermediate of formula (XVIII). This reaction can be run in an aprotic solvent such as DCM, ether or MTBE and at low temperatures, preferably 0° C. to −78° C. and most optimally at −25° C. In addition to triethyl amine, many other non-nucleophilic bases can be used such as DIEA or DBU can be used. The product of this reaction can be used directly in the next reaction, or the amine salts generated in the reaction, such as triethyl ammonium hydrochloride, can be filtered off prior to the next step. The reaction should be protected from moisture at all times, as the phosphorodichloridate product, is very moisture sensitive. Subsequent reaction of (XVIII) with the amino ester salt of formula (XII) is carried out in the presence of a base to produce the compound of formula (XIX). This reaction can be done at 0° C. to −78° C., and most optimally at −25° C. A variety of non-polar aprotic solvents may be used such as ether, MTBE, and DCM. The base may be selected from a wide variety on non-nucleophilic organic amines such as, but not limited to, TEA, DIEA, or DBU. This reaction must be protected from moisture at all times. Upon completion of the reaction it is critical to remove the corresponding organic amine salts, such as triethyl ammonium hydrochloride, or triethyl ammonium p-toluene sulfonic acid. This can be accomplished by concentrating the reaction mixture and precipitating the salt with EtOAc and Hexanes and filtering them off, or by passing the crude product through a silica gel plug. Removal of solvents during the work up must be done at temperatures at or below 25° C. to avoid decomposition of the phosphorochloridate.

In Step 4, coupling of the formula (XIX) and formula (XV) or formula (XVI) compounds to provide the compound of formula (Ia) [formula (I) where $R^3$ is OH] is carried out using an nucleophilic catalyst such as NMI in an inert organic solvent such as THF. Other nucleophilic catalysts such as DMAP, Trimethylamine, pyridine, or 4-(pyrrolidin-1-yl)pyridine, can be used as well as other aprotic solvents such as diethyl ether, MTBE chloroform or DCM. These reactions can be carried out between 0° C. and 50° C., and most optimally at 25° C. Alternatively a strong non-nucleophilic base, e.g., tert-butyl magnesium chloride can be used in a solvent such as THF, or diethyl ether, or MTBE. Other strong proton selective organic or inorganic bases can be used such as n-butyl lithium, potassium tert-butoxide, 2,4,6-collidine, DBU, or lithium bis(trimethylsilyl)amide. This reaction can be carried out at −78° C. to 40° C. and most optimally at 0-25° C.

Reaction Scheme 2 illustrates that the phosphorous diastereomers produced in Step 4, can be separated using chiral chromatography.

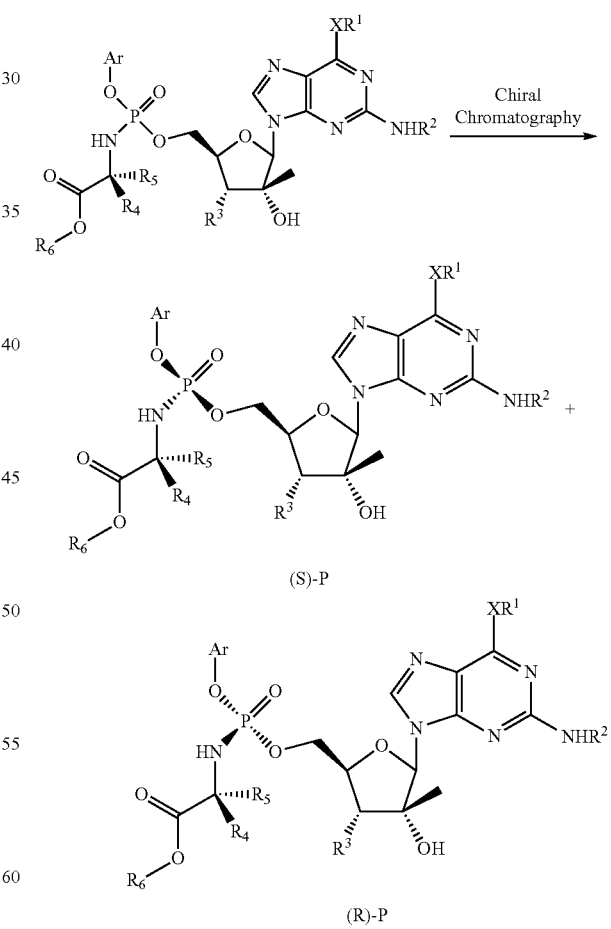

Reaction Scheme 2 (Separation of phosphorous diastereomers)

In this Scheme, the chiral chromatography can be performed on a variety of different chiral resins such as CHIRALPAK AD®, CHIRALPAK AS®, CHIRALCEL OD®, CHIRALCEL OJ®, CHIRALCEL OB®, and CHIRALCEL OC® AD-H®, AS-H®, OD-H®, OJ-H®, OB-H® and OC-H®. Alternatively the chiral resin could be selected from the list below:
CHIRALPAK® IA™
CHIRALPAK® IA-3
CHIRALPAK® AD-H
CHIRALPAK® AD
CHIRALPAK® AD-3
CHIRALPAK® AD-3R
CHIRALPAK® AS-H
CHIRALPAK® AS
CHIRALPAK® AY-H
CHIRALPAK® AY
CHIRALPAK® AZ-H
CHIRALPAK® AZ
CHIRALPAK® IB™
CHIRALCEL® OD-H
CHIRALCEL® OD
CHIRALCEL® OD-3
CHIRALCEL® OD-3R
CHIRALCEL® OD-I
CHIRALPAK® IC™
CHIRALPAK® IC-3
CHIRALCEL® OC-H
CHIRALCEL® OC
CHIRALCEL® OA
CHIRALCEL® OB-H
CHIRALCEL® OB
CHIRALCEL® OG
CHIRALCEL® OJ-H
CHIRALCEL® OJ
CHIRALCEL® OF
CHIRALCEL® OK
CHIRALCEL® OZ-H
CHIRALCEL® OZ Optimally a Chiral Pak AD column can be used with a mixture of 1:1 ethanol:hexanes as the mobile phase. Other solvents such as ethyl acetate, isopropanol, acetonitrile, and methanol can be used as the mobile phase, or other solvents familiar to those skilled in the art.

Reaction Scheme 3 illustrates a general method of preparation of the compounds of formula (I) where R³ is H (also referred to herein as "formula 1b").

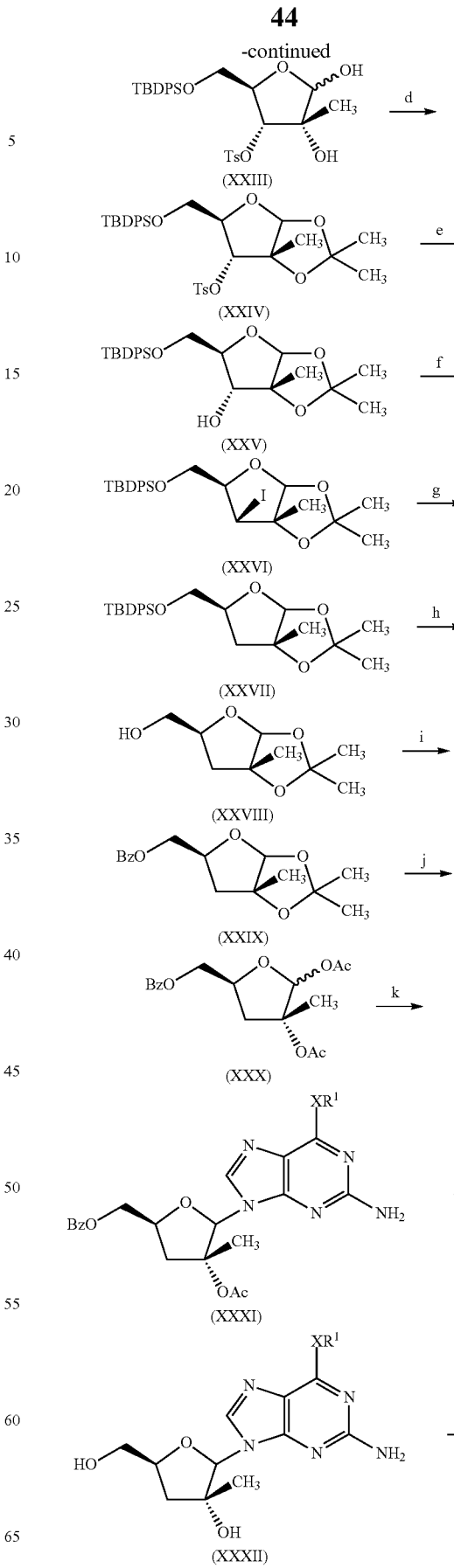

-continued

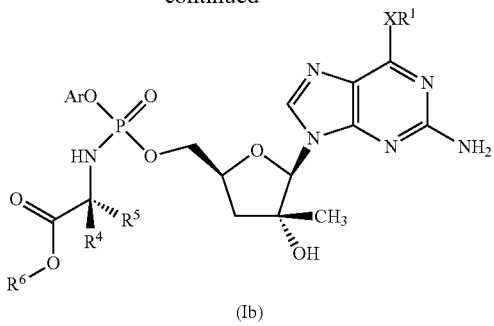

(Ib)

Reagents: a) TBDPSCl, DMAP, pyridine; b) TsCl, DMAP; c) Red-Al, ethanol, toluene; d) 2,2-dimethoxypropane, 5% PTSA, DCM; e) Lithium triethylborohydride, THF; f) triphenylphosphine, imidazole, iodine, toluene; g), tributyl tin hydride, AIBN, toluene; h) TBAF, THF; i) benzoyl chloride, pyridine, DMAP; j) (i) 70% acetic acid, (ii) acetic anhydride, DMAP, pyridine; k)

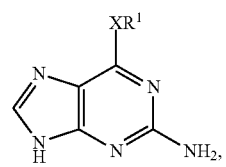

BSA, TMSOTf, acetonitrile; l) methanolic ammonia; m)

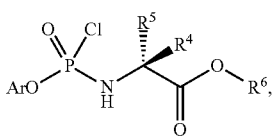
(XIX)

tert-butyl magnesium chloride/THF

In this scheme, the primary alcohol group present in the compound of formula (XX) is selected protected with, for example, TBDPSCl to provide an intermediate of formula (XXI). Protecting the secondary alcohol group with, for example, TsCl, gives the doubly protected intermediate of formula (XXII). Reduction of the lactone to a lactol of formula (XXIII) is carried out using a suitable reducing agent, such as Red-Al, and the diol is then converted to the acetonide of formula (XXIV) by reaction with acetone dimethylacetal and PTSA. Selective deprotection of the secondary alcohol is carried out, using, e.g., Li(Et)$_3$BH where the protecting group is Ts, provides the intermediate of formula (XXV). The hydroxy group is converted to an iodo group, using, e.g., triphenylphosphine, imidazole, and iodine, to give the compound of formula (XXVI). Removal of the iodo group is accomplished using tributyltin hydride, giving the intermediate of formula XXVII. By carrying out a series of deprotection/protection steps (h, i and j), the intermediate of formula (XXX) is prepared. This compound is analogous to the earlier described intermediate of formula (XIII), and by reaction with an appropriate guanine derivative followed by deprotection, the compounds of formula (XXXI) and (XXXII), respectively, can be prepared. The formula (XXXII) compound is converted to the compound of formula (Ib) [formula (I) where $R^3$=H] by reaction with the compound of formula (XIX) using the above described Method B.

The general schemes above are preferably carried out in the presence of a suitable solvent. Suitable solvents include hydrocarbon solvents such as benzene and toluene; ether type solvents such as diethyl ether, tetrahydrofuran, diphenyl ether, anisole and dimethoxybenzene; halogenated hydrocarbon solvents such as methylene chloride, chloroform and chlorobenzene; ketone type solvents such as acetone, methyl ethyl ketone and methyl isobutyl ketone; alcohol type solvents such as methanol, ethanol, propanol, isopropanol, n-butyl alcohol and tert-butyl alcohol; nitrile type solvents such as acetonitiile, propionitrile and benzonitrile; ester type solvents such as ethyl acetate and butyl acetate; carbonate type solvents such as ethylene carbonate and propylene carbonate; and the like. These may be used singly or two or more of them may be used in admixture. Preferably an inert solvent is used in the process of the present invention. The term "inert solvent" means a solvent inert under the conditions of the reaction being described in conjunction therewith including, for example, benzene, toluene, acetonitrile, tetrahydrofuran, dimethylformamide, chloroform, methylene chloride (or dichloromethane), diethyl ether, ethyl acetate, acetone, methylethyl ketone, methanol, ethanol, propanol, isopropanol, tert-butanol, dioxane, pyridine, and the like.

Dosages and Routes of Administration.

In general, the compounds of this invention will be administered in a therapeutically effective amount by any of the accepted modes of administration for agents that serve similar utilities. The effective amount will be that amount of the compound of this invention that would be understood by one skilled in the art to provide therapeutic benefits, i.e., the active ingredient, and will thus depend upon numerous factors such as the severity of the disease to be treated, the age and relative health of the subject, the potency of the compound used, the route and form of administration, and other factors. The drug can be administered more than once a day, and in the preferred mode the drug is administered once or twice a day. As indicated above, all of the factors to be considered in determining the effective amount will be well within the skill of the attending clinician or other health care professional.

For example, therapeutically effective amounts of compounds of Formula I may range from approximately 0.05 to 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-700 mg per day. In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract (see U.S. Pat. No. 5,607,915, said patent incorporated herein by reference).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability. These patents are incorporated herein by reference.

As indicated above, the compositions in accordance with the invention generally comprise a compound of a formula such as one of those recited above in combination with at least one pharmaceutically acceptable carrier, excipient or diluent. Some examples of acceptable excipients are those that are non-toxic, will aid administration, and do not adversely affect the therapeutic benefit of the compound of the invention. Such excipient may be any solid, liquid, semi-solid or, in the case of an aerosol composition, gaseous excipient that is generally available to one of skill in the art.

Solid pharmaceutical excipients useful in the invention may include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990). The amount of the compound in a formulation can vary within the full range employed by those skilled in the art. For example, the formulation will contain, on a weight percent (wt %) basis, from about 0.01-99.99 wt % wherein the compound is a compound of formula I based on the total formulation, with the balance being one or more suitable pharmaceutical excipients. Preferably, the compound is present at a level of about 1-80 wt %. Pharmaceutical formulations containing a compound in accordance with the invention are described further below.

Additionally, the present invention is directed to a pharmaceutical composition comprising a therapeutically effective amount of a compound of the present invention in combination with a therapeutically effective amount of one or more agents active against RNA-dependent RNA virus and, in particular, against HCV. Agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffman-LaRoche, Nutley, N.J.), interferon-α2b (such as Intron-A interferon available from Schering Corp., Kenilworth, N.J., USA), a consensus interferon, and a purified interferon-α product. For a discussion of ribavirin and its activity against HCV, see J. O, Saunders and S. A. Raybuck, "Inosine Monophosphate Dehydrogenase: Consideration of Structure, Kinetics and Therapeutic Potential," *Ann. Rep. Med. Chem.,* 35:201-210 (2000).

Even further, the present invention is directed to a pharmaceutical composition comprising a therapeutically effective amount of a compound of the present invention in combination with a therapeutically effective amount of one or more agents active against hepatitis C virus. Such agents include those that inhibit HCV proteases, HCV polymerase, HCV helicase, HCV NS4B protein, HCV entry, HCV assembly, HCV egress, HCV NS5A protein, and inosine 5'-monophosphate dehydrogenase. Other agents include nucleoside analogs for the treatment of an HCV infection. Still other compounds include those disclosed in WO 2004/014313 and WO 2004/014852 and in the references cited therein. The patent applications WO 2004/014313 and WO 2004/014852 are hereby incorporated by references in their entirety. Specific antiviral agents include Omega IFN (BioMedicines Inc.), BILN-2061 (Boehringer Ingelheim), Summetrel (Endo Pharmaceuticals Holdings Inc.), Roferon A (F. Hoffman-La Roche), Pegasys (F. Hoffman-La Roche), Pegasys/Ribaravin (F. Hoffman-La Roche), CellCept (F. Hoffman-La Roche), Wellferon (GlaxoSmithKline), Albuferon-α (Human Genome Sciences Inc.), Levovirin (ICN Pharmaceuticals), IDN-6556 (Idun Pharmaceuticals), IP-501 (Indevus Pharmaceuticals), Actimmune (InterMune Inc.), Infergen A (InterMune Inc.), ISIS14803 (ISIS Pharmaceuticals Inc.), JTK-003 (Japan Tobacco Inc.), Pegasys/Ceplene (Maxim Pharmaceuticals), Ceplene (Maxim Pharmaceuticals), Civacir (Nabi Biopharmaceuticals Inc.), Intron A/Zadaxin (RegeneRx), Levovirin (Ribapharm Inc.), Viramidine (Ribapharm Inc.), Heptazyme (Ribozyme Pharmaceuticals), Intron A (Schering-Plough), PEG-Intron (Schering-Plough), Rebetron (Schering-Plough), Ribavirin (Schering-Plough), PEG-Intron/Ribavirin (Schering-Plough), Zadazim (SciClone), Rebif (Serono), IFN-β/EMZ701 (Transition Therapeutics), T67 (Tularik Inc.), VX-497 (Vertex Pharmaceuticals Inc.), VX-950/LY-5703 10 (Vertex Pharmaceuticals Inc.), Omniferon (Viragen Inc.), XTL-002 (XTL Biopharmaceuticals), SCH 503034 (Schering-Plough), isatoribine and its prodrugs ANA971 and ANA975 (Anadys), R1479 (Roche Biosciences), Valopicitabine (Idenix), NIM811 (Novartis), and Actilon (Coley Pharmaceuticals).

In some embodiments, the compositions and methods of the present invention contain a compound of a formula as set forth above in combination with interferon. In some aspects, the interferon is selected from the group consisting of interferon alpha 2B, pegylated interferon alpha, consensus interferon, interferon alpha 2A, and lymphoblastiod interferon tau.

In other embodiments the compositions and methods of the present invention utilize a combination of a compound of a formula as set forth above and a compound having anti-HCV activity such as those selected from the group consisting of interleukin 2, interleukin 6, interleukin 12, a compound that enhances the development of a type 1 helper T cell response, interfering RNA, anti-sense RNA, Imiqimod, ribavirin, an inosine 5' monophospate dehydrogenase inhibitor, amantadine, and rimantadine.

Anti-Hepatitis C Activity Assays

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture was disclosed in U.S. Pat. No. 5,738,985 to Miles et al., said patent incorporated herein by reference. In vitro assays have been reported in Ferrari et al. *J. of Vir.,* 73:1649-1654, 1999; Ishii et al., *Hepatology,* 29:1227-1235, 1999; Lohmann et al., *J. Bio. Chem.,* 274:10807-10815, 1999; and Yamashita et al., *J. of Bio. Chem.,* 273:15479-15486, 1998.

WO 97/12033 relates to HCV polymerase assay that can be used to evaluate the activity of the compounds described herein, and this patent publication is incorporated herein by reference. Another HCV polymerase assay has been reported by Bartholomeusz, et al., Hepatitis C Virus (HCV) RNA polymerase assay using cloned HCV non-structural proteins; Antiviral Therapy 1996:1 (Supp 4) 18-24.

Screens that measure reductions in kinase activity from HCV drugs were disclosed in U.S. Pat. No. 6,030,785, to Katze et al., U.S. Pat. No. 6,228,576, Delvecchio, and U.S. Pat. No. 5,759,795 to Jubin et al. Screens that measure the protease inhibiting activity of proposed HCV drugs were disclosed in U.S. Pat. No. 5,861,267 to Su et al., U.S. Pat. No. 5,739,002 to De Francesco et al., and U.S. Pat. No. 5,597,691 to Houghton et al., all of said patents incorporated herein by reference.

The invention is further illustrated in the following non-limiting examples.

EXAMPLES

Embodiments of the present invention will now be described by way of example only with respect to the following examples. Target compounds were prepared by reaction of the appropriate nucleosides, or modified precursor, with the required phosphorochloridate. The latter reagents were prepared by published methods from aryl phosphorodichloridates with amino acid ester hydrochlorides.

General Procedures.

All experiments involving water-sensitive compounds were conducted under scrupulously dry conditions. Anhydrous tetrahydrofuran (THF) and dichloromethane were purchased from Aldrich and used directly. The sugar derivative (2S,3R,4R,5R)-5-(benzoyloxymethyl)-3-methyltetrahydrofuran-2,3,4-triyl tribenzoate or equivalently: 2,3,4,5-tetra-O-benzoyl-2-C-methyl-β-D-ribofuranose was purchased from CarboSynth Limited, 8&9 Old Station Business Park, Compton, Berkshire, RG20 6NE, UK. The purine derivative 2-amino-6-chloropurine or equivalently, 6-chloro-9H-purin-2-amine, was purchased from Aldrich. 2'-C-Methylguanosine (2-amino-9-((3R,4R,5R)-3,4-dihydroxy-5-(hydroxymethyl)-3-methyltetrahydrofuran-2-yl)-1H-purin-6 (9H)-one) is a commercial reagent and was purchased from CarboSynth Limited, 8&9 Old Station Business Park, Compton, Berkshire, RG20 6NE, UK. Tert-Butylmagnesium Chloride was purchased from Aldrich as a 1.0 M solution. This 1.0 M solution was used in the experimental procedures. Column chromatography refers to flash column chromatography carried out using Merck silica gel 60 (40-60 μm) as stationary phase. Proton, carbon, and phosphorus nuclear magnetic resonance ($^{1}$H, $^{13}$C, $^{31}$P NMR) spectra were recorded on Bruker Avance spectrometers operating either at 500, 125, and 202 MHz or at 300, 75, and 121 MHz or a Varian Unity Inova instrument operating at 400, 100, and 161.9 MHz. The solvents used are indicated for each compound. All $^{13}$C and $^{31}$P spectra were recorded proton decoupled. Chemical shifts for $^{1}$H and $^{13}$C spectra are in parts per million downfield from tetramethylsilane. Coupling constants are referred to as J values. Signal splitting patterns are described as singlet (s), doublet (d), triplet (t), quartet (q), broad signal (br), doublet of doublet (dd), doublet of triplet (dt), or multiplet (m). Chemical shifts for $^{31}$P spectra are in parts per million relative to an external phosphoric acid standard. Many proton and carbon NMR signals were split because of the presence of (phosphate) diastereoisomers in the samples. The mode of ionization for mass spectrometry was fast atom bombardment (FAB) using MNOBA (m-nitrobenzyl alcohol) as matrix for some compounds. Electrospray mass spectra were obtained using a Waters LCT time-of-flight mass spectrometer coupled to a Waters M600 HPLC pump. Samples were dissolved in methanol and injected into the solvent stream via a Rheodyne injector. The mobile phase used was methanol at a flow rate of 200 μL/min. The electrospray source was operated at a temperature of 130° C. with a desolvation temperature of 300° C., a capillary voltage of 3 kV, and cone voltage of 30 V. Data were collected in the continuum mode over the mass range 100-2000 amu and processed using Masslynx 4.1 software. Accurate mass measurements were facilitated by the introduction of a single lockmass compound of known elemental composition into the source concurrently with sample.

Example 1

(2R,3R,4R,5R)-2-(2-amino-6-chloro-9H-purin-9-yl)-5-(benzoyloxymethyl)-3-methyltetrahydrofuran-3,4-diyldibenzoate

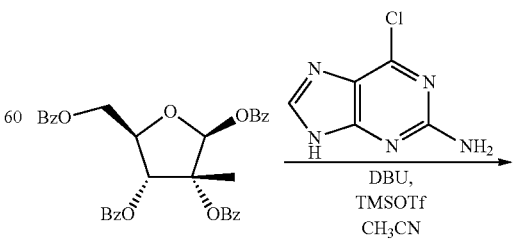

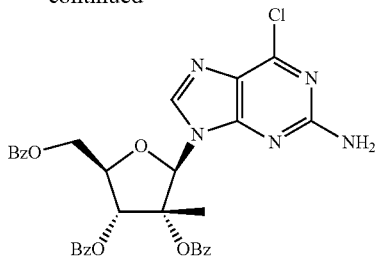

To a pre-cooled (0° C.) solution of (2S,3R,4R,5R)-5-(benzoyloxymethyl)-3-methyltetrahydrofuran-2,3,4-triyl tribenzoate (or 2,3,4,5-tetra-O-benzoyl-2-C-methyl-β-D-ribofuranose) (CarboSynth Ltd, 10.0 g, 17.22 mmol), 2-amino-6-chloropurine (Aldrich, 3.2 g, 18.87 mmol), and 1,8-diazabicycl[5.4.0]undec-7-ene (DBU) (7.7 mL, 51 mmol) in anhydrous acetonitrile (200 mL), was added trimethysilyl triflate (12.5 mL, 68.8 mmol) dropwise. The reaction mixture was then heated at 65° C. for 4 to 6 h, allowed to cool down to room temperature, poured into saturated aqueous sodium bicarbonate (300 mL), and extracted with dichloromethane (3×150 mL). The combined organic phase was dried over sodium sulfate and evaporated under reduced pressure. The residue was precipitated from dichloromethane and methanol, filtrated, the solid was washed 2 times with methanol and dried to give the desired compound (8.5 g, 79%) as a white solid (yields are from 65% (column) up to 90% (precipitation)).

The following are the NMR results analyzing the synthesized compounds:

$^1$H NMR (500 MHz, CDCl$_3$) δ 8.13 (dd, J=1.2, 8.3, 2H), 8.02-7.94 (m, 5H), 7.65-7.60 (m, 1H), 7.58-7.45 (m, 4H), 7.35 (q, J=7.7, 4H), 6.65 (s, 1H), 6.40 (d, J=6.7, 1H), 5.31 (s, 2H), 5.08 (dd, J=4.2, 11.6, 1H), 4.79 (dd, J=6.4, 11.6, 1H), 4.74 (td, J=4.2, 6.5, 1H), 1.60 (s, 3H).

$^{13}$C NMR (126 MHz, CDCl$_3$) δ 166.31 (C=O), 165.38 (C=O), 165.32 (C=O), 159.13 (C2), 152.87 (C6), 152.06 (C4), 141.42 (C8), 133.77 (C—H Bn), 133.69 (C—H Bn), 133.28 (C—H Bn), 129.90 (C—H Bn), 129.82 (C—H Bn), 129.78 (C Bn), 129.70 (C—H Bn), 129.41 (C Bn), 128.78 (C Bn), 128.61 (C—H Bn), 128.50 (C—H Bn), 128.41 (C—H Bn), 126.00 (C5), 88.84 (C1'), 85.68 (C2'), 79.43 (C4'), 76.07 (C3'), 63.57 (C5'), 17.77 (2'-Me).

Example 2

(2R,3R,4R,5R)-2-(2-amino-6-methoxy-9H-purin-9-yl)-5-(hydroxymethyl)-3-methyltetrahydrofuran-3,4-diol

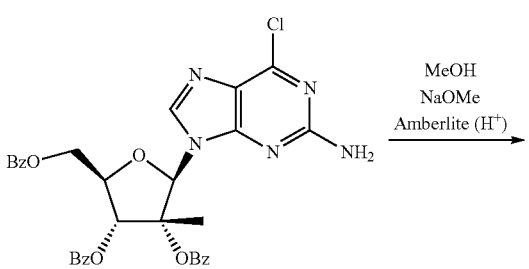

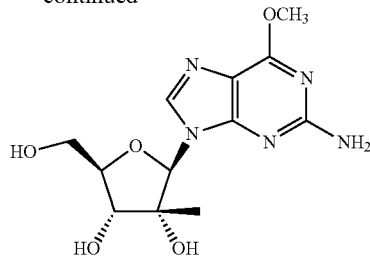

To a suspension of (2R,3R,4R,5R)-2-(2-amino-6-chloro-9H-purin-9-yl)-5-(benzoyloxymethyl)-3-methyltetrahydrofuran-3,4-diyldibenzoate (3.0 g, 4.78 mmol) in methanol (36 mL) at 0° C. was added NaOMe in methanol (5.4 mL, 25% w/w). The mixture was stirred at room temperature for 24 h then quenched by addition of amberlite (H$^+$). The mixture was then filtrated and methanol was removed under reduced pressure. The resultant residue was dissolved in water (50 mL) and extracted with hexane (50 mL). The organic layer was then extracted with water (50 mL), and the combined water fractions were concentrated under reduced pressure. The residue was purified by silica gel chromatography (CHCl$_3$/MeOH 85:15) to give the pure compound (1.125 g, 76%) as a white solid.

The following are the NMR, HPLC and CHN results analyzing the synthesized compound:

$^1$HNMR (500 MHz, CD$_3$OD) δ 8.26 (s, 1H), 5.99 (s, 1H), 4.24 (d, J=9.1, 1H), 4.08 (s, 3H), 4.04 (ddd, J=2.3, 5.7, 8.6, 2H), 3.87 (dd, J=3.0, 12.4, 1H), 0.96 (s, 3H).

$^{13}$C NMR (126 MHz, CD$_3$OD) δ 162.75 (C6), 161.86 (C2), 154.50 (C4), 139.35 (C8), 115.36 (C5), 93.00 (C1'), 84.15 (C4'), 80.34 (C2'), 73.57 (C3'), 61.17 (C5'), 54.25 (6-OMe), 20.35 (2'-Me).

HPLC: t$_R$=9.00 min; column: Varian Pursuit XRs 5, C18, 150×4.6 mm The method is: Linear gradient H$_2$O/ACN: 0% to 100% ACN in 30 mina)

Elemental analysis: calculated for C$_{12}$H$_{17}$N$_5$O$_5$+0.75H$_2$O: C:44.37, H:5.74, N:21.56; Found: C:44.24, H:5.49, N:20.83

Example 3

Naphthalen-1-yl phosphorodichloridate

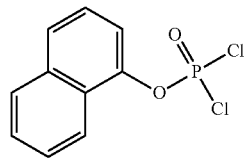 [SMILES: O=P(Cl)(Cl)Oc1cccc2ccccc12]

Phosphorus oxychloride (1.94 mL, 1 equiv) and α-naphthol (Aldrich, 3 g, 1 equiv) were stirred in anhydrous diethyl ether (20 mL). Anhydrous triethylamine was added (2.90 mL, 1 equiv) at −78° C. and the solution was allowed to warm to room temperature after 25 min. The triethylamine hydrochloride salt was filtered off and the solvent was removed under reduced pressure to give a clear pale yellow oil (4.88 g, 90%).

$^1$H NMR (500 MHz, CDCl$_3$) δ 8.11 (d, J=8.4, 1H. H$_8$), 7.90 (d, J=7.5, 1H, H$_5$), 7.80 (d, J=8.3, 1H, H$_4$), 7.65-7.53 (m, 3H, H$_2$, H$_6$, H$_7$), 7.46 (t, J=8.0, 1H, H$_3$)

$^{31}$P NMR (202 MHz, CDCl$_3$) δ 3.69. .

Example 4

Naphthalen-2-yl phosphorodichloridate synthesis

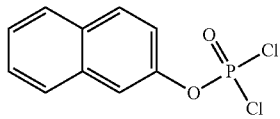 [SMILES: O=P(Cl)(Cl)Oc1ccc2ccccc2c1]

Phosphorus oxychloride (3.23 mL, 1 equiv) and β-naphthol (Aldrich, 5 g, 1 equiv) were stirred in anhydrous diethyl ether (25 mL). Anhydrous triethylamine was added (4.84 mL, 1 equiv) at −78° C. and the solution was allowed to warm to room temperature after 25 min. The triethylamine hydrochloride salt was filtered off and the solvent was removed under reduced pressure to give a clear pale yellow oil (7.95 g, 88%). (oil solidified in the freezer).

The following are the NMR results analyzing the synthesized compound:

$^1$H NMR (500 MHz, CDCl$_3$) δ 7.86-7.77 (m, 2H), 7.70 (s, 1H), 7.52-7.45 (m, 2H), 7.37 (m, 1H).
$^{31}$P NMR (202 MHz, CDCl$_3$) δ 2.71.

Example 5

(S)-methyl 2-(6-(dichlorophosphoryloxy)naphthalen-2-yl)propanoate synthesis

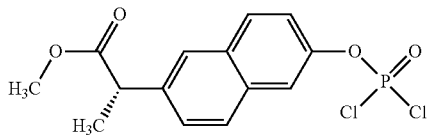

Phosphorus oxychloride (0.202 mL, 1 equiv) and (S)-methyl 2-(6-hydroxynaphthalen-2-yl)propanoate (Aldrich, 500 mg, 1 equiv) were stirred in anhydrous diethyl ether (25 mL). Anhydrous triethylamine was added (0.302 mL, 1 equiv) at −78° C. and the solution was allowed to warm to room temperature after 25 min, the triethylamine hydrochloride salt was filtered off and the solvent was removed under reduced pressure to give a clear pale yellow thick syrup (750 mg, 95%).

The following are the NMR results analyzing the synthesized compound:

$^{31}$P NMR (80 MHz, CDCl$_3$): δ 4.49

Example 6

Quinolin-5-yl phosphorodichloridate synthesis

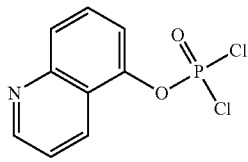 [SMILES: O=P(Cl)(Cl)Oc1cccc2ncccc12]

Phosphorus oxychloride (0.385 mL, 4.14 mmol.) and quinolin-5-ol (Aldrich, 600 mg, 4.14 mmol.) were stirred in anhydrous THF (25 mL). Anhydrous triethylamine was added (0.576 mL, 4.14 mmol.) at −78° C. and the solution was allowed to warm to room temperature. The reaction mixture was monitored by $^{31}$PNMR for completion of phosphorus oxychloride (about 30 min) and this mixture was used directly.

The following are the NMR results analyzing the synthesized compound:

$^{31}$P NMR (80 MHz, CDCl$_3$): δ 4.58.

Example 7

Quinolin-6-yl phosphorodichloridate synthesis

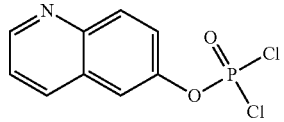 [SMILES: O=P(Cl)(Cl)Oc1ccc2ncccc2c1]

Phosphorus oxychloride (0.385 mL, 4.14 mmol.) and quinolin-5-ol (Aldrich, 600 mg, 4.14 mmol) were stirred in anhydrous THF (25 mL). Anhydrous triethylamine was added (0.576 mL, 4.14 mmol) at −78° C. and the solution was allowed to warm to room temperature. The reaction mixture was monitored by $^{31}$PNMR for completion of phosphorus oxychloride (about 30 min) and this mixture was used directly.

The following are the NMR results analyzing the synthesized compound:

$^{31}$P NMR (80 MHz, CDCl$_3$): δ 4.61.

Example 8

Quinolin-8-yl phosphorodichloridate synthesis

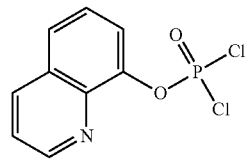 [SMILES: O=P(Cl)(Cl)Oc1cccc2cccnc12]

Phosphorus oxychloride (0.58 mL, 1 equiv) and quinolin-8-ol (Aldrich, 900 mg, 1 equiv) were stirred in anhydrous diethyl ether (25 mL). Anhydrous triethylamine was added (0.86 mL, 1 equiv) at −78° C. and the solution was allowed to warm to room temperature after 25 min. The triethylamine hydrochloride salt was filtered off and the solvent was removed under reduced pressure to give a clear pale yellow syrup (870 mg, 54%). This crude product was used for next step directly.

The following are the NMR results analyzing the synthesized compound:

$^{31}$P NMR (80 MHz, CDCl$_3$): δ 4.53.

Example 9

2-Methylnaphthalen-1-yl phosphorodichloridate synthesis

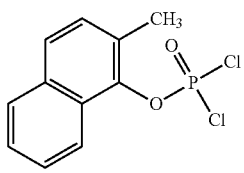 [SMILES: Cc1ccc2ccccc2c1OP(=O)(Cl)Cl]

Phosphorus oxychloride (0.176 mL, 1 equiv) and 2-methylnaphthalen-1-ol (Aldrich, 0.3 g, 1 equiv) were stirred in anhydrous diethyl ether (10 mL). Anhydrous triethylamine was added (0.264 mL, 1 equiv) at −78° C. and stirred for 30 min. The dichloridate was very unstable at room temperature. The progress of the reaction was monitored by $^{31}$P NMR. This crude mixture was considered to be a 100% conversion to dichloridate and was used directly.

The following are the NMR results analyzing the synthesized compound:

$^{31}$P NMR (80 MHz, CDCl$_3$) δ 4.20

Example 10

3-tert-Butylnaphthalen-1-yl phosphorodichloridate synthesis

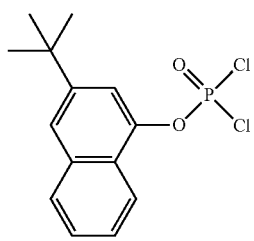 [SMILES: CC(C)(C)c1cc(OP(=O)(Cl)Cl)c2ccccc2c1]

Phosphorus oxychloride (0.143 mL, 1 equiv) and 3-tert-butylnaphthalen-1-ol (J. Org. Chem. 1995, 60, 2909-2911, 0.308 g, 1 equiv), were stirred in anhydrous diethyl ether (8 mL). Anhydrous triethylamine was added (0.214 mL, 1 equiv) at −78° C. and stirred for 30 min. The dichloridate is very unstable at room temperature. The reaction was monitored by $^{31}$P NMR. This crude mixture was considered to be a 100% conversion to dichloridate and was used directly.

The following are the NMR results analyzing the synthesized compound:

$^{31}$P NMR (80 MHz, CDCl$_3$) δ 4.46

Example 11

3,7-Di-tert-butylnaphthalen-1-yl phosphorodichloridate synthesis

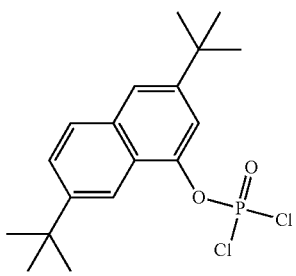 [SMILES: CC(C)(C)c1cc(OP(=O)(Cl)Cl)c2cc(C(C)(C)C)ccc2c1]

Phosphorus oxychloride (0.145 mL, 1 equiv) and 3,7-di-tert-butylnaphthalen-1-ol (J. Org. Chem. 1995, 60, 2909-2911, 0.4 g, 1 equiv) were stirred in anhydrous diethyl ether (10 mL). Anhydrous triethylamine was added (0.217 mL, 1 equiv) at −78° C. and stirred for 30 min. The dichloridate is very unstable at room temperature. The progress of the reaction was monitored by $^{31}$P NMR. This crude mixture was considered to be a 100% conversion to dichloridate and was used directly.

The following are the NMR results analyzing the synthesized compound:

$^{31}$P NMR (80 MHz, CDCl$_3$) δ 4.45

Example 12

Phenyl phosphorodichloridate synthesis

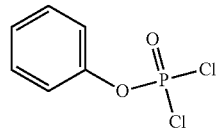 [SMILES: O=P(Cl)(Cl)Oc1ccccc1]

Phosphorus oxychloride (3.23 mL, 1 equiv) and phenol (g, 1 equiv) were stirred in anhydrous diethyl ether (25 mL). Anhydrous triethylamine was added (4.84 mL, 1 equiv) at −78° C. and the solution was allowed to warm to room temperature after 25 min. The triethylamine hydrochloride salt was filtered off and the solvent was removed under reduced pressure to give a clear pale yellow oil (g, %). (oil solidified in the freezer).

The following are the NMR results analyzing the synthesized compound:

Amino acid esters were either purchased, or prepared using literature procedures familiar to those skilled in the art. In general BOC (tert-butoxy carbonyl) protected amino acids were coupled with the corresponding alcohol in dichloromethane with EDCI (1-(3-dimethylaminopropyl)-3-ethylcarbodiimide hydrochloride, Aldrich) and DMAP (4-dimethylaminopyridine, Aldrich). The BOC groups were removed with PTSA (para-toluene sulfonic acid) and isolated as the para-toluene sulfonic acid salts.

Naphthyl (aminoacid ester) phosphorochloridates were prepared by the procedures known to one skilled in the art. In general, the naphthalene phosphorodichloridate (1 equiv) and the appropriate amino ester as the PTSA salt (1 equiv) were suspended in anhydrous dichloromethane (20 mL/g of phosphorodichloridate). Anhydrous triethylamine (2 equiv) was added dropwise at −78° C. and after one h, the reaction was left to rise to room temperature and stirred for 2 to 4 h (reaction can be monitored by phosphorus NMR). The solvent was removed under reduced pressure keeping the rotoevaporator heating bath below 25° C. and the crude residue was purified by a very quick chromatography on silica gel (hexane/ethyl acetate 1:1). The ethyl acetate was then carefully removed keeping the rotoevaporator heating bath below 25° C. This same general procedure was used for the substituted naphthol derivatives and for the quinoline and isoquinoline derivatives.

The nucleoside derivatives other than 2-amino-6-methoxy-9-(2-C-methyl-β-D-ribofuranosyl)purine were synthesized as described below in the examples.

The 5'-phosphoramidates of 2-amino-6-methoxy-9-(2-C-methyl-β-D-ribofuranosyl)purine were synthesized by procedures available to one skilled in the art, including the Methods A and B below:

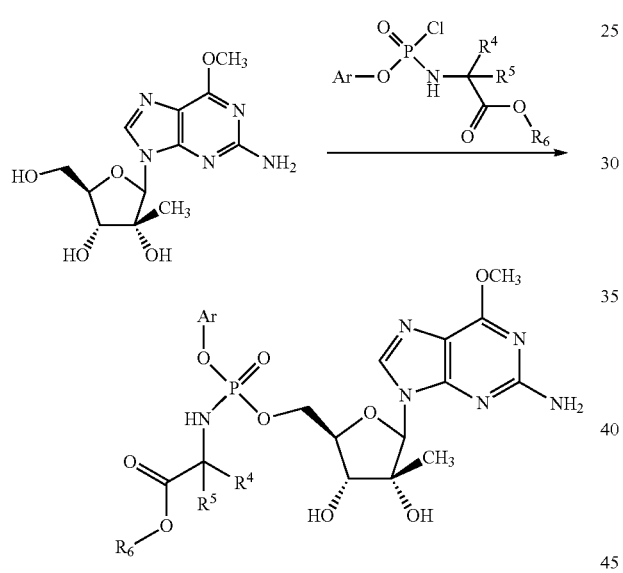

Method A: To 2-amino-6-methoxy-9-(2-C-methyl-β-D-ribofuranosyl)purine (1 equiv) dissolved in THF (20 mL/g) was added N-methyl-imidazole (NMI, Aldrich, 5 equiv) followed by the chloro(naphthalen-1-yloxy)phosphorylamino acid derivative (3 equiv) dissolved in THF (20 mL). The mixture was stirred overnight and the solvent was removed under reduced pressure. The residue was then purified on silica gel (CHCl₃/MeOH 95:5) to give the pure phosphoramidate in 20 to 30% yield. In some cases, some trace on N-methyl-imidazole remains: to remove the N-methyl-imidazole, the phosphoramidate was dissolved in chloroform and washed 3 times with hydrochloric acid (HCl 0.1N). The organic layer was then dried over sodium sulfate and evaporated under reduced pressure to afford the pure compound. In some cases, the latter needed to be purified a second time (100% CHCl₃ to 95:5 CHCl₃/MeOH).

Method B. To a solution of 2-amino-6-methoxy-9-(2-C-methyl-β-D-ribofuranosyl)purine (Aldrich, 1 equiv) in anhydrous THF (4 mL/mmol) was added 1M solution of tert-butylMgCl in THF (Aldrich, 2 equiv) at 0° C. After stirring 15 min, a solution of the chloro(naphthalen-1-yloxy)phosphorylamino acid derivative (2 equiv) in THF (30 mL) was added dropwise into the reaction mixture, which was then allowed to warm to room temperature and stirred overnight. The reaction was monitored by TLC. The reaction mixture was washed with a saturated NH₄Cl solution (300 mL) and brine (100 mL). The organic layer was dried over anhydrous sodium sulfate and concentrated. The crude material was purified by column chromatography on silica gel using CH₂Cl₂/MeOH (96:4) to obtain phosphoramidate in 10-50% yields.

Example 13

The synthesis of benzyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)propanoate was performed according to the following steps

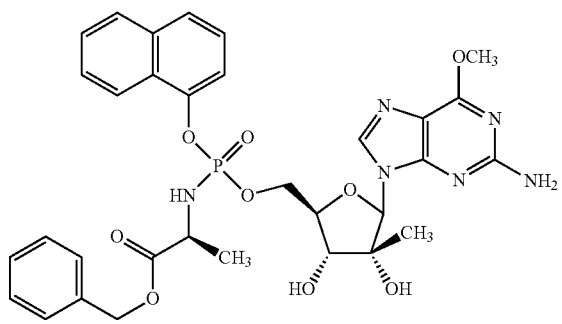 [SMILES: COc1nc(N)nc2c1ncn2C1O[C@H](COP(=O)(N[C@@H](C)C(=O)OCc2ccccc2)Oc2cccc3ccccc23)[C@@H](O)[C@@]1(C)O]

Step 1: (2S)-benzyl 2-(chloro(naphthalen-1-yloxy)-phosphorylamino)-propanoate

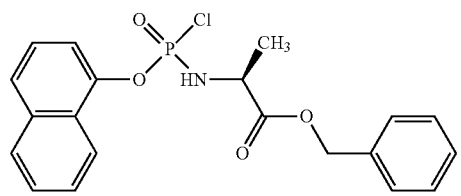 [SMILES: C[C@H](NP(=O)(Cl)Oc1cccc2ccccc12)C(=O)OCc1ccccc1]

Using the general procedure for synthesizing naphthyl (aminoacid ester) phosphorochloridates the tosylate salt of benzyloxy-L-alanine (1.5 g), naphthalen-1-yl phosphorodichloridate (1.10 g), TEA (1.14 mL), and DCM (20 mL) were combined to give (2S)-benzyl 2-(chloro(naphthalen-1-yloxy)-phosphorylamino)-propanoate in an 89% yield (1.53 g), as a pale yellow thick oil.

The following are the NMR results analyzing the synthesized compound:

¹H NMR (500 MHz, CDCl₃) δ 8.08 (m, 1H, H₈-napht), 7.90 (m, 1H, H₅-napht), 7.75 (d, J=8.2, 1H, H₄-napht), 7.58 (m, 3H, H₆, H₇, H₂-napht), 7.48-7.42 (m, 1H, H₃-napht), 7.36 (m, 5H, phe), 5.31-5.16 (m, 2H, CH₂ ester), 4.59-4.48 (m, 0.5H, NH), 4.38 (m, 1.5H. NH and H₃), 1.59 (d, J=7.1, 1.5H, CH₃ ala), 1.57 (d, J=6.9, 1.5H, CH₃ ala).

³¹P NMR (202 MHz, CDCl₃) δ 8.16, 7.89.

Step 2: Synthesis of Protide

Using the general procedure (Method A) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, 1.12 g (1.6 mmol) of nucleoside in 25 mL of THF, N-methyl imidazole 1.44 mL (0.018 mmol), was added followed by (2S)-benzyl 2-(chloro(naphthalen-1-yloxy)phosphorylamino)propanoate 4.38 g (0.11 mmol) in 25 mL of THF. After workup and silica gel column chromatography, 68 mg of pure protide was obtained in a 28% yield, as an off-white solid.

The following are the NMR results analyzing the synthesized compound:

$^1$H NMR (500 MHz, CD$_3$OD) δ 8.20-8.13 (m, 1H), 7.98, 7.95 (2×s, 1H), 7.83-7.77 (m, 1H), 7.63, 7.62 (2×d, J=7.7, 1H), 7.54-7.49 (m, 1H), 7.49-7.40 (m, 2H), 7.32 (t, J=7.5, 1H), 7.27-7.16 (m, 5H), 6.04, 6.02 (2×s, 1H), 5.03, 4.93 (AB, J$_{AB}$=12.00 Hz, 2H), 4.67-4.57 (m, 2H), 4.34-4.24 (m, 2H), 4.16-4.06 (m, 1H), 4.01, 4.00 (2×s, 3H), 1.30, 1.29 (2×d, J=7.1, 3H), 0.97, 0.95 (s, 3H).

$^{13}$C NMR (126 MHz,) δ 174.85 (d, $^3J_{C-C-N-P}$=4.4), 174.62 (d, $^3J_{C-C-N-P}$=5.5,), 162.74, 161.83, 154.56, 154.51, 147.99 (d, $^2J_{C-O-P}$=1.9), 147.93 (d, $^2J_{C-O-P}$=1.7), 139.31, 139.04, 137.08, 136.24, 136.22, 129.54, 129.26, 129.25, 129.17, 129.12, 128.87, 128.83, 127.90 (d, $^3J_{C-C-O-P}$=4.1), 127.85 (d, $^3J_{C-C-O-P}$=4.2), 127.77, 127.53, 126.56, 126.53, 126.00, 122.83, 122.76, 116.28, 116.27, 115.68, 115.65, 93.30, 93.12, 82.29 (d, $^3J_{C-C-O-P}$=8.0), 82.12 (d, $^3J_{C-C-O-P}$=8.4), 80.03, 79.99, 79.53, 74.96, 74.64, 68.03 (d, $^2J_{C-O-P}$=4.7), 67.98, 67.96, 67.48 (d, $^2J_{C-O-P}$=4.9), 51.84, 51.75, 20.67 (d, $^3J_{C-C-N-P}$=6.1), 20.48 (d, $^3J_{C-C-N-P}$=4.6), 20.44.

$^{31}$P NMR (202 MHz,) δ 4.28, 4.27.

Example 14

The (2S)-2,4-difluorobenzyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

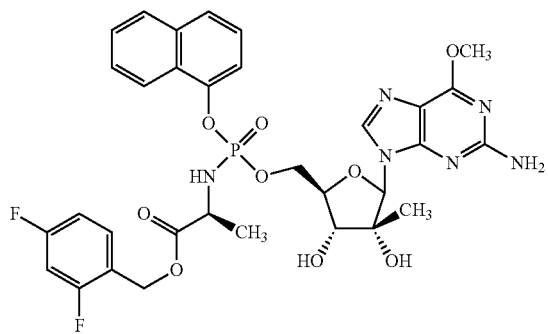 [SMILES: COc1nc(N)nc2c1ncn2C1O[C@H](COP(=O)(N[C@@H](C)C(=O)OCc2ccc(F)cc2F)Oc2cccc3ccccc23)[C@@H](O)[C@@]1(C)O]

Step 1: (2S)-2,4-difluorobenzyl 2-(chloro(naphthalen-1-yloxy)phosphorylamino) propanoate

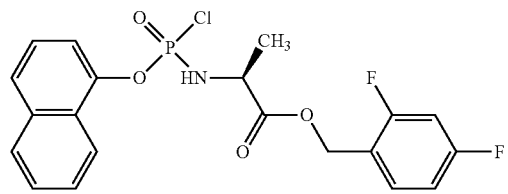 [SMILES: C[C@H](NP(=O)(Cl)Oc1cccc2ccccc12)C(=O)OCc1ccc(F)cc1F]

Using the general procedure for synthesizing naphthyl (aminoacid ester) phosphorochloridates the tosylate salt of 2,4-difluorobenzyl-L-alanine (4 g), naphth-1-yl phosphorodichloridate (2.69 g), TEA (2.9 mL) and DCM (52 mL) were combined to give naphth-1-yl-(2,4-di-fluorobenzyl-L-alaninyl)phosphorochloridate (2.77 g) which was used directly in the next step.

The following are the NMR results analyzing the synthesized compound:

$^{31}$P NMR (202 MHz, CDCl$_3$) δ 8.10, 7.92.

Step 2. Synthesis of the Protide

Using the general procedure (Method A) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol to a solution of 300 mg of nucleoside in 3.6 mL of THF, was added N-methyl imidazole (384 µL) followed by (2S)-2,4-difluorobenzyl 2-(chloro(naphthalen-1-yloxy)phosphorylamino)propanoate (1.27 g) in THF (3.6 mL). After workup and silica gel column chromatography, 217 mg of pure protide was obtained (30% yield) as an off-white solid. HPLC: t$_R$=20.56, 20.89 min. (column: Varian Pursuit XRs 5, C18, 150×4.6 mm. The method is: Linear gradient H$_2$O/ACN: 0% to 100% ACN in 30 min.)

The following are the NMR results analyzing the synthesized compound:

$^1$H NMR (500 MHz, CD$_3$OD) δ 8.14 (m, 1H), 8.00 and 7.97 (2s, 1H), 7.82 (m, 1H), 7.65 (d, J=7.7, 1H), 7.52-7.41 (m, 3H), 7.38-7.26 (m, 2H), 6.89-6.77 (m, 2H), 6.01 and 6.00 (2s, 1H), 5.09-4.95 (m, 2H), 4.67-4.57 (m, 2H), 4.36-4.22 (m, 2H), 4.08 (m, 1H), 4.02 and 4.01 (2s, 3H), 1.29 (d, J=7.1, 3H), 0.97 and 0.95 (2s, 3H).

$^{31}$P NMR (202 MHz, CD$_3$OD) δ 4.21

Example 15

The 1(S)-phenylethyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)propanoate was synthesized as follows

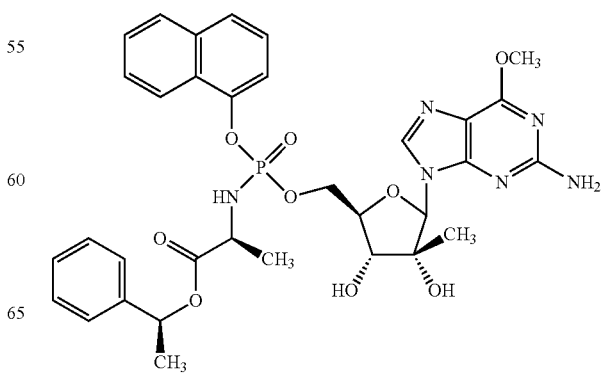

Step 1: (2S)-((S)-1-phenylethyl) 2-(chloro(naphthalen-1-yloxy) phosphorylamino)propanoate

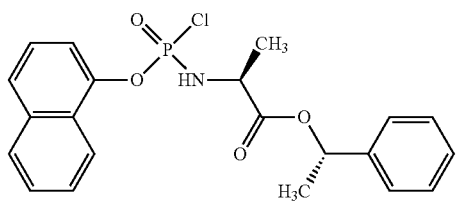 [SMILES: C[C@H](NP(=O)(Cl)Oc1cccc2ccccc12)C(=O)O[C@@H](C)c1ccccc1]

Using the general procedure for synthesizing naphthyl (aminoacid ester) phosphorochloridates the tosylate salt of (S)-((S)-1-phenylethyl) 2-aminopropanoate (10 g), naphthalen-1-yl phosphorodichloridate (7.14 g), TEA (7.60 mL), and DCM (120 mL) were combined to give naphth-1-yl((S)-1-phenylethoxy-L-alaninyl)phosphorochloridate in an 85% yield (9.7 g) as a pale yellow thick oil.

The following are the NMR results analyzing the synthesized compound:

$^1$H NMR (500 MHz, CDCl$_3$) δ 8.08 (m, 1H, H$_8$-napht), 7.89 (m, 1H, H$_5$-napht), 7.74 (m, 1H, H$_4$-napht), 7.63-7.50 (m, 3H, H$_7$, H$_6$, H$_2$-napht), 7.49-7.27 (m, 6H, H$_3$-napht and phe), 5.96 (dd, J=6.7, 13.3, 0.5H, CH ester), 5.93 (dd, J=6.6, 13.2, 0.5H, CH ester), 4.40-4.21 (m, 2H, NH and CHα), 1.61 (d, J=6.6, 1.5H, CH$_3$ Ala), 1.57 (d, J=6.6, 1.5H, CH$_3$ Ala), 1.52 (d, J=6.8, 1.5H, CH$_3$ ester), 1.49 (d, J=6.8, 1.5H, CH$_3$ ester).

$^{31}$P NMR (202 MHz, CDCl$_3$) δ 8.17, 7.86.

Step 2: Synthesis of Protide

Using the general procedure (Method A) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, 1.5 g (4.82 mmol) of nucleoside in 30 mL of THF, NMI 1.9 mL (24.10 mmol), was added followed by (2S)-((S)-1-phenylethyl) 2-(chloro(naphthalen-1-yloxy) phosphorylamino)propanoate 6.04 g (14.5 mmol) in 20 mL of THF. After workup and silica gel column chromatography, 571 mg of pure protide was obtained in a 17% yield, as an off-white solid. MS (ES+) m/e: 693.25 (MH$^+$, 100%); Accurate mass: C$_{33}$H$_{38}$N$_6$O$_9$P$_1$ calculated 693.2438. found 693.2468.

The following are the NMR results analyzing the synthesized compound:

$^1$H NMR (500 MHz, CD$_3$OD) δ 8.20-8.16 (m, 1H), 7.98, 7.94 (2×s, 1H), 7.92-7.85 (m, 1H), 7.71-7.69 (m, 1H), 7.54-7.46 (m, 3H), 7.41-7.35 (m, 1H), 7.29-7.22 (m, 5H), 6.00, 5.99 (2×s, 1H), 5.74, 5.68 (2×q, J=6.7 Hz, 1H), 4.65-4.59 (m, 1H), 4.57-4.55 (m, 1H), 4.36-4.28 (m, 1H), 4.28-4.21 (m, 1H), 4.06-4.01 (m, 4H), 1.40, 1.41 (2×d, J=6.1 Hz, 3H), 1.26 (2×s, 3H), 0.98, 0.96 (2×s, 3H).

$^{31}$P NMR (202 MHz, CD$_3$OD) δ 4.30, 4.27.

Example 16

The (2S)-2,3-dihydro-1H-inden-2-yl 2-((((2R,3R,4R)-5-(2-amino-6-methoxy-9H-purin-9-yl)-3,4-dihydroxy-4-methyltetrahydrofuran-2-yl)methoxy) (naphthalen-1-yloxy)phosphorylamino)propanoate was synthesized as follows

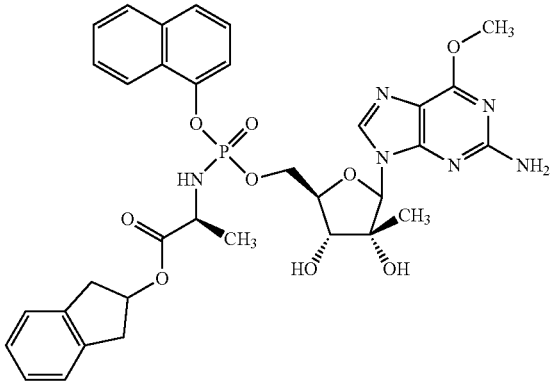 [SMILES: COc1nc(N)nc2c1ncn2C1O[C@H](COP(=O)(N[C@@H](C)C(=O)OC2Cc3ccccc3C2)Oc2cccc3ccccc23)[C@@H](O)[C@@]1(C)O]

Step 1: (2S)-2,3-dihydro-1H-inden-2-yl 2-(chloro (naphthalen-1-yloxy)phosphorylamino)propanoate

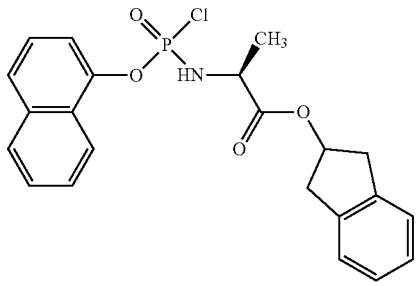 [SMILES: C[C@H](NP(=O)(Cl)Oc1cccc2ccccc12)C(=O)OC1Cc2ccccc2C1]

Using the general procedure for synthesizing naphthyl (aminoacid ester) phosphorochloridates the tosylate salt of (S)-2,3-dihydro-1H-inden-2-yl 2-aminopropanoate (2.00 g, 5.30 mmol), naphthalen-1-yl phosphorodichloridate (1.38 g, 5.30 mmol) and TEA (1.48 mL, 10.60 mmol) in 30 mL of dry DCM, were combined to give (2S)-2,3-dihydro-1H-inden-2-yl 2-(chloro(naphthalen-1-yloxy)phosphorylamino)propanoate in 65% yield (1.48 g), as a yellow, thick oil.

The following are the NMR results analyzing the synthesized compound:

$^1$H NMR (500 MHz, CDCl$_3$) δ 8.08-8.05 (m, 1H, H$_8$-napht), 7.90-7.88 (m, 1H, H$_5$-napht), 7.75 (d, J=8.5 Hz, 1H, H$_4$-napht), 7.62-7.52 (m, 3H, H$_7$, H$_6$, H$_2$-napht), 7.45, 7.44 (2×t, J=8.0 Hz, 1H, H$_3$-napht), 7.29-7.20 (m, 4H, 4×CH Ar ester), 5.68-5.65, 5.63-5.59 (2×m, 1H, CH ester), 4.51, 4.25 (2×bs, 1H, NH), 4.31-4.22 (m, 1H, CHα), 3.42-3.32 (m, 2H, 2×CH ester), 3.11-3.00 (m, 2H, 2×CH ester), 1.54, 1.52 (2×d, J=7.0 Hz, 3H, CH$_3$).

$^{31}$P NMR (202 MHz, CDCl$_3$) δ 8.16, 7.90

Step 2: Synthesis of Protide

Using the general procedure (Method B) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, to a solution of 250 mg (0.803 mmol) of nucleoside in 5 mL of THF, was added tBuMgCl 1.61 mL (1.61 mmol), followed by (2S)-2,3-dihydro-1H-inden-2-yl 2-(chloro(naphthalen-1-yloxy)phosphorylamino)propanoate 690 mg (1.60 mmol) in 5 mL of THF. After workup and silica gel column chromatography, 255 mg of pure protide was obtained in a 45% yield, as an off-white solid.

The following are the NMR results analyzing the synthesized compound:

$^1$H NMR (500 MHz, CD$_3$OD) δ 8.17-8.10 (m, 1H, H$_8$-napht), 7.95, 7.93 (2×s, 1H, H$_8$) 7.81 (d, J=8.5 Hz, 1H, H$_5$-napht), 7.65, 7.63 (2×d, J=8.5 Hz, 1H, H$_4$-napht), 7.50-7.42 (m, 3H, H$_7$, H$_6$, H$_2$-napht), 7.37-7.33 (m, 1H, H$_3$-napht), 7.15-7.08 (m, 4H, 4×CH ester), 6.00 (s, 1H, H$_1$), 5.34-5.31 (m, 1H, CH ester), 4.59-4.51 (m, 2H, H$_5$), 4.33-4.21 (m, 2H, H$_3$ and H$_4$), 4.02, 4.01 (2×s, 3H, 6OCH$_3$), 3.98-3.95 (m, 1H, Hα), 3.20-3.01 (m, 2H, 2×CH ester), 2.85-2.78 (m, 2H, 2×CH ester), 1.26, 1.25 (2×d, J=7.00 Hz, 3H, CH$_3$ Ala), 0.97, 0.94 (2×s, 3H, 2'-CH$_3$).

$^{13}$C NMR (126 MHz, CD$_3$OD) δ 174.97, 174.73 (d, $^3J_{C-C-N-P}$=3.8, C=O ester), 162.73 (C6), 161.83 (C2), 154.53, 154.48 (C4), 147.97, 147.91 (d, $^2J_{C-O-P}$=3.8 Hz, ipso Naph), 141.52, 141.48, 141.36, 141.35, 139.28, 138.97, 136.24, 136.22, 128.87, 128.83, 127.88, 127.82, 127.81, 127.77, 127.52, 126.55, 126.51, 125.99, 125.60, 125.57, 125.52, 122.81, 122.75 (Naph, C9-Naph, 2×ipso ester and 4×CH ester), 116.24, 16.22 (d, $^3J_{C-C-O-P}$=3.8, C2-Naph), 115.67, 115.65 (C5), 93.32, 93.11 (C1'), 82.28, 82.08 (2×d, $^3J_{C-C-O-P}$=8.8, C4'), 79.98, 79.96 (C2'), 77.73, 77.69 (CH ester), 74.91, 74.57 (C3'), 67.97, 67.34 (2×d, $^2J_{C-O-P}$=5.0, C5'), 54.36, 54.34 (6OCH$_3$), 51.82, 51.71 (Cα Ala), 40.49, 40.44, 40.33, 40.25 (2×CH$_2$ ester), 20.63, 20.49 (CH$_3$ Ala), 26.9, 28.8, 28.7 (3×$\underline{C}$H$_3$ ester) 20.4, 20.3 (2'CCH$_3$), $^{31}$P NMR (202 MHz, CD$_3$OD) δ 4.26

Example 17

The (2S)-propyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

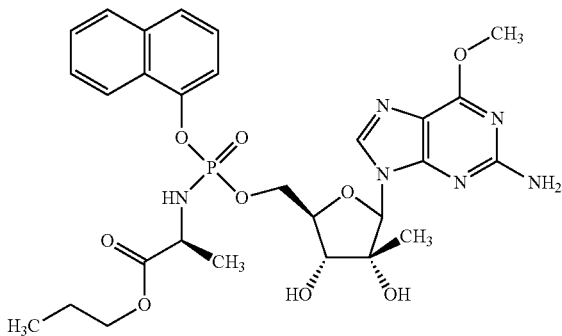 [SMILES: CCCOC(=O)[C@H](C)NP(=O)(OC[C@H]1OC(n2cnc3c(OC)nc(N)nc32)[C@](C)(O)[C@@H]1O)Oc1cccc2ccccc12]

Step 1: (2S)-propyl 2-(chloro(naphthalen-1-yloxy)phosphorylamino)propanoate

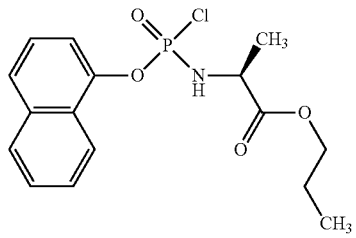 [SMILES: CCCOC(=O)[C@H](C)NP(=O)(Cl)Oc1cccc2ccccc12]

Using the general procedure for synthesizing naphthyl (aminoacid ester) phosphorochloridates the tosylate salt of (S)-propyl 2-aminopropanoate (2.00 g, 11.93 mmol), naphth-1-yl phosphorodichloridate (3.11 g, 11.93 mmol) and TEA (3.32 mL, 23.86 mmol) in 30 mL of dry DCM, were combined to give (2S)-propyl 2-(chloro(naphthalen-1-yloxy)phosphorylamino)propanoate in 82% yield (3.50 g), as a clear, yellow, thick oil.

The following are the NMR results analyzing the synthesized compound:

$^1$H NMR (500 MHz, CDCl$_3$) δ 8.13-8.04 (m, 1H, H$_8$-napht), 7.89, 7.88 (2×d, J=7.5 Hz, 1H, H$_5$-napht), 7.75 (d, J=8.0 Hz, 1H, H$_4$-napht), 7.64-7.55 (m, 3H, H$_7$, H$_6$, H$_2$-napht), 7.45 (t, J=8.0 Hz, 1H, H$_3$-napht), 4.51, 4.25 (2×bs, 1H, NH), 4.28-4.27 (m, 1H, CHα), 4.15, 4.14 (2×q, J=7.0 Hz, 2H, O—CH$_2$ ester), 1.76-1.65 (m, 2H, O—CH$_2$—CH$_2$ ester), 1.59, 1.56 (2×d, J=7.0 Hz, 3H, CH$_3$ Ala), 0.99, 0.96 (2×t, J=6.5 Hz, 3H, CH$_3$ ester).

$^{31}$P NMR (202 MHz, CDCl$_3$) δ 8.29, 8.04

Step 2: Synthesis of Protide

Using the general procedure (Method B) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, to a solution of 250 mg (0.803 mmol) of nucleoside in 5 mL of THF was added tert-BuMgCl 1.61 mL (1.61 mmol), followed by (2S)-propyl 2-(chloro(naphthalen-1-yloxy)phosphorylamino)propanoate 571 mg (1.60 mmol) in 5 mL of THF. After workup and silica gel column chromatography, 163 mg of pure product was obtained in a 32% yield, as an off-white solid.

The following are the NMR results analyzing the synthesized compound:

$^1$H NMR (500 MHz, CD$_3$OD) δ 8.19-8.15 (m, 1H, H$_8$-naph), 7.99, 7.97 (2×s, 1H, H$_8$), 7.90-7.82 (m, 1H, H$_5$-napht), 7.68, 7.65 (2×d, J=8.5 Hz, 1H, H$_4$-napht), 7.54-7.45 (m, 3H, H$_2$, H$_7$, H$_6$-napht), 7.38, 7.36 (2×t, J=8.0 Hz, 1H, H$_3$-napht), 6.04, 6.03 (2×s, 1H, H$_1$), 4.70-4.61 (m, 2H, H$_5$), 4.37-4.26 (m, 2H, H$_3'$, H$_4'$), 4.10-4.04 (m, 1H, Hα), 4.03 (s, 3H, 6OCH$_3$), 3.95-3.84 (m, 2H, OCH$_2$ ester), 1.53-1.45 (m, 2H, OCH$_2$CH$_2$ ester), 1.31 (d, J=7.0 Hz, 3H, CH$_3$ Ala), 0.99, 0.97 (2×s, 3H, 2'CCH$_3$), 0.82 (t, J=7.5 Hz, 3H, CH$_3$ ester).

$^{13}$C NMR (126 MHz, CD$_3$OD) δ 175.13, 174.89 (2×d, $^3J_{C-C-N-P}$=5.0 Hz, C=O ester), 162.75 (C6), 161.84 (C2), 156.56, 154.52 (C4), 148.02, 147.96 (2×d, $^2J_{C-O-P}$=3.0 Hz, ipso Naph), 139.33, 139.07 (CH8), 136.25, 136.22 (C10-Naph), 128.86, 128.82, (CH-napht), 127.85, 127.76 (2×d, $^3J_{C-C-O-P}$=6.3 Hz, C9-Naph), 127.49, 126.55, 126.51, 125.97, 125.95, 122.81, 122.76

(CH-Naph), 116.24, 116.17 (2×d, $^3J_{C-C-O-P}$=4.5 Hz, C2-Naph), 115.67, 115.66 (C5), 93.32, 93.17 (C1'), 82.30, 82.16 (2×d, $^3J_{C-C-O-P}$=8.8 Hz, C4'), 80.04, 80.01 (C2'), 74.94, 74.71 (C3'), 68.00 (OCH$_2$ ester), 67.87, 67.54 (d, $^2J_{C-O-P}$=5.0 Hz, C5'), 54.36 (6OCH$_3$), 51.77, 51.17 (Cα Ala), 20.84, 20.62 (2×d, $^3J_{C-C-N-P}$=6.3 Hz, CH$_3$ Ala), 20.46, 20.44 (2'CCH$_3$), 10.67, 10.65 (CH$_3$ ester).
$^{31}$P NMR (202 MHz, CD$_3$OD) δ 4.33, 4.22.

Example 18

The (2S)-3,3-dimethylbutyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

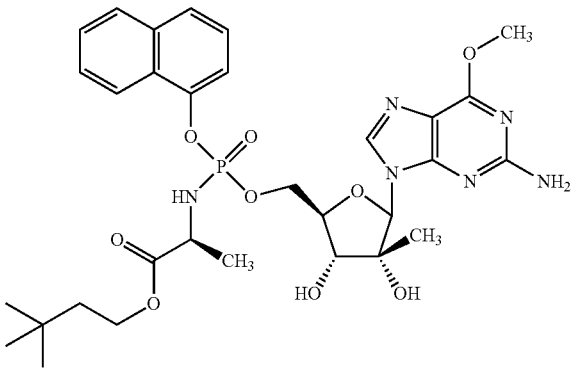 [SMILES: COc1nc(N)nc2c1ncn2C1O[C@H](COP(=O)(N[C@@H](C)C(=O)OCCC(C)(C)C)Oc2cccc3ccccc23)[C@@H](O)[C@@]1(C)O]

Step 1: (2S)-3,3-dimethylbutyl 2-(chloro(naphthalen-1-yloxy) phosphorylamino)propanoate

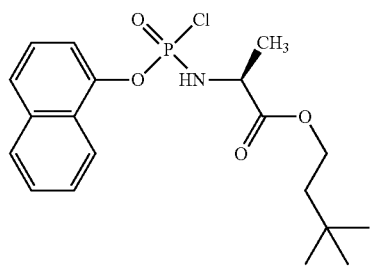 [SMILES: C[C@H](NP(=O)(Cl)Oc1cccc2ccccc12)C(=O)OCCC(C)(C)C]

Using the general procedure for synthesizing naphthyl (aminoacid ester) phosphorochloridates the tosylate salt of (S)-3,3-dimethylbutyl 2-aminopropanoate (2.00 g, 5.79 mmol), naphthalen-1-yl phosphorodichloridate (1.51 g, 5.79 mmol) and TEA (1.61 mL, 11.58 mmol) in 30 mL of dry DCM, were combined to give (2S)-3,3-dimethylbutyl 2-(chloro(naphthalen-1-yloxy)phosphorylamino)propanoate in 91% yield (2.10 g), as a clear, yellow, thick oil.
The following are the NMR results analyzing the synthesized compound:
$^1$H NMR (500 MHz, CDCl$_3$) δ 8.11, 8.09 (2×d, J=7.5 Hz 1H, H$_8$-napht), 7.90-7.89 (m, 1H, H$_5$-napht), 7.75 (d, J=8.5 Hz, 1H, H$_4$-napht), 7.64-7.55 (m, 3H, H$_6$, H$_7$, H$_2$-napht), 7.46 (t, J=7.5 Hz, 1H, H$_3$—napht), 4.56-4.45 (m, 1H, NH), 4.32-4.26 (m, 2H, OCH$_2$ ester), 4.25-4.21 (m, 1H, CHa), 1.64-1.60 (m, 2H, CH$_2$ ester), 1.58, 1.55 (2×d, J=7.0 Hz, CH$_3$ Ala), 0.98, 0.96 (2×s, 9H, 3×CH$_3$ ester).
$^{31}$P NMR (202 MHz, CDCl$_3$) δ 8.46, 8.02

Step 2: Synthesis of Protide

Using the general procedure (Method A) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, to a solution of 250 mg (0.803 mmol) of nucleoside in 5 mL of THF, was added tBuMgCl 1.61 mL (1.61 mmol), followed by (2S)-3,3-dimethylbutyl 2-(chloro(naphthalen-1-yloxy)phosphorylamino)propanoate 640 mg (1.60 mmol) in 5 mL of THF. After workup and silica gel column chromatography, 190 mg of pure product was obtained in a 35% yield, as an off-white solid.
The following are the NMR results analyzing the synthesized compound:
$^1$H NMR (500 MHz, CD$_3$OD) δ 8.20-8.16 (m, 1H, H$_8$-naph), 8.00, 7.98 (2×s, 1H, H$_8$), 7.85-7.81 (m, 1H, H$_5$-napht), 7.66, 7.64 (2×d, J=8.5 Hz, 1H, H$_4$-napht), 7.54-7.45 (m, 3H, H$_2$, H$_7$, H$_6$-napht), 7.39, 7.37 (2×t, J=8.0 Hz, 1H, H$_3$-napht), 6.04, 6.03 (2×s, 1H, H$_{1'}$), 4.71-4.61 (m, 1H, H$_{5'}$), 4.36-4.27 (m, 1H, H$_{3'}$, H$_{4'}$), 4.03 (s, 3H, 6OCH$_3$), 4.02-3.91 (m, 2H, Hα and OCH$_2$ ester), 1.39-1.29 (m, 5H, CH$_3$ Ala and OCH$_2$CH$_2$ ester), 0.99, 0.97 (2×s, 3H, 2'CCH$_3$), 0.82, 0.81 (2×s, 9H, 3×CH$_3$ ester).
$^{13}$C NMR (126 MHz, CD$_3$OD) δ 175.06, 174.80 (2×d, $^3J_{C-C-N-P}$=5.0 Hz, C=O ester), 162.73 (C6), 161.86 (C2), 154.55, 154.51 (C4), 148.00, 147.95 (d, $^2J_{C-O-P}$=3.8 Hz, ipso Naph), 139.36, 139.08 (CH8), 136.27, 136.25 (C10-Naph), 128.86, 128.80 (CH-Naph), 127.88, 127.73 (2×d, $^3J_{C-C-O-P}$=6.3 Hz, C9-Naph), 127.78, 127.76, 127.51, 126.51, 125.53, 125.98, 125.93, 122.83, 122.79 (CH-Naph), 116.22, 116.09 (2×d, $^3J_{C-C-O-P}$=3.8 Hz, C2-Naph), 115.67 (C5), 93.30, 93.16 (C1'), 82.29, 82.15 (2×d, $^3J_{C-C-O-P}$=8.8 Hz, C4'), 80.06, 80.03 (C2'), 74.90, 74.67 (C3'), 67.97, 67.50 (2×d, $^2J_{C-O-P}$=5.0 Hz, C5'), 64.01, 63.99 (OCH$_2$ ester), 54.37, 54.35 (6OCH$_3$), 51.74, 51.71 (Cα Ala), 42.67, 42.60 (OCH$_2$CH$_2$ ester), 30.08, 30.00 (3×CH$_3$ ester), 20.73, 20.52 (2×d, $^3J_{C-C-N-P}$=6.3 Hz, CH$_3$ Ala), 20.46, 20.44 (2'CCH$_3$).
$^{31}$P NMR (202 MHz, CDCl$_3$) δ 4.33, 4.29.

Example 19

The (2S)-isobutyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy) phosphorylamino)propanoate was synthesized as follows

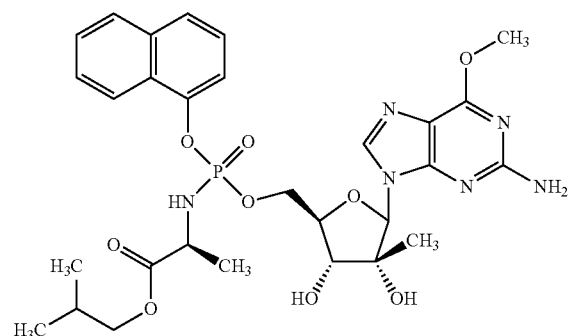

Step 1: (2S)-isobutyl 2-(chloro(naphthalen-1-yloxy)phosphorylamino)propanoate

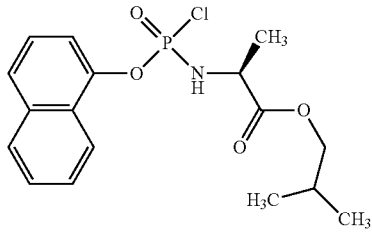 [SMILES: CC(C)COC(=O)[C@H](C)NP(=O)(Cl)Oc1cccc2ccccc12]

Using the general procedure for synthesizing naphthyl (aminoacid ester) phosphorochloridates, the tosylate salt of (S)-isobutyl 2-aminopropanoate (2.5 g), naphthalen-1-yl phosphorodichloridate (2.06 g), TEA (2.19 mL) and DCM (50 mL) were combined to give (2S)-isobutyl 2-(chloro (naphthalen-1-yloxy)phosphorylamino)propanoate as a crude pale yellow thick oil. The crude compound was taken forward without further purification.

The following are the NMR results analyzing the synthesized compound:
$^{31}$P NMR (202 MHz, CDCl$_3$) δ 8.27, 7.96

Step 2: Synthesis of Protide

Using the general procedure (Method B) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, to a solution of 205 mg of nucleoside in 4 mL of THF was added tert-BuMgCl (1.31 mL) followed by (2S)-isobutyl 2-(chloro(naphthalen-1-yloxy)phosphorylamino)propanoate (730 mg) in THF (2.6 mL). After workup and silica gel column chromatography, 66 mg of pure protide was obtained (16% yield). HPLC t$_R$=27.61, 28.29 min (column: Varian Pursuit XRs 5, C$_{18}$, 150×4.6 mm; method: linear gradient of MeOH (10% to 100%) in H$_2$O in 30 min).

The following are the NMR results analyzing the synthesized compound:
$^1$H NMR (500 MHz, CD$_3$OD) δ 8.21-8.14 (m, 1H), 7.98 and 7.95 (2s, 1H), 7.91-7.84 (m, 1H), 7.73-7.66 (m, 1H), 7.56-7.36 (m, 4H), 6.02 and 5.98 (2s, 1H), 4.67-4.52 (m, 2H), 4.36-4.21 (m, 2H), 4.09-3.98 (m, 4H), 3.80-3.64 (m, 2H), 1.84-1.74 (m, 1H), 1.32 (d, J=7.1, 3H), 0.98 and 0.96 (2s, 3H), 0.87-0.82 (m, 6H).
$^{31}$P NMR (202 MHz, CD$_3$OD) δ 4.30, 4.19

Example 20

The 2,2-dimethylpropyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)propanoate was synthesized as follows

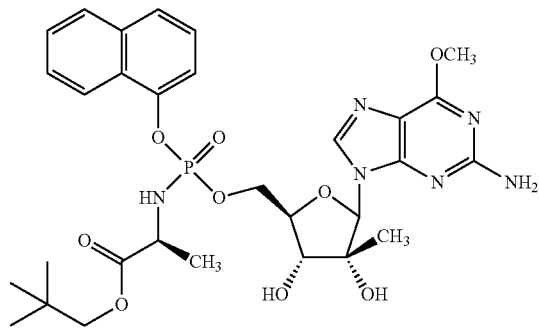 [SMILES: COc1nc(N)nc2c1ncn2C1O[C@H](COP(=O)(N[C@@H](C)C(=O)OCC(C)(C)C)Oc2cccc3ccccc23)[C@@H](O)[C@@]1(C)O]

Step 1: (2S)-neopentyl 2-(chloro(naphthalen-1-yloxy)phosphorylamino)-propanoate

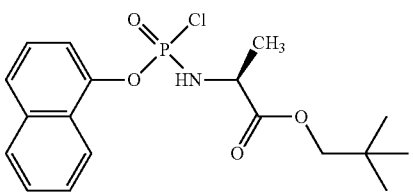 [SMILES: C[C@H](NP(=O)(Cl)Oc1cccc2ccccc12)C(=O)OCC(C)(C)C]

Using the general procedure for synthesizing naphthyl (aminoacid ester) phosphorochloridates the tosylate salt of (2,2-dimethylpropyloxy)-L-alanine (1.5 g), was combined with naphthalene-1-yl phosphorodichloridate (1.18 g), TEA (1.26 mL), and DCM (20 mL) to give (2S)-neopentyl 2-(chloro(naphthalen-1-yloxy)phosphorylamino)-propanoate in an 81% yield (1.4 g) as a pale yellow thick oil:

The following are the NMR results analyzing the synthesized compound:
$^1$H NMR (500 MHz, CDCl$_3$) δ 8.11 (m, 1H, H$_8$-napht), 7.89 (m, 1H, H$_5$-napht), 7.76 (m, 1H, H$_4$-napht), 7.66-7.53 (m, 3H, H$_6$, H$_7$, H$_2$-napht), 7.46 (td, J=2.0, 8.0, 1H, H$_3$-napht), 4.54 (m, 0.5H, NH), 4.46 (m, 0.5H, NH), 4.41-4.30 (m, 1H, Hα), 3.99-3.84 (m, 2H, CH$_2$ ester), 1.61 (d, J=7.1, 1.5H, CH$_3$ ala), 1.59 (d, J=7.0, 1.5H, CH$_3$ ala), 1.00 (s, 4.5H, tBu), 0.98 (s, 4.5H, tBu).
$^{31}$P NMR (202 MHz, CDCl$_3$) δ 8.25, 7.96.

Step 2: Synthesis of Protide

Using the general procedure (Method A) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, the nucleoside (6.0 g, 19.29 mmol) in anhydrous THF (50 mL) was added a solution of (2S)-neopentyl 2-(chloro(naphthalen-1-yloxy)phosphorylamino)propanoate (14.8 g, 38.58 mmol) at −78° C. followed by addition of NMI (7.65 mL, 96.45 mmol). The reaction mixture was allowed to warm to room temperature and stirred overnight. After normal work-up the crude product was purified by column chromatography on silica gel using CH$_2$Cl$_2$/MeOH (96:4) to give 3.5 g of protide as an off-white solid in a 27.5% yield.

The following are the NMR results analyzing the synthesized compound:
$^1$H NMR (200 MHz, CDCl$_3$) δ 8.18-8.10 (m, 1H), 7.93 (d, J=5.0 Hz, 1H), 7.87-7.62 (m, 1H), 7.65 (t, J=8.2 Hz, 1H), 7.52-7.31 (m, 4H), 5.96 (d, J=3.0 Hz, 1H), 4.63-4.53 (m, 2H), 4.33-4.19 (m, 2H), 4.07-3.96 (m, 1H), 4.02 (s, 3H), 3.76-3.52 (m, 2H), 1.30 (d, J=7.2 Hz, 3H), 0.95-0.91 (2 s, 3H), 0.84-0.82 (2 s, 9H).
$^{31}$P NMR (50 MHz, CDCl$_3$) δ 5.37, 5.32.

Improved synthesis of 2,2-dimethylpropyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)propanoate:

Step 1. Preparation of (S)-neopentyl 2-(tert-butoxycarbonylamino)propanoate

In a 22 L 3-neck flask equipped with a mechanical stirrer, an internal thermocouple, a cooling bath using ice/salt and a nitrogen inlet were placed Boc-L-alanine (900 g, 4.75 mol 99% grade, Product No 01322, Chem-Impex) and neopentyl alcohol (502.4 g, 5.70 mol, 1.2 equiv, 99% grade, Product No N7206, Aldrich) in 9 L of anhydrous dichloromethane. To this mixture solution EDCI (1.37 kg, 7.12 mol, 1.5 equiv, Product No 00050, Chem-Impex) was added as a single portion followed by portion-wise addition of DMAP (58 g, 0.475 mmol, 99% grade, Product No 107700, Aldrich) at 0° C. The mixture was allowed to warm slowly in ice bath and stir at room temperature for 15 h. The progress of reaction was monitored by TLC ($R_f$=0.4, hexanes:ethyl acetate (85:15), Ninhydrin stain). The reaction mixture was diluted with DCM (2 L) and washed successively with saturated $NaHCO_3$ solution (2×2 L) and brine (2 L). The organic layer was dried over anhydrous sodium sulfate (EMD grade), filtered and concentrated under reduced pressure. Purification was performed by column chromatography on silica gel (4 kg, Silicycle, SiliaFlash® P60) using a constant gradient mixture of hexanes:ethyl acetate (85:15) to give 903 g (3.48 mol, 74%) of compound 2 as a light yellow oil after concentration in vacuo.

Step 2. Preparation of (S)-neopentyl 2-aminopropanoate p-toluenesulfonic acid The conversion was carried out using a 22 L 3-neck open head flask equipped with a mechanical stirrer and an internal thermocouple. To a stirred solution of (S)-neopentyl 2-(tert-butoxycarbonylamino)propanoate (900 g, 3.47 mol) in 14 L of ethyl acetate was added $PTSA.H_2O$ (660 g, 3.47 mol, 98% reagent grade, Product No 161993, Aldrich) and heated at 65° C. for 10 h. The mixture was cooled to give white solid at room temperature and cooled at ice bath for 30 min prior to filtration. The mixture solution was filtered and dried in a vacuum oven (40° C., Welch Model 2034, ca. 10 mmHg) for 15 hr to yield 907 g (2.74 mol, 79%) of desired product.

Step 3. Preparation of naphthalene-1-yl phosphorodichloridate

In a 22 L 3-neck flask equipped with a mechanical stirrer, an internal thermocouple, a cooling bath of dry/acetone, an additional funnel and a nitrogen inlet was placed 1-naphthol (780 g, 5.41 mol, 491 g used from Aldrich, ≥99% grade, Product No N1000 and 289 g used from Alfa Aesar 99% grade, Product No A11862) in 10 L of MTBE at room temperature. $POCl_3$ (495 mL, 5.41 mol, ReagentPlus® 99%, Product No 201170, Aldrich) in an additional funnel was dropwise added in 5 min (note: no exothermic observed) under nitrogen pressure. To this solution at −25° C. (an internal temperature) was slowly added by triethylamine (754 mL, 5.41 mol, ≥99.5% grade, Product No 471283, Aldrich) for one h (note: exotherm observed) and then the cooling bath was removed after the addition was completed. The reaction mixture was aged for 3 h at room temperature under nitrogen pressure. The triethylamine hydrochloride salt was filtered off using a 3 L sintered funnel (Medium size) and the filtrate was concentrated to dryness under reduced pressure at <20° C. of water bath to give desired product as clear dark yellow oil (1219 g, 86.3%) which was used without further purification.

Step 4. Preparation of (2S)-neopentyl 2-(chloro-(naphthalene-1-yl)phosphorylamino)-propanoate Naphthalene-1-yl phosphorodichloridate (1219 g, 4.67 mol) and (S)-neopentyl 2-aminopropanoate p-toluenesulfonic acid (1547 g, 4.67 mol) were suspended in anhydrous dichloromethane (15 L) in a 22 L 3-neck flask equipped with a mechanical stirrer, an internal thermocouple, a cooling bath of dry/acetone, an additional funnel and a nitrogen inlet. Anhydrous triethylamine (1.3 L, 9.34 mmol, ≥99.5% grade, Product No 471283, Aldrich) was slowly added at −25° C. for one h. Later the reaction mixture was warmed to room temperature and stirred for overnight and monitored by $^{31}P$ NMR. After completion, the solvent was removed under reduced pressure and the resulting crude residue that was triturated with a 1:1 mixture of ethyl acetate (2 L)/hexanes (2 L) was filtered by short pad of silica gel (Silicycle, SiliaFlash® P60, 3 inch high, funnel: 3 L medium size) and eluted using a mixture of ethyl acetate/hexanes (3 L: 3 L) followed by rinse with a mixture of ethyl acetate/hexanes (1.5 L: 1.5 L). Upon concentration, the dark oil was diluted with 3 L THF and was concentrated again under reduced pressure to deliver 1700 g (94%) of product which was used without further purification.

Step 5. Synthesis of (2S)-neopentyl 2-(((2R,3R,4R,5R)-5-(2-amino-6-methoxy-9H-purin-9-yl)-3,4-dihydroxy-4-methyl-tetrahydrofuran-2-yl)methoxy)(naphthalene-1-yl)phosphorylamino)-propanoate To a solution of (3R,4R,5R)-2-(2-amino-6-methoxy-9H-purin-9-yl)-5-(hydroxymethyl)-3-methyltetrahydrofuran-3,4-diol, (450 g, 1.45 mol, 1.0 equiv) in anhydrous THF (7 L) in a 22 L 3-neck flask equipped with a mechanical stirrer, an internal thermocouple, a cooling bath, an additional funnel and a nitrogen inlet was added slowly 1.0M tert-BuMgCl in THF (Aldrich, 2.89 L, 2.89 mol, 2.0 equiv) at dry ice/acetone bath (internal temp=−2±1° C.) over 45 min under nitrogen. The resulting reaction mixture gave a white suspension after stirring 30 min and to this a solution of (2S)-neopentyl 2-(chloro-(naphthalene-1-yl)phosphorylamino)-propanoate (1.11 kg, 2.895 mol, 2.0 equiv) in THF (1.6 L) was dropwise added over 40 min. The mixture was allowed to warm to room temperature and stirred overnight (15 h). The progress of the reaction was monitored by TLC (97:3 DCM:MeOH, $\lambda_{254}$ nm, $R_f$=0.3 see below typical TLC diagram) and LC/MS. The reaction mixture was cooled in an ice-bath was quenched with saturated $NH_4Cl$ solution (7 L) dropwise over ca. 20 min and stirred vigorously for 20 min. The reaction mixture (THF layer) was separated from aqueous $NH_4Cl$ solution. The aqueous layer was extracted with THF (3 L). The combined organic layer (THF) was washed with brine (2 L), dried over anhydrous sodium sulfate and concentrated under reduced pressure below 39±1° C. The crude product (1600 g) was purified by both silica gel column and Biotage chromatography. Crude product (1600 g) dissolved in 1.2 L DCM was loaded onto a glass column (11"×20" high) with silica gel (13 kg, Silicycle, SiliaFlash® P60) and was purified by an eluent of 1% MeOH in DCM→4% MeOH in DCM (300 L used) collecting fractions (4 L size amber bottles×55) to give three fractions for a total of 730 g. Further purification of this material was required.

Purification Run 1 from Part A: The first batch A (140 g) dissolved in 300 mL was purified again by Biotage (column F75L, 800 g) to give 92 g of product as a pure material. It was eluted by a mixture of 0.5% MeOH in DCM→3% MeOH in DCM (60 L DCM used) collecting fraction (1 L size×20 and 2 L size×20 Erlenmeyer flasks). It gave a diastereomeric ratio (68:32) by HPLC. The diastereomeric ratio from crude mixture before purification was about 50:50.

Purification Run 2 from Part B: Major batch B (420 g) dissolved in 1 L DCM was purified again by Biotage (column F150M, 2.5 kg) to give 296 g of a pure product. It was eluted by a mixture of 0.5% MeOH in DCM→3% MeOH in DCM (200 L DCM used) collecting fraction (4 L size bottle×45). It gave a diastereomeric ratio (49:51) by HPLC. The impure fractions were combined and purified together in "Run" 3.

Purification Run 3 from Part C: The last batch C (170 g) dissolved in 500 mL DCM was purified again by Biotage (F75L, 800 g) using 50 L of DCM. It was eluted by a mixture of 1% MeOH in DCM→3% MeOH in DCM collecting fraction (4 L size bottle×45). Unfortunately, the required purity was not achieved in any of the fractions collected. All combined impure materials (a total of crude 220 g) from Runs 1, 2 and 3 dissolved in 600 mL DCM were loaded onto a glass column (11'×20' high) with silica gel (11 kg, Silicycle, SiliaFlash® P60). With the similar eluent mixture of 1% MeOH in DCM→3% MeOH in DCM (200 L DCM used), it gave 152 g of pure product. The diastereomeric ratio was (41:59) by HPLC.

It is clear from this work that the ratio of diastereomers can be controlled by selection of the proper chromatographic fractions.

In summary the three purification runs on the 730 g provided a total of 540 g of pure product. To remove trace amounts of DCM the 540 g was dissolved in 3 L (×2) of MeOH then evaporated in a 20 L rotovap flask. The product was completely dried by a 20 L rotovap at 39° C.±1° C. for 15 h to yield an off-white powder solid. The product in glass trays was dried in an oven (3 days, 39° C.±1° C., <5-10 mmHg) until a constant weight was achieved to afford 517 g (0.785 mol, 54.3%, <2000 ppm MeOH) as an off-white solid.

Example 21

The separated diastereomer (peak 1) (S)-P 2,2-dimethylpropyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate was purified from the diastereomeric mixture as follows

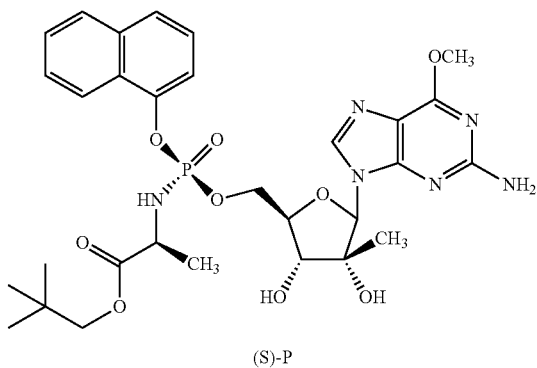 [SMILES: COc1nc(N)nc2c1ncn2C1O[C@H](CO[P@@](=O)(N[C@@H](C)C(=O)OCC(C)(C)C)Oc2cccc3ccccc23)[C@@H](O)[C@@]1(C)O]

(S)-P

A 1:1 mixture of diastereomers of 2,2-dimethylpropyl 2(S)-((((2R,3R,4R,5R>5-(2- amino-6-methoxy-9H-purin-9-yl)-3,4-dihydroxy-4-methyltetrahydrofuran-2- yl)methoxy (naphthalene-l-yloxy) phosphorylamino)propanoate (10.0 g) was taken up in 1:1 ethanol:hexanes and loaded onto a Chiral Pak AD chiral column and eluted with the same solvent. UV detection was done at 300 nm. Analysis of the fractions was done on a Chiral Pak AD (5 um, 4.6 mm ID×250 mm; S/N AD[Eta]OCE-LD001) chiral column at a flow rate of 1 mL/min and detection at 300 nM. Complete separation of the two diastereomers was obtained (see FIG. 1).

Peak 1 with a retention time of 6 min on the analytical column, and provided 4.75 g, (95.9% yield) of a single diastereomer with 99.9% ee (enantiomeric excess).

The following are the NMR results analyzing the synthesized compound:

$^1$H NMR (500 MHz, MeOD) δ 8.16 (d, J=8.50 Hz, 1H, H$_8$-naph), 7.97 (s, 1H, H$_8$), 7.85 (d, J=7.50 Hz, 1H, H$_5$-napht), 7.67 (d, J=8.00 Hz, 1H, H$_4$-napht), 7.52-7.45 (m, 3H, H$_2$, H$_7$, H$_6$-napht), 7.38 (t, J=8.00 Hz, 1H, H$_3$-napht), 6.00 (s, 1H, H$_{1'}$), 4.68-4.57 (m, 1H, H$_{5'}$), 4.31-4.25 (m, 2H, H$_{3'}$, H$_{4'}$), 4.09-4.03 (m, 4H, Hα, 6OCH$_3$), 3.76, 3.64 (AB, J$_{AB}$=10.50 Hz, 2H, CH$_2$ ester), 1.33 (d, J=7.50 Hz, 3H, CH$_3$ Ala), 0.96 (s, 3H, 2'CCH$_3$), 0.87 (s, 9H, 3×CH$_3$ ester)

$^{13}$C NMR (126 MHz, MeOD) δ 175.05 (d, $^3$J$_{C-C-N-P}$=5.00 Hz, C=O ester), 162.73 (C6), 161.87 (C2), 154.55 (C4), 147.97 (d, $^2$J$_{C-O-P}$=6.30 Hz, ipso Naph), 139.09 (CH8), 136.26 (C10-Naph), 128.78 (CH-Naph), 127.89 (d, $^3$J$_{C-C-O-P}$=6.30 Hz, C9-Naph), 127.71, 127.46, 126.46, 125.93, 122.80 (CH-Naph), 116.17 (d, $^3$J$_{C-C-O-P}$=2.50 Hz, C2-Naph), 115.58 (C5), 93.21 (C1'), 82.16 (d, $^3$J$_{C-C-O-P}$=8.80 Hz, C4'), 79.97 (C2'), 75.36 (CH$_2$ ester), 74.69 (C3'), 67.64 (d, $^2$J$_{C-O-P}$=5.00 Hz, C5'), 54.23 (6OCH$_3$), 51.78 (Cα Ala), 32.24 (C ester), 26.69 (3×CH$_3$ ester), 20.60 (d, $^3$J$_{C-C-N-P}$=6.30 Hz, CH$_3$ Ala), 20.30 (2'CCH$_3$)

$^{31}$P NMR (202 MHz, CDCl$_3$) δ 4.22

The absolute configuration of peak 1 product was determined to be (S)-P by VCD.

Experimental Measurement of VCD spectra: A 6-mg sample of peak 1 compound was dissolved in 125 μL CDCl$_3$ and placed in a 100 μm pathlength cell with BaF$_2$ windows. IR and VCD spectra were recorded on a ChiralIR VCD spectrometer (BioTools, Inc., Jupiter, Fla.) equipped with DualPEM, with 4 cm$^{-1}$ resolution, 8-h collection for sample and solvent, and instrument optimized at 1400 cm$^{-1}$.

Theoretical Calculations: The (S)-P and (R)-P diastereomeric configurations shown above were built with Hyperchem molecular modeling software (Hypercube, Inc., Gainesville, Fla.). Conformational searches were carried out with Spartan 06 (Wavefunction, Inc., Irvine, Calif.) at the molecular mechanics level. These conformational searches identified well over 100 possible conformations for each diastereomer. Geometry, frequency, and IR and VCD intensity calculations were carried out at the DFT level (B3LYP functional/6-31G(d) basis set) with Gaussian 03 (Gaussian Inc., Wallingford, Conn.) for 9 low-energy conformations of each diastereomer identified in the conformational search. The calculated frequencies were scaled by 0.97 and the IR and VCD intensities were converted to Lorentzian bands with 6-cm$^{-1}$ half-width for comparison to experiment.

Analysis: The calculated VCD for the two diastereomers exhibit nearly mirror-image VCD intensity for the bands at ~1000 cm$^{-1}$, which correspond to the observed features at ~1030 cm$^{-1}$ (the distinct IR features in this region also occur at higher frequency in the observed spectra compared to the calculated spectra). These bands correspond to antisymmetric stretch of the H$_2$C—O—P bonds (determined by animating the calculated normal modes). This stretching mode serves as a marker for the chirality at the phosphorus, allowing assignment of the configuration of peak 1 to (S)-P and peak 2 to (R)-P. In several other regions of the spectra between 1000 and 1300 cm$^{-1}$, the calculated (S)-P VCD spectra exhibit more positive VCD intensity than the (R)-P VCD spectra. These differences are also in general reflected in the differences between the experimental spectra. This VCD analysis of the two diastereomers provides assignment of the chirality at the phosphorus as (S)-P for the peak 1 diastereomer and (R)-P for the peak2 diastereomer, and is consistent with the R-configurations for the four chiral carbons in the five-membered ring and S-configuration at the peptide.

Figure 2:
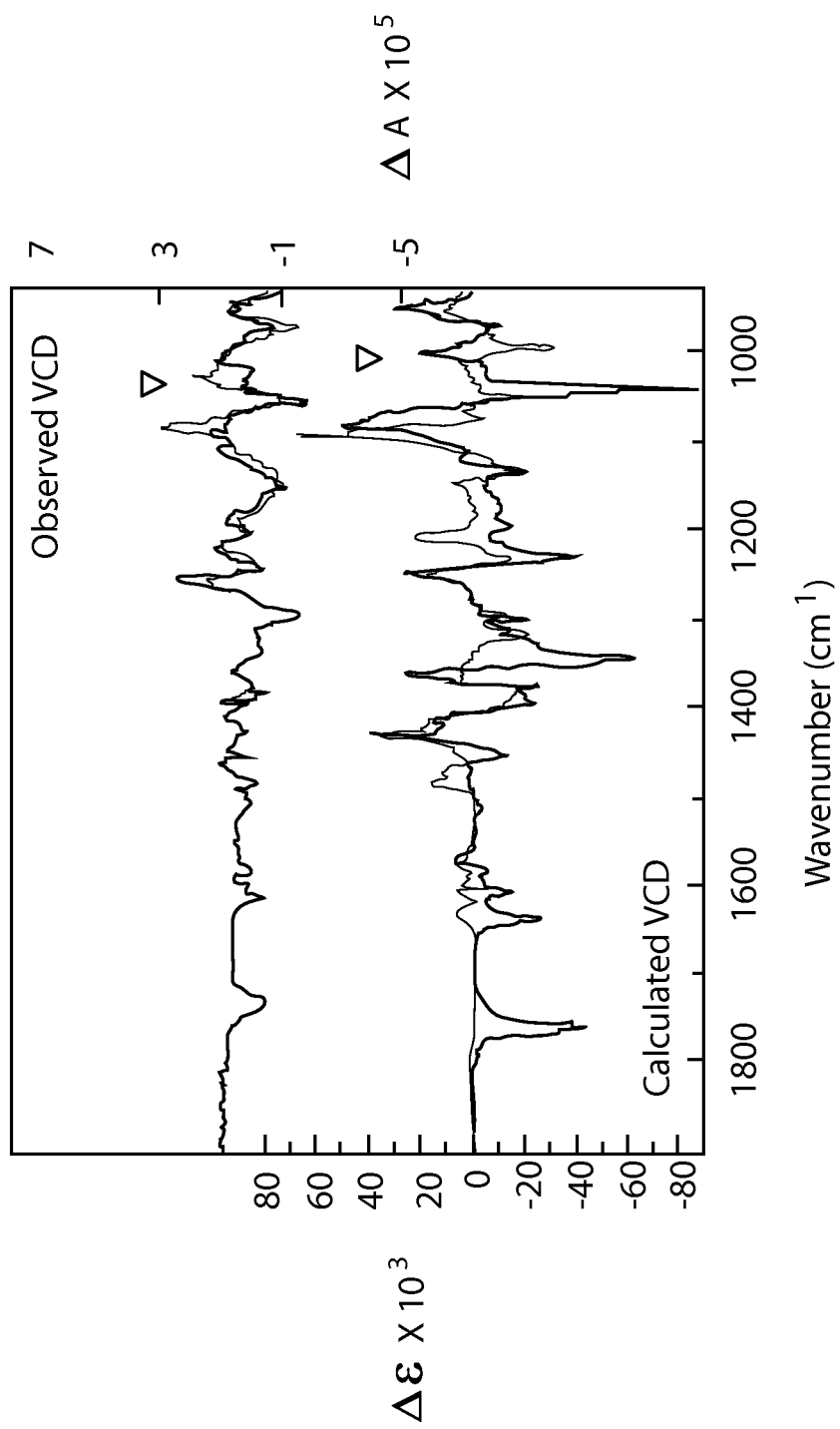
FIG. 2 is a graph showing observed and calculated VCD Spectra for Peak 1.

Observed and Calculated VCD Spectra for Peak 1 (Orange) and Peak 2 (Blue) is shown in FIG. 2.

Example 22

The separated diastereomer (Peak 2) (R)-P 2,2-dimethylpropyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)propanoate was purified from the diastereomeric mixture as follows

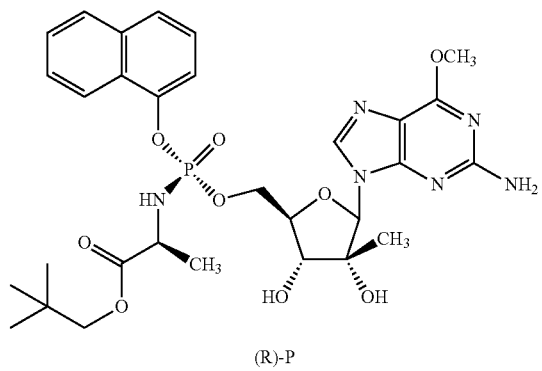 [SMILES: COc1nc(N)nc2c1ncn2C1O[C@H](CO[P@](=O)(N[C@@H](C)C(=O)OCC(C)(C)C)Oc2cccc3ccccc23)[C@@H](O)[C@@]1(C)O]

(R)-P

As described above, Peak 2, with a retention time of 10.7 min on the analytical column, provided 5.29 g (100% yield) of a single diastereomer with 99.8% diasteromeric excess. (95.9% yield) of a single diastereomer with 99.9% ee (enantiomeric excess). The absolute configuration of the Peak 2 diastereomer was determined by VCD to be (R)-P as described above.

The following are the NMR results analyzing the synthesized compound:

$^1$H NMR (500 MHz, MeOD) δ 8.20-8.18 (m, 1H, H$_8$-naph), 7.95 (s, 1H, H$_8$), 7.89-7.87 (m, 1H, H$_5$-napht), 7.70 (d, J=8.50 Hz, 1H, H$_4$-napht), 7.54-7.50 (m, 3H, H$_2$, H$_7$, H$_6$-napht), 7.41 (t, J=7.00 Hz, 1H, H$_3$-napht), 5.99 (s, 1H, H$_{1'}$), 4.63-4.55 (m, 1H, H$_{5'}$), 4.34 (d, J=9.00 Hz, 1H, H$_{3'}$), 4.28-4.23 (m, 1H, H$_{4'}$), 4.08-4.03 (m, 4H, Hα, 6OCH$_3$), 3.72, 3.59 (AB, J$_{AB}$=10.50 Hz, 2H, CH$_2$ ester), 1.33 (d, J=7.50 Hz, 3H, CH$_3$ Ala), 0.98 (s, 3H, 2'CCH$_3$), 0.85 (s, 9H, 3×CH$_3$ ester)

$^{13}$C NMR (126 MHz, MeOD) δ 174.78 (d, $^3$J$_{C-C-N-P}$=6.00 Hz, C=O ester), 162.72 (C6), 161.89 (C2), 154.51 (C4), 148.00 (d, $^2$J$_{C-O-P}$=7.00 Hz, ipso Naph), 139.38 (CH8), 136.30 (C10-Naph), 128.84 (CH-Naph), 127.88 (d, $^3$J$_{C-C-O-P}$=6.30 Hz, C9-Naph), 127.74, 127.46, 126.51, 125.95, 122.76 (CH-Naph), 116.21 (d, $^3$J$_{C-C-O-P}$=3.20 Hz, C2-Naph), 115.60 (C5), 93.37 (C1'), 82.32 (d, $^3$J$_{C-C-O-P}$=8.00 Hz, C4'), 79.91 (C2'), 75.34 (CH$_2$ ester), 74.94 (C3'), 68.12 (d, $^2$J$_{C-O-P}$=5.00 Hz, C5'), 54.21 (6OCH$_3$), 51.71 (Cα Ala), 32.21 (C ester), 26.66 (3×CH$_3$ ester), 20.81 (d, $^3$J$_{C-C-N-P}$=6.30 Hz, CH$_3$ Ala), 20.27 (2'CCH$_3$)

$^{31}$P NMR (202 MHz, CDCl$_3$) δ 4.28

Example 23

The (2S)-isopropyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

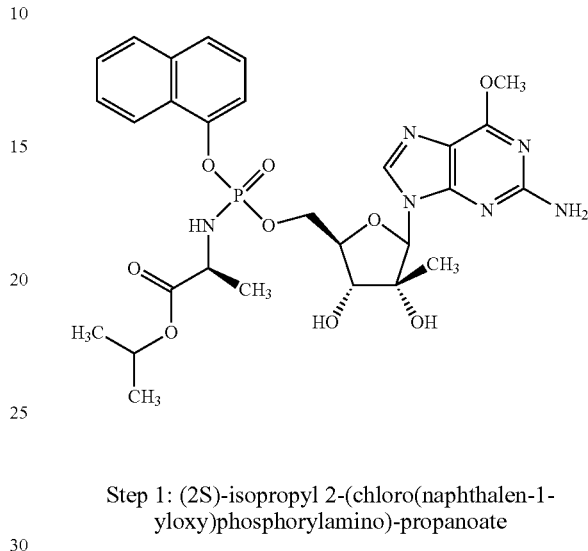

Step 1: (2S)-isopropyl 2-(chloro(naphthalen-1-yloxy)phosphorylamino)-propanoate

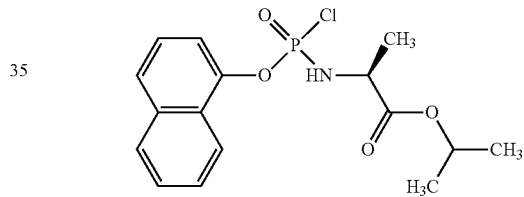

Using the general procedure for synthesizing naphthyl phosphoroaminochloridates, the HCl salt of isopropyloxy-L-alanine (5 g), naphthalen-1-yl phosphorodichloridate (7.30 g), TEA (8.31 mL) and DCM (146 mL) were combined to give (2S)-isopropyl 2-(chloro(naphthalen-1-yloxy)phosphorylamino)-propanoate in an 61% yield (6.52 g), as a pale yellow thick oil. HPLC: t$_R$=18.71, 18.95 min. (column: Varian Pursuit XRs 5, C18, 150×4.6 mm. The method is: Linear gradient H$_2$O/ACN: 0% to 100% ACN in 30 min.)

The following are the NMR results analyzing the synthesized compound:

$^1$H NMR (500 MHz, CDCl$_3$) δ 8.14-8.08 (m, 1H), 7.91-7.87 (m, 1H), 7.75 (d, J=8.3, 1H), 7.65-7.54 (m, 3H), 7.48-7.43 (m, 1H), 5.17-5.05 (m, 1H), 4.60-4.45 (m, 1H), 4.32-4.21 (m, 1H), 1.57 and 1.55 (2d, J=7.1, 3H), 1.34 and 1.26 (2s, 3H)

$^{31}$P NMR (202 MHz, CDCl$_3$) δ 8.31, 8.01.

Step 2. Synthesis of Protide

Using the general procedure (Method A) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, to a solution of 1.2 g (3.85 mmol) of nucleoside and 1.53 mL (19.25 mmol) of NMI in 12 mL of THF, was added (2S)-isopropyl 2-(chloro(naphthalen-1-yloxy)phosphorylamino)-propanoate 4.10 g (11.55 mmol) dissolved in 12 mL of THF. After workup and silica gel column chromatography, 505 mg of pure protide was obtained in a 21% yield, as an off white solid. HPLC $t_R$=18.27, 18.81 min; (column: Varian Pursuit XRs 5, C18, 150×4.6 mm. The method is: Linear gradient $H_2O$/ACN: 0% to 100% ACN in 30 min.)

The following are the NMR results analyzing the synthesized compound:

$^1$H NMR (500 MHz, $CD_3OD$) δ8.19-8.165 (m, 1H, $H_8$-napht), 8.03, 8.00 (2×s, 1H, $H_8$), 7.89-7.85 (m, 1H, $H_5$-napht), 7.71-7.67 (m, 1H, $H_4$-napht), 7.56-7.46 (m, 3H, $H_2$, $H_7$, $H_6$-napht), 7.42-7.37 (m, 1H, $H_3$-napht), 6.00, 5.99 (2×s, 1H), 4.93-4.88 (m, 1H, CH ester), 4.64-4.59 (m, 1H, $H_5$'), 4.37-4.23 (m, 2H, $H_3$', and $H_4$'), 4.05 (s, 3H, $6OCH_3$), 3.98-3.92 (m, 1H, CHα), 1.32 (d, J=7.20 Hz, 3H, $CH_3Ala$), 1.16-1.12 (m, 6H, $2×CH_3$ester), 0.98, 0.97 (2×s, 3H, 2'$CCH_3$).

$^{31}$P NMR (202 MHz, $CD_3OD$) δ 4.35, 4.25.

Example 24

The (2S)-cyclopentyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

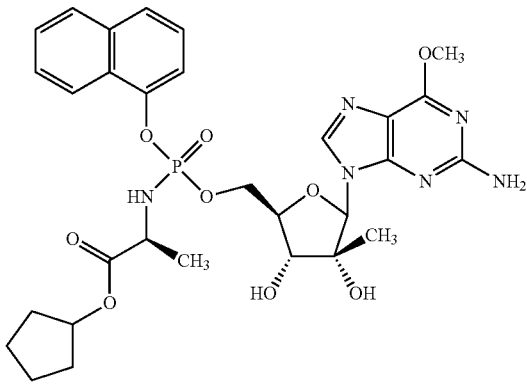 [SMILES: COc1nc(N)nc2c1ncn2C1O[C@H](COP(=O)(N[C@@H](C)C(=O)OC2CCCC2)Oc2cccc3ccccc23)[C@@H](O)[C@@]1(C)O]

Step 1: Synthesis of (2S)-cyclopentyl 2-(chloro(naphthalen-1-yloxy)-phosphorylamino)propanoate Using the general procedure for synthesizing naphthyl (amino acid ester) phosphorochloridates the tosylate salt of (S)-cyclopentyl 2-aminopropanoate (4.00 g, 12.14 mmol), naphthalen-1-yl phosphorodichloridate (3.17 g, 12.14 mmol) and TEA (1.60 mL, 24.28 mmol) in 30 mL of dry DCM, were combined to give (2S)-cyclopentyl 2-(chloro(naphthalen-1-yloxy)-phosphorylamino)propanoate in 65% yield (3.01 g), as a clear, yellow, thick oil.

The following are the NMR results analyzing the synthesized compound:

$^1$H NMR (500 MHz, $CDCl_3$) δ 8.13-8.09 (m, 1H, $H_8$-napht), 7.95-7.88 (m, 1H, $H_5$-napht), 7.74 (d, J=8.0 Hz, 1H, $H_4$-napht), 7.64-7.54 (m, 3H, $H_7$, $H_6$, $H_2$-napht), 7.50-7.40 (m, 1H, $H_3$-napht), 5.30-5.28, 5.25-5.23 (2×m, 1H, CH ester), 4.63-4.57 (m, 1H, NH), 4.28-4.25 (s, 1H, CHa), 1.94-1.85 (m, 2H, $2×CH_{2a}$ ester), 1.79-1.69 (m, 4H, $2×CH_{2b}$ ester, $2×CH_{2c}$, ester), 1.66-1.59 (m, 2H, $2×CH_{2d}$ ester) 1.57, 1.54 (2×d, J=7.0 Hz, 3H, $CH_3$ Ala).

$^{31}$P NMR (202 MHz, $CDCl_3$) δ 8.38, 8.13.

Step 2: Synthesis of the Protide

Using the general procedure (Method A) for the synthesis of 5'-phosphoramidates of 2-amino-6-methoxy-9-(2-C-methyl-β-D-ribofuranosyl)purine, to a solution of 250 mg (0.80 mmol) of nucleoside in 5 mL of THF, and NMI 0.47 mL (4.02 mmol), was added (2S)-cyclopentyl 2-(chloro(naphthalen-1-yloxy)-phosphorylamino)propanoate 920 mg (2.40 mmol) in 5 mL of THF. After workup and silica gel column chromatography, 75 mg of pure protide was obtained in a 14% yield, as an off-white solid. HPLC: $t_R$=19.52, 19.96 min. (column: Varian Pursuit XRs 5, C18, 150×4.6 mm. The method is: Linear gradient $H_2O$/ACN: 0% to 100% ACN in 30 min.)

The following are the NMR results analyzing the synthesized compound:

$^1$H NMR (500 MHz, $CD_3OD$) δ 8.19-8.15 (m, 1H, $H_8$-naph), 7.98, 7.96 (2×s, 1H, $H_8$), 7.86-7.82 (m, 1H, $H_5$-napht), 7.68, 7.65 (2×d, J=8.0 Hz, 1H, $H_4$-napht), 7.53-7.44 (m, 3H, $H_2$, $H_7$, $H_6$-napht), 7.39, 7.37 (2×t, J=8.0 Hz, 1H, $H_3$-napht), 6.02, 6.00 (2×s, 1H, $H_1$'), 5.00-4.97 (m, 1H, CH ester), 4.66-4.58 (m, 2H, $H_5$'), 4.37-4.24 (m, 2H, $H_3$', $H_4$'), 4.04 (s, 3H, $6OCH_3$), 4.01-3.93 (m, 1H, CHα Ala), 1.78-1.69 (m, 2H, $2×CH_{2a}$, $2×CH_2$ ester), 1.60-1.47 (m, 6H, $2×CH_{2b}$, $2×CH_2$ ester), 1.28 (d, J=7.0 Hz, 3H, $CH_3$ Ala), 0.98, 0.96 (2×s, 3H, 2'$CCH_3$).

$^{13}$C NMR (126 MHz, $CD_3OD$) δ 174.87, 174.62 (2×d, $^3J_{C-C-N-P}$=5.0 Hz, C=O ester), 162.73 (C6), 161.86 (C2), 154.55, 154.50 (C4), 148.01, 147.95 (d, $^2J_{C-O-P}$=3.8 Hz, ipso Naph), 139.38, 139.08 (CH8), 136.27, 136.24 (C10-Naph), 128.86, 128.81 (CH-Naph), 127.86, 127.78 (2×d, $^3J_{C-C-O-P}$=5.0 Hz, C9-Naph), 127.73, 127.47, 126.52, 126.48, 125.96, 125.93, 122.78, 122.74 (CH-Naph), 116.21, 116.13 (2×d, $^3J_{C-C-O-P}$=3.8 Hz, C2-Naph), 115.63, 115.60 (C5), 93.37, 93.19 (C1'), 82.31, 82.16 (2×d, $^3J_{C-C-O-P}$=8.8 Hz, C4'), 80.00, 79.96 (C2'), 79.52, 79.50 (CH ester), 74.95, 74.71 (C3'), 68.06, 67.59 (2×d, $^2J_{C-O-P}$=5.0 Hz, C5'), 54.30, 54.29 ($6OCH_3$), 51.81, 51.75 (Cα Ala) 33.52, 33.39 ($2×CH_2$-2 and 5 ester), 24.60, 24.58 ($2×CH_2$-3 and 4 ester), 20.67, 20.63 (2×d, $^3J_{C-C-N-P}$=6.3 Hz, $CH_3$ Ala), 20.44, 20.36 (CH3).

$^{31}$P NMR (202 MHz, $CD_3OD$) δ 4.36, 4.20.

Example 25

The (2S)-cyclohexyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

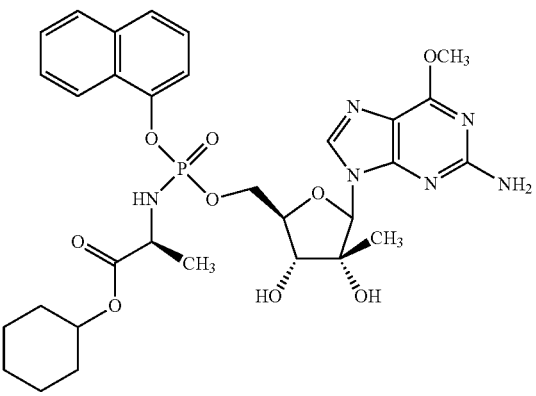 [SMILES: COc1nc(N)nc2c1ncn2C1O[C@H](COP(=O)(N[C@@H](C)C(=O)OC2CCCCC2)Oc2cccc3ccccc23)[C@@H](O)[C@@]1(C)O]

Step 1: Synthesis of (2S)-cyclohexyl 2-(chloro(naphthalen-1-yloxy)-phosphorylamino)propanoate

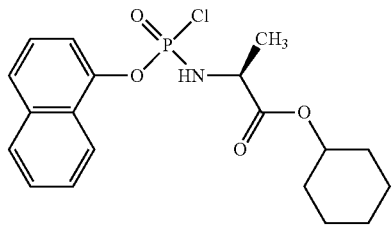 [SMILES: C[C@H](NP(=O)(Cl)Oc1cccc2ccccc12)C(=O)OC1CCCCC1]

Using the general procedure for synthesizing naphthyl (aminoacid ester) phosphorochloridates the hydrochloride salt of cyclohexyloxy-L-alanine (2 g), was combined with naphthalen-1-yl phosphorodichloridate (2.54 g), TEA (2.7 mL), and DCM (55 mL) to give (2S)-cyclohexyl 2-(chloro (naphthalen-1-yloxy)-phosphorylamino)propanoate in a 69% yield (2.64 g) as a pale yellow thick oil:

The following are the NMR results analyzing the synthesized compounds:

$^1$H NMR (500 MHz, CDCl$_3$) δ 8.11 (m, 1H, H$_8$-napht), 7.89 (m, 1H, H$_5$-napht), 7.76 (m, 1H, H$_4$-napht), 7.60 (m, 3H, H$_7$, H$_6$, H$_2$-napht), 7.46 (td, J=2.4, 7.9, 1H, H$_3$-napht), 4.93-4.83 (m, 1H, CH ester), 4.51-4.42 (m, 0.5H, NH), 4.40-4.33 (m, 0.5H, NH), 4.28 (s, 1H, CHα), 1.82 (m, 4H, CH$_2$ cyclohexyl), 1.58 (d, J=7.1, 1.5H, CH$_3$ Ala), 1.56 (d, J=6.9, 1.5H, CH$_3$ Ala), 1.61-1.31 (m, 6H, CH$_2$ cyclohexyl).

$^{31}$P NMR (202 MHz, CDCl$_3$) δ 8.29, 7.94.

Step 2: Synthesis of Protide

Using the general procedure (Method A) for the synthesis of 5'-phosphoramidates of 2-amino-6-methoxy-9-(2-C-methyl-β-D-ribofuranosyl)purine, to a solution of 980 mg (3.15 mmol) of nucleoside and NMI 1.25 mL (15.74 mmol) in 30 mL of THF, was added (2S)-cyclohexyl 2-(chloro(naphthalen-1-yloxy)-phosphorylamino)propanoate 3.82 g (9.44 mmol) in 20 mL of THF. After workup and silica gel column chromatography, 730 mg of pure protide was obtained in a 14% yield, as an off-white solid. MS (ES+) m/e: 671.26 (MH$^+$, 100%); Accurate mass: C$_{31}$H$_{40}$N$_6$O$_9$P$_1$ calculated 671.2594. found 671.2584.

The following are the NMR results analyzing the synthesized compound:

$^1$H NMR (500 MHz, CD$_3$OD) δ 8.19-8.15 (m, 1H, H$_8$-naph), 7.98, 7.96 (2×s, 1H, H$_8$), 7.84-7.82 (m, 1H, H$_5$-napht), 7.67, 7.65 (2×d, J=8.00 Hz, 1H, H$_4$-napht), 7.53-7.44 (m, 3H, H$_2$, H$_7$, H$_6$-napht), 7.41-7.36 (m, 1H, H$_3$-napht), 6.02, 6.00 (2×s, 1H, H$_{1'}$), 4.69-4.60 (m, 3H, CH ester and H$_{5'}$), 4.35-4.29 (m, 2H, H$_{3'}$, H$_{4'}$), 4.04 (s, 3H, 6OCH$_3$), 4.00 (q, J=7.77 Hz, 1H, CHα Ala), 1.69-1.60 (m, 4H, 2×CH$_2$ ester), 1.31-1.19 (m, 9H, 3×CH$_2$ ester and CH$_3$ Ala), 0.98, 0.96 (2×s, 3H, 2'CCH$_3$).

$^{13}$C NMR (126 MHz, CD$_3$OD) δ 174.51, 174.25 (2×d, $^3J_{C-C-N-P}$=5.00 Hz, C=O ester), 162.72 (C6), 161.86 (C2), 154.55, 154.50 (C4), 148.03, 148.01 (d, $^2J_{C-O-P}$=3.80 Hz, ipso Naph), 139.33, 139.05 (CH8), 136.28, 136.25 (C10-Naph), 128.85, 128.79 (CH-Naph), 127.88, 127.73 (2×d, $^3J_{C-C-O-P}$=6.3 Hz, C9-Naph), 127.46, 126.82, 126.53, 126.48, 125.95, 125.91, 122.81, 122.76, 122.27 (CH-Naph), 116.21, 116.12 (2×d, $^3J_{C-C-O-P}$=3.80 Hz, C2-Naph), 115.62, 115.59 (C5), 93.35, 93.17 (C1'), 82.31, 82.15 (2×d, $^3J_{C-C-O-P}$=8.80 Hz, C4'), 79.99, 79.96 (C2'), 74.94, 74.92 (CH ester), 74.95, 74.71 (C3'), 68.05, 67.56 (2×d, $^2J_{C-O-P}$=5.00 Hz, C5'), 54.29 (6OCH$_3$), 51.85, 51.79 (Cα Ala), 32.35, 32.39 (2×CH$_2$-2 and 6 ester), 26.35 (2×CH$_2$-3 and 4 ester), 24.57 (CH$_2$-5 ester), 20.81, 20.60 (2×d, $^3J_{C-C-N-P}$=6.30 Hz, CH$_3$ Ala), 20.36, 20.33 (CH$_3$).

$^{31}$P NMR (202 MHz, CD$_3$OD) δ 4.34, 4.26.

Example 26

The (2S)-tetrahydro-2H-pyran-4-yl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

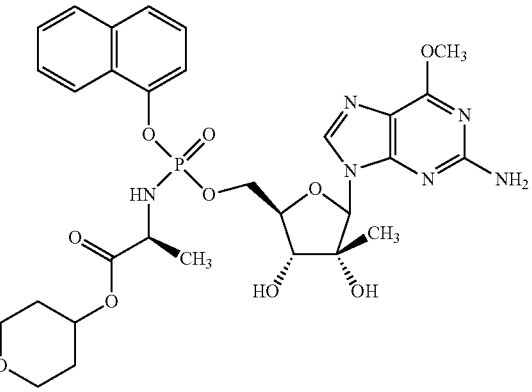

Step 1. Synthesis of (2S)-tetrahydro-2H-pyran-4-yl 2-(chloro(naphthalen-1-yloxy)phosphorylamino) propanoate

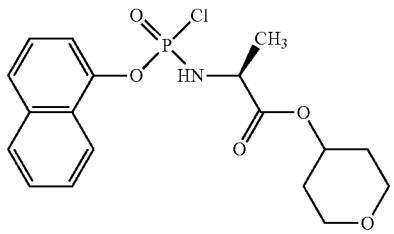 [SMILES: C[C@H](NP(=O)(Cl)Oc1cccc2ccccc12)C(=O)OC1CCOCC1]

Using the general procedure for synthesizing naphthyl (amino acid ester) phosphorochloridates the tosylate salt of (S)-tetrahydro-2H-pyran-4-yl 2-aminopropanoate (1.00 g, 2.90 mmol), naphthalen-1-yl phosphorodichloridate (0.76 g, 2.90 mmol) and TEA (0.80 mL, 5.79 mmol) in 30 mL of dry DCM, were combined to give (2S)-tetrahydro-2H-pyran-4-yl 2-(chloro(naphthalen-1-yloxy)phosphorylamino)propanoate in 70% yield (0.84 g), as a clear, yellow, thick oil.

The following are the NMR results analyzing the synthesized compound:

$^1$H NMR (500 MHz, CDCl$_3$) δ 8.11, 8.08 (2×d, J=8.00 Hz, 1H, H$_8$-napht), 7.91, 7.89 (2×d, J=8.50 Hz, 1H, H$_5$-napht), 7.72, 7.66 (2×d, J=8.0 Hz, 1H, H$_4$-napht), 7.61-7.51 (m, 3H, H$_7$, H$_6$, H$_2$,), 7.47 (t, J=8.00 Hz, 1H, H$_3$-napht), 5.12-4.99 (m, 1H, CH ester), 4.57 (bs, 1H, NH), 4.31-4.22 (m, 1H, CHα Ala), 3.98-3.80 (m, 2H, 2×CH$_{2a}$ ester), 3.53-3.45 (m, 2H, CH$_{2b}$ ester), 1.97-1.88 (m, 2H, CH$_{2c}$, ester), 1.71-1.62 (m, 2H, CH$_{2d}$ ester), 1.54, 1.51 (2×d, J=7.00 Hz, 3H, CH$_3$ Ala).
$^{31}$P NMR (202 MHz, CDCl$_3$) δ 8.19, 8.00

Step 2. Synthesis of the Protide

Using the general procedure (Method B) for the synthesis of 5'-phosphoramidates of 2-amino-6-methoxy-9-(2-C-methyl-β-D-ribofuranosyl)purine, to a solution of 250 mg (0.80 mmol) of nucleoside in 3 mL of THF, was added 1.60 mL of a 1 M solution of tert-BuMgCl in THF, followed by (2S)-tetrahydro-2H-pyran-4-yl 2-(chloro(naphthalen-1-yloxy)phosphorylamino)propanoate 640 mg (1.6 mmol) in THF (3 mL). Standard workup and silica gel column chromatography provided 142 mg of final protide as an off-white solid in a 26% yield. HPLC: t$_R$=16.72, 17.08 min. (column: Varian Pursuit XRs 5, C18, 150×4.6 mm. The method is: Linear gradient H$_2$O/ACN: 0% to 100% ACN in 30 min.)

The following are the NMR results analyzing the synthesized compound:

$^1$H NMR (500 MHz, CD$_3$OD) δ 8.19-8.15 (m, 1H), 7.99, 7.97 (2×s, 1H), 7.87-7.83 (m, 1H), 7.69-7.65 (m, 1H), 7.54-7.44 (m, 3H), 7.42-7.36 (m, 1H), 6.02, 6.00 (2×s, 1H), 4.81-4.73 (m, 1H), 4.67-4.59 (m, 2H), 4.36-4.24 (m, 2H), 4.06-4.03 (m, 4H), 3.79-3.72 (m, 2H), 3.47-3.37 (m, 2H), 1.80-1.70 (m, 2H), 1.54-1.49 (m, 2H), 1.32, 1.30 (2×d, J=5.45 Hz, 3H), 0.98, 0.97 (2×s).

$^{13}$C NMR (126 MHz, CD$_3$OD) δ 174.31, 174.07 (2×d, $^3J_{C-C-N-P}$=5.0 Hz, C=O ester), 162.73 (C6), 161.89, 161.87 (C2), 154.58, 154.53 (C4), 148.00, 147.96 (ipso Naph), 139.39, 139.11 (CH8), 136.28, 136.25 (C10-Naph), 128.85, 128.79 (CH-Naph), 127.86, 127.77 (2×d, $^3J_{C-C-O-P}$=5.0 Hz, C9-Naph), 127.49, 127.25, 126.97, 126.69, 126.54, 126.51, 125.98, 125.92, 122.79, 122.74 (CH-Naph), 116.24, 116.12 (2×d, $^3J_{C-C-O-P}$=3.8 Hz, C2-Naph), 115.61 (C5), 93.37, 93.20 (C1'), 82.34, 82.16 (2×d, $^3J_{C-C-O-P}$=8.8 Hz, C4'), 79.99, 79.95 (C2'), 74.96, 74.73 (CH ester), 71.33 (C3'), 68.14, 67.65 (2×d, $^2J_{C-O-P}$=5.0 Hz, C5'), 66.04, 66.02 (2×CH$_2$O ester), 54.29 (6OCH$_3$), 51.85, 51.76 (Cα Ala), 32.52, 32.48 (2×CH$_2$ ester), 20.67, 20.50 (2×d, $^3J_{C-C-N-P}$=6.3 Hz, CH$_3$ Ala), 20.35, 20.31 (CH$_3$)

$^{31}$P NMR (202 MHz, CD$_3$OD) δ 4.25, 4.12.

Example 27

The protide (2S)-2,4-difluorobenzyl 2-((((2R,3R,4R)-5-(2-amino-6-methoxy-9H-purin-9-yl)-3,4-dihydroxy-4-methyltetrahydrofuran-2-yl)methoxy)(6-((S)-1-methoxy-1-oxopropan-2-yl)naphthalen-2-yloxy)phosphorylamino)propanoate was synthesized as follows

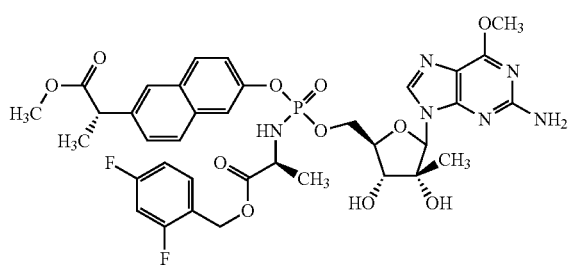 [SMILES: COC(=O)[C@@H](C)c1ccc2cc(OP(=O)(N[C@@H](C)C(=O)OCc3ccc(F)cc3F)OC[C@H]3OC(n4cnc5c(OC)nc(N)nc54)[C@](C)(O)[C@@H]3O)ccc2c1]

Step 1: Synthesis of (2S)-2,4-difluorobenzyl 2-(chloro(6-((S)-1-methoxy-1-oxopropan-2-yl)naphthalen-2-yloxy)phosphorylamino)propanoate

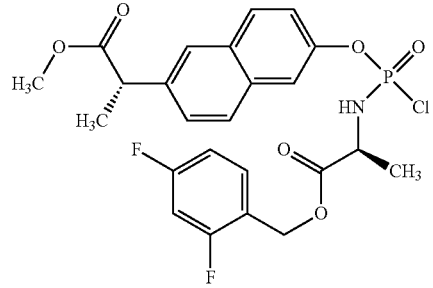 [SMILES: COC(=O)[C@@H](C)c1ccc2cc(OP(=O)(Cl)N[C@@H](C)C(=O)OCc3ccc(F)cc3F)ccc2c1]

Using the general procedure for synthesizing naphthyl (amino acid ester) phosphorochloridates the tosylate salt of (S)-2-amino propionic acid 2,4-difluoro benzyl ester (1.0 g, 2.6 mmol), (S)-methyl 2-(6-(dichlorophosphoryloxy)naphthalen-2-yl)propanoate (900 mg, 2.6 mmol), TEA (0.73 mL, 5.19 mmol) and DCM (20 mL) were combined to give 1.25 g of desired phosphorochloridate in 91% yield as a semi-solid.

The following are the NMR results analyzing the synthesized compound:

$^1$H NMR (200 MHz, CDCl$_3$): δ 7.83-7.68 (m, 4H), 7.5-7.28 (m, 3H), 6.84 (m, 2H), 5.21 (m, 2H), 4.3 (m, 1H), 5.67 (d, J=1.2 Hz, 3H), 1.55 (m, 6H), 1.36 (m, 1H).

$^{31}$P NMR (80 MHz, CDCl$_3$) δ 8.94, 8.63

Step 2: Synthesis of the Protide

Using the general procedure (Method B) for the synthesis of 5'-phosphoramidates of 2-amino-6-methoxy-9-(2-C-methyl-β-D-ribofuranosyl)purine, the nucleoside (370 mg, 1.19 mmol) in anhydrous THF (20 mL) was combined with (2S)-2,4-difluorobenzyl 2-(chloro(6-((S)-1-methoxy-1-oxopropan-2-yl)naphthalen-2-yloxy)phosphorylamino)propanoate (1.25 mg, 2.37 mmol) and t-butyl magnesium chloride (2.9 mL, 2.96 mmol). After normal work-up the crude product was purified by column chromatography on silica gel using CH$_2$Cl$_2$/MeOH (95:5) to give 240 mg of protide in 25% yield.

The following are the NMR results analyzing the synthesized compound:

$^1$H NMR (200 MHz, CD$_3$OD): δ 7.94 (d, J=1.8 Hz, 1H), 7.8-7.66 (m, 4H), 7.44-7.2 (m, 3H), 6.92-6.76 (m, 2H), 5.95 (d, J=1.8 Hz, 1H), 5.06-4.95 (m, 2H), 4.55-4.5 9m, 2H), 4.32-4.15 (m, 2H), 4.03 (d, J=4.4 Hz, 3H), 3.92 (m, 2H), 3.64 (d, J=1.8 Hz, 3H), 1.54 (dd, J=2.6 Hz, J=2.4 Hz, 3H), 1.30 (d, J=7.2 Hz, 3H), 0.9 (d, J=19 Hz, 9H).

$^{31}$P NMR (80 MHz, CD$_3$OD): 5.14

Example 28

The protide (2S)-methyl 2-(6-((((2R,3R,4R)-5-(2-amino-6-methoxy-9H-purin-9-yl)-3,4-dihydroxy-4-methyltetrahydrofuran-2-yl)methoxy)((S)-1-(neopentyloxy)-1-oxopropan-2-ylamino)phosphoryloxy)naphthalen-2-yl)propanoate was synthesized as follows

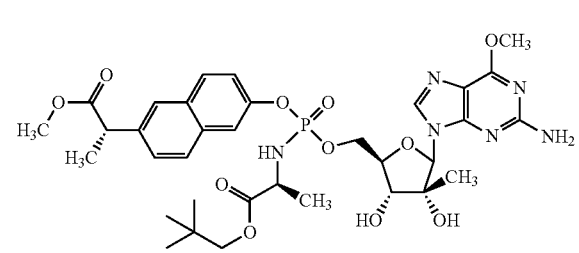 [SMILES: COC(=O)[C@@H](C)c1ccc2cc(OP(=O)(N[C@@H](C)C(=O)OCC(C)(C)C)OC[C@H]3OC(n4cnc5c(OC)nc(N)nc54)[C@](C)(O)[C@@H]3O)ccc2c1]

Step 1: Synthesis of (2S)-methyl 2-(6-(chloro((S)-1-(neopentyloxy)-1-oxopropan-2-ylamino)phosphoryloxy)naphthalen-2-yl)propanoate

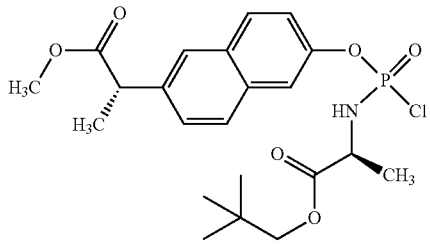 [SMILES: COC(=O)[C@@H](C)c1ccc2cc(OP(=O)(Cl)N[C@@H](C)C(=O)OCC(C)(C)C)ccc2c1]

Using the general procedure for synthesizing naphthyl (amino acid ester) phosphorochloridates and tosylate salt of (S)-neopentyl 2-aminopropanoate (1.0 g, 2.8 mmol), (S)-methyl 2-(6-(dichlorophosphoryloxy)naphthalen-2-yl)propanoate (990 mg, 2.8 mmol), TEA (0.8 mL, 5.6 mmol) and DCM (20 mL) were combined to give 1.13 g of desired (2S)-methyl 2-(6-(chloro((S)-1-(neopentyloxy)-1-oxopropan-2-ylamino)phosphoryloxy)naphthalen-2-yl)propanoate in 83% yield as a gummy syrup.

The following are the NMR results analyzing the synthesized compound:

$^1$H NMR (200 MHz, CDCl$_3$): δ 7.9-7.68 (m, 4H), 7.52-7.3 (m, 2H), 4.3 (m, 1H), 3.97-3.8 (m, 3H), 3.67 (s, 3H), 1.6 (m, 6H), 1.45 (dd, J=4.0 Hz, J=4.2 Hz, 1H), 0.96 (d, J=3.2 Hz, 9H).

$^{31}$P NMR (80 MHz, CDCl$_3$) δ 9.13, 8.77

Step 2: Synthesis of the Protide

Using the general procedure (Method A) for the synthesis of 5'-phosphoramidates of 2-amino-6-methoxy-9-(2-C-methyl-β-D-ribofuranosyl)purine, the nucleoside (250 mg, 0.801 mmol) in anhydrous THF (20 mL) was combined with (2S)-methyl 2-(6-(chloro((S)-1-(neopentyloxy)-1-oxopropan-2-ylamino)phosphoryloxy)naphthalen-2-yl)propanoate (1.13 g, 2.4 mmol) and N-methylimidazole (0.32 mL, 4.0 mmol). After normal work-up the crude product was purified by column chromatography on silica gel using CH$_2$Cl$_2$/MeOH (96:4) to give 200 mg of protide in 33% yield.

The following are the NMR results analyzing the synthesized compound:

$^1$H NMR (200 MHz, CD$_3$OD): δ 7.94 (d, J=1.2 Hz, 1H), 7.83-7.6 (m, 4H), 7.4 (m, 2H), 5.96 (d, J=2.4 Hz, 1H), 4.56 (m, 2H), 4.22 (m, 2H), 4.02 (d, J=3.0 Hz, 3H), 3.94 (m, 1H), 3.8-3.62 (m, 6H), 1.53 (dd, J=2.4 Hz, J=3.0 Hz, 3H), 1.33 (d, J=7.4 Hz, 3H), 0.95-0.8 (m, 12H).

$^{31}$P NMR (80 MHz, CD$_3$OD) δ 5.23

Example 29

The protide (2S)-methyl 2-(6-((((2R,3R,4R)-5-(2-amino-6-methoxy-9H-purin-9-yl)-3,4-dihydroxy-4-methyltetrahydrofuran-2-yl)methoxy)((S)-1-oxo-1-(tetrahydro-2H-pyran-4-yloxy)propan-2-ylamino)phosphoryloxy)naphthalen-2-yl)propanoate was synthesized as follows

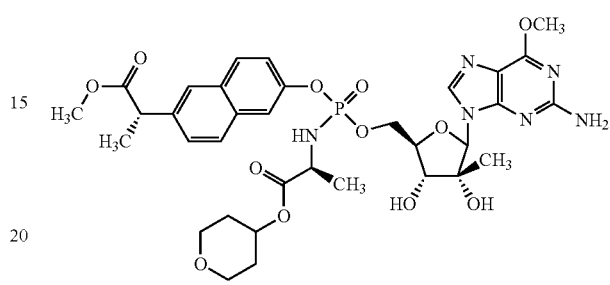

Step 1: Synthesis of (2S)-methyl 2-(6-(chloro((S)-1-oxo-1-(tetrahydro-2H-pyran-4-yloxy)propan-2-ylamino)phosphoryloxy)naphthalen-2-yl)propanoate

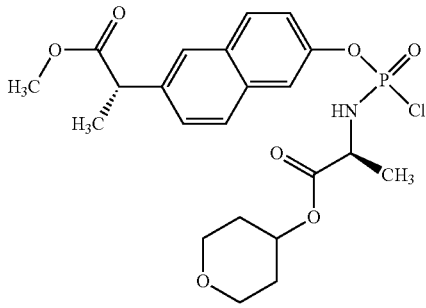 [SMILES: COC(=O)[C@@H](C)c1ccc2cc(OP(=O)(Cl)N[C@@H](C)C(=O)OC3CCOCC3)ccc2c1]

Using the general procedure for synthesizing naphthyl (amino acid ester) phosphorochloridates and tosylate salt of (S)-2-amino propionic acid tetrahydro pyran-4-yloxy ester (892 mg, 2.6 mmol), 6-[(S)-1-methoxy carbonyl ethyl]naphthalene-2-yl phosphorodichloridate (900 mg, 2.6 mmol), TEA (0.73 mL, 5.19 mmol) and DCM (20 mL) were combined to give 683 mg of desired phosphorochloridate in 55% yield as a gummy syrup.

The following are the NMR results analyzing the synthesized compound:

$^1$H NMR (200 MHz, CDCl$_3$): δ 7.85-7.7 (m, 4H), 7.52-7.44 (dd, J=1.8 Hz, 1H), 7.36 (m, 1H), 5.02 (m, 1H), 4.22 (m, 1H), 4.0-3.8 (m, 3H), 3.67 (s, 3H), 3.55 (m, 2H), 1.91 (m, 2H), 1.8-1.5 (m, 9H).

$^{31}$P NMR (80 MHz, CDCl$_3$) δ 9.07, 8.72

Step 2: Synthesis of the Protide

Using the general procedure (Method B) for the synthesis of 5'-phosphoramidates of 2-amino-6-methoxy-9-(2-C-methyl-β-D-ribofuranosyl)purine, the nucleoside (200 mg, 0.64 mmol) in anhydrous THF (20 mL) was combined with (2S)-methyl 2-(6-(chloro((S)-1-oxo-1-(tetrahydro-2H-pyran-4- yloxy)propan-2-ylamino)phosphoryloxy)naphthalen-2-yl) propanoate (680 mg, 1.48 mmol) and t-butyl magnesium chloride (1.6 mL, 1.6 mmol). After normal work-up the crude product was purified by column chromatography on silica gel using DCM/MeOH (95:5) to give 140 mg of protide in 29% yield as an off-white solid.

The following are the NMR results analyzing the synthesized compound:

$^1$H NMR (200 MHz, CD$_3$OD): δ 7.96 (s, 1H), 7.83-7.68 (m, 4H), 7.45-7.35 (m, 2H), 5.98 (d, J=3.6 Hz, 1H), 4.85-4.5 (m, 3H), 4.32-4.15 (m, 2H), 4.04 (d, J=2.2 Hz, 3H), 3.98-3.86 (m, 2H), 3.8-3.67 (m, 2H), 3.65 (d, J=2.6 Hz, 3H), 3.46-3.34 (m, 2H), 1.7 (m, 2H), 1.55-1.36 (m, 6H), 1.3 (d, J=7.0 Hz, 3H), 0.94 (d, J=15.2 Hz, 3H).

$^{31}$P NMR (80 MHz, CD$_3$OD): 5.26, 5.08

Example 30

The protide (2S)-2,4-difluorobenzyl 2-((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)propanoate was synthesized as follows

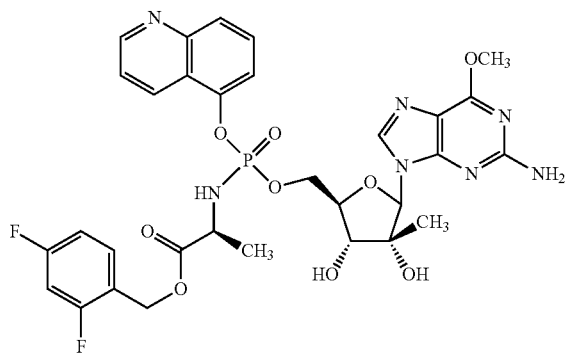 [SMILES: COc1nc(N)nc2c1ncn2C1O[C@H](COP(=O)(N[C@@H](C)C(=O)OCc2ccc(F)cc2F)Oc2cccc3ncccc23)[C@@H](O)[C@@]1(C)O]

Step 1: Synthesis of (2S)-2,4-difluorobenzyl 2-(chloro(quinolin-5-yloxy)phosphorylamino)propanoate

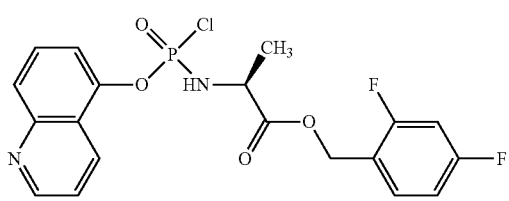 [SMILES: C[C@H](NP(=O)(Cl)Oc1cccc2ncccc12)C(=O)OCc1ccc(F)cc1F]

Using the general procedure for synthesizing naphthyl (amino acid ester) phosphorochloridates, the tosylate salt of (S)-2-amino propionic acid 2,4-difluoro benzyl ester (1.4 g, 3.45 mmol), quinoline 5-yloxy phosphorodichloridate (904 mg, 3.45 mmol), TEA (0.96 mL, 6.9 mmol) and DCM (40 mL) were combined to give 400 mg of desired phosphorochloridate in 25% yield as pale yellow thick syrup.

The following are the NMR results analyzing the synthesized compound:

$^1$H NMR (200 MHz, CDCl$_3$): δ 9.0 (d, J=4.0 Hz, 1H), 8.6 (d, J=8.4 Hz, 1H), 8.26 (d, J=8.4 Hz, 1H), 7.8-7.6 (m, 3H), 7.4-7.2 (m, 1H), 6.8 (m, 2H), 5.0-5.3 (m, 2H), 4.7 (m, 1H), 4.3 (m, 1H), 1.6-1.4 (m, 3H).

$^{31}$P NMR (80 MHz, CDCl$_3$) δ 9.51, 9.3

Step 2: Synthesis of the Protide

Using the general procedure (Method B) for the synthesis of 5'-phosphoramidates of 2-amino-6-methoxy-9-(2-C-methyl-β-D-ribofuranosyl)purine, the nucleoside (125 mg, 0.4 mmol) in anhydrous THF (25 mL) was combined with (2S)-2,4-difluorobenzyl 2-(chloro(quinolin-5-yloxy)phosphorylamino)propanoate (407 mg, 0.88 mmol) and t-butyl magnesium chloride (0.881 mL, 0.881 mmol). After normal work-up the crude product was purified by column chromatography on silica gel using DCM/MeOH (95:5) to give 72 mg of protide in 25% yield as an of white solid.

The following are the NMR results analyzing the synthesized compound:

$^1$H NMR (200 MHz, CD$_3$OD): δ 8.87-8.79 (dddd, J=1.6 Hz, J=1.8 Hz, 1H), 8.63-8.5 (m, 1H), 7.92 (s, 1H), 7.81 (m, 1H), 7.7-7.2 (m, 4H), 6.8 (m, 2H), 5.95 (d, J=2.2 Hz, 1H), 5.0 (m, 2H), 4.6 (m, 2H), 4.4-4.0 (m, 6H), 1.3 (dddd, J=1.0 Hz, J=1.4 Hz, J=1.2 Hz, 3H), 0.95 (d, J=5.6 Hz, 3H).

$^{31}$P NMR (80 MHz, CD$_3$OD): δ 5.43, 5.16

Example 31

The protide (2S)-neopentyl 2-((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)propanoate was synthesized as follows

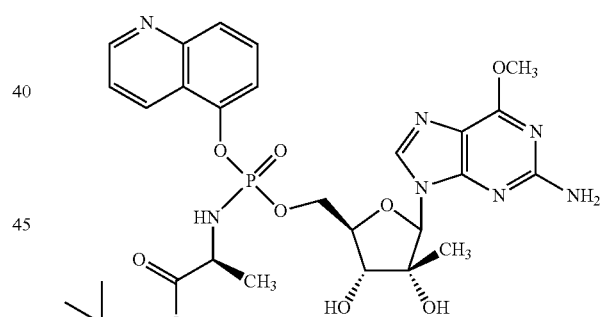

Step 1: Synthesis of (2S)-neopentyl 2-(chloro(quinolin-5-yloxy)-phosphorylamino)propanoate

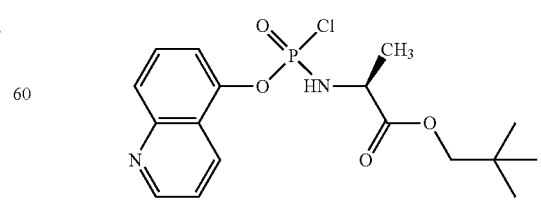

Using the general procedure for synthesizing naphthyl (amino acid ester) phosphorochloridates, the tosylate salt of (S)-2-amino propionic acid 2,2-dimethylpropyl ester (1.068 g, 3 mmol), quinoline 5-yloxy phosphorodichloridate (800 mg, 3 mmol), TEA (0.85 mL, 6 mmol) and DCM (30 mL) were combined to give 450 mg of desired phosphorochloridate in 36% yield as pale yellow thick oil.

The following are the NMR results analyzing the synthesized compound:

$^1$H NMR (200 MHz, CDCl$_3$): δ 8.94 (m, 1H), 8.6-8.45 (m, 1H), 8.0-7.9 (m, 1H), 7.62 (m, 2H), 7.45 (m, 1H), 4.12 (m, 1H), 3.7 (m, 3H), 1.4 (dd, J=6.8 Hz, J=7.0 Hz, 3H), 0.91 (d, J=2.6 Hz, 9H).

$^{31}$P NMR (80 MHz, CDCl$_3$) δ 9.29

Step 2: Synthesis of the Protide

Using the general procedure (Method B) for the synthesis of 5'-phosphoramidates of 2-amino-6-methoxy-9-(2-C-methyl-β-D-ribofuranosyl)purine, the nucleoside (100 mg, 0.32 mmol) in anhydrous THF (25 mL) was combined with (2S)-neopentyl 2-(chloro(quinolin-5-yloxy)-phosphorylamino) propanoate (400 mg, 0.96 mmol) and t-butyl magnesium chloride (0.96 mL, 0.96 mmol). After normal work-up the crude product was purified by column chromatography on silica gel using DCM/MeOH (95:5) to give 40 mg of protide in 20% yield.

The following are the NMR results analyzing the synthesized compound:

$^1$H NMR (200 MHz, CD$_3$OD): δ 8.87-8.80 (dddd, J=1.6 Hz, J=1.8 Hz, J=2.2 Hz, 1H), 8.65-8.53 (m, 1H), 7.94 (d, J=0.8 Hz, 1H), 7.83 (m, 1H), 7.72-7.4 (m, 3H), 5.95 (d, J=1.2 Hz, 1H), 4.62 (m, 2H), 4.3 (m, 2H), 4.1-3.96 (m, 4H), 3.76-3.52 (m, 3H), 1.34 (dddd, J+0.8 Hz, J=1.2 Hz, 3H), 0.95 (d, J=3.8 Hz, 3H), 0.82 (d, J=1.2 Hz, 9H).

$^{31}$P NMR (80 MHz, CD$_3$OD): δ 5.5, 5.2

Example 32

The protide (2S)-tetrahydro-2H-pyran-4-yl 2-((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)propanoate was synthesized as follows

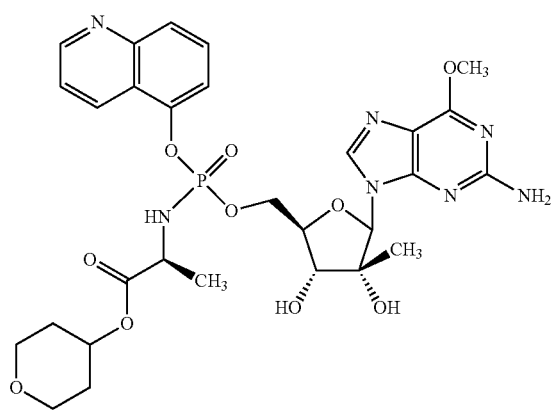 [SMILES: COc1nc(N)nc2c1ncn2C1O[C@H](COP(=O)(N[C@@H](C)C(=O)OC2CCOCC2)Oc2cccc3ncccc23)[C@@H](O)[C@@]1(C)O]

Step 1: Synthesis of (2S)-tetrahydro-2H-pyran-4-yl 2-(chloro(quinolin-5-yloxy)phosphorylamino)propanoate

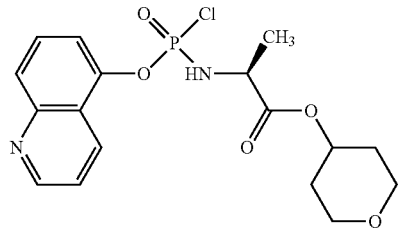 [SMILES: C[C@H](NP(=O)(Cl)Oc1cccc2ncccc12)C(=O)OC1CCOCC1]

Using the general procedure for synthesizing naphthyl (amino acid ester) phosphorochloridates, the tosylate salt of (S)-2-amino propionic acid 4-yloxy tetrahydropyran ester (1.18 g, 3.4 mmol), quinoline 5-yloxy phosphorodichloridate (900 mg, 3.4 mmol), TEA (0.95 mL, 6.87 mmol) and DCM (40 mL) were combined to give 350 mg of desired phosphorochloridate in 26% yield as pale yellow thick syrup.

The following are the NMR results analyzing the synthesized compound:

$^1$H NMR (200 MHz, CD$_3$OD): δ 9.0 (d, J=3.0 Hz, 1H), 8.5 (d, J=8.8 Hz, 1H), 8.1 (d, J=7.8 Hz, 1H), 7.76-7.6 (m, 2H), 7.5 (dddd, J=2.6 Hz, J=2.2 Hz, 1H), 5.0 (m, 1H), 4.7 (m, 1H), 4.3 (m, 1H), 3.9 (m, 2H), 3.5 (m, 2H), 1.9 (m, 2H), 1.7 (m, 2H), 1.55 (dd, J=4.4 Hz, J=4.4 Hz, 3H).

$^{31}$P NMR (80 MHz, CD$_3$OD): δ 9.5, 9.33

Step 2: Synthesis of the Protide

Using the general procedure (Method B) for the synthesis of 5'-phosphoramidates of 2-amino-6-methoxy-9-(2-C-methyl-β-D-ribofuranosyl)purine, the nucleoside (133 mg, 0.426 mmol) in anhydrous THF (20 mL) was combined with quinoline 5-yloxy tetrahydropyran-4-yloxy alaninyl phosphorochloridate (338 mg, 0.852 mmol) and t-butyl magnesium chloride (0.851 mL, 0.851 mmol). After normal work-up the crude product was purified by column chromatography on silica gel using DCM/MeOH (95:5) to give 52 mg of protide in 19% yield as off-white solid The following are the NMR results analyzing the synthesized compound:

$^1$H NMR (200 MHz, CD$_3$OD): δ 8.9-8.8 (dddd, J=1.8 Hz, J=1.4 Hz, 1H), 8.67-8.55 (m, 1H), 7.94 (d, J=1.0 Hz, 1H), 7.9-7.8 (m, 1H), 7.74-7.42 (m, 3H), 5.95 (d, J=4.0 Hz, 1H), 4.8-4.5 (m, 4H), 4.4-4.1 (m, 2H), 4.02 (d, J+1.2 Hz, 3H), 3.8 (m, 2H), 3.2 (m, 2H), 1.8 (m, 2H), 1.5 (m, 2H), 1.35-1.28 (dddd, J=1.2 Hz, J=1.4 Hz, j=0.8 Hz, J=1.0 Hz, 3H), 0.95 (d, J=3.2 Hz, 3H).

$^{31}$P NMR (80 MHz, CD$_3$OD): δ 5.46, 5.19

Example 33

The protide (2S)-neopentyl 2-((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)propanoate was synthesized as follows

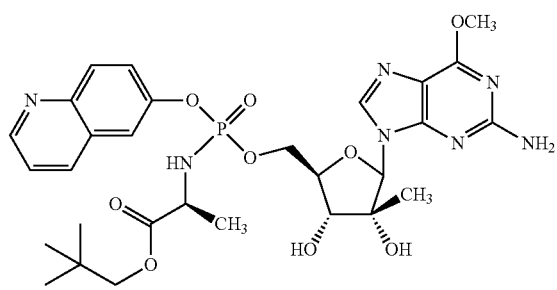 [SMILES: COc1nc(N)nc2c1ncn2C1O[C@H](COP(=O)(N[C@@H](C)C(=O)OCC(C)(C)C)Oc2ccc3ncccc3c2)[C@@H](O)[C@@]1(C)O]

Step 1: (2S)-neopentyl 2-(chloro(quinolin-6-yloxy)phosphorylamino)-propanoate

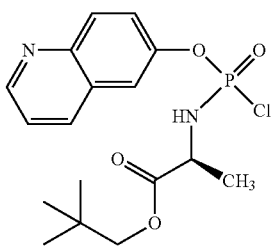 [SMILES: C[C@H](NP(=O)(Cl)Oc1ccc2ncccc2c1)C(=O)OCC(C)(C)C]

Using the general procedure for synthesizing naphthyl (amino acid ester) phosphorochloridates, the tosylate salt of (S)-2-amino propionic acid 2,2-dimethyl propyl ester (870 mg, 2.6 mmol), quinoline 6-yloxy phosphorodichloridate (698 mg, 2.6 mmol), TEA (0.73 mL, 5.2 mmol) and DCM (20 mL) were combined to give 250 mg of desired phosphorochloridate in 24% yield as pale yellow thick oil The following are the NMR results analyzing the synthesized compound:

$^1$H NMR (200 MHz, CDCl$_3$): δ 8.92 (d, J=3.2 Hz, 1H), 8.2 (d, J=8.8 Hz, 2H), 7.82 (dd, J=3.0 Hz, J=2.4 Hz, 1H), 7.6 (m, 1H), 7.51-7.45 (dd, J=4.0 Hz, J=4.0 Hz, 1H), 4.5 (m, 1H), 4.3 (m, 1H), 3.9 (m, 2H), 1.56 (dd, J=3.2 Hz, J=3.2 Hz, 3H), 0.96 (d, J=2.6 Hz, 9H).

$^{31}$P NMR (80 MHz, CDCl$_3$) δ 9.26, 8.92

Step 2: Synthesis of the Protide

Using the general procedure (Method B) for the Synthesis of 5'-phosphoramidates of 2-amino-6-methoxy-9-(2-C-methyl-β-D-ribofuranosyl)purine, the nucleoside (100 mg, 0.32 mmol) in anhydrous THF (25 mL) was combined with (2S)-neopentyl 2-(chloro(quinolin-6-yloxy)phosphorylamino)-propanoate (250 mg, 0.64 mmol) and t-butyl magnesium chloride (0.64 mL, 0.64 mmol). After normal work-up the crude product was purified by column chromatography on silica gel using CH$_2$Cl$_2$/MeOH (95:5) to give 72 mg of protide in 34% yield.

The following are the NMR results analyzing the synthesized compound:

$^1$H NMR (200 MHz, CD$_3$OD): δ 8.75-8.8 (dt, J=1.8 Hz, J=4.4 Hz, 1H), 8.23 (m, 1H), 8.0 (m, 1H), 7.93 (d, J=2.2 Hz, 1H), 7.79 (m, 1H), 7.7-7.64 (m, 1H), 7.44-7.54 (dddd, J=2.6 Hz, J=4.4 Hz, 1H), 5.95 (d, J=1.4 Hz, 1H), 4.62-4.53 (m, 2H), 4.34-4.2 (m, 2H), 4.03 9d, J=2.2 Hz, 3H), 3.79-3.55 (m, 3H), 1.4-1.32 (dddd, J=0.8 Hz, J=1.0 Hz, 3H), 0.95 (d, J=13.2 Hz, 3H), 0.86 (d, J=6.6 Hz, 9H).

$^{31}$P NMR (80 MHz, CD$_3$OD): δ 5.19, 5.10

Example 34

The protide (2S)-tetrahydro-2H-pyran-4-yl 2-((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)propanoate was synthesized as follows

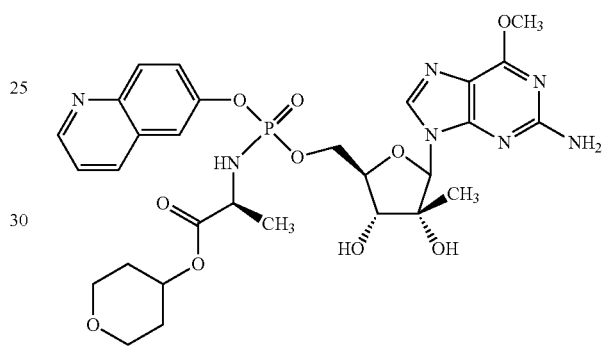

Step 1: Synthesis of (2S)-tetrahydro-2H-pyran-4-yl 2-(chloro(quinolin-6-yloxy)phosphorylamino)propanoate

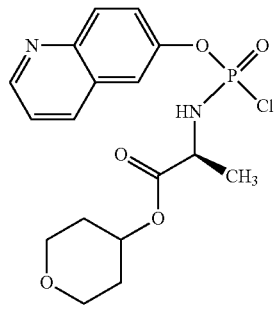 [SMILES: C[C@H](NP(=O)(Cl)Oc1ccc2ncccc2c1)C(=O)OC1CCOCC1]

Using the general procedure for synthesizing naphthyl (amino acid ester) phosphorochloridates, the tosylate salt of (S)-2-amino propionic acid tetrahedropyran-4-yloxy ester (880 mg, 2.62 mmol), quinoline 6-yloxy phosphorodichloridate (682 mg, 2.62 mmol), TEA (0.74 mL, 5.2 mmol) and DCM (40 mL) were combined to give 300 mg of desired (2S)-tetrahydro-2H-pyran-4-yl 2-(chloro(quinolin-6-yloxy)phosphorylamino)propanoate in 29% yield as pale yellow thick oil.

The following are the NMR results analyzing the synthesized compound:

$^1$H NMR (200 MHz, CDCl$_3$): δ 8.96 (d, J=3.2 Hz, 1H), 8.31 (m, 2H), 7.88-7.84 (dd, J=2.6 Hz, J=2.4 Hz, 1H), 7.64 (m, 1H), 7.55 (dd, J=4.0 Hz, J=4.4 Hz, 1H), 5.0 (m, 1H), 4.6-4.1 (m, 2H), 3.9 (m, 2H), 3.5 (m, 2H), 1.9 (m, 2H), 1.7 (m, 2H), 1.59 (dd, J=2.8 Hz, J=2.6 Hz, 3H).
$^{31}$P NMR (80 MHz, CDCl$_3$) δ 9.18, 9.88

Step 2: Synthesis of the Protide

Using the general procedure (Method B) for the synthesis of 5′-phosphoramidates of 2-amino-6-methoxy-9-(2-C-methyl-β-D-ribofuranosyl)purine, the nucleoside (120 mg, 0.38 mmol) in anhydrous THF (25 mL) was combined with (2S)-tetrahydro-2H-pyran-4-yl 2-(chloro(quinolin-6-yloxy)phosphorylamino)propanoate (300 mg, 0.76 mmol) and t-butyl magnesium chloride (0.76 mL, 0.76 mmol). After normal work-up the crude product was purified by column chromatography on silica gel using DCM/MeOH (95:5) to give 52 mg of protide in 20% yield as an off-white solid.

The following are the NMR results analyzing the synthesized compound:
$^1$H NMR (200 MHz, CD$_3$OD): δ 8.81-8.76 (dt, J=1.8 Hz, J=1.6 Hz, 1H), 8.24 (m, 1H), 8.02-7.97 (dd, J=2.2 Hz, J=9.2 Hz, 1H), 7.94 (d, J=2.8 Hz, 1H), 7.78 (m, 1H), 7.64-7.72 (m, 1H), 7.5 (m, 1H), 5.96 (d, J=2.6 Hz, 1H), 4.8 (m, 1H), 4.58 (m, 2H), 4.4-4.2 (m, 2H), 4.03 (d, J=1.8 Hz, 3H), 3.95 (m, 1H), 3.8-3.7 (m, 2H), 3.4-3.5 (m, 2H), 1.8 (m, 2H), 1.6-1.4 (m, 2H), 1.3 (dddd, J=1.2 Hz, J=1.0 Hz, J=0.8 Hz, 3H), 0.95 (d, J=11.4 Hz, 9H).
$^{31}$P NMR (80 MHz, CD$_3$OD): 5.18, 5.06

Example 35

The protide (2S)-neopentyl 2-(((((2R,3R,4R)-5-(2-amino-6-methoxy-9H-purin-9-yl)-3,4-dihydroxy-4-methyltetrahydrofuran-2-yl)methoxy)(phenoxy)phosphorylamino)propanoate was synthesized as follows

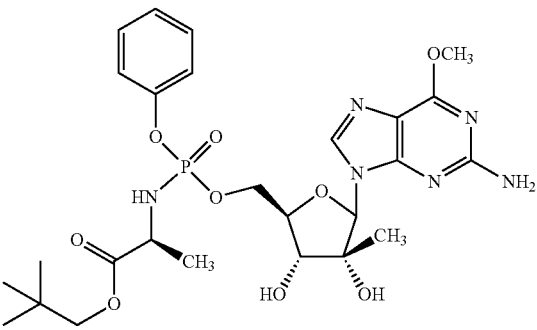 [SMILES: COc1nc(N)nc2c1ncn2C1O[C@H](COP(=O)(N[C@@H](C)C(=O)OCC(C)(C)C)Oc2ccccc2)[C@@H](O)[C@@]1(C)O]

Step 1: Synthesis of (2S)-neopentyl 2-(chloro(phenoxy)phosphorylamino)propanoate

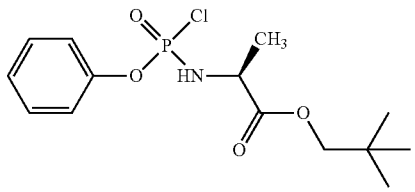 [SMILES: C[C@H](NP(=O)(Cl)Oc1ccccc1)C(=O)OCC(C)(C)C]

Using the general procedure for synthesizing naphthyl (amino acid ester) phosphorochloridates, the tosylate salt of (S)-neopentyl 2-aminopropanoate (2.00 g, 6.03 mmol), phenyl phosphorodichloridate (0.90 mL, 12.06 mmol) and TEA (1.68 mL, 12.06 mmol) were combined in 66 mL of dry DCM. The product, (2S)-neopentyl 2-(chloro(phenoxy)phosphorylamino)propanoate was obtained as a clear, thick oil (1.91 g, 95%).

The following are the NMR results analyzing the synthesized compound:
$^1$H NMR (500 MHz, CDCl$_3$) δ 7.40-7.23 (m, 5H, phe), 4.53-4.43 (m, 1H, NH), 4.30-4.18 (m, 1H, CHa), 3.94, 3.92, 3.88, 3.85 (2×AB, J$_{AB}$=10.5 Hz, 2H, CH$_2$ ester), 1.56, 1.55 (2×d, J=5.5 Hz, 3H, CH$_3$ Ala), 0.98, 0.97 (2×s, 9H, 3×CH$_3$ ester).
$^{31}$P NMR (202 MHz, CDCl$_3$) δ 8.02, 7.73.

Step 2: Synthesis of the Protide

Using the general procedure for the synthesis of nucleoside 5′-phosphoramidates, to a solution of (3R,4R,5R)-2-(2-amino-6-methoxy-9H-purin-9-yl)-5-(hydroxymethyl)-3-methyltetrahydrofuran-3,4-diol 250 mg, (0.803 mmol), and NMI 0.32 mL (4.01 mmol), in 5 mL of THF, was added (2S)-neopentyl 2-(chloro(phenoxy)phosphorylamino)propanoate 0.804 g (2.41 mmol) dissolved in 5 mL of THF. After workup and silica gel column chromatography, 97.2 mg of protide was obtained in a 20% yield, as an off-white solid. MS (ES+) m/e: 609.23 (MH$^+$, 100%); Accurate mass: C$_{26}$H$_{38}$N$_6$O$_9$P$_1$ calculated 609.2438. found 609.2443.

The following are the NMR results analyzing the synthesized compound:
$^1$H NMR (500 MHz, CD$_3$OD) δ7.96, 7.95 (2×s, 1H, H$_8$), 7.36-7.32 (m, 2H, Ph), 7.28-7.26 (m, 2H, Ph), 7.19-7.15 (m, 1H, Ph), 6.03, 6.00 (2×s, 1H, H$_{1'}$), 4.63-4.50 (m, 1H, H$_{5'}$), 4.30-4.20 (m, 1H, H$_{3'}$, H$_{4'}$), 4.07, 4.06 (2×s, 3H, 6OCH$_3$), 4.03-4.06 (m, 1H, Hα), 3.83, 3.80, 3.72, 3.66 (2×AB, J$_{AB}$=10.50 Hz, 2H, CH$_2$ester), 1.36, 1.35 (2×d, J=7.50 Hz, 3H, CH$_3$ Ala), 0.99, 0.96 (2×s, 3H, 2′CCH$_3$), 0.91, 0.88 (2×s, 9H, 3×CH$_3$ester).
$^{13}$C NMR (126 MHz, CD$_3$OD) δ 175.07, 174.85 (2×d, $^3$J$_{C-C-N-P}$=5.00 Hz, C=O ester), 162.75 (C6), 161.93, 161.89 (C2), 154.63 (C4), 152.21, 152.15 (d, $^2$J$_{C-O-P}$=3.80 Hz, ipsoPh), 139.26, 138.92 (CH8), 130.28, 130.78 (C$_3$ and C$_5$ Ph), 126.15 (C$_4$ Ph), 121.50, 121.47 (C$_2$ and C$_6$ Ph), 115.59, 115.47 (C5), 93.24, 92.91 (C1′), 82.23, 82.03 (2×d, $^3$J$_{C-C-O-P}$=8.8 Hz, C4′), 80.04, 19.97 (C2′), 75.42, 75.39 (CH$_2$ ester), 74.77, 74.28 (C3′), 67.71, 66.80 (2×d, $^2$J$_{C-O-P}$=5.00 Hz, C5′), 54.29 (6OCH$_3$), 51.73, 51.60 (Cα Ala), 32.32, 32.25 (C ester), 26.77, 26.73 (3×CH$_3$ester), 20.86, 20.65 (2×d, $^3$J$_{C-C-N-P}$=6.3 Hz, CH$_3$ Ala), 20.33 (2′CCH$_3$)
$^{31}$P NMR (202 MHz, CDCl$_3$) δ 4.04, 3.89.

Example 36

The benzyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)-3-methylbutanoate was synthesized as follows

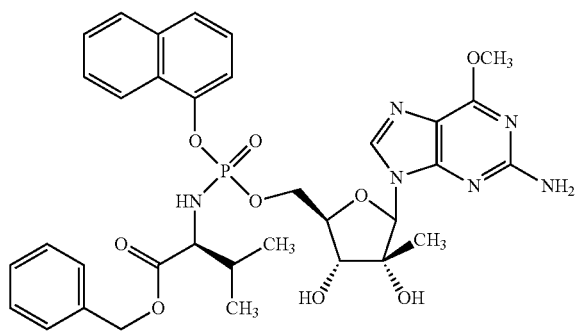 [SMILES: COc1nc(N)nc2c1ncn2C1O[C@H](COP(=O)(N[C@H](C(=O)OCc2ccccc2)C(C)C)Oc2cccc3ccccc23)[C@@H](O)[C@@]1(C)O]

Step 1: Synthesis of (2S)-benzyl 2-(chloro(naphthalen-1-yloxy)-phosphorylamino)-3-methylbutanoate

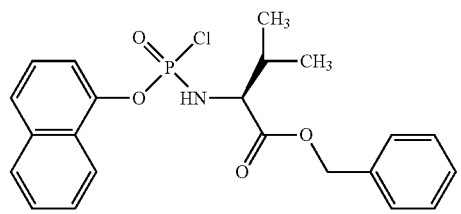 [SMILES: CC(C)[C@H](NP(=O)(Cl)Oc1cccc2ccccc12)C(=O)OCc1ccccc1]

Using the general procedure for synthesizing naphthyl (aminoacid ester) phosphorochloridates the tosylate salt of benzyloxy-L-valine (1.5 g), was combined with naphtha-1-yl phosphorodichloridate (1.03 g), TEA (1.09 mL), and DCM (22 mL) to give naphth-1-yl (benzyloxy-L-valinyl)phosphorochloride in a 72% yield (1.23 g) as a pale yellow thick oil:

The following are the NMR results analyzing the synthesized compounds:

$^1$H NMR (500 MHz, CDCl$_3$) δ 8.07 (m, 1H, H$_8$-napht), 7.90 (m, 1H, H$_5$-napht), 7.76 (m, 1H, H$_4$-napht), 7.65-7.54 (m, 3H, H$_7$, H$_6$, H$_2$-napht), 7.46 (d, J=8.1, 1H, H$_3$-napht), 7.42-7.31 (m, 5H, phe), 5.20 (m, 2H, CH$_2$ ester), 4.15 (m, 2H, NH and CH), 2.28-2.15 (m, 1H, CHβ), 1.05 (d, J=6.8, 1.2H, CH$_3$ val), 1.02 (d, J=6.8, 1.7H, CH$_3$ val), 0.96 (d, J=6.9, 1.3H, CH$_3$ val), 0.91 (d, J=6.9, 1.8H, CH$_3$ val).

$^{31}$P NMR (202 MHz, CDCl$_3$) δ 9.78, 9.29.

Step 2: Synthesis of Protide

Using the general procedure (Method A) for the synthesis of 5'-phosphoramidates of 2-amino-6-methoxy-9-(2-C-methyl-β-D-ribofuranosyl)purine. To a suspension of nucleoside (6.0 g, 19 mmol, 1 equiv) in anhydrous THF (50 mL) was added a solution of (2S)-benzyl 2-(chloro(naphthalen-1-yloxy)-phosphorylamino)-3-methylbutanoate (18.2 g, 42 mmol) at −78° C. followed by addition of 1-methylimidazole (7.63 mL, 96 mmol). The reaction mixture was allowed to warm to room temperature and stirred overnight. Standard work-up and purification provided desired protide in 25% yield (3.3 g) as an off-white solid.

The following are the NMR results analyzing the synthesized compounds:

$^1$H NMR (200 MHz, CDCl$_3$) δ 8.1 (m, 1H), 7.9 (d, J=2.4 Hz, 1H), 7.84 (m, 1H), 7.64 (dd, J=4.8 Hz, 4.8 Hz, 1H), 7.2-7.5 (m, 9H), 5.95 (d, J=1.2 Hz, 1H), 4.9-5.0 (m, 2H), 4.56 (m, 2H), 4.2-4.4 (m, 2H), 4.0 (s, 3H), 3.75 (m, 1H), 2.0 (m, 1H), 0.93 (d, J=9.6 Hz, 3H), 0.73-0.80 (m, 6H).

$^{31}$P NMR (50 MHz, CDCl$_3$) δ 6.1, 6.0

Example 37

The 2,4-Difluorobenzyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)-3-methylbutanoate was synthesized accordingly

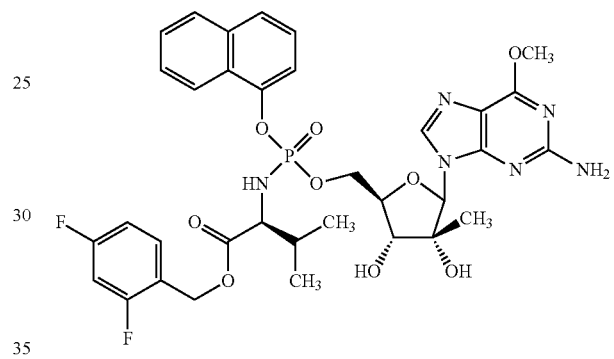

Step 1: Synthesis of (2S)-2,4-difluorobenzyl 2-(chloro(naphthalen-1-yloxy)-phosphorylamino)-3-methylbutanoate

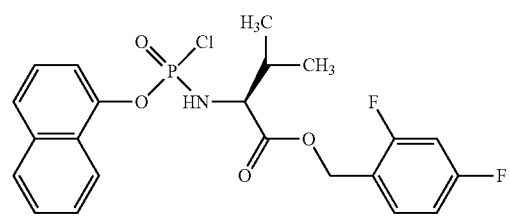 [SMILES: CC(C)[C@H](NP(=O)(Cl)Oc1cccc2ccccc12)C(=O)OCc1ccc(F)cc1F]

Using the general procedure for synthesizing naphthyl (amino acid ester) phosphorochloridates and tosylate salt of 2-amino-3-methyl (2,4-difluoro benzyl)butanoate (5.65 g, 1.36 mmol), naphthalene-1-yl phosphorodichloridate (3.55 g, 1.36 mmol), triethylamine (3.8 mL, 1.36 mmol) and dichloromethane (75 mL) were combined to give 4.1 g of desired phosphorochloridate as a pale yellow viscous oil in 65% yield.

The following are the NMR results analyzing the synthesized compounds:

$^1$H NMR (200 MHz, CDCl$_3$): δ 8.0-8.6 (m, 1H), 7.8-7.9 (m, 1H), 7.7-7.75 (d, J=8.4 Hz, 1H), 7.3-7.6 (m, 5H), 6.7-6.9 (m, 2H), 4.9-5.3 (m, 2H), 4.2-4.3 (m, 1H), 2.0 (m, 1H), 0.88-1.03 (m, 6H)

$^{31}$P NMR (80 MHz, CDCl$_3$) δ 10.83, 10.30

Step 2: Synthesis of Protide

Using the general procedure (Method A) for the Synthesis of 5'-phosphoramidates of 2-amino-6-methoxy-9-(2-C-methyl-β-D-ribofuranosyl)purine, the nucleoside (500 mg, 1.6 mmol) in anhydrous THF (70 mL) was combined with naphthalene-1-yloxy 2,4-difluoro benzyloxy valinyl phosphorochloridate (3.6 g, 7.7 mmol) and N-methyl imidazole (0.76 mL, 9.6 mmol). After normal work-up the crude product was purified by column chromatography on silica gel using $CH_2Cl_2$/MeOH (97:3) to give 400 mg of protide in 50% yield as an off-white solid.

The following are the NMR results analyzing the synthesized compounds:
$^1$H NMR (200 MHz, $CD_3OD$): δ 8.1-8.2 (m, 1H), 7.95 (s, 1H), 7.8 (m, 1H), 7.6-7.7 (m, 1H), 7.2-7.54 (m, 5H), 6.7-6.9 (m, 2H), 5.95 (s, 1H), 4.9-5.1 (m, 2H), 4.6 (m, 2H), 4.2-4.4 (m, 2H), 4.0 (s, 3H), 3.65-3.8 (m, 1H), 2.0 (m, 1H), 0.95 (d, J=8.6 Hz, 3H), 0.7-0.85 (m, 6H)
$^{31}$P NMR (80 MHz, $CD_3OD$): δ 6.14, 6.04

Example 38

The (2S)-((S)-1-phenylethyl) 2-((((2R,3R,4R)-5-(2-amino-6-methoxy-9H-purin-9-yl)-3,4-dihydroxy-4-methyltetrahydrofuran-2-yl)methoxy) (naphthalen-1-yloxy)phosphorylamino)-3-methylbutanoate was synthesized as follows

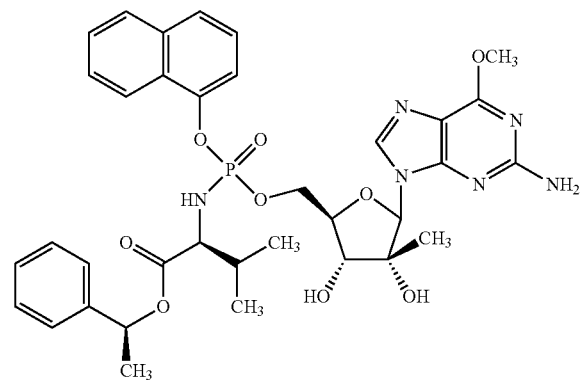

Step 1: Synthesis of (2S)-((S)-1-phenylethyl) 2-(chloro(naphthalen-1-yloxy)phosphorylamino)-3-methylbutanoate

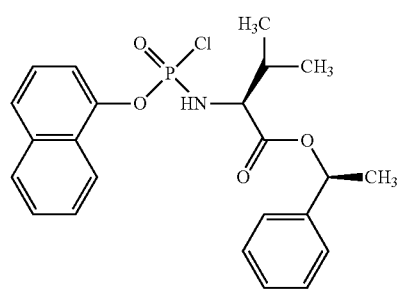 [SMILES: CC(C)[C@H](NP(=O)(Cl)Oc1cccc2ccccc12)C(=O)O[C@@H](C)c1ccccc1]

Using the general procedure for synthesizing naphthyl (aminoacid ester) phosphorochloridates, the tosylate salt of (S)-((S)-1-phenylethyl) 2-amino-3-methylbutanoate (2 g), naphthalen-1-yl phosphorodichloridate (1.33 g), TEA (1.41 mL) and DCM (60 mL) were combined to give (2S)-((S)-1-phenylethyl)-2-(chloro(naphthalen-1-yloxy)phosphorylamino)-3-methylbutanoate in an 96% yield (2.17 g) as a pale yellow thick oil.

The following are the NMR results analyzing the synthesized compounds:
$^1$H NMR (500 MHz, $CDCl_3$) δ 8.15-8.08 (m, 1H), 7.91-7.86 (m, 1H), 7.74 (d, J=8.3, 1H), 7.70-7.52 (m, 3H), 7.47-7.26 (m, 6H), 6.04-5.93 (m, 1H), 4.56-4.42 (m, 1H), 4.19-4.08 (m, 1H), 2.25-2.15 (m, 1H), 1.62 and 1.58 (2d, J=6.6, 3H), 1.01, 0.97, 0.86 and 0.79 (4d, J=6.8, 6H)
$^{31}$P NMR (202 MHz, $CDCl_3$) δ 10.03, 9.50.

Step 2: Synthesis of the Protide

Using the general procedure for the synthesis of 5'-phosphoramidates of 2-amino-6-methoxy-9-(2-C-methyl-β-D-ribofuranosyl)purine, to a solution of 420 mg of nucleoside in 5 mL of THF was added NMI (0.54 mL) followed by (2S)-2,4-difluorobenzyl 2-(chloro(naphthalen-1-yloxy)-phosphorylamino)-3-methylbutanoate (1.81 g) in THF (5 mL). After workup and silica gel column chromatography, 427 mg of pure protide was obtained (44% yield). HPLC $t_R$=26.33 min (column: Varian Pursuit XRs 5, $C_{18}$, 150×4.6 mm; method: linear gradient of ACN (10% to 100%) in $H_2O$ in 30 min).

The following are the NMR results analyzing the synthesized compounds:
$^1$H NMR (500 MHz, $CD_3OD$) δ 8.21-8.14 (m, 1H), 7.94 and 7.93 (2s, 1H), 7.90-7.83 (m, 1H), 7.75-7.64 (m, 1H), 7.56-7.20 (m, 9H), 5.99 and 5.97 (2s, 1H), 5.80-5.65 (m, 1H), 4.60-4.54 (m, 2H), 4.40-4.19 (m, 2H), 4.05 (s, 3H), 3.81-3.74 (m, 1H), 2.07-1.90 (m, 1H), 1.41 and 1.39 (2d, J=6.5, 3H), 0.99 and 0.95 (2s, 3H), 0.79, 0.75, 0.71 and 0.70 (4d, J=6.8, 6H)
$^{31}$P NMR (202 MHz, $CD_3OD$) δ 5.15, 5.05

Example 39

The (2S)-((S)-1-(4-bromophenyl)ethyl) 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate was synthesized as follows

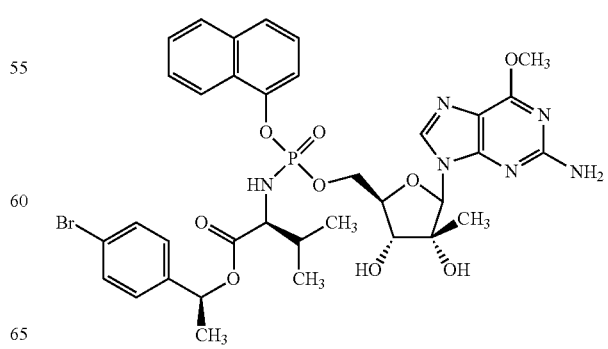

Step 1: (2S)-((S)-1-(4-bromophenyl)ethyl) 2-(chloro (naphthalen-1-yloxy)phosphorylamino)-3-methylbutanoate

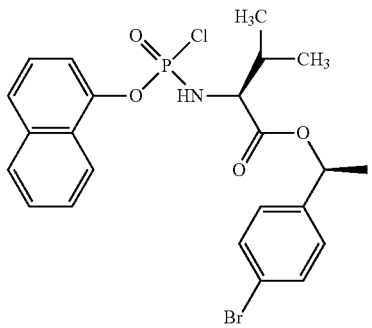 [SMILES: CC(C)[C@H](NP(=O)(Cl)Oc1cccc2ccccc12)C(=O)O[C@@H](C)c1ccc(Br)cc1]

Using the general procedure for synthesizing naphthyl (amino acid ester) phosphorochloridates, the tosylate salt of (S)-4-bromo-α-methyl benzyl-2-amino-3-methylbutanoate (1.2 g), naphthalen-1-yl phosphorodichloridate (660 mg), TEA (0.7 mL) and DCM (20 mL) were combined to give 1.0 g of desired phosphorochloridate as pale yellow thick oil.

The following are the NMR results analyzing the synthesized compounds:

$^1$H NMR (200 MHz, CDCl$_3$): δ δ 8.02-8.1 (m, 1H), 7.85-7.89 (m, 1H), 7.71-7.75 (d, J=8.4 Hz, 1H), 7.38-7.64 (m, 7H), 7.20-7.27 (m, 2H), 5.9 (m, 1H), 4.0-4.4 (m, 2H), 2.1 (m, 1H), 1.5 (dd, J=6.6 Hz, 8.4 Hz, 3H), 0.97 (t, J=6.6 Hz, 3H), 0.75-0.85 (dd, J=7.0 Hz, 7.0 Hz, 3H).

$^{31}$P NMR (80 MHz, CDCl$_3$) δ 11.00, 10.47

Step 2: Synthesis of the Protide

Using the general procedure (Method A) for the synthesis of 5'-phosphoramidates of 2-amino-6-methoxy-9-(2-C-methyl-β-D-ribofuranosyl)purine, the nucleoside (300 mg, 0.928 mmol) in anhydrous THF (15 mL) was combined with (2S)-((S)-1-(4-bromophenyl)ethyl) 2-(chloro(naphthalen-1-yloxy)phosphorylamino)-3-methylbutanoate (1.0 g, 1.92 mmol) and N-methyl imidazole (0.3 mL, 3.64 mmol). After normal work-up the crude product was purified by column chromatography on silica gel using CH$_2$Cl$_2$/MeOH (97:3) to give 126 mg of protide in 16% yield as an off-white solid.

The following are the NMR results analyzing the synthesized compound:

$^1$H NMR (200 MHz, CD$_3$OD): δ8.1-8.15 (m, 1H), 7.96 (s, 1H), 7.78-7.87 (m, 1H), 7.60-7.67 (m, 1H), 7.30-7.52 (m, 5H), 7.15-7.23 (m, 2H), 5.97 (s, 1H), 5.66 (m, 1H), 4.56 (d, J=5.4 Hz, 2H), 4.22-4.38 (m, 2H), 4.02 (s, 3H), 3.74 (m, 1H), 2.0 (m, 1H), 1.34 (dd, J=3.0 Hz, 3.0 Hz, 3H), 0.94 (d, J=9.2 Hz, 3H), 0.70 (m, 6H).

$^{31}$P NMR (80 MHz, CDCl$_3$) δ 6.2, 6.08

Example 40

The (2S)-((S)-1-(2-bromophenyl)ethyl) 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate was synthesized as follows

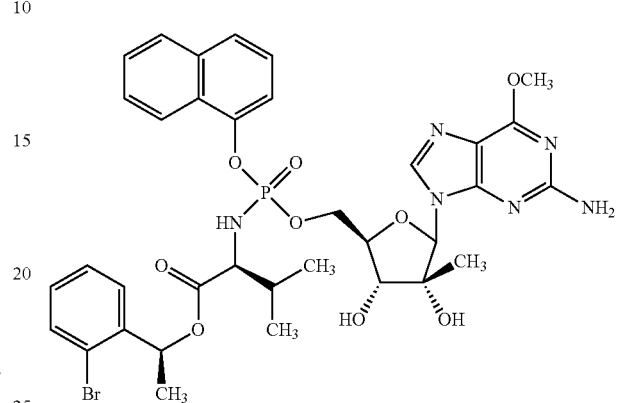

Step 1: Synthesis of (2S)-((S)-1-(2-bromophenyl) ethyl) 2-(chloro(naphthalen-1-yloxy)phosphorylamino)-3-methylbutanoate

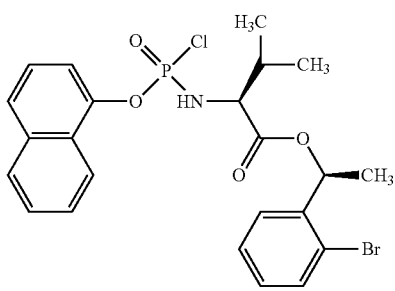 [SMILES: CC(C)[C@H](NP(=O)(Cl)Oc1cccc2ccccc12)C(=O)O[C@@H](C)c1ccccc1Br]

Using the general procedure for synthesizing naphthyl (amino acid ester) phosphorochloridates the tosylate salt of (S)-2-bromo-α-methyl benzyl-2-amino-3-methylbutanoate (1.5 g), naphthalen-1-yl phosphorodichloridate (0.826 g), TEA (0.885 mL) and DCM (20 mL) were combined to give 0.793 g of the desired phosphorochloridate as pale yellow thick oil.

The following are the NMR results analyzing the synthesized compounds:

$^1$H NMR (200 MHz, CDCl$_3$): δ 8.1 (m, 1H), 7.86 (m, 1H), 7.72 (d, J=8.2 Hz, 1H), 7.64 to 7.0 (m, 8H), 6.3 (pentate, J=6.6 Hz, 1H), 4.3 (bs, 1H), 4.1 (m, 1H), 2.2 (m, 1H), 1.55 (dd, J=6.6 Hz, J=8.2 Hz, 3H), 1.0 (dd, J=7.2 Hz, J=7.4 Hz, 3H), 0.85 (dd, J=6.8 Hz, J=7.0 Hz, 3H).

$^{31}$P NMR (80 MHz, CDCl$_3$) δ 11.07, 10.58.

Step 2: Synthesis of the Protide

Using the general procedure for the synthesis of 5'-phosphoramidates of 2-amino-6-methoxy-9-(2-C-methyl-β-D-ribofuranosyl)purine, the nucleoside (314 mg, 1 mmol) in anhydrous THF (30 mL) was combined with (2S)-((S)-1-(2-bromophenyl)ethyl) 2-(chloro(naphthalen-1-yloxy)phosphorylamino)-3-methylbutanoate (793.6 mg, 1.51 mmol) and N-methyl imidazole (248.72 mg, 3.03 mmol). After normal work-up the crude product was purified by column chromatography on silica gel using $CH_2Cl_2$/MeOH (97:3) to give 105 mg of protide in 13% yield as an off-white solid.

The following are the NMR results analyzing the synthesized compound:

$^1$H NMR (200 MHz, $CD_3OD$): δ 8.13 (m, 1H), 7.97 (bs, 1H), 7.8 (m, 1H), 7.68 to 7.06 (m, 9H), 5.97 (s, 1H), 4.6 (m, 2H), 4.25 (m, 2H), 4.0 (s, 3H), 3.8 (m, 1H), 2.0 (m, 1H), 1.3 (m, 3H), 0.8 (m, 6H).

$^{31}$P NMR (80 MHz, $CD_3OD$): δ 6.33, 6.04.

Example 41

The (2S)-methyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate was synthesized as follows

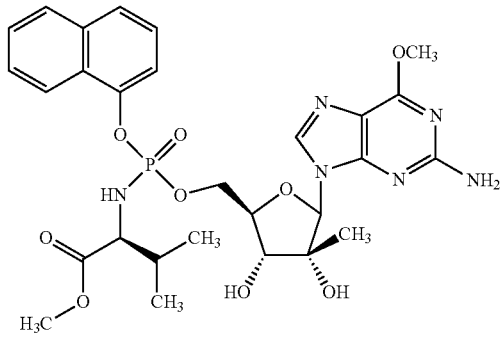 [SMILES: COC(=O)[C@@H](NP(=O)(OC[C@H]1OC(n2cnc3c(OC)nc(N)nc32)[C@](C)(O)[C@@H]1O)Oc1cccc2ccccc12)C(C)C]

Step 1: Synthesis (2S)-methyl 2-(chloro(naphthalen-1-yloxy)-phosphorylamino)-3-methylbutanoate

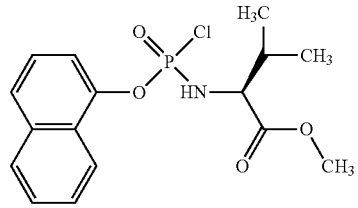 [SMILES: COC(=O)[C@@H](NP(=O)(Cl)Oc1cccc2ccccc12)C(C)C]

Using the general procedure for synthesizing naphthyl (amino acid ester) phosphorochloridates the hydrochloride salt of L-valine methyl ester (2.00 g, 11.93 mmol), naphthalen-1-yl phosphorodichloridate (0.77 g, 11.93 mmol) and TEA (4.11 mL, 23.85 mmol) in 20 mL of dry DCM, were combined to give (2S)-methyl 2-(chloro(naphthalen-1-yloxy)-phosphorylamino)-3-methylbutanoate in 62% yield (2.63 g), as a clear, yellow, thick oil.

The following are the NMR results analyzing the synthesized compounds:

$^1$H NMR (500 MHz, $CDCl_3$) δ 8.12, 8.10 (2×d, J=7.50 Hz, 1H, $H_8$-napht), 7.88 (d, J=8.00 Hz, 1H, $H_5$-napht), 7.74 (d, J=8.00 Hz, 1H, $H_4$-napht), 7.65-7.52 (m, 3H, $H_7$, $H_6$, $H_2$-napht), 7.50, 7.45 (2×t, J=8.00 Hz, 1H, $H_3$-napht), 4.59 (bs, 1H, NH), 4.09-4.06 (m, 1H, Hα Val), 3.81, 3.76 (2×s, 3H, $CH_3$ ester), 2.25-2.18 (m, 1H, Hβ Val), 1.06, 1.03 (2×d, J=6.50 Hz, 3H, $CH_3$ Val), 0.99, 0.96 (2×d, J=6.50 Hz, 3H, $CH_3$ Val).

$^{31}$P NMR (202 MHz, $CDCl_3$) δ 10.02, 9.56.

Step 2: Synthesis of the Protide

Using the general procedure for the synthesis of 5'-phosphoramidates of 2-amino-6-methoxy-9-(2-C-methyl-β-D-ribofuranosyl)purine, to a solution of 250 mg (0.80 mmol) of nucleoside in 5 mL of THF, was added NMI 0.32 mL (4.02 mmol), followed by methyl 2-(chloro(naphthalen-1-yloxy)-phosphorylamino)-3-methylbutanoate 860 mg (2.41 mmol) in 5 mL of THF. After workup and silica gel column chromatography, 78.4 mg of pure protide was obtained in a 15% yield, as an off-white solid. MS (ES+) m/e: 631.23 (MH$^+$, 100%); Accurate mass: $C_{28}H_{36}N_6O_9P_1$ calculated 631.2281. found 631.2252.

The following are the NMR results analyzing the synthesized compounds:

$^1$H NMR (500 MHz, $CD_3OD$) δ 8.19-8.15 (m, 1H, $H_8$-napht), 8.00 (s, 1H, $H_8$), 7.90-7.82 (m, 1H, $H_5$-napht), 7.68, 7.65 (2×d, J=7.7 Hz, 1H, $H_4$-napht), 7.57-7.43 (m, 3H, $H_7$, $H_6$, $H_2$-napht), 7.40-7.34 (m, 1H, $H_3$-napht), 6.01 (s, 1H, $H_{1'}$), 4.64-4.61 (m, 2H, $H_{5'}$), 4.41-4.26 (m, 2H, $H_{3'}$ and $H_{4'}$), 4.04 (s, 3H, 6OCH$_3$), 3.76-3.72 (m, 1H, CHα), 3.53, 3.50 (2×s, 3H, $CH_3$ ester), 2.03-1.92 (m, 1H, CHβ Val), 1.00, 0.96 (2×s, 3H, 2'CCH$_3$), 0.88-0.79 (m, 6H, 2×CH$_3$Val).

$^{13}$C NMR (126 MHz, $CD_3OD$) δ 174.74, 174.41 (2×d, $^3J_{C-C-N-P}$=2.5 Hz, C=O ester), 162.64 (C6), 161.88, 161.87 (C2), 154.39 (C4), 148.03, 147.97 (ipso Naph), 139.33, 139.07 (CH8), 136.27, 136.22 (C10-Naph), 128.81, 128.75, 128.52, 127.87, 127.82, 127.74, 127.70, 127.41, 126.56, 126.50, 126.43, 125.90, 122.79 (Naph), 116.16, 116.14 (C2-Naph), 115.38, 115.30 (C5), 93.47, 93.33 (C1'), 82.37, 82.23 (2×d, $^3J_{C-C-O-P}$=8.8 Hz, C4'), 79.93, 79.91 (C2'), 74.88, 74.75 (C3'), 68.18, 67.70 (d, $^2J_{C-O-P}$=6.3 Hz, C5'), 61.97, 61.92 (OCH$_3$ ester) 54.31, 54.29 (6OCH$_3$), 52.43, 52.39, 52.03 (Cα Val), 33.27, 33.03 (2×d, $^3J_{C-C-N-P}$=8.8 Hz, Cβ Val), 20.35, 20.32 (2'CCH$_3$), 19.45, 19.42, 18.45, 18.39 (2×CH$_3$Val).

$^{31}$P NMR (202 MHz, $CD_3OD$) δ5.15, 4.95.

Example 42

The (2S)-neopentyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate was synthesized accordingly

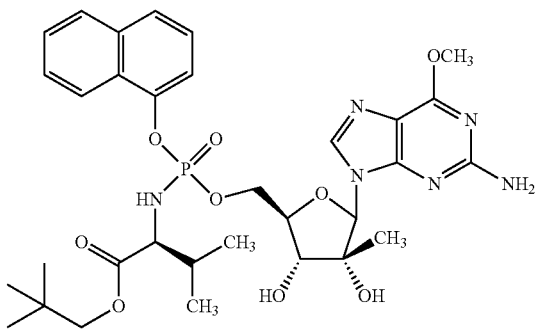 [SMILES: COc1nc(N)nc2c1ncn2C1O[C@H](COP(=O)(N[C@H](C(=O)OCC(C)(C)C)C(C)C)Oc2cccc3ccccc23)[C@@H](O)[C@@]1(C)O]

Step 1: Synthesis of (2S)-neopentyl 2-(chloro(naphthalen-1-yloxy)-phosphorylamino)-3-methylbutanoate

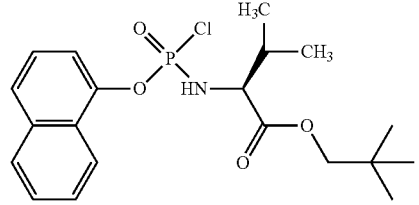 [SMILES: CC(C)[C@H](NP(=O)(Cl)Oc1cccc2ccccc12)C(=O)OCC(C)(C)C]

Using the general procedure for synthesizing naphthyl (amino acid ester) phosphorochloridates and tosylate salt of (S)-neopentyl-2-amino-3-methylbutanoate (4.2 g, 1.18 mmol), naphthalene-1-yl phosphorodichloridate (3.1 g, 1.18 mmol), triethylamine (3.31 mL, 2.37 mmol) and dichloromethane (60 mL) were combined to give 3.8 g of desired phosphorochloridate as a pale yellow viscous oil in 77% yield.

The following are the NMR results analyzing the synthesized compounds:
$^1$H NMR (200 MHz, CDCl$_3$): δ 8.06-8.1 (m, 1H), 7.85-7.89 (m, 1H), 7.73 (d, J=8.6 Hz, 1H), 7.39-7.62 (m, 4H), 4.15 (m, 1H), 3.89 (s, 1H), 3.86 (d, J=2.2 Hz, 1H), 2.2 (m, 1H), 0.8-1.1 (m, 15H).
$^{31}$P NMR (80 MHz, CDCl$_3$): δ10.9, 10.4.

Step 2: Synthesis of Protide

Using the general procedure (Method A) for the synthesis of 5'-phosphoramidates of 2-amino-6-methoxy-9-(2-C-methyl-β-D-ribofuranosyl)purine, the nucleoside (1.0 g, 3.2 mmol) in anhydrous THF (75 mL) was combined with (2S)-neopentyl 2-(chloro(naphthalen-1-yloxy)-phosphorylamino)-3-methylbutanoate (3.8 g, 9.92 mmol) and N-methyl imidazole (1.45 mL, 18.3 mmol). After normal work-up the crude product was purified by column chromatography on silica gel using CH$_2$Cl$_2$/MeOH (97:3) to give 750 mg of protide in 34% yield as an off-white solid.

The following are the NMR results analyzing the synthesized compounds:
$^1$H NMR (200 MHz, CD$_3$OD): δ 8.1-8.17 (m, 1H), 7.96 (s, 1H), 7.8-7.87 (m, 1H), 7.61-7.68 (m, 1H), 7.3-7.54 (m, 4H), 5.95 (s, 1H), 4.6 (m, 2H), 4.24-4.37 (m, 2H), 4.0 (s, 3H), 3.55-3.8 (m, 3H), 2.0 (m, 1H), 0.95 (d, J=7.4 Hz, 3H), 0.8-0.86 (m, 15H)
$^{31}$P NMR (80 MHz, CD$_3$OD): δ 6.21, 6.03.

Example 43

The (2S)-cyclopropylmethyl 2-((((2R,3R,4R)-5-(2-amino-6-methoxy-9H-purin-9-yl)-3,4-dihydroxy-4-methyltetrahydrofuran-2-yl)methoxy) (naphthalen-1-yloxy)phosphorylamino)-3-methylbutanoate was synthesized as follows

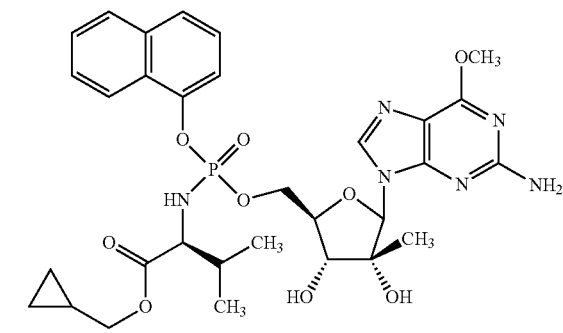 [SMILES: COc1nc(N)nc2c1ncn2C1O[C@H](COP(=O)(N[C@H](C(=O)OCC2CC2)C(C)C)Oc2cccc3ccccc23)[C@@H](O)[C@@]1(C)O]

Step 1: (2S)-cyclopropylmethyl 2-(chloro(naphthalen-1-yloxy)-phosphorylamino)-3-methylbutanoate

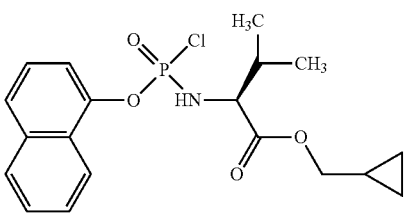 [SMILES: CC(C)[C@H](NP(=O)(Cl)Oc1cccc2ccccc12)C(=O)OCC1CC1]

Using the general procedure for synthesizing naphthyl (amino acid ester) phosphorochloridates, the tosylate salt of cyclopropyl methane 2-amino-3-methylbutanoate (2.92 g), naphthalen-1-yl phosphorodichloridate (2.3 g), TEA (2.47 mL) and DCM (60 mL) were combined to give 2.35 g of desired phosphorochloridate as pale yellow thick oil.

The following are the NMR results analyzing the synthesized compounds:
$^1$H NMR (200 MHz, CDCl$_3$): δ 8.1 (m, 1H), 7.87 (m, 1H), 7.74 (d, J=7.8 Hz, 1H), 7.62 to 7.39 (m, 4H), 4.2 to 3.98 (m, 4H), 2.2 (m, 1H), 1.08 to 0.98 (m, 7H), 0.6 (m, 2H), 0.3 (m, 2H).
$^{31}$P NMR (80 MHz, CDCl$_3$) δ 10.87, 10.34

Step 2: Synthesis of the Protide

Using the general procedure for the synthesis of 5'-phosphoramidates of 2-amino-6-methoxy-9-(2-C-methyl-β-D-ribofuranosyl)purine, the nucleoside (400 mg, 1.28 mmol) in anhydrous THF (40 mL) was combined with (2S)-cyclopropylmethyl 2-(chloro(naphthalen-1-yloxy)-phosphorylamino)-3-methylbutanoate (735.6 mg, 1.92 mmol) and N-methyl imidazole (316.8 mg, 3.85 mmol). After normal work-up the crude product was purified by column chromatography on silica gel using $CH_2Cl_2$/MeOH (97:3) to give 380 mg of protide in 45% yield as an off-white solid.

The following are the NMR results analyzing the synthesized compounds:

$^1$H NMR (200 MHz, $CD_3OD$): δ 8.16 (m, 1H), 7.95 (s, 1H), 7.84 (m, 1H), 7.66 (m, 1H), 7.52 to 7.3 (m, 4H), 5.96 (d, J=1.2 Hz, 1H), 4.6 (m, 2H), 4.23 (m, 2H), 4.0 (s, 3H), 3.86 to 3.64 (m, 3H), 3.5 (dd, J=7.0 Hz, J=6.8 Hz, 1H), 2.0 (m, 1H), 1.0 to 0.8 (m, 10H), 0.45 (m, 2H), 0.15 (m, 2H).

$^{31}$P NMR (80 MHz, $CDCl_3$) δ 6.24, 6.08.

Example 44

The (2S)-cyclobutyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate was synthesized as follows

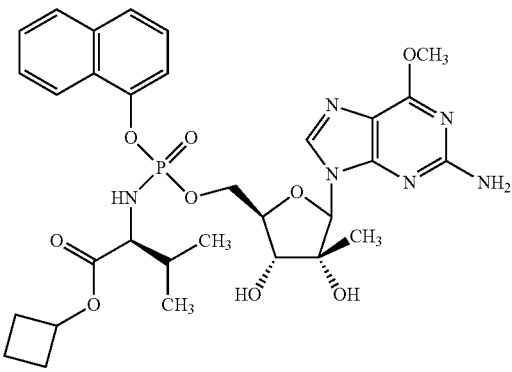 [SMILES: COc1nc(N)nc2c1ncn2C1O[C@H](COP(=O)(N[C@H](C(=O)OC2CCC2)C(C)C)Oc2cccc3ccccc23)[C@@H](O)[C@@]1(C)O]

Step 1: Synthesis of (2S)-cyclobutyl 2-(chloro(naphthalen-1-yloxy)-phosphorylamino)-3-methylbutanoate

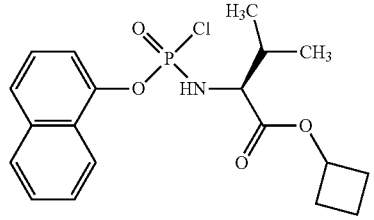 [SMILES: CC(C)[C@H](NP(=O)(Cl)Oc1cccc2ccccc12)C(=O)OC1CCC1]

Using the general procedure for synthesizing naphthyl (amino acid ester) phosphorochloridates and tosylate salt of (S)-cyclobutyl-2-amino-3-methylbutanoate (2.67 g, 7.8 mmol), naphtha-1-yl phosphorodichloridate (2.03 g, 7.8 mmol), triethylamine (2.17 mL, 15.6 mmol) and dichloromethane (20 mL) were combined to give 2.13 g of desired phosphorochloridate as a pale yellow viscous oil in 69% yield.

The following are the NMR results analyzing the synthesized compounds:

$^1$H NMR (200 MHz, $CDCl_3$): δ 8.1 (m, 1H), 7.88 (m, 1H), 7.7 (m, 1H), 7.38-7.64 (m, 4H), 5.12 (m, 1H), 4.0 (m, 2H), 2.3 (m, 2H), 2.0 (m, 2H), 1.6-1.95 (m, 3H), 0.85-1.08 (m, 6H).

$^{31}$P NMR (80 MHz, $CDCl_3$) δ 10.90, 10.47

Step 2: Synthesis of Protide

Using the general procedure (Method A) for the Synthesis of 5'-phosphoramidates of 2-amino-6-methoxy-9-(2-C-methyl-β-D-ribofuranosyl)purine, the nucleoside (200 mg, 0.64 mmol) in anhydrous THF (15 mL) was combined with (2S)-cyclobutyl 2-(chloro(naphthalen-1-yloxy)-phosphorylamino)-3-methylbutanoate (0.303 g, 0.77 mmol) and N-methyl imidazole (0.1 mL, 1.29 mmol). After normal work-up the crude product was purified by column chromatography on silica gel using $CH_2Cl_2$/MeOH (97:3) to give 106 mg of protide in 25% yield as an off-white solid.

The following are the NMR results analyzing the synthesized compounds:

$^1$H NMR (200 MHz, $CD_3OD$): δ 8.1-8.17 (m, 1H), 7.8 (m, 1H), 7.7 (m, 1H), 7.2-7.65 (m, 5H), 5.9 (s, 1H), 4.95 (m, 1H), 4.6-4.9 (m, 2H), 4.2-4.5 (m, 2H), 4.0 (s, 3H), 3.6-3.7 (m, 1H), 1.8-2.4 (m, 4H), 1.4-1.8 (m, 2H), 0.92-0.96 (d, J=8.3 Hz, 3H), 0.79-0.85 (m, 6H).

$^{31}$P NMR (80 MHz, $CD_3OD$): δ 6.22, 6.06.

Example 45

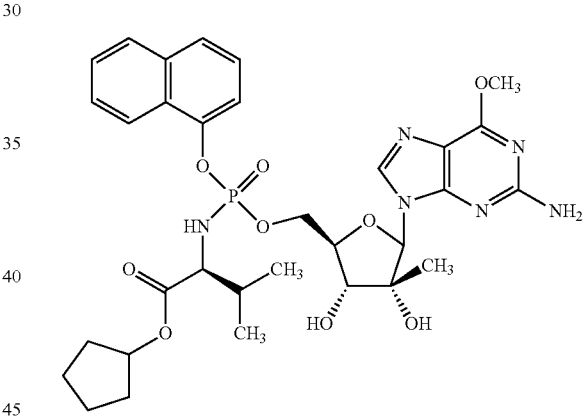

The cyclopentyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)-3-methylbutanoate was synthesized accordingly Step 1: Synthesis of (2S)-cyclopentyl 2-(chloro(naphthalen-1-yloxy)-phosphorylamino)-3-methylbutanoate

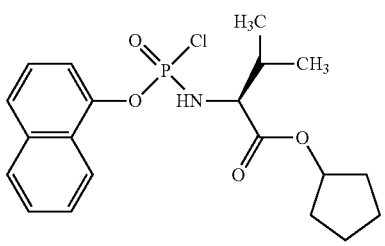 [SMILES: CC(C)[C@H](NP(=O)(Cl)Oc1cccc2ccccc12)C(=O)OC1CCCC1]

Using the general procedure for synthesizing naphthyl (amino acid ester) phosphorochloridates and tosylate salt of (S)-cyclopentyl-2-amino-3-methylbutanoate (2.58 g, 7.2 mmol), naphthalene-1-yl phosphorodichloridate (1.88 g, 7.2 mmol), triethyl amine (2.014 mL, 14.4 mmol) and dichloromethane (20 mL) were combined to give 2.12 g of desired (2S)-cyclopentyl 2-(chloro(naphthalen-1-yloxy)-phosphorylamino)-3-methylbutanoate as a pale yellow viscous oil in 72% yield.

The following are the NMR results analyzing the synthesized compounds:

$^1$H NMR (200 MHz, CDCl$_3$): δ 8.1 (m, 1H), 7.2-7.9 (m, 6H), 5.26 (m, 1H), 3.8-4.1 (m, 2H), 2.15 (m, 1H), 1.6-1.92 (m, 8H), 0.9-1.1 (m, 6H).

$^{31}$P NMR (80 MHz, CDCl$_3$): δ 10.98, 10.5.

Step 2: Synthesis of Protide

Using the general procedure (Method A) for the Synthesis of 5'-phosphoramidates of 2-amino-6-methoxy-9-(2-C-methyl-β-D-ribofuranosyl)purine, the nucleoside (200 mg, 0.64 mmol) in anhydrous THF (15 mL) was combined with (2S)-cyclopentyl 2-(chloro(naphthalen-1-yloxy)-phosphorylamino)-3-methylbutanoate (0.92 g, 2.25 mmol) and N-methyl imidazole (263 mg, 3.2 mmol). After normal work-up the crude product was purified by column chromatography on silica gel using CH$_2$Cl$_2$/MeOH (97:3) to give 60 mg of protide in 14% yield as an off-white solid.

The following are the NMR results analyzing the synthesized compounds:

$^1$H NMR (200 MHz, CD$_3$OD): δ 8.1-8.17 (m, 1H), 8.0 (s, 1H), 7.8-7.9 (m, 1H), 7.6-7.7 (m, 1H), 7.3-7.5 (m, 4H), 5.95 (s, 1H), 4.95 (m, 1H), 4.6 (m, 2H), 4.2-4.4 (m, 2H), 4.0 (s, 3H), 3.6-3.7 (m, 1H), 2.0 (m, 1H), 1.4-1.8 (m, 8H), 0.92-0.96 (d, J=8.4 Hz, 3H), 0.79-0.85 (m, 6H)

$^{31}$P NMR (80 MHz, CD$_3$OD): δ 6.3, 6.0

Example 46

The cyclohexyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)-3-methylbutanoate was synthesized as follows

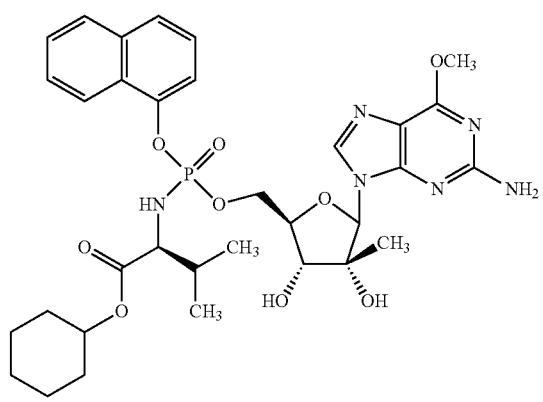 [SMILES: COc1nc(N)nc2c1ncn2C1O[C@H](COP(=O)(N[C@H](C(=O)OC2CCCCC2)C(C)C)Oc2cccc3ccccc23)[C@@H](O)[C@@]1(C)O]

Step 1: Synthesis of (2S)-cyclohexyl 2-(chloro(naphthalen-1-yloxy)-phosphorylamino)-3-methylbutanoate

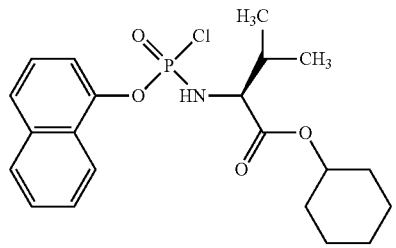 [SMILES: CC(C)[C@H](NP(=O)(Cl)Oc1cccc2ccccc12)C(=O)OC1CCCCC1]

Using the general procedure for synthesizing naphthalene (amino acid ester) phosphorochloridates, the hydrochloride salt of cyclohexyloxy-L-valine (1.8 g), was combined with naphthalene-1-yl phosphorodichloridate (1.99 g), TEA (2.12 mL), and DCM (25 mL) to give (2S)-cyclohexyl 2-(chloro (naphthalen-1-yloxy)-phosphorylamino)-3-methylbutanoate in a 72% yield (2.34 g) as a pale yellow thick oil:

The following are the NMR results analyzing the synthesized compounds:

$^1$H NMR (500 MHz, CDCl$_3$) δ 8.11 (m, 1H, H$_8$-napht), 7.90 (m, 1H, H$_5$-napht), 7.75 (dd, J=0.6, 8.3, 1H, H$_4$-napht), 7.66-7.54 (m, 3H, H$_7$, H$_6$, H$_2$-napht), 7.46 (t, J=8.0, 1H, H$_3$-napht), 4.89 (s, 1H, CH ester), 4.27 (t, J=11.1, 0.4H, NH), 4.23 (t, J=10.5, 0.6H, NH), 4.09-3.99 (m, 1H, CHα), 2.22 (m, 1H, CHβ), 1.89 (m, 2H, CH$_2$ cyclohexyl), 1.76 (s, 2H, CH$_2$ cyclohexyl), 1.63-1.53 (m, 2H), 1.50 (m, 2H, CH$_2$ cyclohexyl), 1.41 (m, 2H, CH$_2$ cyclohexyl), 1.08 (d, J=6.8, 1.3H, CH$_3$ val), 1.05 (d, J=6.8, 1.7H, CH$_3$ val), 1.01 (d, J=6.9, 1.3H, CH$_3$ val), 0.97 (d, J=6.9, 1.7H, CH$_3$ val).

$^{31}$P NMR (202 MHz, CDCl$_3$) δ 9.88, 9.42.

Step 2: Synthesis of Protide

Using the general procedure (Method A) for the synthesis of 5'-phosphoramidates of 2-amino-6-methoxy-9-(2-C-methyl-β-D-ribofuranosyl)purine, to a solution of 150 mg (0.48 mmol) of nucleoside in 5 mL of THF, was added NMI 0.32 mL (4.02 mmol), followed by (2S)-cyclohexyl 2-(chloro (naphthalen-1-yloxy)-phosphorylamino)-3-methylbutanoate 633 mg (1.44 mmol) in 5 mL of THF. After workup and silica gel column chromatography, 45 mg of pure protide was obtained in a 11% yield, as an off-white solid.

The following are the NMR results analyzing the synthesized compounds:

$^1$H NMR (500 MHz, CD$_3$OD) δ 8.21-8.14 (m, 1H, H$_8$-napht), 7.96, 7.94 (s, 1H, H$_8$), 7.89-7.82 (m, 1H, H$_5$-napht), 7.69, 7.65 (2×d, J=8.5 Hz, 1H, H$_4$-napht), 7.55-7.42 (m, 3H, H$_7$, H$_6$, H$_2$-napht), 7.42-7.33 (m, 1H, H$_3$-napht), 5.99 (s, 1H, H$_{1'}$), 4.66-4.54 (m, 3H, CH ester, H$_{5'}$), 4.39-4.22 (m, 2H, H$_{3'}$, and H$_{4'}$), 4.05, 4.04 (s, 3H, 6OCH$_3$), 3.75-3.68 (m, 1H, Hα Val), 2.06-1.93 (m, 1H, Hβ Val), 1.70-1.57 (m, 4H, 2×CH$_2$ cyclohexyl), 1.39-1.15 (m, 6H, 3×CH$_2$ cyclohexyl), 0.99, 0.95 (s, 3H, 2'CCH$_3$), 0.89-0.82 (m, 6H, CH$_3$ Val).

$^{13}$C NMR (126 MHz, CD$_3$OD) δ 173.67 (d, $^3J_{C-C-N-P}$=2.8, C=O ester), 173.39 (d, $^3J_{C-C-N-P}$=3.4, C=O ester), 162.73 (C6), 161.89, 161.86 (C2), 154.53, 154.49 (C4), 148.06 (d, $^2J_{C-O-P}$=1.6, napht-C1), 148.00 (d, $^2J_{C-O-P}$=1.2, napht-C1), 139.44, 139.15 (CH8), 136.30, 136.25 (napht-C10), 128.81, 128.75 (CH-napht), 127.88 (d, $^3J_{C-C-O-P}$=6.6, napht-C9), 127.86 (d, $^3J_{C-C-O-P}$=6.4, napht-C9), 127.72, 127.67 (CH-napht), 127.39 (CH-napht), 126.49, 126.42 (CH-napht), 125.85 (CH-napht), 122.85, 122.83 (CH-napht), 116.12 (d, $^3J_{C-C-O-P}$=3.1, napht-C2), 116.07 (d, $^3J_{C-C-O-P}$=3.2, napht-C2), 115.67, 115.62 (C5), 93.48, 93.29 (C1'), 82.41 (d, $^3J_{C-C-O-P}$=8.0, C4'), 82.22 (d, $^3J_{C-C-O-P}$=8.3, C4'), 79.89 (C2'), 74.98, 74.93 (C3'), 74.86, 74.81 (CH ester), 68.36 (d, $^2J_{C-O-P}$=5.5, C5'), 67.82 (d, $^2J_{C-O-P}$=5.4, C5'), 62.05, 62.01 (Cα Val), 54.23, 54.22 (O$^6$—CH$_3$), 33.34 (d, $^3J_{C-C-N-P}$=6.9, Cβ Val), 33.16, (d, $^3J_{C-C-N-P}$=7.4, Cβ Val), 32.46, 32.39 (CH$_2$ cyclohexyl), 26.35 (CH$_2$ cyclohexyl), 24.62, 24.58 (CH$_2$ cyclohexyl), 20.32, 20.28 (2'—CH$_3$), 19.46, 19.46, 19.44 (CH$_3$ Val), 18.35, 18.23 (CH$_3$ Val)

$^{31}$P NMR (202 MHz, CD$_3$OD) δ 5.15, 4.91

Example 47

The (2S)-tetrahydro-2H-pyran-4-yl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate was synthesized as follows

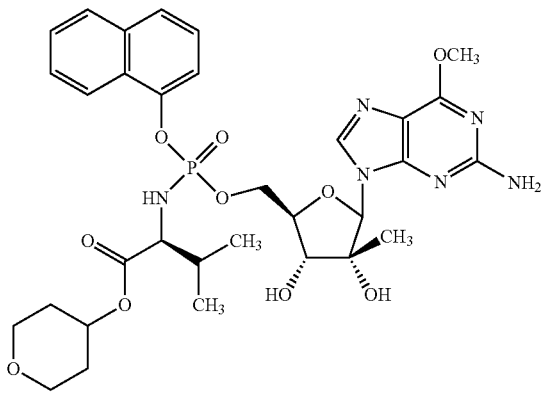 [SMILES: COc1nc(N)nc2c1ncn2C1O[C@H](COP(=O)(N[C@H](C(=O)OC2CCOCC2)C(C)C)Oc2cccc3ccccc23)[C@@H](O)[C@@]1(C)O]

Step 1: Synthesis of (2S)-tetrahydro-2H-pyran-4-yl 2-(chloro(naphthalen-1-yloxy)phosphorylamino)-3-methylbutanoate Using the general procedure for synthesizing naphthylalene (amino acid ester) phosphorochloridates and tosylate salt of (S)-tetrahydro-2H-pyran-4-yl-2-amino-3-methylbutanoate (3.76 g, 10.0 mmol), naphthalene-1-yl phosphorodichloridate (2.62 g, 10.0 mmol), triethylamine (2.81 mL, 2.0 mmol) and dichloromethane (54 mL) were combined to give 2.89 g of desired (2S)-tetrahydro-2H-pyran-4-yl 2-(chloro (naphthalen-1-yloxy)phosphorylamino)-3-methylbutanoate as a pale yellow viscous oil in 67% yield.

The following are the NMR results analyzing the synthesized compounds:

$^1$H NMR (200 MHz, CDCl$_3$): δ 8.05 (m, 1H), 7.85 (m, 1H), 7.7 (m, 1H), 7.4-7.6 (m, 4H), 5.05 (m, 1H), 4.2 (m, 1H), 3.8-4.18 (m, 3H), 3.6-3.8 (m, 2H), 2.1-2.3 (m, 1H) 1.6-2.0 (m, 4H), 0.85-1.08 (m, 6H).

$^{31}$P NMR (80 MHz, CDCl$_3$) δ10.91, 10.36

Step 2: Synthesis of Protide

Using the general procedure (Method A) for the synthesis of 5'-phosphoramidates of 2-amino-6-methoxy-9-(2-C-methyl-β-D-ribofuranosyl)purine, the nucleoside (400 mg, 1.28 mmol) in anhydrous THF (40 mL) was combined with (2S)-tetrahydro-2H-pyran-4-yl 2-(chloro(naphthalen-1-yloxy)phosphorylamino)-3-methylbutanoate (0.82 g, 1.93 mmol) and N-methyl imidazole (0.3 mL, 3.86 mmol). After normal work-up the crude product was purified by column chromatography on silica gel using CH$_2$Cl$_2$/MeOH (97:3) to give 480 mg of protide in 53% yield as an off-white solid.

The following are the NMR results analyzing the synthesized compounds:

$^1$H NMR (200 MHz, CD$_3$OD): δ 8.1-8.17 (m, 1H), 7.96 (s, 1H), 7.8-7.9 (m, 1H), 7.6-7.7 (m, 1H), 7.3-7.6 (m, 4H), 5.95 (s, 1H), 4.65-4.8 (m, 1H), 4.6 (m, 2H), 4.2-4.4 (m, 2H), 4.0 (s, 3H), 3.6-3.8 (m, 2H), 3.3-3.5 (m, 1H), 1.96 (m, 1H), 1.58-1.83 (m, 5), 0.92-0.96 (d, J=8.25 Hz, 3H), 0.79-0.85 (m, 6H)

$^{31}$P NMR (80 MHz, CD$_3$OD): δ 6.19, 6.15, 5.95, 5.91

Example 48

The protide (2S)-neopentyl 2-((((2R,3R,4R)-5-(2-amino-6-methoxy-9H-purin-9-yl)-3,4-dihydroxy-4-methyltetrahydrofuran-2-yl)methoxy) (6-((S)-1-methoxy-1-oxopropan-2-yl)naphthalen-2-yloxy) phosphorylamino)-3-methylbutanoate was synthesized as follows

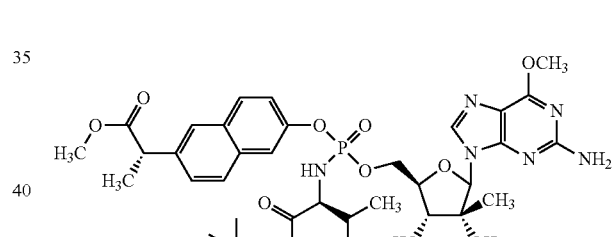

Step 1: Synthesis of (2S)-neopentyl 2-(chloro(6-((S)-1-methoxy-1-oxopropan-2-yl)naphthalen-2-yloxy) phosphorylamino)-3-methylbutanoate

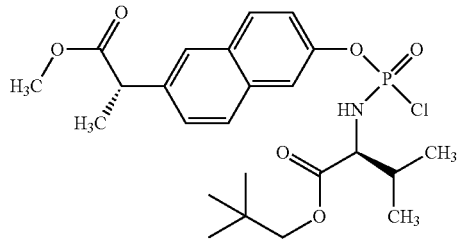 [SMILES: COC(=O)[C@@H](C)c1ccc2cc(OP(=O)(Cl)N[C@H](C(=O)OCC(C)(C)C)C(C)C)ccc2c1]

Using the general procedure for synthesizing naphthyl (amino acid ester) phosphorochloridates the tosylate salt of (S)-neopentyl 2-amino-3-methylbutanoate (776 mg), and (S)-methyl 2-(6-(dichlorophosphoryloxy)naphthalen-2-yl) propanoate (750 mg), TEA (0.6 mL) and DCM (15 mL) were combined to give 580 mg of desired (2S)-neopentyl 2-(chloro (6-((S)-1-methoxy-1-oxopropan-2-yl)naphthalen-2-yloxy) phosphorylamino)-3-methylbutanoate as gummy solid.

The following are the NMR results analyzing the synthesized compound:

$^1$H NMR (200 MHz, CDCl$_3$): δ 7.84-7.72 (m, 4H), 7.49-7.44 (dd, J=1.8 Hz, 8.4 Hz, 1H), 7.36 (m, 1H), 4.2-3.9 (m, 3H), 3.6 (s, 3H), 2.2 (m, 1H), 1.6 (d, J=7.2 Hz, 3H), 1.5 (dd, J=5.4, 6.6 Hz, 3H), 0.95 (m, 12H).

$^{31}$P NMR (80 MHz, CDCl$_3$) δ 10.65, 10.19

Step 2: Synthesis of the Protide

Using the general procedure (Method A) for the synthesis of 5'-phosphoramidates of 2-amino-6-methoxy-9-(2-C-methyl-β-D-ribofuranosyl)purine, the nucleoside (150 mg, 0.48 mmol) in anhydrous THF (20 mL) was combined with (2S)-neopentyl 2-(chloro(6-((S)-1-methoxy-1-oxopropan-2-yl) naphthalen-2-yloxy)phosphorylamino)-3-methylbutanoate (580 mg, 0.96 mmol), N-methyl imidazole (0.2 mL, 2.4 mmol) and triethyl amine (0.07 mL, 0.48 mmol). After normal work-up the crude product was purified by column chromatography on silica gel using CH$_2$Cl$_2$/MeOH (97:3) to give 83 mg of protide in 22% yield as an off-white solid.

The following are the NMR results analyzing the synthesized compound:

$^1$H NMR (200 MHz, CD$_3$OD): δ 8.2-7.9 (m, 1H), 7.8-7.6 (m, 4H), 7.5-7.3 (m, 2H), 5.96 (s, 1H), 4.57 (dd, J=3.4, 3.2 Hz, 2H), 4.35-4.1 (m, 2H), 4.01 (s, 3H), 3.95-3.7 (m, 2H), 3.66 (s, 3H), 3.6-3.4 (m, 1H), 3.3 (m, 1H), 2.0 (m, 1H), 1.5 (dd, J=3.0, 7.0 Hz, 3H), 0.7-0.95 (m, 18H).

$^{31}$P NMR (80 MHz, CD$_3$OD): 6.24, 5.90

Example 49

The (2S)-2,4-difluorobenzyl 2-((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)-3-methylbutanoate was synthesized as follows

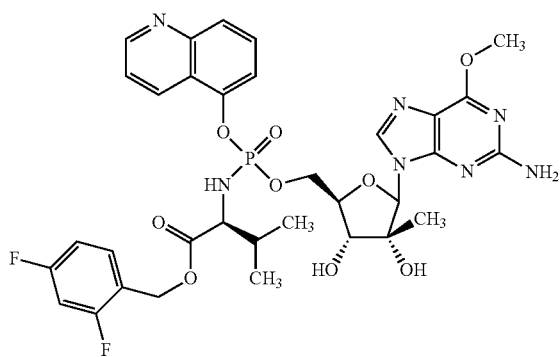 [SMILES: COc1nc(N)nc2c1ncn2C1O[C@H](COP(=O)(N[C@H](C(=O)OCc2ccc(F)cc2F)C(C)C)Oc2cccc3ncccc23)[C@@H](O)[C@@]1(C)O]

Step 1: (2S)-2,4-difluorobenzyl 2-(chloro(quinolin-5-yloxy)phosphorylamino)-3-methylbutanoate

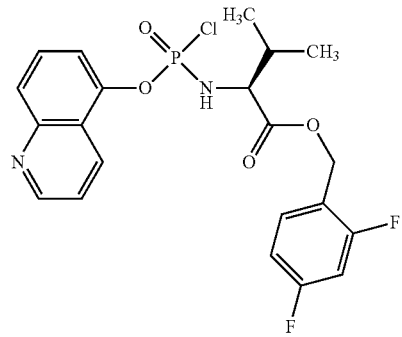 [SMILES: CC(C)[C@H](NP(=O)(Cl)Oc1cccc2ncccc12)C(=O)OCc1ccc(F)cc1F]

Using the general procedure for synthesizing naphthyl (aminoacid ester) phosphorochloridates the tosylate salt of (S)-2,4-difluorobenzyl 2-amino-3-methylbutanoate (1.7 g, 4.1 mmol), quinoline 5-yloxy phosphorodichloridate (1.08 g, 4.01 mmol), triethyl amine (1.15 mL, 8.2 mmol) and dichloromethane (20 mL) were combined to give 770 mg of desired phosphorochloridate in 40% yield as pale yellow thick syrup.

The following are the NMR results analyzing the synthesized compound.

$^1$H NMR (200 MHz, CDCl$_3$): δ 8.96 (d, J=3.4 Hz, 1H), 8.45 (d, J=8.6 Hz, 1H), 8.07 (d, J=8.0 Hz, 1H), 7.65 (m, 2H), 7.27-7.52 (m, 2H), 6.8 (m, 2H), 5.2 (m, 2H), 4.5 (bq, J=8.4 Hz, 1H), 4.0 (m, 1H), 2.2 (m, 1H), 0.9 (m, 6H).

$^{31}$P NMR (80 MHz, CDCl$_3$): δ11.08, 10.62.

Step 2: Synthesis of Protide

Using the general procedure (Method B) for the synthesis of 5'-phosphoramidates of 2-amino-6-methoxy-9-(2-C-methyl-β-D-ribofuranosyl)purine, the nucleoside (256 mg, 0.82 mmol) in anhydrous THF (30 mL) was combined with (2S)-2,4-difluorobenzyl 2-(chloro(quinolin-5-yloxy)phosphorylamino)-3-methylbutanoate (770 mg, 1.64 mmol), and t-butyl magnesium chloride (1.645 mL, 1.645 mmol). After normal work-up the crude product was purified by column chromatography on silica gel using CH$_2$Cl$_2$/MeOH (94:6) to give 169 mg of protide in 28% yield as an off-white solid.

The following are the NMR results analyzing the synthesized compound.

$^1$H NMR (200 MHz, CD$_3$OD): δ 8.84 (m, 1H), 8.61 (m, 1H), 7.78-7.9 (m, 1H), 7.78-7.85 (m, 1H), 7.26-7.69 (m, 4H), 6.75-6.92 (m, 2H), 5.94 (s, 1H), 5.0 (m, 2H), 4.6 (dd, J=4.0 Hz, J=4.4 Hz, 2H), 4.15-4.41 (m, 2H), 4.0 (s, 3H), 3.73 (dd, J=6.2 Hz, J=6.2 Hz, 1H), 2.0 (m, 1H), 0.8-1.0 (m, 9H).

$^{31}$P NMR (80 MHz, CD$_3$OD): δ 6.34, 5.94.

Example 50

The protide (2S)-neopentyl 2-((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)-3-methylbutanoate was synthesized as follows

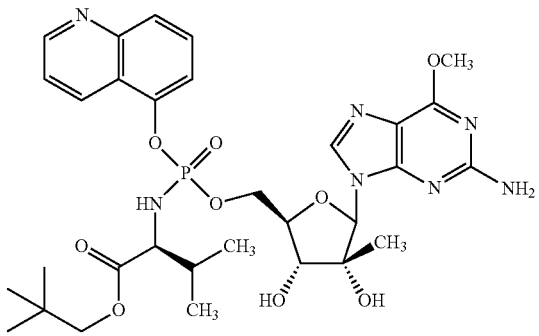 [SMILES: COc1nc(N)nc2c1ncn2C1O[C@H](COP(=O)(N[C@H](C(=O)OCC(C)(C)C)C(C)C)Oc2cccc3ncccc23)[C@@H](O)[C@@]1(C)O]

Step 1: Synthesis of (2S)-neopentyl 2-(chloro(quinolin-5-yloxy)-phosphorylamino)-3-methylbutanoate Using the general procedure for synthesizing naphthyl (amino acid ester) phosphorochloridates, the tosylate salt of neopentyl-2-amino-3-methylbutanoate (1.1 g, 3.06 mmol), quinoline 5-yloxy phosphorodichloridate (800 mg, 3.06 mmol), triethylamine (0.85 mL, 6.1 mmol) and dichloromethane (30 mL) were combined to give 802 mg of desired phosphorochloridate in 64% yield as pale yellow thick oil.

The following are the NMR results analyzing the synthesized compound:

$^1$H NMR (200 MHz, CDCl$_3$): δ 8.98-8.96 (d, J=4.0 Hz, 1H0, 8.44 (d, J=8.4 Hz, 1H), 8.02 (d, J=6.6 Hz, 1H), 7.7 (m, 2H), 7.5 9m, 1H), 4.38 (m, 1H), 4.0 9m, 1H), 3.89 9m, 2H), 2.1 (m, 2H), 1.09-0.85 (m, 15H).

$^{31}$P NMR (80 MHz, CDCl$_3$): δ11.11, 10.7.

Step 2: Synthesis of the Protide

Using the general procedure (Method A) for the synthesis of 5'-phosphoramidates of 2-amino-6-methoxy-9-(2-C-methyl-β-D-ribofuranosyl)purine, the nucleoside (168 mg, 0.53 mmol) in anhydrous THF (25 mL) was combined with (2S)-neopentyl 2-(chloro(quinolin-5-yloxy)-phosphorylamino)-3-methylbutanoate (650 mg, 1.61 mmol), triethylamine (0.12 mL, 0.538 mmol) and N-methyl imidazole (0.25 mL, 2.7 mmol). After normal work-up the crude product was purified by column chromatography on silica gel using CH$_2$Cl$_2$/MeOH (96:4) to give 38 mg of protide in 10% yield.

The following are the NMR results analyzing the synthesized compound:

$^1$H NMR (200 MHz, CD$_3$OD): δ 8.86-8.8 (dd, J=4.4 Hz, J=6.6 Hz, 1H), 8.64-8.53 (dd, J=7.6 Hz, J=8.4 hz, 1H), 7.94-7.92 (d, J=4.4 Hz, 1H), 7.82 (m, 1H), 7.63 9m, 1H), 7.55-7.49 (dd, J=4.4 Hz, J=8.4 Hz, 1H), 7.45-7.38 (dd, J=4.4 Hz, J=8.4 Hz, 1H), 5.95 (s, 1H), 4.62 (m, 2H), 4.42-4.21 (m, 2H), 4.11-4.0 (d, J=2.2 Hz, 3H), 3.8-3.54 (m, 3H), 2.0 9m, 1H), 0.97-0.81 (m, 18H).

$^{31}$P NMR (80 MHz, CD$_3$OD): δ 6.41, 5.94.

Example 51

The (2S)-2,4-difluorobenzyl 2-((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)-3-methylbutanoate was synthesized as follows

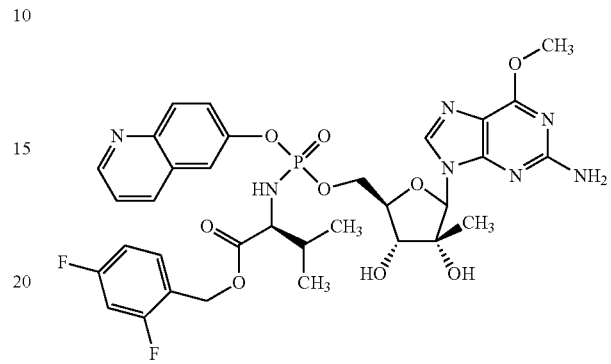

Step 1: (2S)-2,4-difluorobenzyl 2-(chloro(quinolin-6-yloxy)phosphorylamino)-3-methylbutanoate

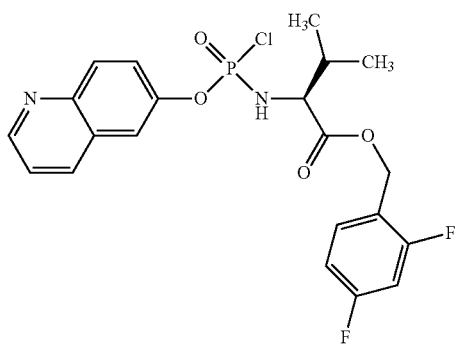 [SMILES: CC(C)[C@H](NP(=O)(Cl)Oc1ccc2ncccc2c1)C(=O)OCc1ccc(F)cc1F]

Using the general procedure for synthesizing naphthyl (aminoacid ester) phosphorochlorides the tosylate salt of (S)-2,4-difluorobenzyl 2-amino-3-methylbutanoate (1.7 g, 4.1 mmol), quinoline 6-yloxy phosphorodichloridate (1.08 g, 4.1 mmol), triethyl amine (1.15 mL, 8.2 mmol) and dichloromethane (30 mL) were combined to give 462 mg of desired (2S)-2,4-difluorobenzyl 2-(chloro(quinolin-6-yloxy)phosphorylamino)-3-methylbutanoate after short silica gel chromatography as pale yellow gummy syrup in 24% yield.

The following are the NMR results analyzing the synthesized compound.

$^1$H NMR (200 MHz, CDCl$_3$): δ 8.95 (d, J=4.0 Hz, 1H), 8.3 (dd, J=5.0 Hz, J=8.3 Hz, 2H), 7.84 (m, 1H), 7.6 (m, 2H), 7.38 (m, 1H), 6.84 (m, 2H), 5.2 (m, 2H), 4.3 (m, 2H), 2.2 (m, 1H), 0.8 (m, 6H).

$^{31}$P NMR (80 MHz, CDCl$_3$): δ 10.66, 10.2

Step 2: Synthesis of Protide

Using the general procedure (Method B) for the synthesis of 5'-phosphoramidates of 2-amino-6-methoxy-9-(2-C-methyl-β-D-ribofuranosyl)purine, (154 mg, 0.493 mmol) in anhydrous THF (20 mL) was combined with (2S)-2,4-difluorobenzyl 2-(chloro(quinolin-6-yloxy)phosphorylamino)-3-methylbutanoate (462 mg) and t-butyl magnesium chloride (1.0 mL, 0.987 mmol). After normal work-up the crude product was purified by column chromatography on silica gel using CH$_2$Cl$_2$/MeOH (92:8) to give 55 mg of protide in 15% yield as off-white solid.

The following are the NMR results analyzing the synthesized compound.

$^1$H NMR (200 MHz, CD$_3$OD): δ 8.78 (ddd, J=1.8 Hz, J=1.4 Hz, J=1.6 Hz, 1H), 8.24 (m, 1H), 7.94 (m, 2H), 7.72 (s, 1H), 7.62 (m, 1H), 7.25-7.5 (m, 2H), 6.88 (m, 2H), 5.93 (d, J=1.6 Hz, 1H), 5.0 (m, 2H), 4.56 (m, 2H), 4.2-4.4 (m, 2H), 3.62-3.88 (m, 2H), 2.0 (m, 1H), 0.8-1.0 (m, 9H).

$^{31}$P NMR (80 MHz, CD$_3$OD): δ 5.98, 5.81.

Example 52

The protide (2S)-neopentyl 2-((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)-3-methylbutanoate was synthesized as follows

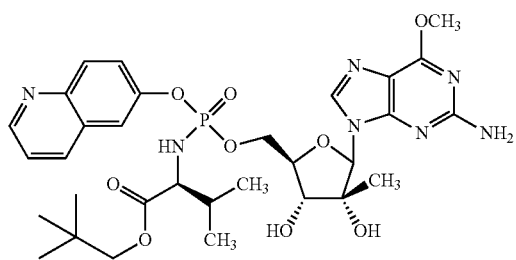 [SMILES: COc1nc(N)nc2c1ncn2C1O[C@H](COP(=O)(N[C@H](C(=O)OCC(C)(C)C)C(C)C)Oc2ccc3ncccc3c2)[C@@H](O)[C@@]1(C)O]

Step 1: Synthesis of (2S)-neopentyl 2-(chloro(quinolin-6-yloxy)phosphorylamino)-3-methylbutanoate

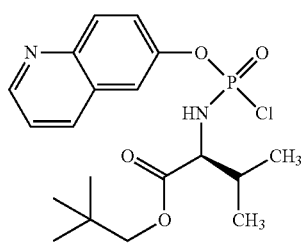 [SMILES: CC(C)[C@H](NP(=O)(Cl)Oc1ccc2ncccc2c1)C(=O)OCC(C)(C)C]

Using the general procedure for synthesizing naphthyl (amino acid ester) phosphorochloridates the tosylate salt of (S)-neopentyl-2-amino-3-methylbutanoate (1.9 g), quinolin-6-yl phosphorodichloridate (1.4 g), TEA (1.49 mL) and DCM (20 mL) were combined to give 600 mg of desired (2S)-neopentyl 2-(chloro(quinolin-6-yloxy)phosphorylamino)-3-methylbutanoate as thick oil.

The following are the NMR results analyzing the synthesized compound:

$^1$H NMR (200 MHz, CDCl$_3$): δ δ 8.9-8.93 (dd, J=1.4 Hz, 3.0 Hz, 1H), 8.13 (m, 2H), 7.78 (dd, J=2.6 Hz, 4.8 Hz, 1H), 7.56-7.62 (ddd, J=1.2, 2.6, 9.2 Hz, 1H), 7.45 (dd, J=4.0 Hz, 8.4 Hz, 1H), 4.0-4.2 (m, 2H), 3.88 (d, 2H, J=2.8 Hz), 2.2 (m, 1H), 1.0 (m, 15H).

$^{31}$P NMR (80 MHz, CDCl$_3$) δ 10.74, 10.27

Step 2: Synthesis of the Protide

Using the general procedure (Method A) for the synthesis of 5'-phosphoramidates of 2-amino-6-methoxy-9-(2-C-methyl-β-D-ribofuranosyl)purine, the nucleoside (150 mg, 0.48 mmol) in anhydrous THF (20 mL) was combined with (2S)-neopentyl 2-(chloro(quinolin-6-yloxy)phosphorylamino)-3-methylbutanoate (600 mg, 1.44 mmol), N-methyl imidazole (0.2 mL 2.40 mmol) and triethyl amine (0.07 mL, 0.48 mmol). After normal work-up the crude product was purified by column chromatography on silica gel using CH$_2$Cl$_2$/MeOH (94:6) to give 126 mg of protide in 38% yield as an off-white solid.

The following are the NMR results analyzing the synthesized compound:

$^1$H NMR (200 MHz, CD$_3$OD): δ 8.76 (m, 1H), 8.2 (m, 1H), 7.9 (m, 2H), 7.75 (d, J=1.2 Hz, 1H), 7.62-7.68 (dd, J=2.6, 9.2 Hz, 1H), 7.46 (m, 1H), 5.92 (s, 1H), 4.6 (m, 2H), 4.2 (m, 2H), 4.01 (s, 3H), 3.74-3.82 (dd, J=5.8 Hz, 5.2 Hz, 1H), 3.74-3.5 (m, 3H), 2.0 (m, 1H), 0.75-0.95 (m, 18H).

$^{31}$P NMR (80 MHz, CD$_3$OD): δ 6.12, 5.85

Example 53

The protide (2S)-neopentyl 2-((((2R,3R,4R)-5-(2-amino-6-methoxy-9H-purin-9-yl)-3,4-dihydroxy-4-methyltetrahydrofuran-2-yl)methoxy)(quinolin-8-yloxy)phosphorylamino)-3-methylbutanoate was synthesized as follows

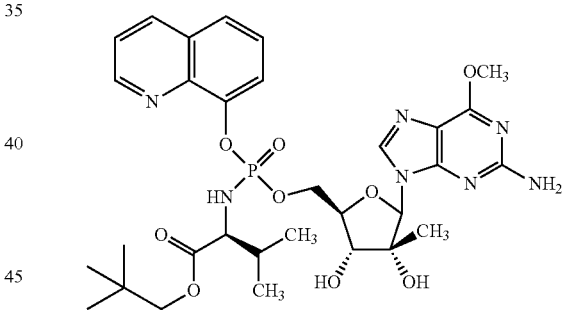

Step1: Synthesis of (2S)-neopentyl 2-(chloro(quinolin-8-yloxy)phosphorylamino)-3-methylbutanoate

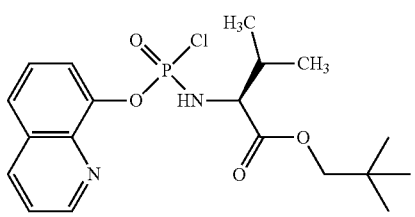 [SMILES: CC(C)[C@H](NP(=O)(Cl)Oc1cccc2cccnc12)C(=O)OCC(C)(C)C]

Using the general procedure for synthesizing naphthyl (amino acid ester) phosphorochloridates, the tosylate salt of neopentyl-2-amino-3-methylbutanoate (1.2 g, 3.4 mmol), quinoline 8-yloxy phosphorodichloridate (900 mg, 3.4 mmol), triethyl amine (0.96 mL, 6.9 mmol) and dichloromethane (30 mL) were combined to give 3.1 g crude desired (2S)-neopentyl 2-(chloro(quinolin-8-yloxy)phosphorylamino)-3-methylbutanoate which was used directly to next step.

Step 2: Synthesis of the Protide

Using the general procedure (Method A) for the synthesis of 5'-phosphoramidates of 2-amino-6-methoxy-9-(2-C-methyl-β-D-ribofuranosyl)purine, the nucleoside (160 mg, 0.52 mmol) in anhydrous THF (25 mL) was combined with (2S)-neopentyl 2-(chloro(quinolin-8-yloxy)phosphorylamino)-3-methylbutanoate (3.1 g) and N-methyl imidazole (0.2 mL, 2.56 mmol). After normal work-up the crude product was purified by column chromatography on silica gel using $CH_2Cl_2$/MeOH (96:4) to give 8 mg of protide in 3% yield as an off-white solid.

The following are the NMR results analyzing the synthesized compound:

$^1$H NMR (200 MHz, $CD_3OD$): δ 8.92-8.89 (dd, J=1.4 Hz, J=1.8 Hz, 1H), 8.37-8.32 (dd, J=1.8 Hz, J=1.8 Hz, 1H), 7.89 (s, 1H), 7.75 (m, 2H), 7.55 (m, 2H), 5.9 (s, 1H), 4.6 (m, 2H), 4.2 (m, 2H), 4.02-3.9 (m, 4H), 3.86 (s, 1H), 3.7-3.67 (m, 2H), 2.03 (m, 1H), 1.0-0.81 (m, 18H).

$^{31}$P NMR (80 MHz, $CD_3OD$): δ 6.48.

Example 54

The protide (2S)-neopentyl 2-(((((2R,3R,4R))-5-(2-amino-6-methoxy-9H-purin-9-yl)-3,4-dihydroxy-4-methyltetrahydrofuran-2-yl)methoxy)(2-methylnaphthalen-1-yloxy)phosphorylamino)-3-methylbutanoate was synthesized as follows

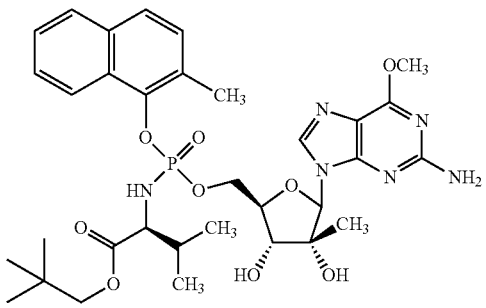 [SMILES: COc1nc(N)nc2c1ncn2C1O[C@H](COP(=O)(N[C@H](C(=O)OCC(C)(C)C)C(C)C)Oc2c(C)ccc3ccccc23)[C@@H](O)[C@@]1(C)O]

Step 1: Synthesis of (2S)-neopentyl 2-(chloro(2-methylnaphthalen-1-yloxy)phosphorylamino)-3-methylbutanoate

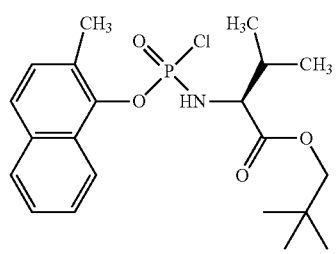 [SMILES: Cc1ccc2ccccc2c1OP(=O)(Cl)N[C@H](C(=O)OCC(C)(C)C)C(C)C]

Using the general procedure for synthesizing naphthyl (amino acid ester) phosphorochloridates, the tosylate salt (S)-neopentyl 2-amino-3-methylbutanoate (680 mg, 1.89 mmol), 2-methyl naphthalen-1-yloxy phosphorodichloridate (523.38 mg, 1.89 mmol), triethyl amine (0.528 mL, 3.79 mmol) and dichloromethane (10 mL) were combined to give desired product, which was used directly in the next step.

The following are the NMR results analyzing the synthesized compound:

$^{31}$P NMR (80 MHz, $CD_3OD$): δ 10.48, 9.89

Step 2: Synthesis of the Protide

Using the general procedure for the synthesis of 5'-phosphoramidates of 2-amino-6-methoxy-9-(2-C-methyl-β-D-ribofuranosyl)purine, the nucleoside (393 mg, 1.26 mmol) in anhydrous THF (30 mL) was combined with (2S)-neopentyl 2-(chloro(2-methylnaphthalen-1-yloxy)phosphorylamino)-3-methylbutanoate (805.9 mg, 1.89 mmol) and N-methyl imidazole (415.21 mg 5.05 mmol). After normal work-up the crude product was purified by column chromatography on silica gel using $CH_2Cl_2$/MeOH (98:2) to give 450 mg of protide in 51% yield as an off-white solid.

The following are the NMR results analyzing the synthesized compound:

$^1$H NMR (200 MHz, $CD_3OD$): δ 8.2 (m, 1H), 7.89 (d, J=3.6 Hz, 1H), 7.82 to 7.25 (m, 5H), 5.92 (d, J=4.0 Hz, 1H), 4.5 (m, 1H), 4.4 (m, 1H), 4.15 (m, 2H), 4.03 (s, 3H), 3.8 to 3.7 (m, 2H), 2.53 (m, 3H), 2.0 (m, 1H), 0.98 to 0.7 (m, 18H).

$^{31}$P NMR (80 MHz, $CD_3OD$): δ 6.8, 6.4

Example 55

The protide (2S)-neopentyl 2-(((((2R,3R,4R)-5-(2-amino-6-methoxy-9H-purin-9-yl)-3,4-dihydroxy-4-methyltetrahydrofuran-2-yl)methoxy)(3-tert-butyl-naphthalen-1-yloxy)phosphorylamino)-3-methylbutanoate was synthesized as follows

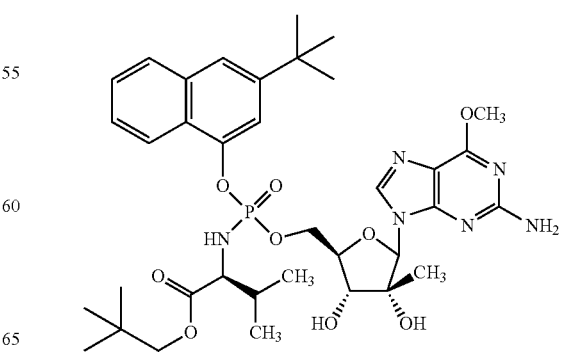

Step 1: Synthesis of (2S)-neopentyl 2-((3-tert-butyl-naphthalen-1-yloxy)chlorophosphorylamino)-3-methylbutanoate

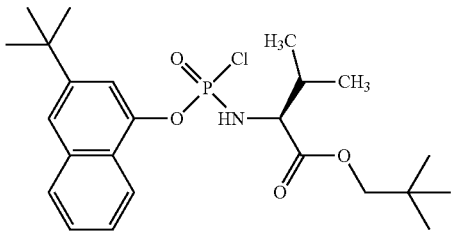 [SMILES: CC(C)[C@H](NP(=O)(Cl)Oc1cc(C(C)(C)C)cc2ccccc12)C(=O)OCC(C)(C)C]

Using the general procedure for synthesizing naphthyl (amino acid ester) phosphorochloridates, the tosylate salt of (S)-neopentyl 2-amino-3-methylbutanoate (552 mg, 1.54 mmol), 3-tert-butyl naphthalen-1-yloxy phosphorodichloridate (486 mg, 1.54 mmol), triethylamine (0.43 mL, 3.08 mmol) and dichloromethane (20 mL) were combined to give desired phosphorochloridate as pale yellow thick syrup, which was used directly in the next step.

The following are the NMR results analyzing the synthesized compound:

$^{31}$P NMR (80 MHz, CD$_3$OD): δ10.83, 10.31.

Step 2: Synthesis of the Protide

Using the general procedure for the synthesis of 5'-phosphoramidates of 2-amino-6-methoxy-9-(2-C-methyl-β-D-ribofuranosyl)purine, the nucleoside (239 mg, 0.77 mmol) in anhydrous THF (20 mL) was combined with (2S)-neopentyl 2-((3-tert-butylnaphthalen-1-yloxy)chlorophosphorylamino)-3-methylbutanoate (719 mg, 1.54 mmol) and N-methyl imidazole (0.35 mL, 3.85 mmol). After normal work-up the crude product was purified by column chromatography on silica gel using CH$_2$Cl$_2$/MeOH (97:3) to give 388 mg of protide in 68% yield as an off-white solid.

The following are the NMR results analyzing the synthesized compound:

$^{1}$H NMR (200 MHz, CD$_3$OD): δ8.06 (m, 1H), 7.96 (d, J=2.6 Hz, 1H), 7.89 (s, 1H), 7.8 (m, 1H), 7.62 (m, 2H), 7.4 (m, 2H), 5.98 (d, J=2.6 Hz, 1H), 4.6 (m, 2H), 4.37-4.25 (m, 2H), 4.02 (s, 3H), 3.82-3.56 (m, 3H), 2.0 (m, 1H), 1.34 (d, J=8.2 Hz, 9H), 0.95 (d, J=4.6 Hz, 3H), 0.86-0.81 (m, 15H).

$^{31}$P NMR (80 MHz, CD$_3$OD): δ 6.12, 6.02.

Example 56

The protide (2S)-neopentyl 2-(((((2R,3R,4R)-5-(2-amino-6-methoxy-9H-purin-9-yl)-3,4-dihydroxy-4-methyltetrahydrofuran-2-yl)methoxy)(3,7-di-tert-butylnaphthalen-1-yloxy)phosphorylamino)-3-methylbutanoate was synthesized as follows

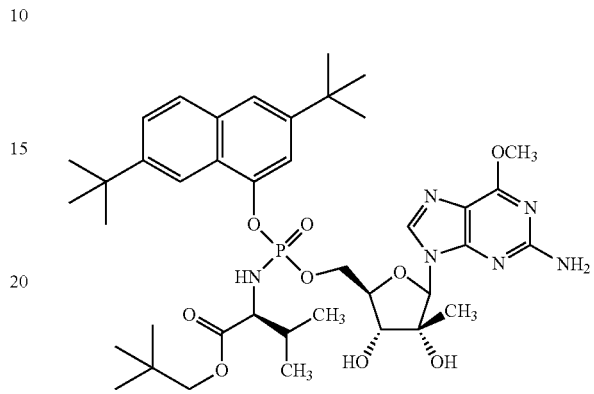

Step 1: Synthesis of (2S)-neopentyl 2-(chloro(3,7-di-tert-butylnaphthalen-1-yloxy)phosphorylamino)-3-methylbutanoate

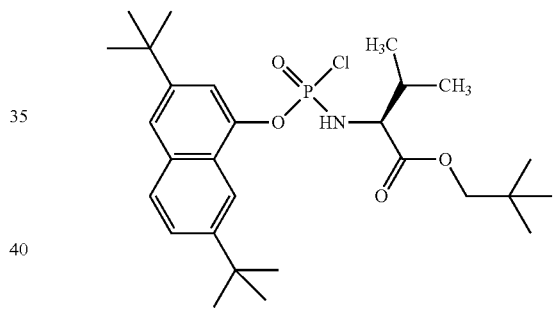

Using the general procedure for synthesizing naphthyl (amino acid ester) phosphorochloridates, the tosylate salt of (S) neopentyl-2-amino-3-methylbutanoate (560 mg, 1.56 mmol), 3,7-di-tert-butyl naphthalen-1-yloxy phosphorodichloridate (581 mg, 1.56 mmol), triethylamine (0.43 mL, 3.12 mmol) and dichloromethane (20 mL) were combined to give desired phosphorochloridate as pale yellow thick syrup, which was used in next step without any purification.

The following are the NMR results analyzing the synthesized compound:

$^{31}$P NMR (80 MHz, CD$_3$OD): δ10.71, 10.04.

Step 2: Synthesis of the Protide

Using the general procedure (Method A) for the synthesis of nucleoside 5'-phosphoramidates, (3R,4R,5R)-2-(2-amino-6-methoxy-9H-purin-9-yl)-5-(hydroxymethyl)-3-methyltetrahydrofuran-3,4-diol (243 mg, 0.78 mmol) in anhydrous THF (20 mL) was combined with (2S)-neopentyl 2-(chloro (3,7-di-tert-butylnaphthalen-1-yloxy)phosphorylamino)-3-methylbutanoate (817 mg, 1.56 mmol) and N-methyl imidazole (0.31 mL, 3.9 mmol). After normal work-up the crude product was purified by column chromatography on silica gel using CH$_2$Cl$_2$/MeOH (97:3) to give 393 mg of protide in 65% yield as off-white solid The following are the NMR results analyzing the synthesized compound:

$^1$H NMR (200 MHz, CD$_3$OD): δ 8.03 (m, 1H), 7.95 (m, 1H), 7.89 (s, 1H), 7.74 (m, 1H), 7.62-7.57 (m, 2H), 5.96 (d, J=2.2 Hz, 1H), 4.57 (m, 2H), 4.28 (m, 2H), 4.03 (s, 3H), 3.83-3.5 (m, 3H), 2.0 (m, 1H), 1.37 (m, 18H), 0.97-0.77 (m, 18H).

$^{31}$P NMR (80 MHz, CD$_3$OD): δ 6.14, 6.10.

Example 57

The (2R)-neopentyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

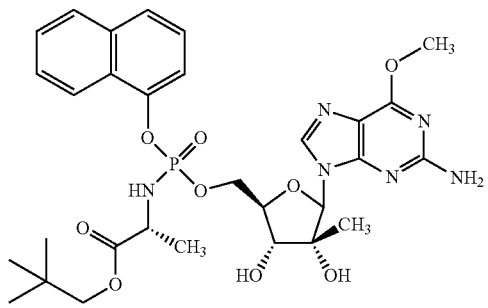 [SMILES: COc1nc(N)nc2c1ncn2C1O[C@H](COP(=O)(N[C@H](C)C(=O)OCC(C)(C)C)Oc2cccc3ccccc23)[C@@H](O)[C@@]1(C)O]

Step 1: (2R)-neopentyl 2-(chloro(naphthalen-1-yloxy)phosphorylamino)propanoate

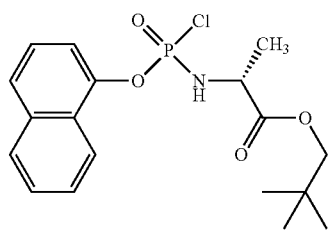 [SMILES: C[C@@H](NP(=O)(Cl)Oc1cccc2ccccc12)C(=O)OCC(C)(C)C]

Using the general procedure for synthesizing naphthyl (aminoacid ester) phosphorochloridates the tosylate salt of (R)-neopentyl 2-aminopropanoate (3 g), naphthalene-1-yl phosphorodichloridate (2.36 g), TEA (2.52 mL) and DCM (90 mL) were combined to give (2R)-neopentyl 2-(chloro(naphthalen-1-yloxy)phosphorylamino)propanoate as a crude pale yellow thick oil. The crude compound was taken forward without further purification.

The following are the NMR results analyzing the synthesized compound:

$^{31}$P NMR (202 MHz, CDCl$_3$) δ 8.18, 7.88

Step 2: Synthesis of Protide

Using the general procedure (Method B) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, to a solution of 250 mg of nucleoside in 5 mL of THF was added tert-BuMgCl (1.61 mL) followed by (2R)-neopentyl-2-(chloro(naphthalen-1-yloxy)phosphorylamino)propanoate (925 mg) in THF (3 mL). After workup, silica gel column chromatography and preparative HPLC, 57.9 mg of pure protide was obtained (11% yield). HPLC t$_R$=27.61, 28.29 min (column: Varian Pursuit XRs 5, C$_{18}$, 150×4.6 mm; method: linear gradient of MeOH (10% to 100%) in H$_2$O in 30 min).

The following are the NMR results analyzing the synthesized compound:

$^1$H NMR (500 MHz, CD$_3$OD) δ 8.21-8.15 (m, 1H), 8.01 and 7.98 (2s, 1H), 7.91-7.85 (m, 1H), 7.71 and 7.69 (2d, J=8.0, 1H), 7.56-7.46 (m, 3H), 7.42 and 7.39 (2t, J=8.0, 1H), 6.00 and 5.98 (2s, 1H), 4.67-4.53 (m, 2H), 4.41-4.20 (m, 2H), 4.09-4.00 (m, 4H), 3.81, 3.79, 3.68, 3.66 (2×AB, J$_{AB}$=10.5, 2H), 1.32 and 1.27 (2d, J=7.2, 3H), 1.00 and 0.99 (2s, 3H), 0.88 and 0.86 (2s, 9H)

$^{13}$C NMR (126 MHz, CD$_3$OD) δ 175.20 and 174.90 (2d, $_3$J$_{C-C-N-P}$=5.1), 162.64, 162.62, 161.95, 161.93, 154.49, 154.48, 148.00, 147.95 (d, $_2$J$_{C-O-P}$=6.7), 139.46, 139.05, 136.31, 136.28, 129.17, 128.83, 127.91 and 127.84 (2d, $_3$J$_{C-C-O-P}$=6.3), 127.77, 127.54, 127.46, 126.50, 125.99, 125.94, 122.83, 122.70, 116.28, 116.26, 116.11, 116.08, 93.39, 93.20, 82.32 and 82.10 (2d, $_3$J$_{C-C-O-P}$=8.3), 79.97, 79.90, 75.38, 74.77, 74.54, 67.82 and 67.38 (2d, $_2$J$_{C-O-P}$=5.0), 54.29, 54.27, 51.78, 51.67, 32.24, 26.69, 26.66, 20.70 and 20.43 (2d, $_3$J$_{C-C-N-P}$=7.2), 20.31, 20.29

$^{31}$P NMR (202 MHz, CD$_3$OD) δ 4.48, 4.09

Example 58

The (2S)-benzyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-4-(methylthio)butanoate was synthesized as follows

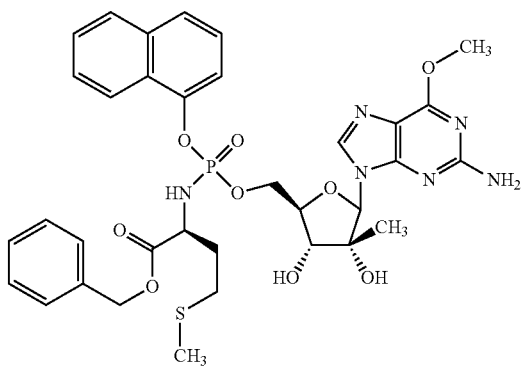 [SMILES: COc1nc(N)nc2c1ncn2C1O[C@H](COP(=O)(N[C@@H](CCSC)C(=O)OCc2ccccc2)Oc2cccc3ccccc23)[C@@H](O)[C@@]1(C)O]

Step 1: (2S)-benzyl 2-(chloro(naphthalen-1-yloxy)phosphorylamino)-4-(methylthio)butanoate

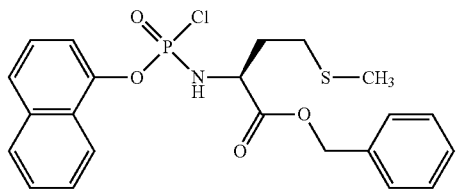 [SMILES: CSCC[C@H](NP(=O)(Cl)Oc1cccc2ccccc12)C(=O)OCc1ccccc1]

Using the general procedure for synthesizing naphthyl (amino acid ester) phosphorochloridates the tosylate salt of (2S)-benzyl 2-(chloro(naphthalen-1-yloxy)phosphorylamino)-4-(methylthio)butanoate (2.00 g, 4.70 mmol), naphthalen-1-yl phosphorodichloridate (1.23 g, 4.70 mmol) and TEA (1.31 mL, 9.40 mmol) were combined in 30 mL of dry DCM to give (2S)-benzyl 2-(chloro(naphthalen-1-yloxy)phosphorylamino)-4-(methylthio)butanoate in 74% yield (1.67 g), as a clear, yellow, thick oil.

The following are the NMR results analyzing the synthesized compound:

$^1$H NMR (500 MHz, CDCl$_3$) δ 8.13-8.08 (m, 1H, H$_8$-napht), 7.90-7.88 (m, 1H, H$_5$-napht), 7.75 (d, J=9.00 Hz, 1H, H$_4$-napht), 7.64-7.54 (m, 3H, H$_7$, H$_6$, H$_2$-napht), 7.44 (t, J=8.20 Hz, 1H, H$_3$-napht), 7.35-7.31 (m, 5H, Ph), 5.25, 5.22 (AB, J$_{AB}$=8.50 Hz, 2H, CH$_2$ ester), 4.75-4.69 (m, 1H, NH), 4.48-4.41 (m, 1H, CHα), 2.62-2.52 (m, 2H, CH$_2$—S), 2.18-1.96 (m, 2H, CH—CH$_2$ Met), 2.03, 2.01 (2×s, 3H, CH$_3$ Met).

$^{31}$P NMR (202 MHz, CDCl$_3$) δ 8.72, 8.63

Step 2: Synthesis of Protide

Using the general procedure (Method B) for the synthesis of nucleoside 5'-phosphoramidates, to a solution of (3R,4R,5R)-2-(2-amino-6-methoxy-9H-purin-9-yl)-5-(hydroxymethyl)-3-methyltetrahydrofuran-3,4-diol, 250 mg (0.803 mmol) in 5 mL of THF was added tert-BuMgCl 1.61 mL (1.61 mmol), followed by (2S)-benzyl 2-(chloro(naphthalen-1-yloxy)phosphorylamino)-4-(methylthio)butanoate 742 mg (1.60 mmol) of THF. After workup and silica gel column chromatography, 246 mg of pure protide was obtained in a 42% yield, as an off-white solid.

The following are the NMR results analyzing the synthesized compound:

$^1$H NMR (500 MHz, CD$_3$OD) δ 8.19, 8.16 (2×d, J=7.80 Hz, 1H, H$_8$-napht), 7.98, 7.94 (2×s, 1H, H$_8$) 7.86, 7.84 (2×d, J=9.00 Hz, 1H, H$_5$-napht), 7.68, 7.66 (2×d, J=8.20 Hz, 1H, H$_4$-napht), 7.53-7.44 (m, 3H, H$_7$, H$_6$, H$_2$-napht), 7.36, 7.35 (2×t, J=8.00 Hz, 1H, H$_3$-napht), 7.26-7.25 (m, 5H, Ph), 6.00, 5.99 (2×s, 1H, H$_{1'}$), 5.08-4.95 (m, 2H, CH$_2$ ester), 4.66-4.58 (m, 2H, H$_{5'}$), 4.35, 4.29 (2×d, J=9.0 Hz, 1H, H$_{3'}$), 4.26-4.22 (m, 1H, H$_{4'}$), 4.18-4.13 (m, 1H, Hα Met), 4.03, 4.02 (2×s, 3H, 6O-CH$_3$), 2.35, 2.24 (2×t, J=7.50 Hz, 2H, CH$_2$—S), 1.98-1.77 (m, 5H, CHCH$_2$ Met and CH$_3$ Met) 0.98, 0.96 (2×s, 3H, 2'-CH$_3$).

$^{13}$C NMR (126 MHz, CD$_3$OD) δ 174.21 (d, $^3$J$_{C-C-N-P}$=3.8 Hz, C=O ester), 173.89 (d, $^3$J$_{C-C-N-P}$=3.8 Hz, C=O ester), 162.72 (C6), 161.85 (C2), 154.56, 154.51 (C4), 148.00, 147.94 (ipso Naph), 139.34, 139.09 (CH8), 137.08, 137.06 (ipso Ph), 136.28, 136.25 (napht-C10), 129.53, 129.36, 129.31, 128.85, 128.83 (Naph, Ph), 127.89 (d, $^3$J$_{C-C-O-P}$=3.8 Hz, naph-C9), 127.80 (d, $^3$J$_{C-C-O-P}$=5.0 Hz, naph-C9), 127.54, 127.52, 126.52, 126.03, 125.97, 122.86, 122.82 (Naph, Ph), 116.35, 116.25 (d, $^3$J$_{C-C-O-P}$=3.8 Hz, C2-Naph), 116.15 (d, $^3$J$_{C-C-O-P}$=2.5 Hz, C2-Naph), 115.64, 115.60 (C5), 93.35, 93.16 (C1'), 82.32 (d, $^3$J$_{C-O-P}$=8.8 Hz, C4'), 82.13 (d, $^3$J$_{C-C-O-P}$=8.8 Hz, C4'), 79.98, 79.93 (C2'), 74.91, 74.63 (C3'), 68.17 (d, $^2$J$_{C-O-P}$=5.0 Hz, C5'), 68.04 (d, $^2$J$_{C-O-P}$=6.25 Hz, C5'), 67.59, 67.55 (CH$_2$ ester), 55.23, 55.11 (CαMet), 54.26 (6OCH$_3$), 34.35 (d, $^3$J$_{C-C-N-P}$=6.25 Hz, CβMet), 34.13 (d, $^3$J$_{C-C-N-P}$=7.5 Hz, CβMet), 30.74, 30.72 (CH$_2$S Met), 20.36 (2'CCH$_3$), 15.13, 15.09 (CH$_3$ Met)

$^{31}$P NMR (202 MHz, CD$_3$OD) δ 4.54, 4.42

Example 59

The (2S)-((S)-1-phenylethyl) 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-4-(methylthio)butanoate was synthesized as follows

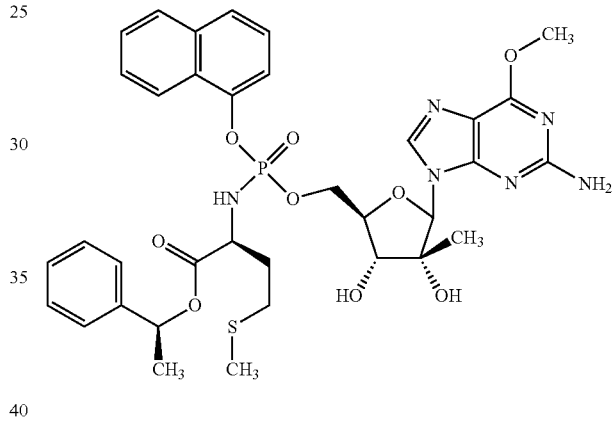

Step 1: (2S)-((S)-1-phenylethyl) 2-(chloro(naphthalen-1-yloxy)phosphorylamimo)-4-(methylthio)butanoate

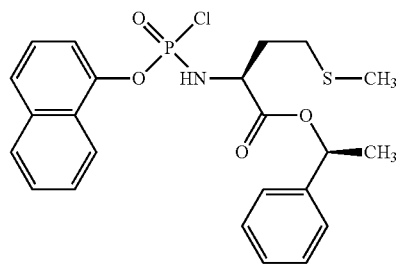 [SMILES: CSCC[C@H](NP(=O)(Cl)Oc1cccc2ccccc12)C(=O)O[C@@H](C)c1ccccc1]

Using the general procedure for synthesizing naphthyl (aminoacid ester) phosphorochloridates the tosylate salt of (S)-((S)-1-phenylethyl) 2-amino-4-(methylthio)butanoate (2.00 g, 4.70 mmol), naphthalene-1-yl phosphorodichloridate (1.23 g, 4.70 mmol) and TEA (1.31 mL, 9.40 mmol) in 30 mL of dry DCM, were combined to give (2S)-((S)-1-phenylethyl) 2-(chloro(naphthalen-1-yloxy)phosphorylamino)-4-(methylthio)butanoate in 74% yield (1.67 g), as a clear, yellow, thick oil.

The following are the NMR results analyzing the synthesized compound:

¹H NMR (500 MHz, CDCl₃) δ 8.12, 8.10 (2×d, J=8.00 Hz, 1H, H₈-napht), 7.91-7.88 (m, 1H, H₅-napht), 7.76 (d, J=8.50 Hz, 1H, H₄-napht), 7.65-7.55 (m, 3H, H₇, H₆, H₂-napht), 7.46, 7.45 (2×t, J=8.00 Hz, 1H, H₃-napht), 7.40-7.31 (m, 5H, Ph), 6.00, 5.97 (2×q, J=7.50 Hz, 1H, CH ester), 4.58-4.47 (m, 1H, NH), 4.47-4.40 (m, 1H, CHa), 2.55-2.34 (m, 2H, CH₂—S), 2.18-1.96 (m, 5H, CH₂ and CH₃ Met), 1.64, 1.60 (2×d, J=7.50 Hz, 3H, CH₃ ester).

³¹P NMR (202 MHz, CDCl₃) δ 8.64, 8.59

Step 2: Synthesis of Protide

Using the general procedure (Method B) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, to a solution of 250 mg (0.803 mmol) of nucleoside in 5 mL of THF, was added tert-BuMgCl 1.61 mL (1.61 mmol), followed by (2S)-((S)-1-phenylethyl) 2-(chloro (naphthalen-1-yloxy)phosphorylamino)-4-(methylthio)butanoate 768 mg (1.60 mmol) in 5 mL of THF. After workup and silica gel column chromatography, 226 mg of pure protide was obtained in a 37% yield, as an off-white solid.

The following are the NMR results analyzing the synthesized compound:

¹H NMR (500 MHz, CD₃OD) δ 8.22-8.17 (m, 1H, H₈-napht), 7.99, 7.96 (2×s, 1H, H₈) 7.86-7.82 (m, 1H, H₅-napht), 7.67, 7.65 (2×d, J=8.5 Hz, 1H, H₄-napht), 7.55-7.46 (m, 3H, H₇, H₆, H₂-napht), 7.37, 7.35 (2×t, J=8.0 Hz, 1H, H₃-napht), 7.29-7.26 (m, 5H, Phe), 6.03, 6.01 (2×s, 1H, H₁ᵢ), 5.77, 5.69 (2×q, J=5.0 Hz, CH ester), 4.68-4.54 (m, 2H, H₅ᵢ), 4.35, 4.31 (2×d, J=9.0 Hz, 1H, H₃ᵢ), 4.28-4.23 (m, 1H, H₄ᵢ), 4.16-4.12 (m, 1H, Hα Met), 4.04, 4.03 (2×s, 3H, 6O-CH₃), 2.33-2.11 (m, 1H, CH₂—S), 1.93-1.86, 1.80-1.72 (2×m, 2H, CHCH₂ Met), 1.82, 1.81 (2×s, 3H, S—CH₃), 1.40, 1.39 (2×d, J=5.0 Hz, 3H, CH₃ ester), 0.98, 0.97 (2×s, 3H, 2'-CH₃).

¹³C NMR (126 MHz, CD₃OD) δ 173.63 (d, ³J_{C—C—N—P}=3.8 Hz, C═O ester), 173.33 (d, ³J_{C—C—N—P}=3.8 Hz, C═O ester), 162.75 (C6), 161.87 (C2), 154.58, 154.54 (C4), 147.98, 147.95 (2×d, ²J_{C—O—P}=6.3 Hz, ipso Naph), 139.42, 139.12 (CH8), 137.68 (ipso Ph), 136.29, 136.25 (napht-C10), 129.68, 129.57, 129.55, 129.08, 128.88, 128.86, (Naph, Ph), 127.89 (d, ³J_{C—C—O—P}=3.8 Hz, naph-C9), 127.79 (d, ³J_{C—C—O—P}=3.8 Hz, naph-C9), 127.55, 127.53, 127.25, 126.53, 126.00, 122.86, 122.83 (Naph, Ph), 116. 27, 116.25 (C2-Naph), 115.67, 115.62 (C5), 93.37, 93.17 (C1'), 82.36 (d, ³J_{C—C—O—P}=7.5 Hz, C4'), 82.15 (d, ³J_{C—C—O—P}=8.8 Hz, C4'), 80.00, 79.94 (C2'), 75.03, 74.96 (C3'), 74.92, 74.70 (CH ester), 68.26, 67.66 (2×d, ²J_{C—O—P}=6.25 Hz, C5'), 55.20, 55.12 (CαMet), 55.02, 54.32 (6OCH₃), 34.34, 34.17 (2×d, ³J_{C—C—N—P}=7.5 Hz, CβMet), 30.65, 30.61 (CH₂S Met), 22.47, 22.41 ( CH₃ ester) 20.40, 20.38 (2'CCH₃), 15.13, 15.11 (CH₃ Met).

³¹P NMR (202 MHz, CD₃OD) δ 4.53, 4.44

Example 60

The (2S)-neopentyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy) phosphorylamino)-4-(methylthio)butanoate was synthesized as follows

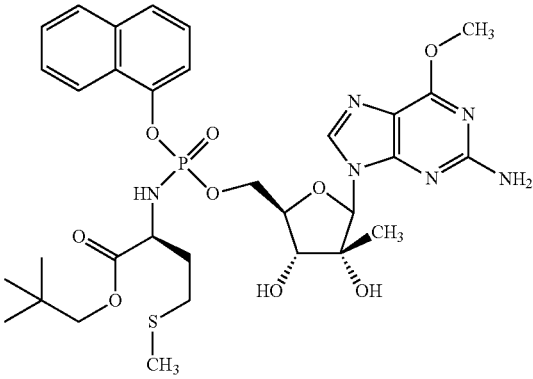 [SMILES: COc1nc(N)nc2c1ncn2C1O[C@H](COP(=O)(N[C@@H](CCSC)C(=O)OCC(C)(C)C)Oc2cccc3ccccc23)[C@@H](O)[C@@]1(C)O]

Step 1: (2S)-neopentyl 2-(chloro(naphthalen-1-yloxy)phosphorylamino)-4-(methylthio)butanoate

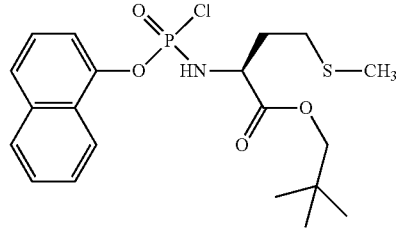 [SMILES: CSCC[C@H](NP(=O)(Cl)Oc1cccc2ccccc12)C(=O)OCC(C)(C)C]

Using the general procedure for synthesizing naphthyl (aminoacid ester) phosphorochloridates the tosylate salt of (S)-neopentyl 2-amino-4-(methylthio)butanoate (2.00 g, 5.11 mmol), naphthalene-1-yl phosphorodichloridate (1.30 g, 5.11 mmol) and TEA (1.42 mL, 10.22 mmol) in 30 mL of dry DCM, were combined to give (2S)-neopentyl 2-(chloro (naphthalen-1-yloxy)phosphorylamino)-4-(methylthio)butanoate in 41% yield (0.92 g), as a clear, yellow, thick oil.

The following are the NMR results for the synthesized compound:

¹H NMR (500 MHz, CDCl₃) δ 8.15-8.11 (m, 1H, H₈-napht), 7.87 (d, J=8.20 Hz, 1H, H₅-napht), 7.73 (d, J=8.85, 1H, H₄-napht), 7.67-7.52 (m, 3H, H₇, H₆, H₂-napht), 7.43 (t, J=8.00 Hz, 1H, H₃-napht), 4.97 (bs, 1H, NH), 4.48-4.41 (m, 1H, CHa), 3.93, 3.90, 3.89, 3.86 (AB, J_{AB}=10.50 Hz, 2H, CH₂ ester) 2.65-2.58 (m, 2H, CH₂—S), 2.25-2.07 (m, 5H, CH₂ and CH₃ Met), 0.99, 0.96 (2×s, 9H, 3×CH₃ ester).

³¹P NMR (202 MHz, CDCl₃) δ 8.92, 8.74

Step 2: Synthesis of Protide

Using the general procedure (Method B) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, to a solution of 250 mg (0.803 mmol) of nucleoside in 5 mL of THF, was added tert-BuMgCl 1.61 mL (1.61 mmol), followed by (2S)-neopentyl 2-(chloro(naphthalen-1-yloxy)phosphorylamino)-4-(methylthio)butanoate 713 mg (1.61 mmol) in 5 mL of THF. After workup and silica gel column chromatography, 214 mg of pure protide was obtained in a 37% yield, as an off-white solid.

The following are the NMR results analyzing the synthesized compound:

$^1$H NMR (500 MHz, CD$_3$OD) δ 8.23-8.16 (m, 1H, H$_8$-napht), 7.99, 7.97 (2×s, 1H, H$_8$) 7.88-7.8. (m, 1H, H$_5$-napht), 7.69, 7.66 (2×d, J=8.6 Hz, 1H, H$_4$-napht), 7.55-7.45 (m, 3H, H$_7$, H$_6$, H$_2$-napht), 7.41, 7.37 (2×t, J=8.0 Hz, 1H, H$_3$-napht), 6.01, 6.00 (2×s, 1H, H$_{1'}$), 4.72-4.59 (m, 2H, H$_{5'}$), 4.35-4.23 (m, 2H, H$_{3'}$ and H$_{4'}$), 4.18-4.13 (m, 1H, Ha), 4.05, 4.04 (2×s, 3H, 6O -CH$_3$), 3.75, 3.71, 3.66, 3.62 (2×AB, J$_{AB}$=10.0 Hz, 2H, CH$_2$ ester), 2.47-2.38, 2.32-2.29 (2×m, 1H, CH$_2$—S), 2.02-1.81 (m, 5H, S—CH$_3$ and CH$_2$ Met), 0.98, 0.97 (2×s, 3H, 2'-CH$_3$), 0.88, 0.85 (2×s, 9H, 3×CH$_3$).

$^{13}$C NMR (126 MHz, CD$_3$OD) δ 174.52 (d, $^3J_{C-C-N-P}$=3.8, C=O ester), 174.2 (d, $^3J_{C-C-N-P}$=3.8, C=O ester), 162.7 (C6), 161.9, 161.8 (C2), 154.5, 154.5 (C4), 148.00 (d, $^2J_{C-O-P}$=6.3, napht-C1), 147.95 (d, $^2J_{C-O-P}$=6.3, napht-C1), 139.4, 139.2 (CH8), 136.3, 136.25 (napht-C10), 128.9, 128.8 (napht-O5), 127.9 (d, $^3J_{C-C-O-P}$=3.8, napht-C9), 127.8 (d, $^3J_{C-C-O-P}$=5.0, napht-C9), 127.7 (CH-napht), 127.6, 127.5 (CH-napht), 126.5 (CH-napht), 126.0 (CH-napht), 122.8 (CH-napht), 116.3 (d, $^3J_{C-C-O-P}$=3.8, napht-C2), 116.1 (d, $^3J_{C-C-O-P}$=2.5, napht-C2), 115.7, 115.6 (C5), 93.3, 93.2 (C1'), 82.3 (d, $^3J_{C-C-O-P}$=7.5, C4'), 82.2 (d, $^3J_{C-C-O-P}$=8.8, C4'), 80.0, 79.9 (C2'), 75.6 (CH$_2$ ester), 74.9, 74.8 (C3'), 68.2 (d, $^2J_{C-O-P}$=5.0, C5'), 67.8 (d, $^2J_{C-O-P}$=3.8, C5'), 55.2, 55.1 (CaMet), 54.2, 54.0 (O$^6$—CH$_3$), 34.5 (d, $^3J_{C-C-N-P}$=6.3, CbMet), 34.3, (d, $^3J_{C-C-N-P}$=7.5, Cb Met), 32.2, 32.1 (C-ester), 31.0, 30.9 (CH$_2$S? Met), 26.9, 28.8, 28.7 (3×CH$_3$ ester) 20.4, 20.3 (2'-CH$_3$), 15.2, 15.1 (CH$_3$ Met).

$^{31}$P NMR (202 MHz, CD$_3$OD) δ 4.50, 4.44

Example 61

The (2S)-neopentyl 2-(((((2R,3R,4R,5R)-5-(2-amino-6-methoxy-9H-purin-9-yl)-3,4-dihydroxy-4-methyltetrahydrofuran-2-yl)methoxy)(naphthalen-1-yloxy)phosphorylamino)-4-methylpentanoate was synthesized as follows

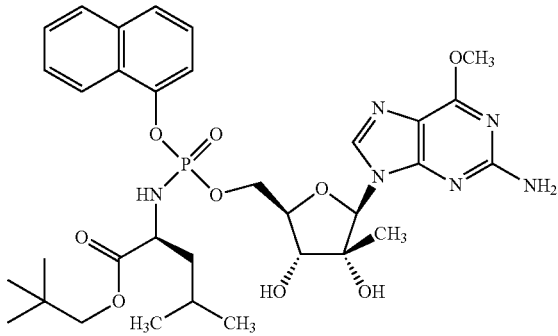 [SMILES: COc1nc(N)nc2c1ncn2[C@@H]1O[C@H](COP(=O)(N[C@@H](CC(C)C)C(=O)OCC(C)(C)C)Oc2cccc3ccccc23)[C@@H](O)[C@@]1(C)O]

Step 1: (2S)-neopentyl 2-(chloro(naphthalen-1-yloxy)phosphorylamino)-4-methylpentanoate

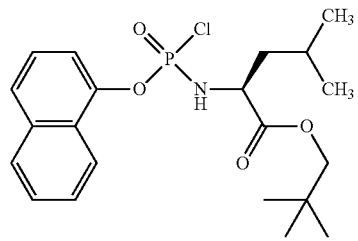 [SMILES: CC(C)C[C@H](NP(=O)(Cl)Oc1cccc2ccccc12)C(=O)OCC(C)(C)C]

Using the general procedure for synthesizing naphthyl (aminoacid ester) phosphorochloridates the tosylate salt of (S)-neopentyl 2-amino-4-methylpentanoate (2.33 g), naphthalen-1-yl phosphorodichloridate (1.63 g), TEA (1.74 mL) and DCM (70 mL) were combined to give (2S)-neopentyl 2-(chloro(naphthalen-1-yloxy)phosphorylamino)-4-methylpentanoate in an 77% yield (2.04 g), as a pale yellow thick oil.

The following are the NMR results analyzing the synthesized compound:

$^1$H NMR (500 MHz, CDCl$_3$) δ 8.15-8.08 (m, 1H), 7.91-7.86 (m, 1H), 7.74 (d, J=7.9, 1H), 7.66-7.42 (m, 4H), 4.52-4.40 (m, 1H), 4.32-4.23 (m, 1H), 3.96-3.83 (m, 2H), 1.92-1.62 (m, 3H), 1.04-0.87 (m, 15H)

$^{31}$P NMR (202 MHz, CDCl$_3$) δ 8.70, 8.48

Step 2: Synthesis of Protide

Using the general procedure (Method B) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, to a solution of 250 mg of nucleoside in 5 mL of THF was added tert-BuMgCl (1.61 mL) followed by (2S)-neopentyl 2-(chloro(naphthalen-1-yloxy)phosphorylamino)-4-methylpentanoate (1.03 g) in THF (3 mL). After workup, silica gel column chromatography and preparative TLC, 39.4 mg of pure protide was obtained (7% yield). HPLC t$_R$=32.79, 33.31 min (column: Varian Pursuit XRs 5, C$_{18}$, 150×4.6 mm; method: linear gradient of MeOH (50% to 100%) in H$_2$O in 45 min).

The following are the NMR results analyzing the synthesized compound:

$^1$H NMR (500 MHz, CD$_3$OD) δ 8.22-8.13 (m, 1H), 7.98 and 7.96 (2s, 1H), 7.92-7.83 (m, 1H), 7.73-7.65 (m, 1H), 7.58-7.34 (m, 4H), 5.99 and 5.98 (2s, 1H), 4.68-4.54 (m, 2H), 4.37-4.20 (m, 2H), 4.06 and 4.05 (2s, 3H), 4.00-3.90 (m, 1H), 3.75-3.60 (m, 2H), 1.70-1.60 (m, 1H), 1.53-1.41 (m, 2H), 1.01-0.70 (m, 18H)

$^{31}$P NMR (202 MHz, CD$_3$OD) δ 4.51, 4.40

Example 62

The (2S,3R)-neopentyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylpentanoate was synthesized as follows

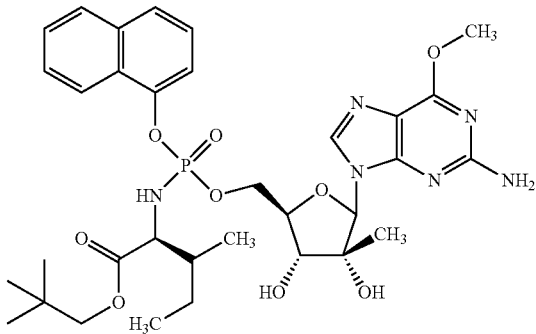 [SMILES: CCC(C)[C@H](NP(=O)(OC[C@H]1OC(n2cnc3c(OC)nc(N)nc32)[C@](C)(O)[C@@H]1O)Oc1cccc2ccccc12)C(=O)OCC(C)(C)C]

Step 1: (2S,3R)-neopentyl 2-(chloro(naphthalen-1-yloxy)phosphorylamino)-3-methylpentanoate

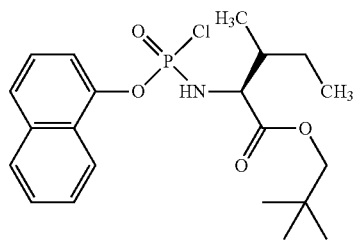 [SMILES: CCC(C)[C@H](NP(=O)(Cl)Oc1cccc2ccccc12)C(=O)OCC(C)(C)C]

Using the general procedure for synthesizing naphthyl (aminoacid ester) phosphorochloridates the tosylate salt of (2S,3R)-neopentyl 2-amino-3-methylpentanoate (2.5 g), naphthalen-1-yl phosphorodichloridate (1.75 g), TEA (1.86 mL) and DCM (50 mL) were combined to give (2S,3R)-neopentyl 2-(chloro(naphthalen-1-yloxy)phosphorylamino)-3-methylpentanoate in a 37% yield (1.06 g) as a pale yellow thick oil.

The following are the NMR results analyzing the synthesized compound:

$^1$H NMR (500 MHz, CDCl$_3$) δ 8.14-8.08 (m, 1H), 7.92-7.87 (m, 1H), 7.76 (d, J=8.3, 1H), 7.65-7.43 (m, 4H), 4.43-4.28 (m, 1H), 4.24-4.15 (m, 1H), 3.96-3.83 (m, 2H), 2.02-1.92 (m, 1H), 1.62-1.47 (m, 1H), 1.33-1.18 (m, 1H), 1.08-0.93 (m, 15H)

$^{31}$P NMR (202 MHz, CDCl$_3$) δ 9.49, 9.07

Step 2: Synthesis of Protide

Using the general procedure (Method B) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, to a solution of 243 mg of nucleoside in 5 mL of THF was added tert-BuMgCl (1.56 mL) followed by (2S,3R)-neopentyl 2-(chloro(naphthalen-1-yloxy)phosphorylamino)-3-methylpentanoate (1 g) in THF (2.8 mL). After workup and silica gel column chromatography, 98 mg of pure protide was obtained (18% yield). HPLC t$_R$=24.63 min (column: Varian Pursuit XRs 5, C$_{18}$, 150×4.6 mm; method: linear gradient of ACN (10% to 100%) in H$_2$O in 30 min).

The following are the NMR results analyzing the synthesized compound:

$^1$H NMR (500 MHz, CD$_3$OD) δ 8.21-8.13 (m, 1H), 7.95 (s, 1H), 7.90-7.83 (m, 1H), 7.72-7.65 (m, 1H), 7.56-7.34 (m, 4H), 5.98 (s, 1H), 4.65-4.55 (m, 2H), 4.40-4.22 (m, 2H), 4.05 (s, 3H), 3.90-3.82 (m, 1H), 3.72-3.57 (m, 2H), 1.78-1.67 (m, 1H), 1.48-1.37 (m, 1H), 1.14-1.02 (m, 1H), 1.02-0.75 (m, 18H)

$^{31}$P NMR (202 MHz, CD$_3$OD) δ 4.97, 4.80

Example 63

The (2S)-benzyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate was synthesized as follows

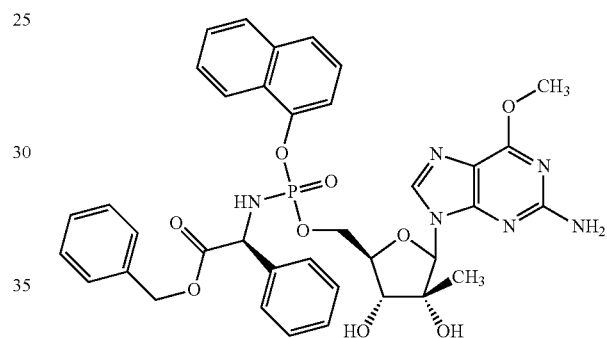

Step 1: (2S)-benzyl 2-(chloro(naphthalen-1-yloxy)phosphorylamino)-2-phenylacetate

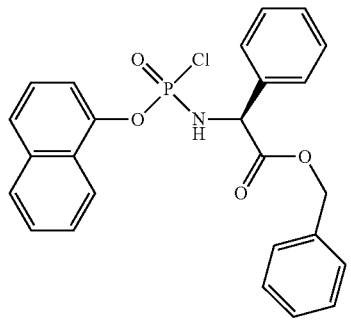 [SMILES: O=C(OCc1ccccc1)[C@@H](NP(=O)(Cl)Oc1cccc2ccccc12)c1ccccc1]

Using the general procedure for synthesizing naphthyl (aminoacid ester) phosphorochloridates the tosylate salt of (S)-benzyl 2-amino-2-phenylacetate (1.11 mg, 2.69 mmol) was dissolved with the naphthalen-1-yl phosphorodichloridate (0.72 mg, 2.74 mmol) in 5 mL anhydrous dichloromethane. The solution was cooled down to −78° C. at which 0.76 mL of triethylamine (5.45 mmol) was added dropwise. Then the mixture was left stirring for 1 h at −78° C. and then 30 min at room temperature. The solvent was removed under reduced pressure and the residue was purified by flash chromatography using Hexane/Ethyl acetate (1:1) as eluents, to provide (2S)-benzyl 2-(chloro(naphthalen-1-yloxy)phosphorylamino)-2-phenylacetate in 74% yield.

The following are the NMR results analyzing the synthesized compound:

$^1$H NMR (CDCl$_3$): 8.11-8.01 ppm (m, 1H, H$_8$-naphtyl), 7.82 ppm (d, J=8.0 Hz, H$_5$-naphtyl), 7.68 ppm (d, J=8.0 Hz, H$_4$-naphtyl), 7.55-7.46 ppm (m, H$_2$, H$_6$, H$_7$-naphtyl), 7.40-7.08 ppm (m, 12H, Phenyl, Phenylglycine & H$_3$-naphthyl), 5.31-4.91 ppm (m, 5H, NH & CH phenylglycine & CH$_2$ ester).

$^{31}$P NMR (CDCl$_3$): 7.50 ppm (s), 7.24 ppm (s)

Step 2: Synthesis of Protide

Using the general procedure (Method B) for the synthesis of nucleoside 5'-phosphoramidates, tert-BuMgCl (1.49 mL, 2 equiv) was added dropwise to (3R,4R,5R)-2-(2-amino-6-methoxy-9H-purin-9-yl)-5-(hydroxymethyl)-3-methyltetrahydrofuran-3,4-diol (234.7 mg, 0.75 mmol) in anhyd tetrahydrofuran (1.5 mL). The solution was stirred for 20 min and (2S)-benzyl 2-(chloro(naphthalen-1-yloxy)phosphorylamino)-2-phenylacetate in 1.5 mL anhydrous tetrahydrofuran was added. The solution was stirred overnight at room temperature and the solvent was removed under reduced pressure and the residue was purified on silica gel using chloroform/methanol to yield (2S)-benzyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate 0.16 g (0.22 mmol, 32%) as an off-white solid.

The following are the NMR results analyzing the synthesized compound:

$^1$H NMR (CDCl$_3$): 8.02-8.00 ppm (dd, J=8 Hz, 1H, H$_8$ naphthyl), 7.85 ppm (td, J=9.5 Hz, 2H, H$_5$ naphthyl & H$_8$), 7.66 ppm (d, J=8.5 Hz, 1H, H$_4$ naphthyl), 7.58-7.13 ppm (m, 14H, naphthyl & phenyl), 5.81 ppm (s, 1H, H$_1$'), 5.18-5.07 ppm (m, 4H, CH$_2$ ester & CH phenylglycine), 4.53-4.49 ppm (m, 1H, H$_5$'), 4.36-4.34 ppm (m, 1H), 4.30-4.25 ppm (m, 1H, H$_4$'), 4.18-4.16 (m, 1H, H$_3$'), 4.1 ppm (s, 3H, 6OCH$_3$), 0.90 ppm (2×s, 3H, 2'CH$_3$)

$^{31}$P NMR (CDCl$_3$): 3.82 ppm (s), 3.41 ppm (s)

Example 64

The (2S)-methyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate was synthesized as follows

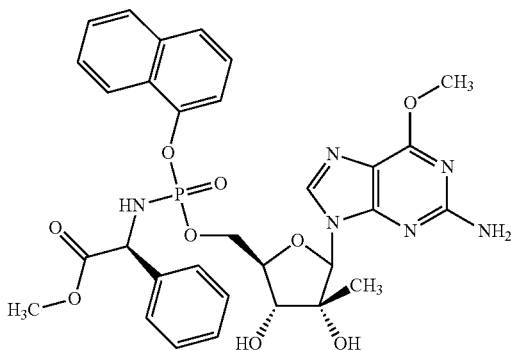 [SMILES: COC(=O)[C@@H](NP(=O)(OC[C@H]1OC(n2cnc3c(OC)nc(N)nc32)[C@](C)(O)[C@@H]1O)Oc1cccc2ccccc12)c1ccccc1]

Step 1: (2S)-methyl 2-(chloro(naphthalen-1-yloxy)phosphorylamino)-2-phenylacetate

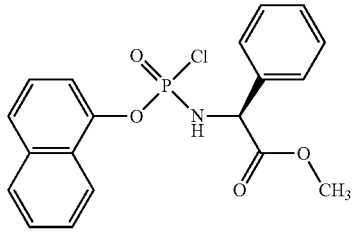 [SMILES: COC(=O)[C@@H](NP(=O)(Cl)Oc1cccc2ccccc12)c1ccccc1]

Using the general procedure for synthesizing naphthyl (aminoacid ester) phosphorochloridates, the HCl salt of (S)-methyl 2-amino-2-phenylacetate (2 g), naphthalen-1-yl phosphorodichloridate (2.59 g), TEA (2.76 mL) and DCM (60 mL) were combined to give (2S)-methyl 2-(chloro(naphthalen-1-yloxy)phosphorylamino)-2-phenylacetate as a pale yellow thick oil. The crude compound was taken forward without further purification.

The following are the NMR results analyzing the synthesized compound:

$^{31}$P NMR (202 MHz, CDCl$_3$) δ 7.64, 7.46

Step 2: Synthesis of Protide

Using the general procedure (Method B) for the synthesis of nucleoside 5'-phosphoramidates, to a solution of 250 mg of (3R,4R,5R)-2-(2-amino-6-methoxy-9H-purin-9-yl)-5-(hydroxymethyl)-3-methyltetrahydrofuran-3,4-diol in 5 mL of THF was added tert-BuMgCl (1.61 mL) followed by (2S)-methyl 2-(chloro(naphthalen-1-yloxy)phosphorylamino)-2-phenylacetate (0.94 g) in THF (5 mL). After workup and silica gel column chromatography, 314 mg of (2S)-methyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate was obtained (59% yield). HPLC t$_R$=16.24, 16.50 min (column: Varian Pursuit XRs 5, C$_{18}$, 150×4.6 mm; method: linear gradient of ACN (10% to 100%) in H$_2$O in 30 min).

The following are the NMR results analyzing the synthesized compound:

$^1$H NMR (500 MHz, CD$_3$OD) δ 8.00-7.88 (m, 2H), 7.87-7.81 (m, 1H), 7.79-7.62 (m, 1H), 7.53-7.18 (m, 9H), 5.99 and 5.97 (2s, 1H), 5.10 and 5.05 (2d, J=9.4, 1H), 4.67-4.48 (m, 2H), 4.31-4.19 (m, 2H), 4.06 and 4.05 (2s, 3H), 3.56 and 3.51 (2s, 3H), 0.97 and 0.95 (2s, 3H)

$^{31}$P NMR (202 MHz, CD$_3$OD) δ 3.95, 3.92

Example 65

The (2S)-propyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate was synthesized as follows

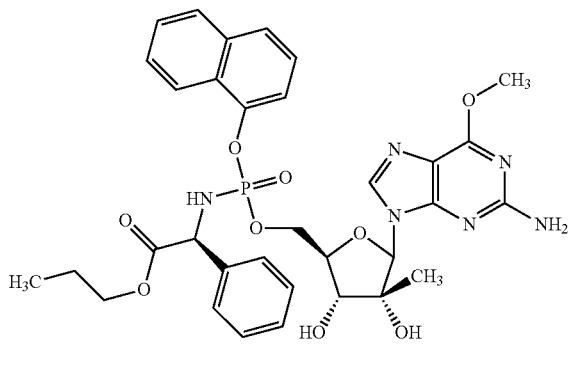 [SMILES: CCCOC(=O)[C@@H](NP(=O)(OC[C@H]1OC(n2cnc3c(OC)nc(N)nc32)[C@](C)(O)[C@@H]1O)Oc1cccc2ccccc12)c1ccccc1]

Step 1: (2S)-propyl 2-(chloro(naphthalen-1-yloxy)phosphorylamino)-2-phenylacetate

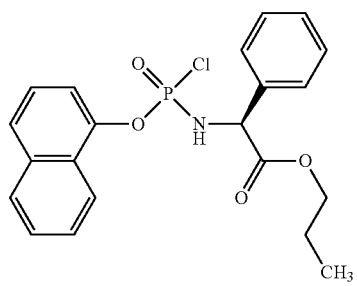 [SMILES: CCCOC(=O)[C@@H](NP(=O)(Cl)Oc1cccc2ccccc12)c1ccccc1]

Using the general procedure for synthesizing naphthyl (aminoacid ester) phosphorochloridates, the HCl salt of (S)-propyl 2-amino-2-phenylacetate (1 g), naphthalen-1-yl phosphorodichloridate (1.14 g), TEA (1.21 mL) and DCM (30 mL) were combined to give (2S)-propyl 2-(chloro(naphthalen-1-yloxy)phosphorylamino)-2-phenylacetate in an 83% yield (1.51 g) as a pale yellow thick oil.

The following are the NMR results analyzing the synthesized compound:

$^1$H NMR (500 MHz, CDCl$_3$) δ 8.13-8.00 (m, 1H), 7.95-7.86 (m, 1H), 7.73 and 7.68 (2d, J=8.2, 1H), 7.62-7.33 (m, 9H), 5.38-5.19 and 5.07-4.99 (2m, 2H), 3.80-3.77 (2s, 3H $^{31}$P NMR (202 MHz, CDCl$_3$) δ 7.62, 7.36.

Step 2: Synthesis of Protide

Using the general procedure (Method B) for the synthesis of nucleoside 5'-phosphoramidates, to a solution of (3R,4R,5R)-2-(2-amino-6-methoxy-9H-purin-9-yl)-5-(hydroxymethyl)-3-methyltetrahydrofuran-3,4-diol (250 mg) in 5 mL of THF was added tert-BuMgCl (1.61 mL) followed by (2S)-propyl 2-(chloro(naphthalen-1-yloxy)phosphorylamino)-2-phenylacetate (1.01 g) in THF (5 mL). After workup and silica gel column chromatography, 150 mg of (2S)-propyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate was obtained (22% yield). HPLC t$_R$=17.53 min (column: Varian Pursuit XRs 5, C$_{18}$, 150×4.6 mm; method: linear gradient of ACN (10% to 100%) in H$_2$O in 30 min).

The following are the NMR results analyzing the synthesized compound:

$^1$H NMR (500 MHz, CD$_3$OD) δ 8.10-7.89 (m, 2H), 7.83-7.77 (m, 1H), 7.59-7.65 (m, 1H), 7.49-7.14 (m, 9H), 6.01 and 5.99 (2s, 1H), 5.10 and 5.05 (2d, J=9.3, 1H), 4.68-4.50 (m, 2H), 4.30-4.22 (m, 2H), 4.05 and 4.04 (2s, 3H), 3.97-3.77 (m, 2H), 1.48-1.35 (m, 2H), 0.96 and 0.95 (2s, 3H), 0.72-0.64 (m, 3H)

$^{31}$P NMR (202 MHz, CD$_3$OD) δ 3.98, 3.89

Example 66

The (2S)-neopentyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate was synthesized as follows

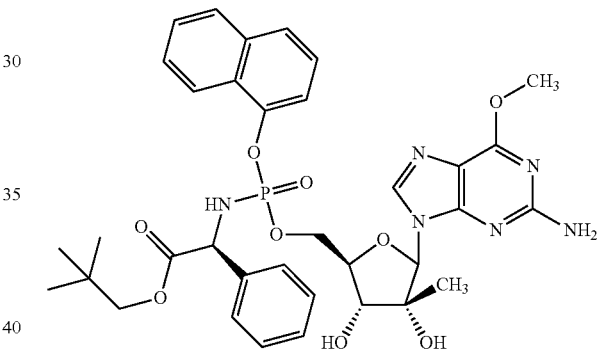

Step 1: (2S)-neopentyl 2-(chloro(naphthalen-1-yloxy)phosphorylamino)-2-phenylacetate

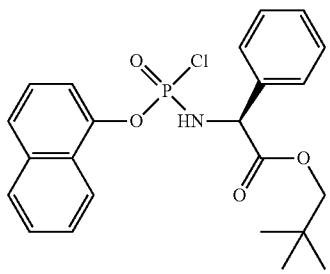 [SMILES: CC(C)(C)COC(=O)[C@@H](NP(=O)(Cl)Oc1cccc2ccccc12)c1ccccc1]

Using the general procedure for synthesizing naphthyl (aminoacid ester) phosphorochloridates the tosylate salt of (S)-neopentyl 2-amino-2-phenylacetate (1.92 g, 4.86 mmol), naphthalene-1-yloxy phosphorodichloridate (1.27 g, 4.86 mmol), triethyl amine (1.36 mL, 9.77 mmol) and dichloromethane (50 mL) were combined to give 1.6 g of desired phosphorochloridate in 74% yield as pale yellow thick oil.

The following are the NMR results analyzing the synthesized compound:

$^1$H NMR (200 MHz, CDCl$_3$): δ 8.01-7.12 (m, 24H), 5.38-5.20 (m, 1H), 5.07 (m, 1H), 3.92 (m, 2H), 3.80 (m, 2H), 0.78 (m, 9H), 0.70 (m, 9H)

$^{31}$P NMR (80 MHz, CDCl$_3$): δ 8.81, 8.50

Step 2: Synthesis of Protide

Using the general procedure (Method B) for the synthesis of nucleoside 5'-phosphoramidates, a solution of (3R,4R,5R)-2-(2-amino-6-methoxy-9H-purin-9-yl)-5-(hydroxymethyl)-3-methyltetrahydrofuran-3,4-diol (560 mg, 1.19 mmol) in anhydrous THF (25 mL) was combined with (2S)-neopentyl 2-(chloro(naphthalen-1-yloxy)phosphorylamino)-2-phenylacetate (1.6 g, 3.6 mmol), and tert-butyl magnesium chloride (3.6 mL, 3.6 mmol). After normal work-up the crude product was purified by column chromatography on silica gel twice using CH$_2$Cl$_2$/MeOH (95:5) and then with ethyl acetate/methanol (97:3) to give 498 mg of protide in 38% yield as an off-white solid.

The following are the NMR results analyzing the synthesized compound.

$^1$H NMR (200 MHz, CD$_3$OD): δ 7.96-7.86 (m, 3H), 7.64-7.15 (m, 10H), 5.94 (d, J=2.6 Hz, 1H), 5.96 (d, J=2.6 Hz, 1H), 5.05 (dd, J=9.6 Hz, 9.6 Hz, 1H), 4.57 (m, 2H), 4.21 (m, 2H), 4.03 (s, 3H), 3.73 (m, 1H), 0.93 (d, J=3.6 Hz, 3H), 0.62 (m, 9H).

$^{31}$P NMR (80 MHz, CD$_3$OD): δ 5.06

Example 67

The (2S)-cyclohexyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate was synthesized as follows

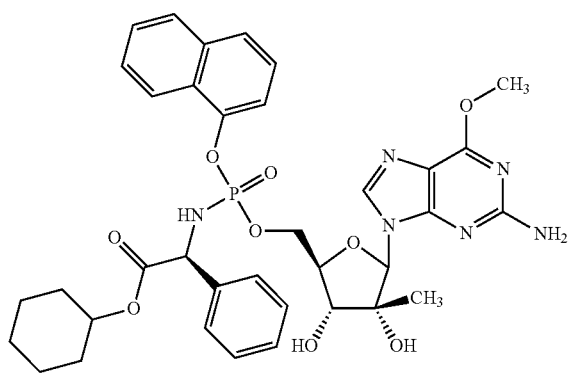 [SMILES: COc1nc(N)nc2c1ncn2C1O[C@H](COP(=O)(N[C@H](C(=O)OC2CCCCC2)c2ccccc2)Oc2cccc3ccccc23)[C@@H](O)[C@@]1(C)O]

Step 1: (2S)-cyclohexyl 2-(chloro(naphthalen-1-yloxy)phosphorylamino)-2-phenylacetate

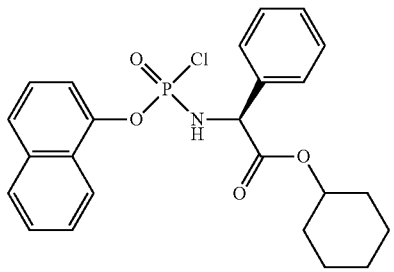 [SMILES: O=C(OC1CCCCC1)[C@@H](NP(=O)(Cl)Oc1cccc2ccccc12)c1ccccc1]

Using the general procedure for synthesizing naphthyl (aminoacid ester) phosphorochloridates, the HCl salt of (S)-cyclohexyl 2-amino-2-phenylacetate (1 g), naphthalen-1-yl phosphorodichloridate (967 mg), TEA (1.03 mL) and DCM (30 mL) were combined to give (2S)-cyclohexyl-2-(chloro(naphthalen-1-yloxy)phosphorylamino)-2-phenylacetate in an 78% yield (1.32 g) as a pale yellow thick oil.

The following are the NMR results analyzing the synthesized compound:

$^1$H NMR (500 MHz, CDCl$_3$) δ 8.13-8.00 (m, 1H), 7.94-7.86 (m, 1H), 7.74 and 7.68 (2d, J=8.2, 1H), 7.62-7.30 (m, 9H), 5.34-5.13 and 5.01-4.92 (2m, 2H), 4.91-4.83 (m, 1H), 1.90-1.20 (m, 10H)

$^{31}$P NMR (202 MHz, CDCl$_3$) δ 7.72, 7.47

Step 2: Synthesis of Protide

Using the general procedure (Method B) for the synthesis of nucleoside 5'-phosphoramidates to a solution of 250 mg of (3R,4R,5R)-2-(2-amino-6-methoxy-9H-purin-9-yl)-5-(hydroxymethyl)-3-methyltetrahydrofuran-3,4-diol in 5 mL of THF was added tert-BuMgCl (1.61 mL) followed by (2S)-cyclohexyl 2-(chloro(naphthalen-1-yloxy)phosphorylamino)-2-phenylacetate (1.10 g) in THF (5 mL). After workup and silica gel column chromatography, 310 mg of (2S)-cyclohexyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate was obtained (53% yield). HPLC t$_R$=21.47, 21.65 min (column: Varian Pursuit XRs 5, C$_{18}$, 150×4.6 mm; method: linear gradient of ACN (10% to 100%) in H$_2$O in 30 min).

The following are the NMR results analyzing the synthesized compound:

$^1$H NMR (500 MHz, CD$_3$OD) δ 8.00-7.81 (m, 3H), 7.69-7.62 (m, 1H), 7.54-7.17 (m, 9H), 6.00 and 5.97 (2s, 1H), 5.04 and 5.00 (2d, J=9.4, 1H), 4.68-4.50 (m, 3H), 4.28-4.20 (m, 2H), 4.07 and 4.06 (2s, 3H), 1.69-1.09 (m, 10H), 0.96 and 0.95 (2s, 3H)

$^{31}$P NMR (202 MHz, CD$_3$OD) δ 4.00, 3.84

Example 68

The (2R)-benzyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate was synthesized as follows

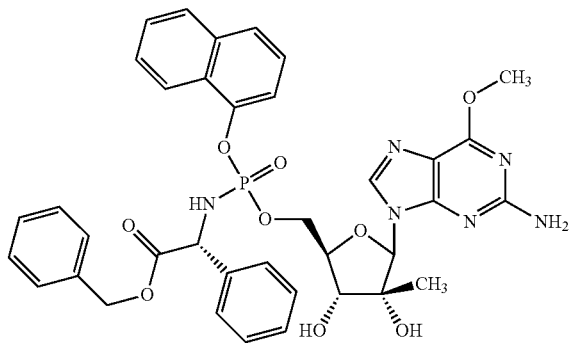 [SMILES: COc1nc(N)nc2c1ncn2C1O[C@H](COP(=O)(N[C@@H](C(=O)OCc2ccccc2)c2ccccc2)Oc2cccc3ccccc23)[C@@H](O)[C@@]1(C)O]

Step 1: (2R)-benzyl 2-(chloro(naphthalen-1-yloxy)phosphorylamino)-2-phenylacetate

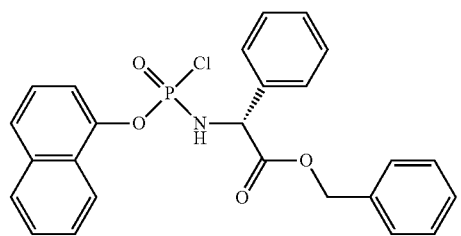 [SMILES: O=C(OCc1ccccc1)[C@H](NP(=O)(Cl)Oc1cccc2ccccc12)c1ccccc1]

Using the general procedure for synthesizing naphthyl (aminoacid ester) phosphorochloridates the tosylate salt of (R)-benzyl 2-amino-2-phenylacetate (1.50 g, 3.63 mmol), and naphthalen-1-yl phosphorodichloridate (0.95 g, 3.63 mmol) and TEA (1.01 mL, 7.26 mmol) in 20 mL of dry DCM, were combined to give (2R)-benzyl 2-(chloro(naphthalen-1-yloxy)phosphorylamino)-2-phenylacetate in 72% yield (1.21 g), as a clear, yellow, thick oil.

The following are the NMR results analyzing the synthesized compound:

$^1$H NMR (500 MHz, CDCl$_3$) δ 8.11-8.01 (m, 1H, H$_8$-napht), 7.87, 7.81 (2×d, J=8.50 Hz, 1H, H$_5$-napht), 7.72, 7.67 (2×d, J=8.0 Hz, 1H, H$_4$-napht), 7.58-7.48 (m, 3H, H$_7$, H$_6$, H$_2$,), 7.40-7.19 (m, 11H, Ph, PhG and H$_3$-napht), 5.42-5.09 (m, 2H, NH and CHα PhG).

$^{31}$P NMR (202 MHz, CDCl$_3$) δ 7.60, 7.42

Step 2: Synthesis of Protide

Using the general procedure (Method B) for the synthesis of nucleoside 5'-phosphoramidates, to a solution of (3R,4R,5R)-2-(2-amino-6-methoxy-9H-purin-9-yl)-5-(hydroxymethyl)-3-methyltetrahydrofuran-3,4-diol 250 fmg (0.803 mmol) in 5 mL of THF was added tert-BuMgCl 1.61 mL (1.61 mmol), followed by (2R)-benzyl 2-(chloro(naphthalen-1-yloxy)phosphorylamino)-2-phenylacetate 932 mg (1.60 mmol) in 5 mL of THF. After workup and silica gel column chromatography, 286 mg of pure protide was obtained in a 48% yield, as an off-white solid.

The following are the NMR results analyzing the synthesized compound.

$^1$H NMR (500 MHz, CD$_3$OD) δ 8.02, 7.99 (2×d, J=7.50 Hz, 1H, H$_8$-napht), 7.95, 7.94 (2×s, 1H, H$_8$) 7.83, 7.81 (2×d, J=8.50 Hz, 1H, H$_5$-napht), 7.65, 7.62 (2×d, J=8.00 Hz, 1H, H$_4$-napht), 7.49-7.06 (m, 14H, H$_7$, H$_6$, H$_2$, H$_3$-napht, Ph,), 5.99, 5.98 (2×s, 1H, H$_{1'}$), 5.15-5.04 (m, 2H, CH$_2$ ester), 5.00, 4.97 (2×d, J=5.00 Hz, 1H, Hα, PhG), 4.65-4.51 (m, 2H, H$_{5'}$), 4.35-4.21 (m, 2H, H$_{3'}$, and H$_{4'}$), 4.05 (s, 3H, 6O-CH$_3$), 0.97, 0.95 (2×s, 3H, 2'-CH$_3$)

$^{13}$C NMR (126 MHz, CD$_3$OD) δ 172.81 (d, $^3J_{C-C-N-P}$=6.3 Hz, C=O ester), 172.55 (d, $^3J_{C-C-N-P}$=6.3 Hz, C=O ester), 162.75, 162.71 (C6), 161.81 (C2), 154.59, 154.49 (C4), 147.87, 147.82 (ipso Naph), 139.44, 139.98 (CH8), 138.90 (ipso Ph), 136.82, 136.76 (napht-C10), 136.18 (ipso-Ph), 129.85, 129.69, 129.47, 129.41, 129.30, 129.16, 129.14, 128.98, 128.89, 128.83, 128.75, 128.26, 127.84, 127.78, 127.71, 127.52, 127.43, 126.45, 126.40, 126.00, 125.96, 122.85, 122.76 (Naph, 2×Ph), 116.37 (d, $^3J_{C-C-O-P}$=3.8 Hz, C2-Naph), 116.03 (d, $^3J_{C-C-O-P}$=2.5 Hz, C2-Naph), 115.72, 115.65 (C5), 93.38, 93.06 (C1'), 82.32 (d, $^3J_{C-C-O-P}$=7.50 Hz, C4'), 81.98 (d, $^3J_{C-C-O-P}$=7.50 Hz, C4'), 80.02 (C2'), 75.00, 74.56 (C3'), 68.24 (d, $^2J_{C-O-P}$=5.00 Hz, C5'), 68.15 (d, $^2J_{C-O-P}$=6.25 Hz, C5'), 67.24 (CH$_2$ ester), 60.00, 59.79 (Cα PhG), 54.38 (6OCH$_3$), 20.48 (2'CCH$_3$)

$^{31}$P NMR (202 MHz, CD$_3$OD) δ 4.37, 3.65

Example 69

The (2R)-propyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate was synthesized as follows

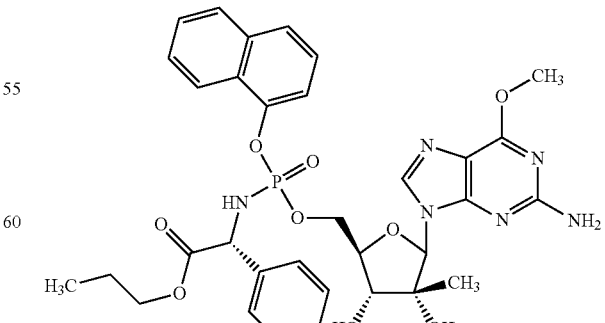

Step 1: (2R)-propyl 2-(chloro(naphthalen-1-yloxy)phosphorylamino)-2-phenylacetate

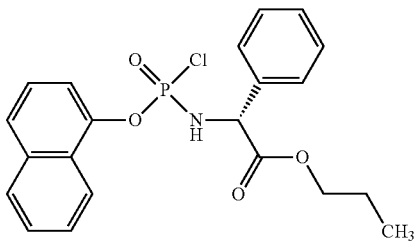 [SMILES: CCCOC(=O)[C@H](NP(=O)(Cl)Oc1cccc2ccccc12)c1ccccc1]

Using the general procedure for synthesizing naphthyl (amino acid ester) phosphorochloridates the hydrochloride salt of (R)-propyl 2-amino-2-phenylacetate (2.00 g, 8.71 mmol), naphthalen-1-yl phosphorodichloridate (2.27, 8.71 mmol) and TEA (2.42 mL, 17.41 mmol) were combined in 20 mL of dry DCM, to give (2R)-propyl 2-(chloro(naphthalen-1-yloxy)phosphorylamino)-2-phenylacetate in 59% yield (2.15 g), as a clear, yellow, thick oil.

The following are the NMR results analyzing the synthesized compound:

$^1$H NMR (500 MHz, CDCl$_3$) δ 8.06-8.04 (m, 1H, H$_8$-napht), 7.87, 7.81 (2×d, J=6.00 Hz, 1H, H$_5$-napht), 7.81, 7.67 (2×d, J=8.0 Hz, 1H, H$_4$-napht), 7.57-7.44 (m, 4H, H$_7$, H$_6$, H$_2$, H$_3$-napht), 7.40-7.37 (m, 5H, PhG), 5.37-5.24 (m, 1H, NH), 5.18-4.991 (m, 1H, CHα), 4.15 (q, J=7.00 Hz, 2H, O—CH$_2$ ester), 1.65-1.59 (m, 2H, O—CH$_2$—CH$_2$ ester), 0.84 (t, J=7.00 Hz, 3H, CH$_3$ ester).

$^{31}$P NMR (202 MHz, CDCl$_3$) δ 7.72, 7.52

Step 2: Synthesis of Protide

Using the general procedure (Method B) for the synthesis of nucleoside 5'-phosphoramidates, to a solution of (3R,4R,5R)-2-(2-amino-6-methoxy-9H-purin-9-yl)-5-(hydroxymethyl)-3-methyltetrahydrofuran-3,4-diol (250 mg, (0.803 mmol) in 5 mL of THF), was added tert-BuMgCl (1.61 mL (1.61 mmol)), followed by (2R)-propyl 2-(chloro(naphthalen-1-yloxy)phosphorylamino)-2-phenylacetate (670 mg (1.60 mmol)) in 5 mL of THF. After workup and silica gel column chromatography, 395 mg of pure protide was obtained in a 71% yield, as an off-white solid.

The following are the NMR results analyzing the synthesized compound:

$^1$H NMR (500 MHz, CD$_3$OD) δ 8.00-7.96 (m, 2H, H$_8$-naph and H$_8$), 7.84, 7.81 (2×d, J=8.00 Hz, 1H, H$_5$-napht), 7.65, 7.62 (2×d, J=8.50 Hz, 1H, H$_4$-napht), 7.50-7.37 (m, 3H, H$_2$, H$_7$, H$_6$-napht), 7.31-7.30 (m, 1H, H$_3$-napht), 7.28-7.18 (m, 5H, PhG), 6.01, 5.99 (2×s, 1H, H$_{1'}$), 5.05, 5.01 (2×d, J=9.00 Hz, 1H, CHα PhG), 4.66-4.53 (m, 2H, H$_{5'}$), 4.36, 4.29 (2×d, J=9.00 Hz, 1H, H$_{3'}$), 4.27-4.20 (m, 1H, H$_{4'}$), 4.06 (s, 3H, 6OCH$_3$), 3.98-3.88 (m, 2H, OCH$_2$ ester), 1.49-1.39 (m, 2H, OCH$_2$CH$_2$ ester), 0.98, 0.97 (2×s, 3H, 2'CCH$_3$), 0.71, 0.69 (2×t, J=7.50 Hz, 3H, CH$_3$ ester)

$^{13}$C NMR (126 MHz, CD$_3$OD) δ 173.05, 172.75 (2×d, $^3J_{C—C—N—P}$=5.0 Hz, C=O ester), 162.77, 162.70 (C6), 161.91, 161.85 (C2), 154.65, 154.50 (C4), 147.89, 147.84 (ipso Naph), 139.45, 139.09 (CH8), 139.29 (d, $^3J_{C—C—N—P}$=6.30 Hz, ipso Ph, PhG), 139.20 (d, $^3J_{C—C—N—P}$=5.0 Hz, ipso Ph, PhG), 136.23, 136.20 (C10-Naph), 129.61, 129.19, 128.72, 128.69, 128.16, 128.14, (CH-napht and Ph), 127.86, 127.76 (2×d, $^3J_{C—C—O—P}$=6.3 Hz, C9-Naph), 127.67, 127.43, 127.37, 126.40, 126.34, 125.93, 125.89, 122.82, 122.76 (CH-Naph and Ph), 116.25, 115.95 (2×d, $^3J_{C—C—O—P}$=2.5 Hz, C2-Naph), 115.64, 115.56 (C5), 93.40, 93.08 (C1'), 82.32 (d, $^3J_{C—C—O—P}$=7.55 Hz, C4'), 82.00 (d, $^3J_{C—C—O—P}$=8.8 Hz, C4'), 79.97, 79.93 (C2'), 74.96, 74.60 (C3'), 68.24 (d, $^2J_{C—O—P}$=2.5 Hz, C5'), 68.15 (d, $^2J_{C—O—P}$=5.0 Hz, C5'), 67.29, 67.25 (OCH$_2$ ester), 59.93, 59.73 (d, $^2J_{C—N—P}$=5.0 Hz, C5', Cα PhG), 54.27, 54.22 (6OCH$_3$), 22.80, 22.77 (O—CH$_2$—CH$_2$ ester), 20.33, 20.28 (2'CHH$_3$), 10.43, 10.41 (CH$_3$ ester)

$^{31}$P NMR (202 MHz, CD$_3$OD) δ 4.38, 3.68

Example 70

The (2R)-neopentyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate was synthesized as follows

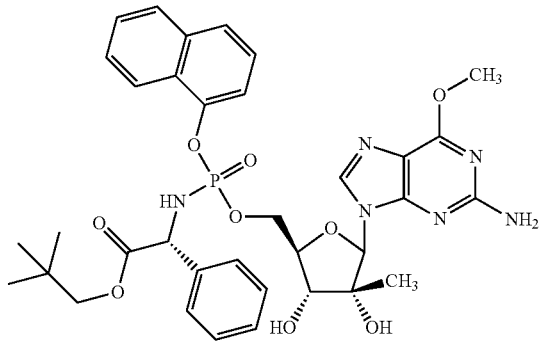 [SMILES: COc1nc(N)nc2c1ncn2C1O[C@H](COP(=O)(N[C@@H](C(=O)OCC(C)(C)C)c2ccccc2)Oc2cccc3ccccc23)[C@@H](O)[C@@]1(C)O]

Step 1: (2R)-neopentyl 2-(chloro(naphthalen-1-yloxy)phosphorylamino)-2-phenylacetate

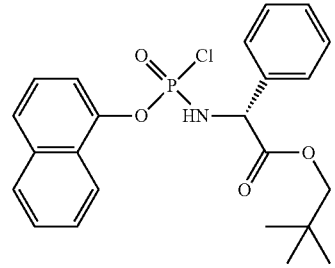 [SMILES: CC(C)(C)COC(=O)[C@H](NP(=O)(Cl)Oc1cccc2ccccc12)c1ccccc1]

Using the general procedure for synthesizing naphthyl (aminoacid ester) phosphorochloridates the tosylate salt of (R)-neopentyl 2-amino-2-phenylacetate (0.81 g, 2.08 mmol), naphthalen-1-yloxy phosphorodichloridate (0.54 g, 2.08 mmol), triethylamine (0.58 mL, 4.16 mmol) and dichloromethane (10 mL) were combined to give 0.51 g of desired (2R)-neopentyl 2-(chloro(naphthalen-1-yloxy)phosphorylamino)-2-phenylacetate in 58% yield as pale yellow thick oil.

The following are the NMR results analyzing the synthesized compound.

$^1$H NMR (200 MHz, CDCl$_3$): δ 8.1-7.25 (m, 12H), 5.3 (m, 1H), 5.2 (m, 1H), 3.8 (m, 2H), 0.79 (s, 9H)

$^{31}$P NMR (80 MHz, CDCl$_3$): δ 8.36, 8.52

Step 2: Synthesis of Protide

Using the general procedure (Method B) for the synthesis of 5'-phosphoramidates of (3R,4R,5R)-2-(2-amino-6-methoxy-9H-purin-9-yl)-5-(hydroxymethyl)-3-methyltetrahydrofuran-3,4-diol, the nucleoside (361 mg, 1.16 mmol) in anhydrous THF (10 mL) was combined with (2R)-neopentyl 2-(chloro(naphthalen-1-yloxy)phosphorylamino)-2-phenylacetate (0.51 g, 1.16 mmol), and tert-butyl magnesium chloride (1.16 mL, 1.16 mmol) was stirred for 12 h. After normal work-up the crude product was purified by column chromatography on silica gel using CH$_2$Cl$_2$/MeOH (96:4) to give 153 mg of protide in 19% yield as an off-white solid. The $^{31}$P NMR data showed that some of the product had epimerized at the amino acid position so that this material was ~10% the L-phenylglycine derivative.

The following are the NMR results analyzing the synthesized compound.

$^1$H NMR (200 MHz, CDCl$_3$): 7.9 (m, 1H), 7.8 (m, 1H), 7.6 (m, 1H), 7.5-7.15 (m, 10H), 5.97 (s, 1H), 5.92 (s, 1H), 5.1 (m, 1H), 4.6 (m, 2H), 4.2 (m, 2H), 4.02 (s, 3H), 3.9-3.6 (m, 2H), 3.44-3.6 (m, 1H), 0.9 (m, 3H), 0.78 (s, 3H), 0.65 (m, 6H)

$^{31}$P NMR (80 MHz, CDCl$_3$): δ 5.608. 5.065, 4.80

Example 71

The (2R)-cyclohexyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate was synthesized as follows

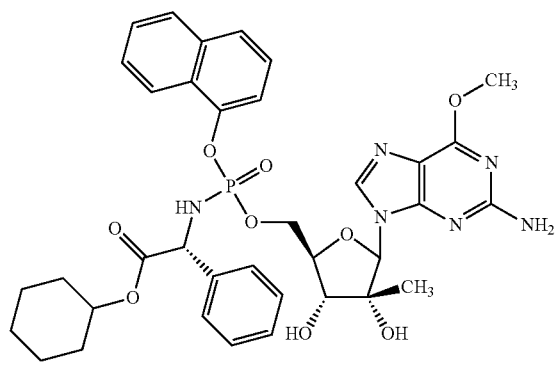 [SMILES: COc1nc(N)nc2c1ncn2C1O[C@H](COP(=O)(N[C@@H](C(=O)OC2CCCCC2)c2ccccc2)Oc2cccc3ccccc23)[C@@H](O)[C@@]1(C)O]

Step 1: (2R)-cyclohexyl 2-(chloro(naphthalen-1-yloxy)phosphorylamino)-2-phenylacetate

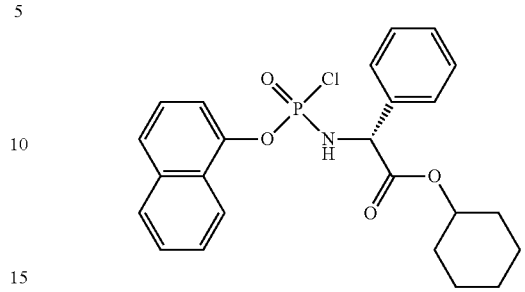

Using the general procedure for synthesizing naphthyl (aminoacid ester) phosphorochloridates the hydrochloride salt of (R)-cyclohexyl 2-amino-2-phenylacetate (2.00 g, 7.41 mmol), naphthalen-1-yl phosphorodichloridate (1.94 g, 7.41 mmol) and TEA (2.06 mL, 14.83 mmol) were combined in 15 mL of dry DCM, to give (2R)-cyclohexyl 2-(chloro(naphthalen-1-yloxy)phosphorylamino)-2-phenylacetate in 60% yield (2.75 g), as a clear, yellow, thick oil.

The following are the NMR results analyzing the synthesized compound:

$^1$H NMR (500 MHz, CDCl$_3$) δ 8.05, 7.88 (2×d, J=8.00 Hz, 1H, H$_8$-napht), 7.87 (d, J=8.50 Hz, 1H, H$_5$-napht), 7.72, 7.66 (2×d, J=8.0 Hz, 1H, H$_4$-napht), 7.58-7.45 (m, 4H, H$_7$, H$_6$, H$_2$, H$_3$-napht), 7.40-7.37 (m, 5H, PhG), 5.38-5.31 (m, 1H, NH), 5.25-5.17 (m, 1H, CHα PhG), 4.89-4.85 (m, 1H, CH ester), 1.88-1.67 (m, 2H, CH$_2$ cyclohexyl), 1.56-1.48 (m, 2H, CH$_2$ cyclohexyl), 1.46-1.33 (m, 6H, 3×CH$_2$ cyclohexyl).

$^{31}$P NMR (202 MHz, CDCl$_3$) δ 7.82, 7.64

Step 2: Synthesis of Protide

Using the general procedure (Method B) for the synthesis of nucleoside 5'-phosphoramidates, to a solution of (3R,4R,5R)-2-(2-amino-6-methoxy-9H-purin-9-yl)-5-(hydroxymethyl)-3-methyltetrahydrofuran-3,4-diol 250 mg (0.803 mmol) in 5 mL of THF, tert-BuMgCl 1.61 mL (1.61 mmol) was added, followed by (2R)-cyclohexyl 2-(chloro(naphthalen-1-yloxy)phosphorylamino)-2-phenylacetate 735 mg (1.60 mmol) in 5 mL of THF. After workup and silica gel column chromatography, 360 mg of pure protide was obtained in a 61% yield, as an off-white solid.

The following are the NMR results analyzing the synthesized compound:

$^1$H NMR (500 MHz, CD$_3$OD) δ 8.00-7.95 (m, 2H, H$_8$-naph and H$_8$), 7.83, 7.80 (2×d, J=8.00 Hz 1H, H$_5$-napht), 7.64, 7.62 (2×d, J=8.00 Hz, 1H, H$_4$-napht), 7.50-7.38 (m, 3H, H$_2$, H$_7$, H$_6$-napht), 7.33-7.18 (m, 6H, H$_3$-napht and 5H PhG), 6.02, 5.99 (2×s, 1H, H$_1$'), 5.03, 4.99 (2×d, J=9.00 Hz, 1H, CHα PhG), 4.67-4.55 (m, 3H, CH ester and H$_5$'), 4.36-4.27 (m, 2H, H$_3$', H$_4$'), 4.06 (s, 3H, 6OCH$_3$), 1.68-1.49 (m, 4H, 2×CH$_2$ ester), 1.40-1.28 (m, 4H, 2×CH$_2$ ester), 1.18-1.13 (m, 2H, CH$_2$ ester), 0.97, 0.97 (2×s, 3H, 2'CCH$_3$).

$^{13}$C NMR (126 MHz, CD$_3$OD) δ 172.40, 172.09 (2×d, $^3$J$_{C—C—N—P}$=5.0 Hz, C=O ester), 162.70, 162.70 (C6), 161.91, 161.84 (C2), 154.65, 154.51 (C4), 147.90, 147.86 (ipso Naph), 139.44, 139.03 (CH8), 139.33, 139.29 (ipso Ph PhG), 136.24, 136.21 (C10-Naph), 129.79, 129.60, 129.15, 128.74, 128.70, 128.16, 128.14

(CH-Naph and Ph), 127.86, 127.77 (2×d, $^3J_{C-C-O-P}$=6.30 Hz, C9-Naph), 127.67, 127.44, 127.37, 126.42, 126.35, 125.93, 125.89, 122.84, 122.77 (CH-Naph and Ph), 116.24, 115.94 (2×d, $^3J_{C-C-O-P}$=3.80 Hz, C2-Naph), 115.65, 115.57 (C5), 93.39, 93.05 (C1'), 82.32, 81.98 (2×d, $^3J_{C-C-O-P}$=8.80 Hz, C4'), 79.98, 79.96 (C2'), 75.26, 75.20 (CH ester), 74.97, 74.78 (C3'), 68.16, 67.25 (2×d, $^2J_{C-O-P}$=5.0 Hz, C5'), 60.02, 59.83 (d, $^2J_{C-N-P}$=3.50 Hz, C5', Cα PhG), 54.30, 54.24 (6OCH$_3$), 32.37, 32.23, 32.19, 32.00 (2×CH$_2$-2 and 6 ester), 26.37, 26.29 (2×CH$_2$-3 and 4 ester), 24.29, 24.21 (CH$_2$-5 ester), 20.36, 20.30 (2'CCH$_3$)

$^{31}$P NMR (202 MHz, CD$_3$OD) δ 4.41, 3.70

Example 72

The nucleoside (3R,4R,5R)-2-(2-amino-6-ethoxy-9H-purin-9-yl)-5-(hydroxymethyl)-3-methyltetrahydrofuran-3,4-diol was synthesized as follows

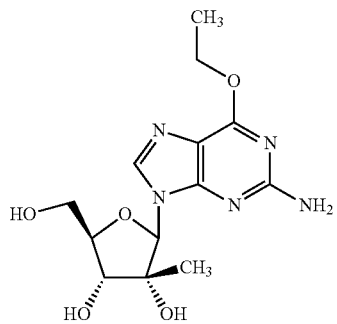 [SMILES: CCOc1nc(N)nc2c1ncn2C1O[C@H](CO)[C@@H](O)[C@@]1(C)O]

To a suspension of 2-amino-6-chloro-9-(2-C-methyl-2,3,5-tri-O-benzoyl-β-D-ribofuranosyl)purine (2.0 g, 3.19 mmol) in anhydrous ethanol (24 mL) at room temperature was added NaOEt in ethanol (1.95 g in 4.9 mL, 9 equiv). The mixture was stirred at 50° C. for 5 h, cooled down to room temperature, filtrated over cotton and quenched by addition of amberlite (H$^+$). The mixture was then filtrated and ethanol was removed under reduced pressure. The residue was purified by silica gel chromatography (CHCl$_3$/MeOH 85:15) to give 0.87 g of the pure compound as a white solid, in an 87% yield. HPLC: t$_R$=10.55 min. (column: Varian Pursuit XRs 5, C18, 150×4.6 mm. The method is: Linear gradient H$_2$O/ACN: 0% to 100% ACN in 30 min.)

The following are the NMR results analyzing the synthesized compound:

$^1$H NMR (500 MHz, CD$_3$OD) δ 8.25 (s, 1H), 5.99 (s, 1H), 4.56 (q, J=7.1), 4.23 (d, J=9.1, 1H), 4.06-4.02 (m, 2H), 3.87 (dd, J=3.0, 12.4, 1H), 1.46 (t, J=7.1, 3H), 0.96 (s, 3H).

Example 73

The (2S)-benzyl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate was synthesized as follows

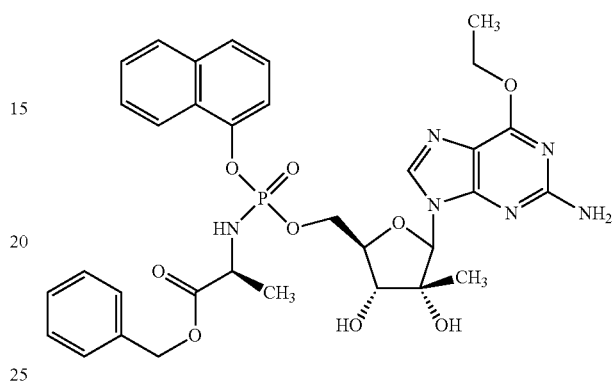

Using the general procedure for the synthesis of nucleoside 5'-phosphoramidates (Method A), to a solution of (3R,4R,5R)-2-(2-amino-6-ethoxy-9H-purin-9-yl)-5-(hydroxymethyl)-3-methyltetrahydrofuran-3,4-diol 250 mg (0.768 mmol) and NMI 0.31 mL (3.54 mmol) in 5 mL of THF, was added (2S)-benzyl 2-(chloro(naphthalen-1-yloxy)phosphorylamino)propanoate, 931 mg (2.31 mmol) in 5 mL of THF. After workup and silica gel column chromatography, 68.7 mg of pure protide was obtained in a 13% yield, as an off-white solid. MS (ES+) m/e: 693.25 (MH$^+$, 100%); Accurate mass: C$_{33}$H$_{38}$N$_6$O$_9$P$_1$ calculated 693.2438. found 693.2452.

The following are the NMR results analyzing the synthesized compound:

$^1$H NMR (500 MHz, CD$_3$OD) δ 8.17-8.15 (m, 1H, H$_8$-napht), 7.96, 7.92 (2×s, 1H, H$_8$), 7.85, 7.84 (2×d, 1H, J=8.00 Hz, H$_5$-napht), 7.67, 7.66 (2×d, J=8.00 Hz, 1H, H$_4$-napht), 7.51-7.43 (m, 3H, H$_2$, H$_7$, H$_6$-napht), 7.36, 7.35 (2×t, J=8.00 Hz, 1H, H$_3$-napht), 7.27-7.22 (m, 5H, phe), 6.00, 5.99 (2×s, 1H, H$_{1'}$), 5.05-4.95 (m, 2H, CH$_2$ ester), 4.61-4.57 (m, 2H, H$_{5'}$), 4.51, 4.50 (2×q, J=7.00 Hz, 2H, 6OCH$_2$CH$_3$) 4.34, 4.27 (2×d, J=9.00 Hz, 1H, H$_{3'}$), 4.25-4.22 (m, 1H, H$_{4'}$), 4.12-4.05 (m, 1H, CHα), 1.42, 1.41 (2×t, J=7.0 Hz, 3H, 6OCH$_2$CH$_3$), 1.30 (d, J=7.50 Hz, CH$_3$ Ala), 0.98, 0.95 (2×s, 3H, 2'CCH$_3$).

$^{13}$C NMR (126 MHz, CD$_3$OD) δ 174.80, 174.61 (d, $^3J_{C-C-N-P}$=5.0 Hz, C=O ester), 162.39, 162.38 (C6), 161.85 (C2), 154.58, 154.52 (C4), 147.98 (ipso Naph), 139.26, 138.98 (CH8), 137.13 (ipso Ph), 136.26, 136.24 (napht-C10), 129.51, 129.22, 129.15, 129.11, 128.93, 128.79 (Naph, Ph), 127.91, 127.88 (2×d, $^3J_{C-C-O-P}$=6.3 Hz, napht-C9), 127.74, 127.72, 127.48, 126.51, 126.48, 125.95, 122.83, 122.75 (Naph, Ph), 116.25, 116.23 (C2-Naph), 115.64, 115.62 (C5), 93.32, 93.14 (C1'), 82.29, 82.11 (2×d, $^3J_{C-C-O-P}$=8.8 Hz, C4'), 79.96, 79.92 (C2'), 74.94, 74.62 (C3'), 68.02, 67.91 (2×d, $^2J_{C-O-P}$=3.7 Hz, C5'), 67.49, 67.45 (CH$_2$ ester), 63.58, 63.56 (6OCH$_2$CH$_3$), 51.81, 51.72 (Cα Ala), 20.59, 20.54, 20.39 (CH$_3$ Ala), 20.36, 20.34 (2'C CH$_3$), 14.89, 14.88 (6OCH$_2$CH$_3$)

$^{31}$P NMR (202 MHz, CD$_3$OD) δ 4.31, 4.26

Example 74

The protide (2S)-2,4-difluorobenzyl 2-(((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate was synthesized as follows

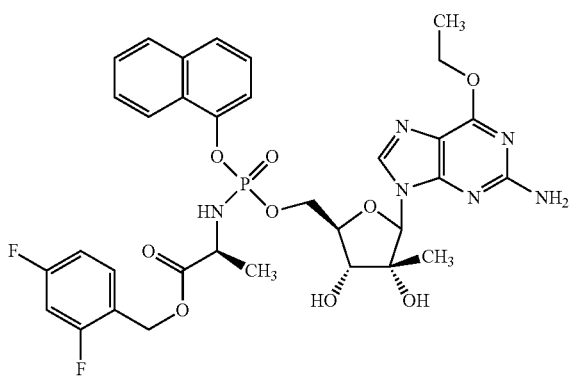 [SMILES: CCOc1nc(N)nc2c1ncn2C1O[C@H](COP(=O)(N[C@@H](C)C(=O)OCc2ccc(F)cc2F)Oc2cccc3ccccc23)[C@@H](O)[C@@]1(C)O]

Using the general procedure for the synthesis of nucleoside 5'-phosphoramidates (Method A), to a solution of 330 mg of nucleoside ((3R,4R,5R)-2-(2-amino-6-ethoxy-9H-purin-9-yl)-5-(hydroxymethyl)-3-methyltetrahydrofuran-3,4-diol) in 3.8 mL of THF, was added (404 μL) of NMI, followed by (2S)-2,4-difluorobenzyl 2-(chloro(naphthalen-1-yloxy)phosphorylamino)propanoate (1.34 g) in 3.8 mL of THF. After workup and silica gel column chromatography, 122 mg of pure protide was obtained (17% yield) as an off-white solid: HPLC: $t_R$=21.65, 21.95 min. (column: Varian Pursuit XRs 5, C18, 150×4.6 mm. The method is: Linear gradient $H_2O$/ACN: 0% to 100% ACN in 30 min.)

The following are the NMR results analyzing the synthesized compound:

$^1$H NMR (500 MHz, $CD_3OD$) δ 8.18-8.12 (m, 1H), 7.93 and 7.91 (2s, 1H), 7.90-7.84 (m, 1H), 7.72 and 7.66 (m, 1H), 7.56-7.29 (m, 5H), 6.93-6.81 (m, 2H), 5.98 and 5.97 (2s, 1H), 5.11-4.97 (m, 2H), 4.62-4.49 (m, 4H), 4.40-4.20 (m, 2H), 4.12-4.03 (m, 1H), 1.46-1.41 (2t, J=7.1, 3H), 1.32 and 1.31 (2d, J=7.2, 3H), 0.99 and 0.96 (2s, 3H)

$^{31}$P NMR (202 MHz, $CD_3OD$-$d_4$) δ 4.22 and 4.19.

Example 75

The Protide (2S)-((S)-1-phenylethyl) 2-(((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate was synthesized as follows

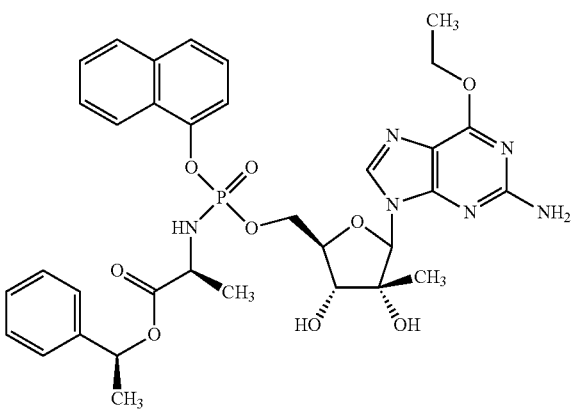 [SMILES: CCOc1nc(N)nc2c1ncn2C1O[C@H](COP(=O)(N[C@@H](C)C(=O)O[C@@H](C)c2ccccc2)Oc2cccc3ccccc23)[C@@H](O)[C@@]1(C)O]

Using the general procedure for the synthesis of 5'-phosphoramidates (Method A), to a solution of 250 mg (0.768 mmol) of (3R,4R,5R)-2-(2-amino-6-ethoxy-9H-purin-9-yl)-5-(hydroxymethyl)-3-methyltetrahydrofuran-3,4-diol and NMI 0.31 mL (3.54 mmol) in 5 mL of THF, was added (2S)-((S)-1-phenylethyl) 2-(chloro(naphthalen-1-yloxy)phosphorylamino)propanoate 963 mg (2.31 mmol) in 5 mL of THF. After workup and silica gel column chromatography, 120 mg of pure protide was obtained in a 22% yield, as an off-white solid.

The following are the NMR results analyzing the synthesized compound:

$^1$H NMR (500 MHz, $CD_3OD$) δ 8.19-8.16 (m, 1H, $H_8$-napht), 8.05, 8.01 (2×s, 1H, $H_8$), 7.84-7.78 (m, 1H, $H_5$-napht), 7.65, 7.63 (2×d, J=8.0 Hz, 1H), 7.55-7.45 (m, 3H, $H_2$, $H_7$, $H_6$-napht), 7.38-7.32 (m, 1H, $H_3$-napht), 7.27-7.19 (m, 5H, Phe), 6.02, 6.01 (2×s, 1H), 5.73, 5.69 (2×q, J=6.50 Hz, 1H, CH ester), 4.67-4.56 (m, 1H, $H_{5'}$), 4.49 (q, J=7.00 Hz, 2H, $6OCH_2CH_3$), 4.32-4.22 (m, 2H, $H_{3'}$ and $H_{4'}$), 4.10-4.03 (m, 1H, CHα), 1.41-1.37 ($6OCH_2CH_3$ and $CH_3$ ester), 1.25 (d, J=8.00 Hz, 3H, $CH_3$ Ala), 0.98, 0.96 (2×s, 3H, 2'$CCH_3$).

$^{13}$C NMR (126 MHz, $CD_3OD$) δ 174.26, 174.00 (d, $^3J_{C-C-N-P}$=5.0 Hz, C=O ester), 162.24, 162.21 (C6), 161.82, 161.75 (C2), 154.25 (C4), 147.99, 147.97, 147.92 (ipso Naph), 142.84, 142.80 (ipso Ph), 139.19, 138.88 (CH8), 136.23, 136.21 (2×d, $^3J_{C-C-O-P}$=3.7 Hz, napht-C10), 129.74, 129.55, 129.51, 128.97, 128.88, 128.84, 128.63 (Naph, Ph), 127.87, 127.81 (2×d, $^3J_{C-C-O-P}$=6.3 Hz, napht-C9), 127.76, 127.50, 127.31, 127.15, 127.02, 126.98, 126.79, 126.72, 126.55, 126.52, 126.38, 126.01, 125.99, 124.22, 123.49, 122.81, 122.75 (Naph, Ph), 116.30, 116.24 (2×d, $^3J_{C-C-O-P}$=3.7 Hz, C2-Naph), 115.06, 114.94 (C5), 93.38, 93.22 (C1'), 82.39, 82.24 (2×d, $^3J_{C-C-O-P}$=8.8 Hz, C4'), 80.00, 79.94 (C2'), 74.91, 74.86, 74.77, 74.64, 74.50 (C3' and CH ester), 68.01, 67.53 (2×d, $^2J_{C-O-P}$=5.0 Hz, C5'), 63.86, 63.81 ($6OCH_2CH_3$), 51.91, 51.82 (Cα Ala), 22.66, 22.60 ($CH_3$ ester), 20.60, 20.55 ($CH_3$ Ala), 20.41, 20.35 (2'$CCH_3$), 14.92 ($6OCH_2CH_3$)

$^{31}$P NMR (202 MHz, $CD_3OD$) δ 4.32, 4.29

Example 76

The protide 2,2-dimethylpropyl 2(S)-(((((2R,3R,4R,5R)-5-(2-amino-6-ethoxy-9H-purin-9-yl)-3,4-dihydroxy-4-methyltetrahydrofuran-2-yl)methoxy(naphthalene-1-yloxy)phosphorylamino)propanoate was synthesized as follows

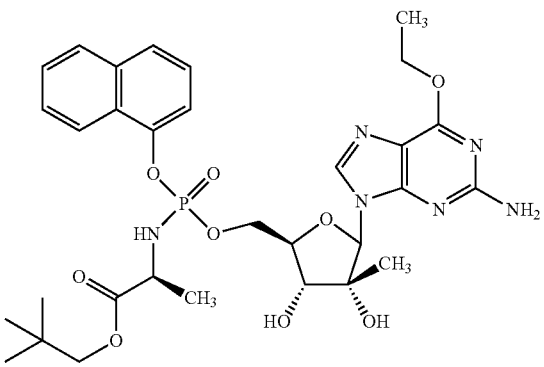 [SMILES: CCOc1nc(N)nc2c1ncn2C1O[C@H](COP(=O)(N[C@@H](C)C(=O)OCC(C)(C)C)Oc2cccc3ccccc23)[C@@H](O)[C@@]1(C)O]

Using the general procedure for the synthesis of nucleoside 5'-phosphoramidates (Method A), to a solution of 500 mg of ((3R,4R,5R)-2-(2-amino-6-ethoxy-9H-purin-9-yl)-5-(hydroxymethyl)-3-methyltetrahydrofuran-3,4-diol) in 6 mL of THF, was added (614 μL) of NMI, followed by (2S)-neopentyl 2-(chloro(naphthalen-1-yloxy)phosphorylamino)propanoate (1.77 g) in 6 mL of THF. After workup and silica gel column chromatography, 285 mg of pure protide was obtained (28% yield) as an off-white solid. HPLC: $t_R$=22.92, 23.16 min. (column: Varian Pursuit XRs 5, C18, 150×4.6 mm. The method is: Linear gradient H₂O/ACN: 0% to 100% ACN in 30 min.)

The following are the NMR results analyzing the synthesized compound:

¹H NMR (500 MHz, CD₃OD) δ 8.20-8.14 (m, 1H), 7.96 and 7.94 (2s, 1H), 7.90-7.84 (m, 1H), 7.71 and 7.78 (2d, J=8.2, 1H), 7.56-7.36 (m, 4H), 5.99 and 5.98 (2s, 1H), 4.65-4.56 (m, 2H), 4.56-4.51 (AB system, J=7.1 and 14.2, 2H), 4.36-4.21 (m, 2H), 4.06-4.02 (m, 1H), 3.78-3.57 (4d, J=10.5, 2H), 1.44 (2t, J=7.1, 3H), 1.33 (2d, J=7.1, 3H), 0.98 and 0.96 (2s, 3H), 0.88 and 0.86 (2s, 9H)

³¹P NMR (202 MHz, CD₃OD-d₄) δ 4.28 and 4.21.

Example 77

The protide (2S)-isopropyl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate was synthesized as follows

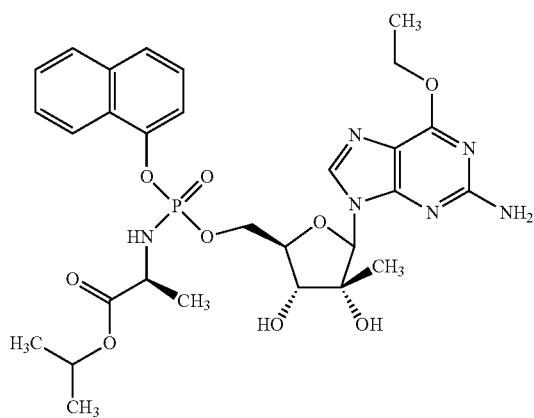 [SMILES: CCOc1nc(N)nc2c1ncn2C1O[C@H](COP(=O)(N[C@@H](C)C(=O)OC(C)C)Oc2cccc3ccccc23)[C@@H](O)[C@@]1(C)O]

Using the general procedure for the synthesis of nucleoside 5'-phosphoramidates (Method A), to a solution of 250 mg of ((3R,4R,5R)-2-(2-amino-6-ethoxy-9H-purin-9-yl)-5-(hydroxymethyl)-3-methyltetrahydrofuran-3,4-diol) in 3.3 mL of THF, was added (306 μL) of NMI followed by (2S)-isopropyl 2-(chloro(naphthalen-1-yloxy)phosphorylamino)propanoate (819.6 mg) in 3.3 mL of THF. After workup and silica gel column chromatography, 277 mg of pure protide was obtained (56% yield) as an off-white solid. HPLC: $t_R$=20.39, 20.65 min. (column: Varian Pursuit XRs 5, C18, 150×4.6 mm. The method is: Linear gradient H₂O/ACN: 0% to 100% ACN in 30 min.)

The following are the NMR results analyzing the synthesized compound:

¹H NMR (500 MHz, CD₃OD) δ 8.21-8.14 (m, 1H), 8.04 and 8.02 (2s, 1H), 7.91-7.83 (m, 1H), 7.71 and 7.68 (2d, J=8.3, 1H), 7.56-7.36 (m, 4H), 5.99 and 5.98 (2s, 1H), 4.85 (m, 1H), 4.66-4.57 (m, 2H), 4.54 (AB system, J=7.1 and 14.2, 2H), 4.38-4.21 (m, 2H), 4.02-3.91 (m, 1H), 1.47-1.42 (2t, J=7.1, 3H), 1.29 (d, J=7.1, 3H), 1.17-1.11 (m, 6H), 0.99 and 0.97 (2s, 3H)

³¹P NMR (202 MHz, CD₃OD) δ 4.39 and 4.29.

Example 78

The protide (2S)-tetrahydro-2H-pyran-4-yl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate was synthesized as follows

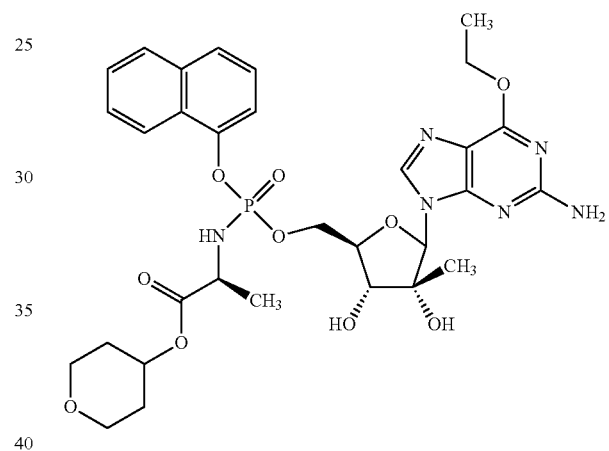

Using the general procedure for the synthesis of nucleoside 5'-phosphoramidates (Method A), to a solution of 250 mg (0.77 mmol) of (3R,4R,5R)-2-(2-amino-6-ethoxy-9H-purin-9-yl)-5-(hydroxymethyl)-3-methyltetrahydrofuran-3,4-diol in 3 mL of THF, was added 0.30 mL (3.6 mmol) of N-methyl imidazole, followed by (2S)-tetrahydro-2H-pyran-4-yl 2-(chloro(naphthalen-1-yloxy)phosphorylamino)propanoate 825 mg (2.1 mmol.) dissolved in 3 mL of THF. After standard workup and purification, 72 mg (14%) of desired protide was obtained as an off-white solid. HPLC: $t_R$=17.85, 18.24 min. (column: Varian Pursuit XRs 5, C18, 150×4.6 mm. The method is: Linear gradient H₂O/ACN: 0% to 100% ACN in 30 min.)

The following are the NMR results analyzing the synthesized compound:

¹H NMR (500 MHz, CD₃OD) δ 8.20-8.15 (m, 1H), 8.00, 7.98 (2×s, 1H), 7.89-7.81 (m, 1H), 7.71-7.67 (m, 1H), 7.58-7.45 (m, 3H), 7.43-7.37 (m, 1H), 6.00, 5.99 (2×s, 1H), 4.81-4.73 (m, 1H), 4.65-4.55 (m, 2H), 4.55, 4.52 (2×d, J=6.70, 2H), 4.35-4.22 (m, 2H), 4.08-3.99 (m, 1H), 3.80-3.75 (m, 2H), 3.48-3.37 (m, 2H), 1.80-1.69 (m, 2H), 1.54-1.49 (m, 2H), 1.44 (t, J=7.20 Hz, 3H), 1.32, 1.30 (2×d, J=6.35 Hz, 3H), 0.98, 0.97 (2×s).

³¹P NMR (202 MHz, CD₃OD) δ 4.26, 4.12.

Example 79

The protide (2S)-neopentyl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)-3-methylbutanoate

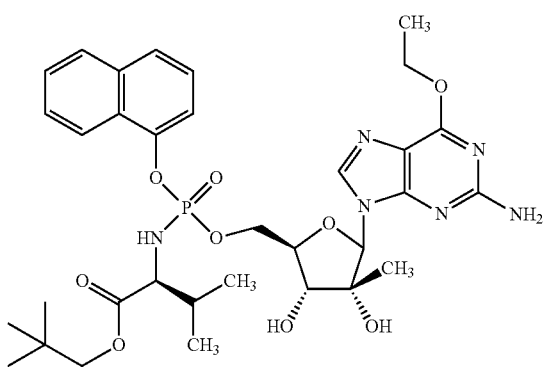 [SMILES: CCOc1nc(N)nc2c1ncn2C1O[C@H](COP(=O)(N[C@H](C(=O)OCC(C)(C)C)C(C)C)Oc2cccc3ccccc23)[C@@H](O)[C@@]1(C)O]

Using the general procedure for the synthesis of nucleoside 5'-phosphoramidates (Method A), to a solution of 300 mg of ((3R,4R,5R)-2-(2-amino-6-ethoxy-9H-purin-9-yl)-5-(hydroxymethyl)-3-methyltetrahydrofuran-3,4-diol) in 4 mL of THF, was added NMI (368 μL) followed by (2S)-neopentyl 2-(chloro(naphthalen-1-yloxy)phosphorylamino)-3-methylbutanoate (1.14 g) in THF (4 mL). After workup and silica gel column chromatography, 77.3 mg of pure protide was obtained (13% yield) as an off-white solid. HPLC: $t_R$=27.96 min. (column: Varian Pursuit XRs 5, C18, 150×4.6 mm. The method is: Linear gradient H$_2$O/ACN: 0% to 100% ACN in 30 min.)

The following are the NMR results analyzing the synthesized compound:

$^1$H NMR (500 MHz, CD$_3$OD) δ 8.20-8.13 (m, 1H), 7.96 and 7.95 (2s, 1H), 7.90-7.83 (m, 1H), 7.70 and 7.66 (2d, J=8.1, 1H), 7.59-7.34 (m, 4H), 5.98 and 5.97 (2s, 1H), 4.65-4.58 (m, 2H), 4.57-4.51 (2×AB system, J=7.0 and 14.2, 2H), 4.40-4.21 (m, 2H), 3.82-3.74 (m, 1H), 3.72-3.59 (4d, J=10.5, 2H), 2.09-1.93 (m, 1H), 1.47-1.42 (2t, J=7.1, 3H), 0.99 and 0.95 (2s, 3H), 0.90-0.82 (m, 15H)

$^{31}$P NMR (202 MHz, CD$_3$OD) δ 5.11 and 4.90.

Example 80

The (3R,4R,5R)-2-(2-amino-6-(methylamino)-9H-purin-9-yl)-5-(hydroxymethyl)-3-methyltetrahydrofuran-3,4-diol was synthesized accordingly

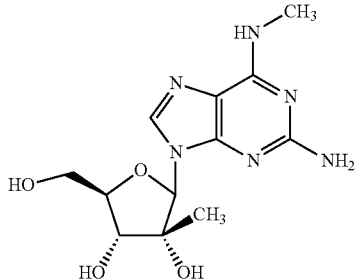 [SMILES: CNc1nc(N)nc2c1ncn2C1O[C@H](CO)[C@@H](O)[C@@]1(C)O]

To a solution of (3R,4R,5R)-2-(2-amino-6-chloro-9H-purin-9-yl)-5-(benzoyloxymethyl)-3-methyltetrahydrofuran-3,4-diyldibenzoate (150 mg, 0.239 mmol) in ethanol was added methyl amine (1 mL, 1.2 mmol) and triethyl amine (0.17 mL, 1.2 mmol) and heated to 85° C. overnight in sealed tube. After cooling and evaporation, the crude product was purified by column chromatography using dichloromethane/methanol (93:7) to give 68 mg (92% yield) of (3R,4R,5R)-2-(2-amino-6-(methylamino)-9H-purin-9-yl)-5-(hydroxymethyl)-3-methyltetrahydrofuran-3,4-diol as an off white solid.

The following are the NMR results analyzing the synthesized compound:

$^1$H NMR (200 MHz, CD$_3$OD): δ 8.06 (s, 1H), 5.9 (s, 1H), 4.25 (d, J=8.8 Hz, 1H), 4.0 (m, 2H), 3.85 9dd, J=3.2 Hz, J=3.2 Hz, 1H), 3.6 (s, 1H), 3.04 (s, 3H), 0.92 (s, 3H).

Example 81

The (2S)-neopentyl 2-((((2R,3R,4R)-5-(2-amino-6-(methylamino)-9H-purin-9-yl)-3,4-dihydroxy-4-methyltetrahydrofuran-2-yl)methoxy)(naphthalen-1-yloxy)phosphorylamino)propanoate was synthesized as follows

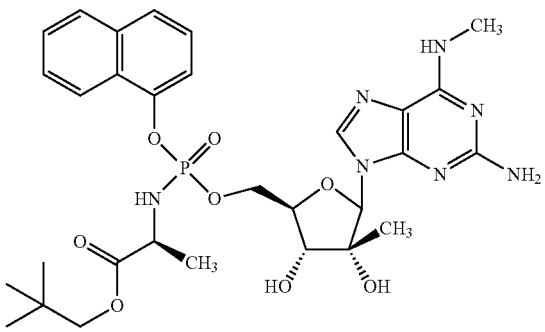 [SMILES: CNc1nc(N)nc2c1ncn2C1O[C@H](COP(=O)(N[C@@H](C)C(=O)OCC(C)(C)C)Oc2cccc3ccccc23)[C@@H](O)[C@@]1(C)O]

Using the general procedure (Method B) for the synthesis of nucleoside 5'-phosphoramidates of (3R,4R,5R)-2-(2-amino-6-(methylamino)-9H-purin-9-yl)-5-(hydroxymethyl)-3-methyltetrahydrofuran-3,4-diol (150 mg, 0.48 mmol) in anhydrous THF (25 mL) was combined with (2S)-neopentyl 2-(chloro(naphthalen-1-yloxy)phosphorylamino)propanoate (463 mg, 1.21 mmol), and tert-butyl magnesium chloride (1.645 mL, 1.645 mmol). After normal work-up the crude product was purified by column chromatography on silica gel using CH$_2$Cl$_2$/MeOH (96:4) to give 51 mg of protide in 17% yield as light yellow solid.

The following are the NMR results analyzing the synthesized compound.

$^1$H NMR (200 MHz, CD$_3$OD): δ 8.15 (m, 1H), 7.85 (m, 2H), 7.65 (m, 1H), 7.3-7.54 (m, 4H), 5.93 (d, J=4.0 Hz, 1H), 4.52 (m, 2H), 4.22 (s, 2H), 4.0 (dd, J=7.4 Hz, J=6.8 Hz, 1H), 3.6 (m, 2H), 3.0 (s, 3H), 1.3 (d, J=7.0 Hz, 3H), 0.95 (d, J=2.6 Hz, 3H), 0.84 (d, J=3.2 Hz, 9H).

$^{31}$P NMR (80 MHz, CD$_3$OD): δ 5.4.

Example 82

The (2S)-((S)-1-phenylethyl) 2-((((2R,3R,4R)-5-(2-amino-6-(methylamino)-9H-purin-9-yl)-3,4-dihydroxy-4-methyltetrahydrofuran-2-yl)methoxy)(naphthalen-1-yloxy)phosphorylamino)propanoate was synthesized as follows

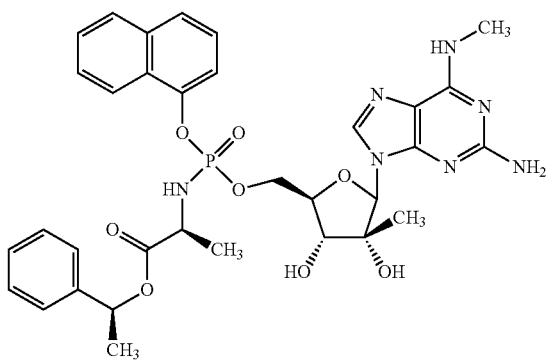 [SMILES: CNc1nc(N)nc2c1ncn2C1O[C@H](COP(=O)(N[C@@H](C)C(=O)O[C@@H](C)c2ccccc2)Oc2cccc3ccccc23)[C@@H](O)[C@@]1(C)O]

Step 1: (2S)-((S)-1-phenylethyl) 2-(chloro(naphthalen-1-yloxy)phosphorylamino)propanoate

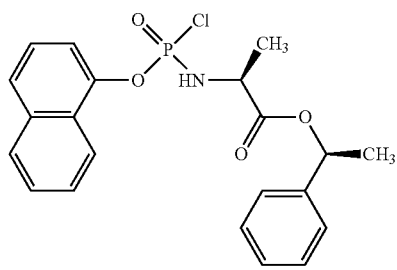 [SMILES: C[C@H](NP(=O)(Cl)Oc1cccc2ccccc12)C(=O)O[C@@H](C)c1ccccc1]

Using the general procedure for synthesizing naphthyl (aminoacid ester) phosphorochloridates the tosylate salt of (S)-((S)-1-phenylethyl) 2-aminopropanoate (1.05 g, 2.85 mmol), naphthalen-1-yloxy phosphorodichloridate (2.85 mmol), triethyl amine (0.76 mL, 5.56 mmol) and dichloromethane (20 mL) were combined to give 610 g of desired (2S)-((S)-1-phenylethyl) 2-(chloro(naphthalen-1-yloxy)phosphorylamino)propanoate in 26% yield as pale yellow oil.

The following are the NMR results analyzing the synthesized compound.

$^1$H NMR (200 MHz, CDCl$_3$): δ 8.07 (m, 1H), 7.86 (m, 1H), 7.71 (d, J=8.4 Hz, 1H), 7.30-7.61 (m, 9H), 5.94 (m, 1H), 4.33 (m, 2H), 1.60-1.46 (m, 6H)

$^{31}$P NMR (80 MHz, CDCl$_3$): δ 9.07, 9.34

Step 2: Synthesis of Protide

Using the general procedure (Method B) for the synthesis of nucleoside 5'-phosphoramidates, (3R,4R,5R)-2-(2-amino-6-(methylamino)-9H-purin-9-yl)-5-(hydroxymethyl)-3-methyltetrahydrofuran-3,4-diol (190 mg, 0.613 mmol) in anhydrous THF (25 mL) was combined with (2S)-((S)-1-phenylethyl) 2-(chloro(naphthalen-1-yloxy)phosphorylamino)propanoate (610 mg, 1.41 mmol), and tert-butyl magnesium chloride (1.41 mL, 1.41 mmol) After normal work-up the crude product was purified by column chromatography on silica gel twice using CH$_2$Cl$_2$/MeOH (95:5) and then with ethyl acetate/methanol (97:3) to give 210 mg of protide in 50% yield as off-white solid.

The following are the NMR results analyzing the synthesized compound.

$^1$H NMR (200 MHz, CD$_3$OD): δ 8.2 (m, 1H), 7.85 (m, 1H), 7.5 (m, 5H), 7.2 (m, 5H), 5.92 (d, J=4.0 Hz, 1H), 5.66 (m, 1H), 4.54 (m, 1H), 4.2 (d, J=2 Hz, 1H), 4.02 (m, 1H), 3.01 (s, 3H), 2.01 (s, 1H), 1.35 (m, 3H), 1.21 (m, 3H), 0.94 (s, 3H)

$^{31}$P NMR (80 MHz, CD$_3$OD): δ 5.36, 5.35.

Example 83

The (2S)-neopentyl 2-((((2R,3R,4R,5R)-5-(2-amino-6-(methylamino)-9H-purin-9-yl)-3,4-dihydroxy-4-methyltetrahydrofuran-2-yl)methoxy)(quinolin-6-yloxy)phosphorylamino)propanoate was synthesized as follows:

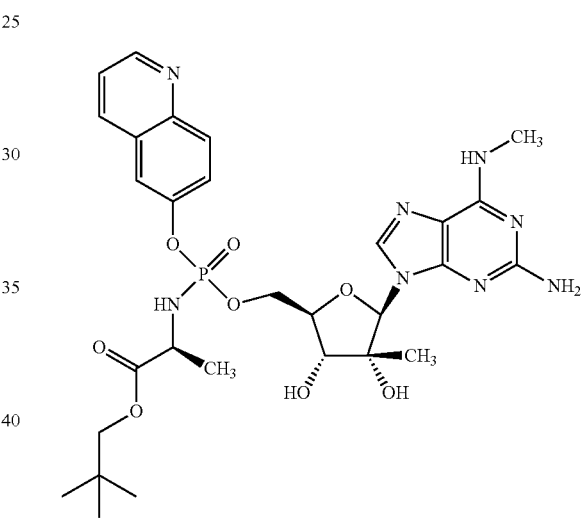

Using the general procedure (Method B) for the synthesis of nucleoside 5'-phosphoramidates of (3R,4R,5R)-2-(2-amino-6-(methylamino)-9H-purin-9-yl)-5-(hydroxymethyl)-3-methyltetrahydrofuran-3,4-diol (200 mg, 0.645 mmol) in anhydrous THF (25 mL) was combined with (2S)-neopentyl 2-(chloro(quinolin-6-yloxy)phosphorylamino)propanoate (650 mg, 1.801 mmol), and tert-butyl magnesium chloride (1.8 mL, 1.8 mmol). After normal work-up the crude product was purified by column chromatography on silica gel twice using CH$_2$Cl$_2$/MeOH (96:4) and then with ethyl acetate/methanol (9:1) to give 110 mg of protide in 26% yield as an off-white solid.

The following are the NMR results analyzing the synthesized compound:

$^1$H NMR (200 MHz, CD$_3$OD): δ 8.77 (ddd, J=1.8 Hz, J=2.0 Hz, J=1.6 Hz, 1H), 8.2 (t, J=8.0 Hz, 1H), 8.0 (d, J=9.2 Hz, 1H), 7.63-7.8 (m, 3H), 7.45 (m, 1H), 5.92 (s, 1H), 4.6 (m, 2H), 4.23 (m, 2H), 4.05 (m, 1H), 3.55-3.8 (m, 2H), 3.0 (d, J=2.4 Hz, 3H), 1.35 (m, 3H), 0.85-0.95 (m, 12H)

$^{31}$P NMR (80 MHz, CD$_3$OD): δ 5.16, 5.06. .

Example 84

The (3R,4R,5R)-2-(2-amino-6-(benzylamino)-9H-purin-9-yl)-5-(hydroxymethyl)-3-methyltetrahydrofuran-3,4-diol was synthesized accordingly:

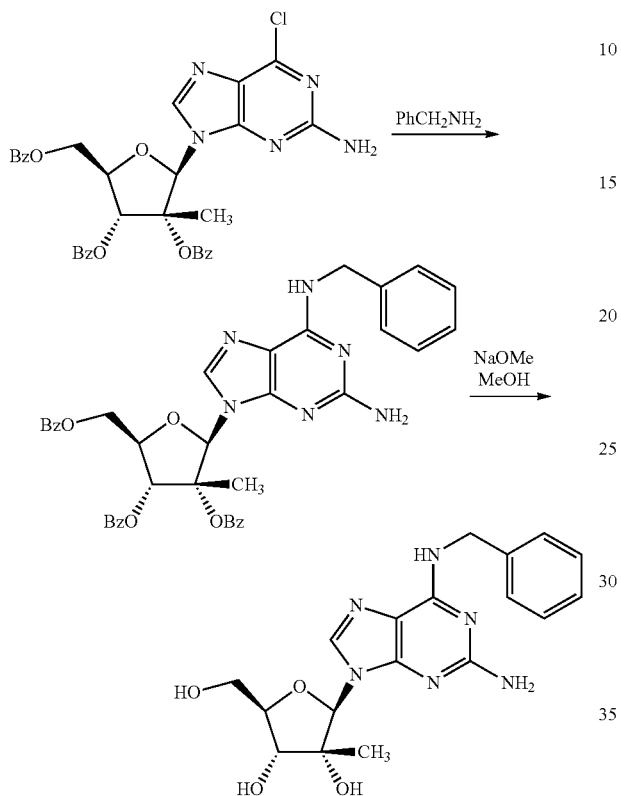

Step 1. Synthesis of (2R,3R,4R,5R)-2-(2-amino-6-(benzylamino)-9H-purin-9-yl)-5-(benzoyloxymethyl)-3-methyltetrahydrofuran-3,4-diyl dibenzoate To a suspension of (3R,4R,5R)-2-(2-amino-6-chloro-9H-purin-9-yl)-5-(benzoyloxymethyl)-3-methyltetrahydrofuran-3,4-diyldibenzoate (1.0 g, 1.60 mmol) in anhydrous ethanol (100 mL), at room temperature, benzylamine (1.75 mL, 10 equiv) was added. The mixture was stirred under reflux overnight, cooled down to room temperature and ethanol was removed under reduced pressure. The residue was then precipitated from CHCl₃/MeOH to give the pure (2R,3R,4R,5R)-2-(2-amino-6-(benzylamino)-9H-purin-9-yl)-5-(benzoyloxymethyl)-3-methyltetrahydrofuran-3,4-diyldibenzoate (1.12 g, 100%) as a white solid.

The following are the NMR results analyzing the synthesized compound:

$^1$H NMR (500 MHz, CD$_3$OD) δ 8.15 (d, J=7.20 Hz, 2H, CH Ph), 8.05 (d, J=7.20 Hz, 2H, CH Ph), 7.96 (d, J=7.30 Hz, 2H, CH Ph), 7.93 (s, 1H, H$_8$), 7.65 (t, J=7.20 Hz, 1H, CH Ph), 7.58 (d, J=7.20 Hz, 2H, CH Ph), 7.52 (t, J=7.80 Hz, 2H, CH Ph), 7.46-7.39 (m, 4H, CH Ph), 7.35 (dd, J=7.80 Hz, 19.1, 4H, CH Ph), 7.26 (s, 1H, CH Ph), 6.68 (s, 1H, H$_{1'}$), 6.30 (d, J=5.60 Hz, 1H, H$_{3'}$), 5.03 (dd, J=5.00 Hz, 11.7, 1H, H$_{5'}$), 4.84 (m, 3H, CH$_2$ benzyl and H$_{5'}$), 4.75 (dd, J=5.50 Hz, 10.8, 1H, H$_{4'}$), 1.65 (s, 3H, 2'-CH$_3$).

Step 2. Deprotection to (3R,4R,5R)-2-(2-amino-6-(benzylamino)-9H-purin-9-yl)-5-(hydroxymethyl)-3-methyltetrahydrofuran-3,4-diol To a solution of protected nucleoside: (2R,3R,4R,5R)-2-(2-amino-6-(benzylamino)-9H-purin-9-yl)-5-(benzoyloxymethyl)-3-methyltetrahydrofuran-3,4-diyl dibenzoate (1.12 g, 1.29 mmol) in anhydrous methanol (18 mL) at room temperature was added sodium methoxide (0.29 g, 3.2 equiv). After being stirred for 2 h, the solvent was removed under reduced pressure and the residue was purified on silica gel using CHCl₃:MeOH 92:8 as an eluent, to yield the pure unprotected nucleoside (0.574 g, 89%) as a white solid. HRMS (ESI): calculated for C$_{18}$H$_{22}$N$_6$O$_4$+Na$^+$ 409.1600. found 409.1593.

The following are the NMR results analyzing the synthesized compound:

$^1$H NMR (500 MHz, DMSO) δ 8.03 (s, 1H, H$_8$), 7.36 (d, J=7.3, 2H, phe), 7.30 (t, J=7.5, 2H, phe), 7.21 (t, J=7.1, 1H, phe), 5.86 (s, 2H, NH$_2$), 5.80 (s, 1H, H$_{1'}$), 5.16 (m, 2H, OH$_{3'}$ and OH$_{5'}$), 5.01 (s, 1H, OH$_{2'}$), 4.64 (bs, 2H, CH$_2$ Bn), 4.02 (d, J=8.1, 1H, H$_{3'}$), 3.86 (m, 2H, H$_{4'}$ and H$_{5'}$), 3.75-3.58 (m, 1H, H$_{5'}$), 0.81 (s, 3H, CH$_3$)

Example 85

2,2-Dimethylpropyl 2(S)-(((((2R,3R,4R,5R)-5-(2-amino-6-benzylamino-9H-purin-9-yl)-3,4-dihydroxy-4-methyltetrahydrofuran-2-yl)methoxy(naphthalene-1-yloxy) phosphorylamino)propionate was synthesized accordingly

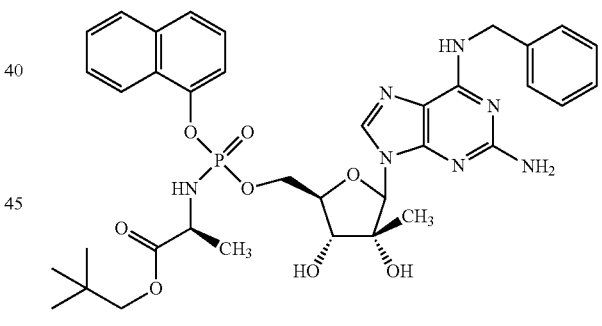

Using the general procedure (Method A) for the synthesis of nucleoside 5'-phosphoramidates, to a solution of (3R,4R,5R)-2-(2-amino-6-(benzylamino)-9H-purin-9-yl)-5-(hydroxymethyl)-3-methyltetrahydrofuran-3,4-diol 150 mg (0.388 mmol) and NMI 0.15 mL (1.94 mmol), in 5 mL of THF, was added naphthalen-1-yl (2,2-dimethylpropyloxy) phosphorchloridate 477 mg (1.16 mmol) in 5 mL of THF. After workup and silica gel column chromatography, 32.3 mg of pure protide was obtained in 11% yield, as an off-white solid.

The following are the NMR results analyzing the synthesized compound:

$^1$H NMR (500 MHz, CD$_3$OD) δ 8.19-8.17 (m, 1H), 7.87 (s, 1H), 7.86-7.81 (m, 1H) 7.70-7.65 (m, 1H), 7.54-7.50 (m, 3H), 7.46-7.36 (m, 3H), 7.32-7.29 (m, 2H), 7.25-7.22 (m, 1H), 5.98, 5.97 (2×s, 1H), 4.75-4.72 (m, 2H), 4.68-

4.57 (m, 2H), 4.30-4.23 (m, 2H), 4.10-4.03 (m, 1H), 3.76, 3.71, 3.63, 3.59 (2×AB, JAB=10.45 Hz, 2H), 1.32 (d, J=7.40 Hz, 1H), 0.99, 0.98 (2×s, 3H), 0.85, 0.84 (2×s, 9H)

$^{13}$C NMR (126 MHz, CD$_3$OD) δ 175.06 (d, $^3J_{C-C-N-P}$=4.70 Hz, C=O ester), 174.82 (d, $^3J_{C-C-N-P}$=5.80 Hz, C=O ester), 162.15 (C6), 156.46 (C4), 148.02 (d, $^2J_{C-O-P}$=2.00 Hz, napht-C1), 147.96 (d, $^2J_{C-O-P}$=2.00 Hz, napht-C1), 140.61 (C1 phe), 137.17, 136.87 (CH8), 136.30 (napht-C10), 129.53 (CH-phe), 129.52 (CH-phe), 128.86, 128.80 (CH-phe), 128.65 (CH-phe), 128.64 (CH-phe), 128.15 (CH-napht), 127.91 (d, $^3J_{C-C-O-P}$=2.50 Hz, napht-C9), 127.86 (d, $^3J_{C-C-O-P}$=2.50 Hz, napht-C9), 127.77, 127.75 (CH-napht), 127.50, 127.49 (CH-napht), 126.53, 126.47 (CH-napht), 125.97 (CH-napht), 122.81, 122.74 (CH-napht), 116.20 (d, $^3J_{C-C-O-P}$=3.3, napht-C2), 116.17 (d, $^3J_{C-C-O-P}$=4.50 Hz, napht-C2), 114.78, 114.75 (C5), 92.98, 92.79 (C1'), 82.13 (d, $^3J_{C-C-O-P}$=8.10 Hz, C4'), 81.98 (d, $^3J_{C-C-O-P}$=8.50 Hz, C4'), 79.98, 79.90 (C2'), 75.37, 75.35 (CH$_2$ ester), 74.82, 74.51 (C3'), 67.87 (d, $^2J_{C-O-P}$=5.2, C5'), 67.29 (d, $^2J_{C-O-P}$=5.00 Hz, C5'), 51.78 (Cα Ala), 44.91 (CH$_2$—NH), 32.24, 32.21 (C t-Bu), 26.70, 26.69 (3×CH$_3$ t-Bu), 20.84 (d, $^3J_{C-C-N-P}$=6.20 Hz, CH$_3$ Ala), 20.62 (d, $^3J_{C-C-N-P}$=7.10 Hz, CH$_3$ Ala), 20.38, 20.35 (2'-CH$_3$)

$^{31}$P NMR (202 MHz, CD$_3$OD) δ 4.43, 4.23

Example 86

The (3R,4R,5R)-2-(2-amino-6-(phenethylamino)-9H-purin-9-yl)-5-(hydroxymethyl)-3-methyltetrahydrofuran-3,4-diol was synthesized accordingly

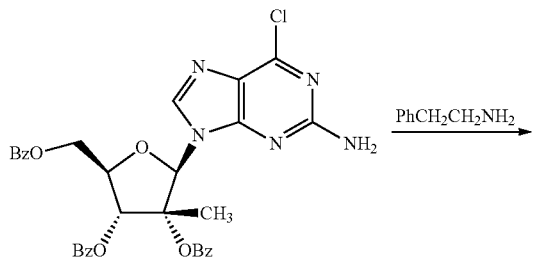

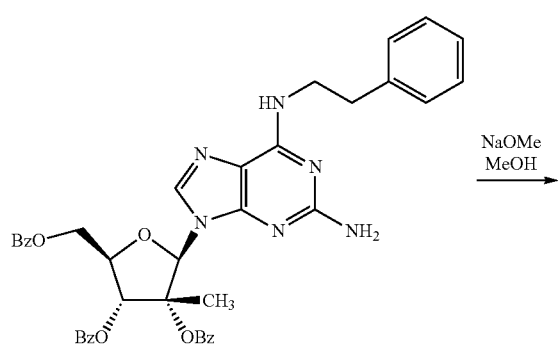

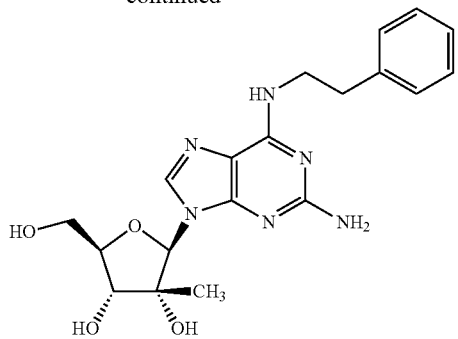

Step 1. (2R,3R,4R,5R)-2-(2-amino-6-(phenethylamino)-9H-purin-9-yl)-5-(benzoyloxymethyl)-3-methyltetrahydrofuran-3,4-diyl dibenzoate To a suspension of (3R,4R,5R)-2-(2-amino-6-chloro-9H-purin-9-yl)-5-(benzoyloxymethyl)-3-methyltetrahydrofuran-3,4-diyldibenzoate (1.0 g, 1.60 mmol) in anhydrous ethanol (100 mL), at room temperature, was added phenylethylamine (2.02 mL, 10 equiv). The mixture was stirred under reflux overnight, cooled down to room temperature and ethanol was removed under reduced pressure. The residue was then precipitated from CHCl$_3$/MeOH to give the pure compound (0.63 g, 55%) as a white solid.

The following are the NMR results analyzing the synthesized compound:

$^1$H NMR (500 MHz, CD$_3$OD) δ 8.12 (d, J=7.20 Hz, 2H, CH Ph), 8.03 (d, J=7.20 Hz, 2H, CH Ph), 7.96 (d, J=7.30 Hz, 2H, CH Ph), 7.90 (s, 1H, H$_8$), 7.65 (t, J=7.50 Hz, 1H, CH Ph), 7.58-7.52 (m, 2H, CH Ph), 7.53 (t, J=7.80 Hz, 2H, CH Ph), 7.43 (t, J=7.80 Hz, 2H, CH Ph), 7.39 (t, J=7.80 Hz, 2H, CH Ph), 7.35-7.26 (m, 5H, CH Ph), 6.65 (s, 1H, H$_{1'}$), 6.28 (d, J=6.00 Hz, 1H, H$_{3'}$), 5.03 (dd, J=4.90 Hz, 12.00 Hz, 1H, H$_{5'}$), 4.84-4.67 (m, 3H, H$_{5'}$, H$_{4'}$), 3.95-3.89 (m, 2H, NH—CH$_2$—CH$_2$-Bn), 3.01 (t, J=7.00 Hz, 2H, NH—CH$_2$—CH$_2$-Bn) 1.65 (s, 3H, 2'-CH$_3$).

Step 2. Deprotection

To a solution of (2R,3R,4R,5R)-2-(2-amino-6-(phenethylamino)-9H-purin-9-yl)-5-(benzoyloxymethyl)-3-methyltetrahydrofuran-3,4-diyldibenzoate (0.63 g, 0.88 mmol) in anhydrous methanol (15 mL) at room temperature was added sodium methoxide (0.15 g, 3.2 equiv). After being stirred for 2 h, the solvent was removed under reduced pressure and the residue was purified on silica gel using CHCl$_3$:MeOH 92:8 as an eluent, to yield the unprotected nucleoside, (3R,4R,5R)-2-(2-amino-6-(phenethylamino)-9H-purin-9-yl)-5-(hydroxymethyl)-3-methyltetrahydrofuran-3,4-diol (0.33 g, 94%) as a white solid. HRMS (ESI): calculated for C$_{19}$H$_{24}$N$_6$O$_4$+Na$^+$423.1757. found 423.1763. Elemental analysis: calculated for C$_{19}$H$_{24}$N$_6$O$_4$+3.5H$_2$O, C, 49.24; H, 6.74; N, 18.13. Found: C, 49.13; H, 5.83; N, 18.05.

The following are the NMR results analyzing the synthesized compound:

$^1$H NMR (500 MHz, CD$_3$OD) δ 8.20 (s, 1H, H$_8$), 7.32-7.19 (m, 5H, Ph), 5.96 (s, 1H, H$_{1'}$), 4.29 (d, J=8.00 Hz, 1H, H$_{3'}$), 4.13-4.05 (m, 3H, H$_{4'}$ and H$_{5'}$), 3.95-3.85 (m, 2H, NH—CH₂—CH₂-Bn), 3.04 (t, J=7.00 Hz, 2H, NH—CH₂—CH₂-Bn) 0.97 (s, 3H, 2'CH₃).

Example 87

The (2S)-neopentyl 2-((((2R,3R,4R)-5-(2-amino-6-(phenethylamino)-9H-purin-9-yl)-3,4-dihydroxy-4-methyltetrahydrofuran-2-yl)methoxy)(naphthalen-1-yloxy)phosphorylamino)propanoate was synthesized accordingly

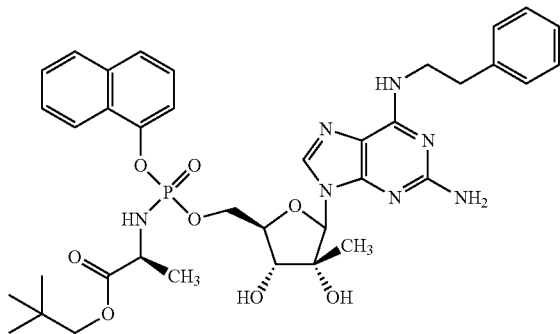 [SMILES: C[C@H](NP(=O)(OC[C@H]1OC(n2cnc3c(NCCc4ccccc4)nc(N)nc32)[C@](C)(O)[C@@H]1O)Oc1cccc2ccccc12)C(=O)OCC(C)(C)C]

Using the general procedure (Method B) for the synthesis of nucleoside 5'-phosphoramidates, to a solution of (3R,4R,5R)-2-(2-amino-6-(phenethylamino)-9H-purin-9-yl)-5-(hydroxymethyl)-3-methyltetrahydrofuran-3,4-diol 200 mg (0.50 mmol) in 5 mL of THF, was added tert-BuMgCl 1.00 mL (1.00 mmol), followed by naphthalen-1-yl (2,2-dimethylpropyloxy)phosphorchloridate 383 mg (1.00 mmol) in 5 mL of THF. After workup and silica gel column chromatography, 246.5 mg of pure protide was obtained in a 24% yield, as an off-white solid.

The following are the NMR results analyzing the synthesized compound:

¹H NMR (500 MHz, CD₃OD) δ 8.19 (d, J=8.50 Hz, 1H, H₈-naph), 7.87-7.81 (m, 2H, H8 and H₅-naph), 7.69, 7.67 (2×d, J=8.50 Hz, 1H, H₄-naph), 7.54-7.47 (m, 3H, H₇, H₆, H₂-naph), 7.42-7.37 (m, 1H, H₃-naph), 7.27-7.16 (m, 5H, Ph), 5.98, 5.97 (2×s, 1H, H1'), 4.69-4.58 (m, 2H, H₅'), 4.27-4.22 (m, 2H, H₃' and H₄'), 4.11-4.03 (m, 1H, Hα, Ala), 3.78-3.58 (m, 4H, CH₂ ester and CH₂—CH₂-Bn), 2.94 (t, J=7.70 Hz, 2H, CH₂—CH₂-Bn), 1.33, 1.32 (2×d, J=7.00 Hz, 3H, CH₃ Ala), 0.98, 0.96 (2×s, 3H, 2'CH₃), 0.86, 0.84 (2×s, 9H, 3×CH₃ ester)

¹³C NMR (126 MHz, CD₃OD) δ 175.06 (d, ³J$_{C-C-N-P}$=4.7, C=O ester), 174.83 (d, ³J$_{C-C-N-P}$=5.8, C=O ester), 162.12 (C6), 156.51 (C4), 148.01 (ipso Naph), 140.69 (ipso Ph), 137.04, 136.76 (CH8), 136.30, 136.28 (napht-C10), 129.91, 129.50, 128.87, 128.82 (CH-napht and Ph), 127.93, 127.76 (C9-naph), 127.52, 127.50, 127.31, 126.53, 126.49, 125.98, 122.82, 122.75 (CH-napht and Ph), 116.22, 116.20 (C2-naph), 114.81 (C5), 92.95, 92.77 (C1'), 82.11 (d, ³J$_{C-C-O-P}$=7.70 Hz, C4'), 81.97 (d, ³J$_{C-C-O-P}$=8.5, C4'), 79.98, 79.91 (C2'), 75.38, 75.36 (CH₂ ester), 74.80, 74.49 (C3'), 67.83, 67.27 (d, ²J$_{C-O-P}$=5.00 Hz, C5'), 51.79, 51.73 (Cα Ala), 44.52 (CH₂—NH), 36.82 (C ester), 32.26, 32.23 (CH₂-Bn), 26.72, 26.71 (3×CH₃ ester), 20.87 (d, ³J$_{C-C-N-P}$=6.20 Hz, CH₃ Ala), 20.64 (d, ³J$_{C-C-N-P}$=7.70 Hz, CH₃ Ala), 20.39, 20.37 (2'CCH₃)

³¹P NMR (202 MHz, CD₃OD) δ 4.25

Example 88

The (2R,3R,4R,5R)-2-(2-amino-6-(methylthio)-9H-purin-9-yl)-5-(hydroxymethyl)-3-methyltetrahydrofuran-3,4-diol was synthesized accordingly

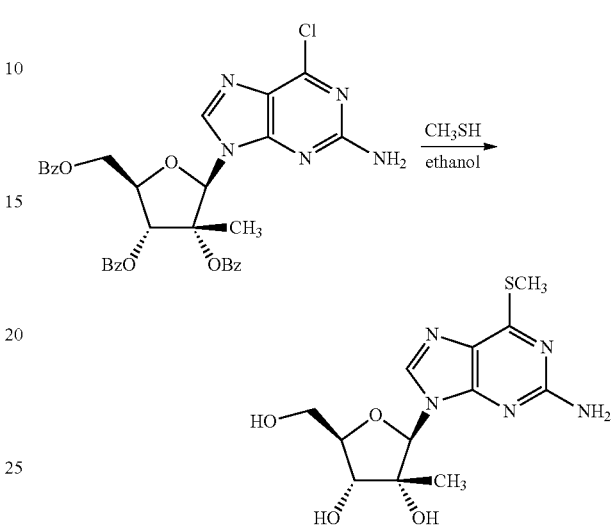

To a suspension of (3R,4R,5R)-2-(2-amino-6-chloro-9H-purin-9-yl)-5-(benzoyloxymethyl)-3-methyltetrahydrofuran-3,4-diyldibenzoate (100 mg, 0.16 mmol) in ethanol (10 mL) was added sodium thiomethoxide (56 mg, 0.8 mmol) and stirred at rt overnight. The mixture was neutralized with acidic resin and evaporated the solvent to dryness. The crude was purified by column chromatography using dichloromethane/methanol (92:8) to give 45 mg (87%) of (2R,3R,4R,5R)-2-(2-amino-6-(methylthio)-9H-purin-9-yl)-5-(hydroxymethyl)-3-methyltetrahydrofuran-3,4-diol as an off white solid.

The following are the NMR results analyzing the synthesized compound:

¹H NMR (200 MHz, CD₃OD): δ 8.31 (s, 1H), 5.98 (s, 1H), 4.2 (d, J=8.8 Hz, 1H), 4.08-3.96 (m, 2H), 3.9-3.8 (dd, J=3.2 Hz, J=3.4 Hz, 1H), 3.6 (s, 1H), 2.6 (s, 3H), 0.93 (s, 3H).

Example 89

The (2S)-((S)-1-phenylethyl) 2-((((2R,3R,4R)-5-(2-amino-6-(methylthio)-9H-purin-9-yl)-3,4-dihydroxy-4-methyltetrahydrofuran-2-yl)methoxy)(naphthalen-1-yloxy)phosphorylamino)propanoate was synthesized accordingly

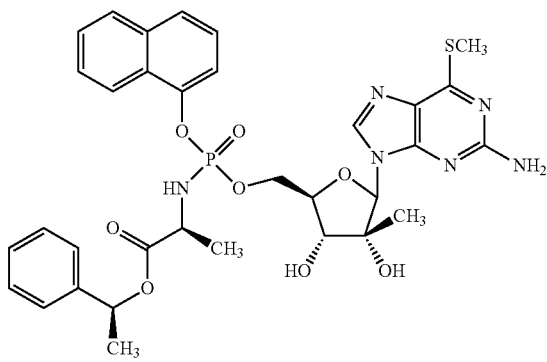 [SMILES: CSc1nc(N)nc2c1ncn2C1O[C@H](COP(=O)(N[C@@H](C)C(=O)O[C@@H](C)c2ccccc2)Oc2cccc3ccccc23)[C@@H](O)[C@@]1(C)O]

Using the general procedure (Method B) for the synthesis of nucleoside 5'-phosphoramidates, to a solution of (2R,3R,4R,5R)-2-(2-amino-6-(methylthio)-9H-purin-9-yl)-5-(hydroxymethyl)-3-methyltetrahydrofuran-3,4-diol (200 mg, 0.611 mmol) in 5 mL of THF, was added tert-BuMgCl (1.55 mL, 2.3 equiv) followed by (2S)-((S)-1-phenylethyl) 2-(chloro(naphthalen-1-yloxy)phosphorylamino)propanoate (610 mg, 1.4 mmol) in 5 mL of THF. After workup and silica gel column chromatography, 160 mg of pure protide was obtained in a 37% yield, as an off white solid.

The following are the NMR results analyzing the synthesized compound:

¹H NMR (200 MHz, CD₃OD): δ 8.2 (m, 2H), 8.0 (d, J=6.6 Hz, 1H), 7.8 (m, 1H), 7.7-7.25 (m, 8H), 5.97 (d, J=2.2 Hz, 1H), 5.65 (m, 1H), 4.55 (m, 2H), 4.35-3.95 (m, 3H), 2.59 (s, 3H), 1.4-1.1 (m, 9H), 0.95 (d, J=5.0 Hz, 3H).

³¹P NMR (80 MHz, CD₃OD): δ 5.35

Example 90

The (2S)-neopentyl 2-((((2R,3R,4R)-5-(2-amino-6-(methylthio)-9H-purin-9-yl)-3,4-dihydroxy-4-methyltetrahydrofuran-2-yl)methoxy)(naphthalen-1-yloxy)phosphorylamino)propanoate was synthesized accordingly

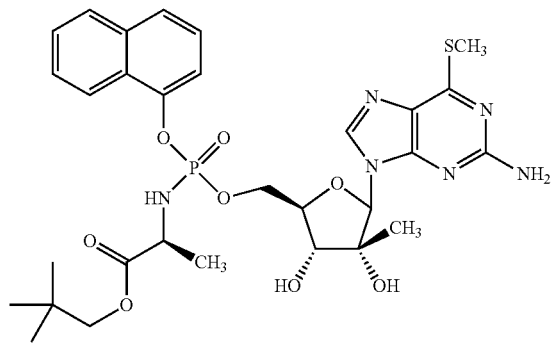 [SMILES: CSc1nc(N)nc2c1ncn2C1O[C@H](COP(=O)(N[C@@H](C)C(=O)OCC(C)(C)C)Oc2cccc3ccccc23)[C@@H](O)[C@@]1(C)O]

Using the general procedure (Method B) for the synthesis of nucleoside 5'-phosphoramidates, to a solution of (2R,3R,4R,5R)-2-(2-amino-6-(methylthio)-9H-purin-9-yl)-5-(hydroxymethyl)-3-methyltetrahydrofuran-3,4-diol (150 mg, 0.459 mmol) in 5 mL of THF, was added tent-BuMgCl (1.14 mL, 2.5 equiv) followed by (2S)-neopentyl 2-(chloro(naphthalen-1-yloxy)phosphorylamino)propanoate (440 mg, 1.146 mmol) in 5 mL of THF. After workup and silica gel column chromatography, 58 mg of pure protide was obtained in a 19% yield, as an off white solid.

The following are the NMR results analyzing the synthesized compound:

¹H NMR (200 MHz, CD₃OD): δ 8.15 (m, 1H), 8.0 (d, J=5.0 Hz, 1H), 7.85 (m, 1H), 7.65 (m, 1H), 7.52-7.3 (m, 4H), 5.96 (d, J=2.2 Hz, 1H), 4.6 (m, 2H), 4.27 (m, 2H), 4.0 (m, 1H), 3.78-3.52 (m, 2H), 2.59 (s, 3H), 1.3 (d, J=7.0 Hz, 3H), 0.95 (d, J=4.0 Hz, 3H), 0.83 (d, J=3.6 Hz, 9H).

³¹P NMR (80 MHz, CD₃OD): δ 5.36, 5.31.

Example 91

The (2S)-neopentyl 2-((((2R,3R,4R,5R)-5-(2-amino-6-(methylthio)-9H-purin-9-yl)-3,4-dihydroxy-4-methyltetrahydrofuran-2-yl)methoxy)(quinolin-6-yloxy)phosphorylamino)propanoate was synthesized accordingly

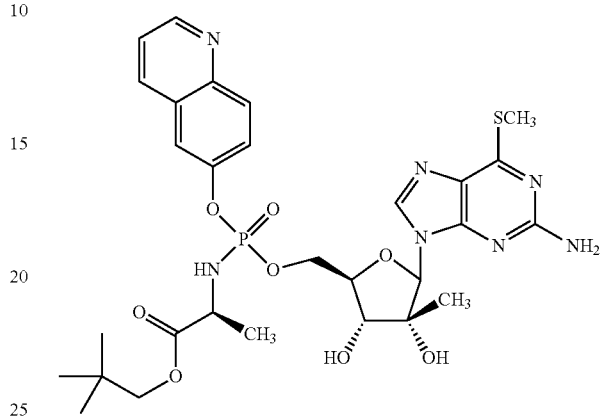

Using the general procedure (Method B) for the synthesis of nucleoside 5'-phosphoramidates, to a solution of (2R,3R,4R,5R)-2-(2-amino-6-(methylthio)-9H-purin-9-yl)-5-(hydroxymethyl)-3-methyltetrahydrofuran-3,4-diol (120 mg, 0.367 mmol) in 5 mL of THF, was added tent-BuMgCl (1.03 mL, 2.5 equiv) followed by (2S)-neopentyl 2-(chloro(quinolin-6-yloxy)phosphorylamino)propanoate (395 mg, 1.027 mmol) in 5 mL of THF. After workup and silica gel column chromatography, 101 mg of pure protide was obtained in a 41% yield, as an off white solid.

The following are the NMR results analyzing the synthesized compound:

¹H NMR (200 MHz, CD₃OD): δ 8.8 (ddd, J=2.0 Hz, J=2.0 Hz, J=1.2 Hz, 1H), 8.2 (bt, J=8.8 Hz, 1H), 8.0 9m, 2H), 7.77 (m, 1H), 7.65 (dd, J=1.8 Hz, J=2.6 Hz, 1H), 7.48 (dddd, J=4.4 Hz, J=1.4 Hz, J=1.8 Hz, J=4.4 Hz, 1H), 5.95 (s, 1H), 4.56 (m, 2H), 4.38-4.2 (m, 2H), 4.05 (m, 1H), 3.8-3.55 (m, 3H), 2.59 (d, J=1.8 Hz, 3H), 1.35 (m, 3H), 1.0-0.8 (m, 12H).

³¹P NMR (80 MHz, CD₃OD): δ 5.17, 5.09.

Example 92

The (2R,3R,4R,5R)-2-(2-(4-fluorobenzylamino)-6-methoxy-9H-purin-9-yl)-5-(hydroxymethyl)-3-methyltetrahydrofuran-3,4-diol was synthesized accordingly

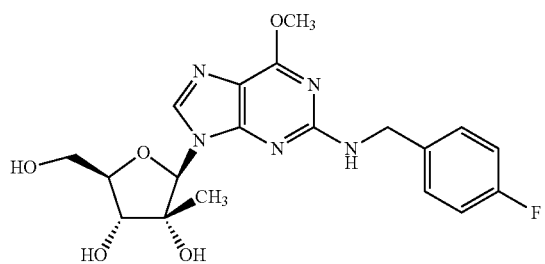 [SMILES: COc1nc(NCc2ccc(F)cc2)nc2c1ncn2[C@@H]1O[C@H](CO)[C@@H](O)[C@@]1(C)O]

Reductive amination of the precursor nucleoside yielded the title compound. The nucleoside (2R,3R,4R,5R)-2-(2-amino-6-methoxy-9H-purin-9-yl)-5-(hydroxymethyl)-3-methyl-tetrahydrofuran-3,4-diol (1.5 g) was dissolved in 50 mL of methanol and p-fluorobenzaldehyde (0.48 mL) was added followed by a catalytic amount of decaborane (0.17 g). The solution was stirred at room temperature for 12 h. The volatiles were evaporated and purified to yield 73% (1.48 g) of title compound as a white powder.

The following are the NMR results analyzing the synthesized compound:

$^1$H NMR (200 MHz, CD$_3$OD): δ 8.25 (s, 1H), 7.4 (m, 2H), 7.03 (m, 2H), 6.01 (s, 1H), 4.55 (s, 2H), 4.02 (s, 3H), 4.2-3.8 (m, 4H), 0.9 (s, 3H)

Example 93

The (2S)-neopentyl 2-((((2R,3R,4R,5R)-5-(2-(4-fluorobenzylamino)-6-methoxy-9H-purin-9-yl)-3,4-dihydroxy-4-methyltetrahydrofuran-2-yl)methoxy)(naphthalen-1-yloxy)phosphorylamino)propanoate was synthesized as follows

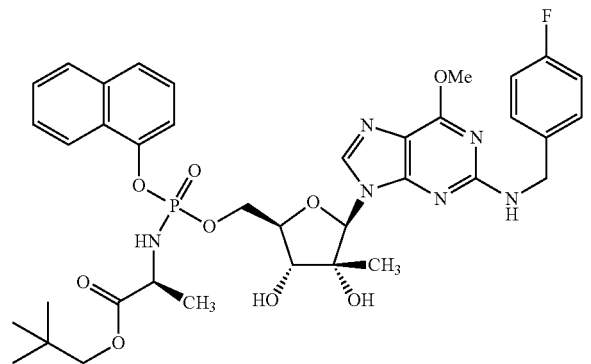 [SMILES: COc1nc(NCc2ccc(F)cc2)nc2c1ncn2[C@@H]1O[C@H](COP(=O)(N[C@@H](C)C(=O)OCC(C)(C)C)Oc2cccc3ccccc23)[C@@H](O)[C@@]1(C)O]

Using the general procedure (Method B) for the synthesis of nucleoside 5'-phosphoramidates, the nucleoside (2R,3R,4R,5R)-2-(2-(4-fluorophenylamino)-6-methoxy-9H-purin-9-yl)-5-(hydroxymethyl)-3-methyl-tetrahydrofuran-3,4-diol (100 mg) was dissolved in THF and cooled to 0° C. To this solution 183 mg of (2S)-neopentyl 2-(chloro(naphthalene-1-yloxy)phosphorylamino)propanoate was added followed by dropwise addition of t-butylmagnesium chloride (0.47 mL) and stirred for 18 h at room temperature. After workup the residue was purified by column chromatography to yield 53% (96 mg) of protide as an off-white solid.

The following are the NMR results analyzing the synthesized compound:

$^1$H NMR (200 MHz, CDCl$_3$): δ 8.0-8.2 (m, 1H), 7.9-7.95 (d, 1H), 7.8-7.9 (m, 1H), 7.6-7.7 (m, 1H), 7.2-7.5 (m, 6H), 6.85-7.02 (m, 2H), 5.95 (d, 1H), 4.45-4.6 (m, 2H), 4.1-4.3 (m, 2H), 3.99 (s, 3H), 3.4-3.7 (m, 3H), 1.28 (d, 3H), 0.9 (d, 3H), 0.81 (d, 9H).

$^{31}$P NMR (80 MHz, CDCl$_3$): δ 5.25, 5.14

Example 94

The nucleoside (3R,5S)-2-(2-amino-6-methoxy-9H-purin-9-yl)-5-(hydroxymethyl)-3-methyl-tetrahydrofuran-3-ol was synthesized as follows

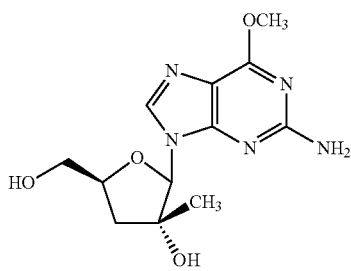 [SMILES: COc1nc(N)nc2c1ncn2C1O[C@H](CO)C[C@@]1(C)O]

Step 1: Preparation of (3R,4R,5R)-5-((tert-butyl-diphenylsilyloxy)methyl)-3,4-dihydroxy-3-methyl-dihydrofuran-2(3H)-one

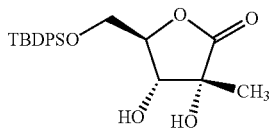

A round bottom flask was charged with 2-methyl-D-ribosolactone (22 g, 0.136 mol) and 200 mL of anhydrous pyridine. This mixture was cooled to 0° C. and TBDPSCl (34.97 mL, 0.136 mol) was added slowly followed by addition of DMAP (5 mol %). This reaction mixture was warmed to room temperature and stirred for 12 h. The reaction progress was monitored by TLC. After the total conversion, pyridine was removed under vacuum and the remaining residue was diluted with CH$_2$Cl$_2$ and washed with 1N HCl followed by saturated NaHCO$_3$ and brine. The combined organic layers were dried over anhydrous Na$_2$SO$_4$, filtered and concentrated. Purification was performed by column chromatography using hexane and ethyl acetate as a gradient mixture to give 48 g of thick viscous title compound in 88% yield.

The following are the NMR results analyzing the synthesized compound:

$^1$H NMR (200 MHz, CDCl$_3$) δ 7.63-7.71 (m, 4H), 7.36-7.5 (m, 6H), 4.3 (td, J=3.2 Hz, 6.4 Hz, 1H), 4.1-4.2 (dd, J=8.0 Hz, 1H), 3.85-4.04 (dq, J=3.2 Hz, 11.8 Hz, 2H), 3.4 (bs, 1H, —OH), 2.9 (bs, 1H, —OH), 1.5 (s, 3H), 1.05 (s, 9H); $^{13}$C (50 MHz, CDCl$_3$) δ 176.1, 135.9, 135.8, 133.0, 132.7, 130.2, 128.1, 83.9, 72.9, 72.5, 62.0, 27.0, 22.0, 19.5.

Step 2: Preparation of (2R,3R,4R)-2-((tert-butyl-diphenylsilyloxy)methyl)-4-hydroxy-4-methyl-5-oxo-tetrahydrofuran-3-yl-4-methylbenzenesulfonate

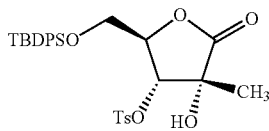

To a stirred solution of (3R,4R,5R)-5-((tert-butyldiphenyl-silyloxy)methyl)-3,4-dihydroxy-3-methyl-dihydrofuran-2(3H)-one (from step 1) (48 g, 0.12 mol) in anhydrous pyridine (250 mL) tosyl chloride (45.825 g, 0.24 mol) was added in small portions over a period of 30 min followed by DMAP (catalytic amount 5 mol %). Then the reaction mixture was slowly warmed to room temperature and stirred for 48 h. After the total conversion, pyridine was removed under vacuum and the remaining residue was washed with 1N HCl followed by saturated NaHCO$_3$ and brine and the extracted using CH$_2$Cl$_2$. The organic layers were dried over anhydrous Na$_2$SO$_4$, filtered and concentrated. Purification was performed by column chromatography using hexane and ethyl acetate as a gradient mixture to give 58.1 g (87% yield) of the title compound.

The following are the NMR results analyzing the synthesized compound:

$^1$H NMR (200 MHz, CDCl$_3$) δ 7.8 (d, J=8.2 Hz, 2H), 7.59-7.7 (m, 4H), 7.32-7.5 (m, 6H), 7.2-7.28 (d, J=8.4 Hz, 2H), 5.1 (d, J=6.6 Hz, 1H), 4.5 (td, J=2.4 Hz, 6.4 Hz, 1H), 3.9 (dd, J=2.2 Hz, 12.2 Hz, 1H), 3.8 (s, 1H), 3.7 (dd, J=2.4 Hz, 12.2 Hz, 1H), 2.38 (s, 3H), 1.39 (s, 3H), 1.05 (s, 9H); $^{13}$C (50 MHz, CDCl$_3$) δ 174.1, 146.2, 135.9, 135.8, 133.0, 132.7, 132.4, 130.4, 130.3, 128.8, 128.4, 128.2, 80.4, 77.9, 72.7, 60.9, 27.0, 22.2, 22.0, 19.5.

Step 3: Preparation of (2R,3R,4R)-2-((tert-butyl-diphenylsilyloxy)methyl)-4,5-dihydroxy-4-methyl-tetrahydrofuran-3-yl 4-methylbenzenesulfonate

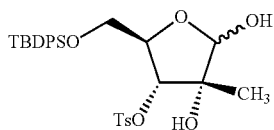

A solution of Red-Al (70.08 mL, 0.2298 mol) in 350 mL anhydrous toluene was cooled to 0° C. and 13.31 mL of anhydrous ethanol was added and stirred for 15 min. This stock solution was slowly added via cannula to a solution of (2R,3R,4R)-2-((tert-butyldiphenylsilyloxy)methyl)-4-hydroxy-4-methyl-5-oxo-tetrahydrofuran-3-yl-4-methyl-benzenesulfonate (from step 2) (58.1 g, 0.105 mol) in 700 mL of anhydrous toluene at −5° C. The progress of the reaction was monitored via TLC. After the complete conversion the reaction mixture was quenched by adding 18 mL of acetone followed by 200 mL water and 200 mL 1N HCl. This mixture was warmed to room temperature slowly. The organic layers were washed with 1N HCl (200 mL) and brine (100 mL) and were dried over anhydrous Na$_2$SO$_4$, filtered and concentrated to dryness. Purification was performed by column chromatography using hexane and ethyl acetate as a gradient mixture to give 58 g (99% yield) of the title compound.

The following are the NMR results analyzing the synthesized compound:

$^1$H NMR (200 MHz, CDCl$_3$) δ 7.26-7.82 (m, 6H), 7.3-7.5 (m, 6H), 7.2 (m, 2H), 5.0 (m, 1H), 4.8 (d, J=5.5 Hz, 1H), 4.2 (m, 1H), 3.44-3.82 (m, 2H), 2.95 (bs, 1H), 2.4 (s, 3H), 1.3 (s, 3H), 1.15 (s, 9H).

Step 4: Preparation of (5R,6R,6aR)-5-((tert-butyl-diphenylsilyloxy)methyl)-2,2,6a-trimethyl-tetrahydrofuro[3,2-d][1,3]dioxol-6-yl 4-methylbenzenesulfonate

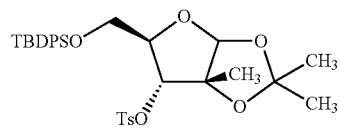

To a mixture of compounds (2R,3R,4R)-2-((tert-butyl-diphenylsilyloxy)methyl)-4,5-dihydroxy-4-methyl-tetrahydrofuran-3-yl 4-methylbenzenesulfonate (from step 3) (58 g, 0.104 mol), 2,2-dimethoxy propane (25.7 mL, 0.209 mol) in 500 mL of anhydrous CH$_2$Cl$_2$ at 0° C., PTSA was added and stirred at room temperature for 2 h. The reaction mixture was poured into saturated NaHCO$_3$ solution and organic layers were washed with brine, dried over anhydrous Na$_2$SO$_4$, filtered and concentrated. Purified by column chromatography using hexane and ethyl acetate as a gradient mixture to give 57.2 g of the title compound (92% yield).

The following are the NMR results analyzing the synthesized compound:

$^1$H NMR (200 MHz, CDCl$_3$) δ 7.8 (d, J=8.1, 2H), 7.62-7.72 (m, 4H), 7.32-7.52 (m, 6H), 7.2 (d, J=8.1 Hz, 2H), 5.45 (s, 1H), 4.9 (d, J=8.2 Hz, 1H), 4.2 (td, J=2.0 Hz, 8.2 Hz, 1H), 3.85 (dd, J=2.0 Hz, 12.3 Hz, 1H), 3.6 (dd, J=2.8, 12.3 Hz, 1H), 2.4 (s, 3H), 1.52 (s, 3H), 1.44 (s, 3H), 1.35 (s, 3H), 1.05 (s, 9H); $^{13}$C (50 MHz, CDCl$_3$) δ 145.3, 136.0 135.9, 133.8, 133.7, 133.3, 130.1, 130.0, 128.3, 128.0, 127.9, 114.1, 108.9, 86.4, 80.9, 80.2, 61.5, 29.5, 28.2, 27.0, 21.9, 21.9, 21.8, 19.6.

Step 5: Preparation of (5R,6R,6aR)-5-((tert-butyl-diphenylsilyloxy)methyl)-2,2,6a-trimethyl-tetrahydrofuro[3,2-d][1,3]dioxol-6-ol

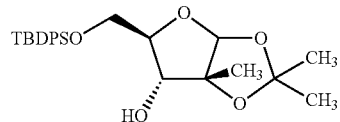

The mixture of (5R,6R,6aR)-5-((tert-butyldiphenylsilyloxy)methyl)-2,2,6a-trimethyl-tetrahydrofuro[3,2-d][1,3]dioxol-6-yl 4-methylbenzenesulfonate (from step 4) (56 g, 0.094 mol) and 1M solution of Li(Et)$_3$BH (376.4 mL, 0.376 mol) in 800 mL of THF was refluxed for 12 h. The reaction mixture was cooled to room temperature and quenched carefully with 200 mL of saturated ammonium chloride solution. Diluted with 500 mL of ethyl acetate and washed with 1N HCl (500 mL) and brine (300 mL). The organic layers were dried over anhydrous Na$_2$SO$_4$, filtered and concentrated. The crude residue was dissolved in ethyl acetate and passed through a pad of celite to remove salts. Purified by column chromatography using hexane and ethyl acetate as a gradient mixture to give 38.4 g of the title compound (93% yield).

The following are the NMR results analyzing the synthesized compound:

$^1$H NMR (200 MHz, CDCl$_3$) δ 7.6-7.7 (m, 4H), 7.26-7.4 (m, 6H), 5.47 (s, 1H), 3.74-3.95 (m, 4H), 5.47 (s, 1H), 3.74-3.95 (m, 4H), 2.3 (m, 1H, —OH), 1.46 (s, 6H), 1.4 (s, 3H), 1.0 (s, 9H); $^{13}$C (50 MHz, CDCl$_3$) δ 136.0, 135.9, 133.7, 133.5, 129.9, 128.0, 127.9, 113.2, 108.9, 87.0, 83.3, 76.1, 62.9, 29.5, 28.2, 27.0, 21.8, 19.6.

Step 6: Preparation of tert-butyl(((5R,6S,6aS)-6-iodo-2,2,6a-trimethyl-tetrahydrofuro[3,2-d][1,3]dioxol-5-yl)methoxy)diphenylsilane

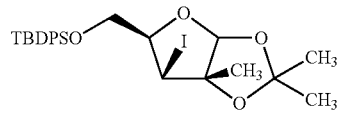

To a mixture of (5R,6R,6aR)-5-((tert-butyldiphenylsilyloxy)methyl)-2,2,6a-trimethyl-tetrahydrofuro[3,2-d][1,3]dioxol-6-ol (from step 5) (32.4 g, 0.0736 mol), triphenylphosphine (57.9 g, 0.2209 mol), Imidazole (15.03 g, 0.2209 mol) in 400 mL anhydrous toluene was added iodine (42.96 g, 0.169 mol) in portions over a period of 30 min and refluxed for 12 h. The mixture was diluted with 300 mL toluene and washed with saturated NaHCO$_3$ solution and saturated sodium thiosulfate solution. The organic layers were dried over anhydrous Na$_2$SO$_4$, filtered and concentrated. Purification was done by column chromatography using a gradient mixture of hexane and ethyl ether to give 32.08 g (80% yield) of the title compound.

The following are the NMR results analyzing the synthesized compound 6:

$^1$H NMR (200 MHz, CDCl$_3$) δ 7.6-7.8 (m, 4H), 7.3-7.44 (m, 6H), 5.56 (s, 1H), 4.5 (d, J=1.4 Hz, 1H), 3.6-4.0 (m, 3H), 1.8 (s, 3H), 1.48 (s, 3H), 1.43 (s, 3H), 1.06 (s, 9H); $^{13}$C (50 MHz, CDCl$_3$) δ 135.9, 135.8, 133.6, 133.5, 130.0, 128.0, 113.4, 108.4, 91.9, 80.3, 69.0, 40.9, 29.3, 28.4, 27.0, 25.1, 19.5; FAB: [M+H]$^+$537.2.

Step 7: Preparation of tert-butyldiphenyl(((5S,6aR)-2,2,6a-trimethyl-tetrahydrofuro[3,2-d][1,3]dioxol-5-yl)methoxy)silane

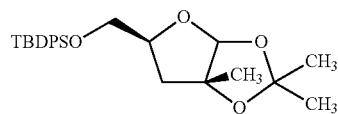

A solution of tert-butyl(((5R,6S,6aS)-6-iodo-2,2,6a-trimethyl-tetrahydrofuro[3,2-d][1,3]dioxol-5-yl)methoxy)diphenylsilane (from step 6) (10.3 g, 0.0186 mol), Bu$_3$SnH (5.9 mL, 0.0224 mol) and AIBN (5 mol %) in 120 mL anhydrous toluene was refluxed for 7 h. The reaction mixture was cooled to room temperature and 100 mL of 1N NaOH was added and stirred for one h. This mixture was then finally washed with brine and extracted with ethyl acetate. The organic layers were dried over anhydrous Na$_2$SO$_4$, filtered and concentrated. Purification was performed by column chromatography using hexane and ethyl ether as a gradient mixture to give 6.8 g of viscous title compound in 86% yield.

The following are the NMR results analyzing the synthesized compound 7:

$^1$H NMR (200 MHz, CDCl$_3$) δ 7.6-7.72 (m, 4H), 7.25-7.32 (m, 6H), 5.48 (s, 1H), 4.3-4.44 (m, 1H), 3.65-3.85 (m, 2H), 2.08-2.22 (dd, J=5.0 Hz, 13.2 Hz, 1H), 1.74-1.90 (dd, J=10.2 Hz, 12.8 Hz, 1H), 1.5 (s, 6H), 1.42 (s, 3H), 1.0 (s, 9H); $^{13}$C (50 MHz, CDCl$_3$) δ 135.9, 135.8, 133.6, 129.9, 127.9, 112.1, 110.1, 90.0, 79.5, 65.2, 41.7, 29.5, 28.6, 27.0, 23.8, 19.5; FAB: [M+H]$^+$411.32.

Step 8: Preparation of ((5S,6aR)-2,2,6a-trimethyl-dihydro-5H-furo[3,2-d][1,3]dioxol-5-yl)methanol

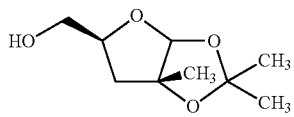

To a solution of tert-butyldiphenyl(((5S,6aR)-2,2,6a-trimethyl-tetrahydrofuro[3,2-d][1,3]dioxol-5-yl)methoxy)silane (from step 7) (7.2 g, 0.0169 mol) in 50 mL of anhydrous THF at 0° C., TBAF (20.28 mL, 0.0203 mol) was added and stirred at room temperature for 3 h. The reaction mixture was diluted with ethyl acetate and washed with water and brine. The organic layers were dried over anhydrous Na$_2$SO$_4$, filtered and concentrated to dryness. Purified by column chromatography using hexane and ethyl ether as a gradient mixture to give 2.72 g of the title compound in 82% yield.

The following are the NMR results analyzing the synthesized compound:

$^1$H NMR (200 MHz, CDCl$_3$) δ 5.5 (s, 1H), 4.4 (m, 1H), 3.8-3.9 (m, 1H), 3.46-3.6 (m, 1H), 2.0-2.15 (dd, J=5.2 Hz, 13.2 Hz, 1H), 1.8 (m, 2H), 1.5 (s, 6H), 1.44 (s, 3H).

Step 9: Preparation of ((5S,6aR)-2,2,6a-trimethyl-dihydro-5H-furo[3,2-d][1,3]dioxol-5-yl)methyl benzoate

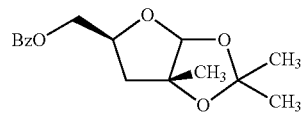

Benzoyl chloride (1.92 mL, 0.0166 mol) was added to a solution of ((5S,6aR)-2,2,6a-trimethyl-dihydro-5H-furo[3,2-d][1,3]dioxol-5-yl)methanol (from step 8) (2.72 g, 0.0138 mol) in 20 mL of anhydrous pyridine at 0° C. To this mixture 5 mol % of DMAP was added and stirred at room temperature for 3 h. Pyridine was removed under vacuum; the residue was diluted with ethyl acetate and washed with 1N HCl, saturated NaHCO$_3$ and brine. The organic layers were dried over anhydrous Na$_2$SO$_4$, filtered and concentrated. The compound was purified via column chromatography using hexane and ethyl acetate as a gradient mixture to give 4.1 g of the title compound (97% yield).

The following are the NMR results analyzing the synthesized compound:

$^1$H NMR (200 MHz, CDCl$_3$) δ 8.0-8.2 (m, 2H), 7.4-7.65 (m, 3H), 5.5 (s, 1H), 4.2-4.65 (m, 3H), 2.2-2.36 (dd,

J=5.0 Hz, 4.8 Hz, 1H), 1.62-1.75 (dd, J=10.8 Hz, 13.2 Hz), 1.54 (s, 6H), 1.46 (s, 3H).

Step 10: Preparation of ((2S,4R)-4,5-diacetoxy-4-methyl-tetrahydrofuran-2-yl)methyl benzoate

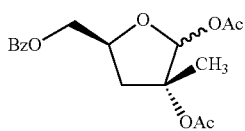

A mixture of 3.8 g of ((5S,6aR)-2,2,6a-trimethyl-dihydro-5H-furo[3,2-d][1,3]dioxol-5-yl)methyl benzoate (from step 9) in 25 mL of 70% acetic acid was heated to 70° C. for 48 h. The reaction mixture was diluted with ethyl acetate and washed with water and saturated NaHCO$_3$. The organic layers were dried over anhydrous Na$_2$SO$_4$, filtered and concentrated. Crude diol obtained was acelyated using Ac$_2$O (0.03373 mol, 3.18 mL) and 20 mL of anhydrous pyridine with catalytic amount of DMAP (5 mol %). The progress of the reaction was monitored by TLC. Pyridine was removed under vacuum and the residue was diluted with ethyl acetate and was washed with 1N HCl and saturated NaHCO$_3$. The organic layers were dried over anhydrous Na$_2$SO$_4$, filtered and concentrated. Purified by column chromatography to give 3.3 g of the title compound (88% yield) and 0.55 g of starting material acetonide was recovered.

The following are the NMR results analyzing the synthesized compound:

$^1$H NMR (200 MHz, CDCl$_3$) δ 8.0-8.1 (m, 2H), 7.36-7.64 (m, 3H), 6.3-6.4 (s, 1H), 4.65-4.24 (m, 3H), 2.6-2.8 (m, 1H), 1.9-2.22 (m, 7H), 1.62 (s, 3H).

Step 11: Preparation of ((2S,4R)-4-acetoxy-5-(2-amino-6-methoxy-9H-purin-9-yl)-4-methyl-tetrahydrofuran-2-yl)methyl benzoate

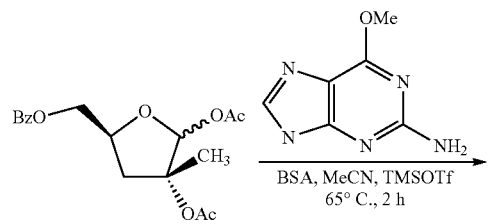

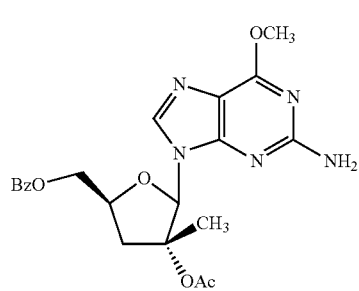

A mixture of 6-O-methyl guanine (0.516 g, 3.125 mmol), BSA (1.99 g, 9.821 mmol), 0.5 g of 3A° molecular sieves in 8 mL of anhydrous CH$_3$CN was heated to 60° C. for 45 min to make a homogeneous solution and then cooled to 0° C. To this mixture was added acetonitrile solution of ((2S,4R)-4,5-diacetoxy-4-methyl-tetrahydrofuran-2-yl)methyl benzoate (from step 10) (1 g, 2.976 mmol) followed by TMSOTf (1.077 mL, 5.95 mmol) and was heated to 60° C. for 2 h. The progress of the reaction was monitored via TLC. The reaction mixture was diluted with 25 mL of ethyl acetate and poured into 20 mL of ice-cold saturated NaHCO$_3$ and stirred for 3 h. The organic layers were washed with water and brine and were dried over anhydrous Na$_2$SO$_4$, filtered, and concentrated. Purified by column chromatography using a gradient mixture of hexane and ethyl acetate to give 0.71 g (54% yield) of the title compound.

The following are the NMR results analyzing the synthesized compound:

$^1$H NMR (200 MHz, CDCl$_3$) δ 8.0-8.1 (m, 2H), 7.7 (s, 1H), 7.4-7.6 (m, 3H), 6.3 (s, 1H), 4.8-5.0 (m, 3H), 4.6-4.76 (m, 2H), 4.0 (s, 3H), 2.7-2.8 (dd, J=4.8 Hz, 13.6 Hz, 1H), 2.52-2.64 (dd, J=10.4 Hz, 13.6 Hz, 1H), 2.1 (s, 3H), 1.36 (s, 3H);

$^{13}$C (50 MHz, CDCl$_3$) δ 170.7, 166.7, 159.6, 138.4, 133.6, 129.9, 128.8, 128.6, 91.5, 90.3, 77.9, 65.3, 54.1, 39.2, 22.4, 18.8.

Step 12: Preparation of (3R,5S)-2-(2-amino-6-methoxy-9H-purin-9-yl)-5-(hydroxymethyl)-3-methyl-tetrahydrofuran-3-ol

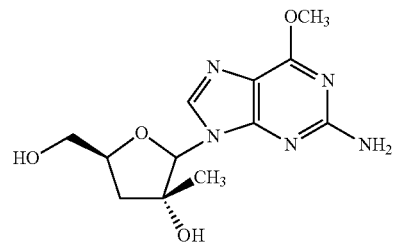 [SMILES: COc1nc(N)nc2c1ncn2C1O[C@H](CO)C[C@@]1(C)O]

Methanolic ammonia (7N, 20 mL) was added to ((2S,4R)-4-acetoxy-5-(2-amino-6-methoxy-9H-purin-9-yl)-4-methyl-tetrahydrofuran-2-yl)methyl benzoate (from step 11) (1.53 g) and stirred at room temperature for 24 h in a sealed tube. The volatiles were evaporated under vacuum and the resulting residue was loaded directly on to the column and eluted with CH$_2$Cl$_2$/MeOH (10:1) as a gradient mixture to give 0.802 g of compound (79% yield). mp: 140° C.-142° C.

The following are the NMR results analyzing the synthesized compound:

$^1$H NMR (200 MHz, DMSO-d$_6$) δ 8.2 (s, 1H), 6.4 (bs, 2H), 5.78 (s, 1H), 5.4 (s, 1H), 5.1 (t, J=5.0 Hz, 1H), 4.26-4.4 (m, 1H), 3.9 (s, 3H), 3.72-3.84 (m, 1H), 3.52-3.66 (m, 1H), 2.04-2.22 (dd, J=12.6 Hz, 10.8 Hz, 1H), 1.76-1.90 (dd, J=5.2 Hz, 12.6 Hz, 1H), 0.8 (s, 3H)

$^{13}$C (50 MHz, DMSO-d$_6$) δ 161.3, 160.5, 154.5, 138.0, 144.3, 92.4, 81.4, 81.1, 62.0, 53.8, 39.4, 22.8;

FAB [M+H]$^+$ 296.02.

Example 95

The protide (2S)-benzyl 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate was synthesized as follows

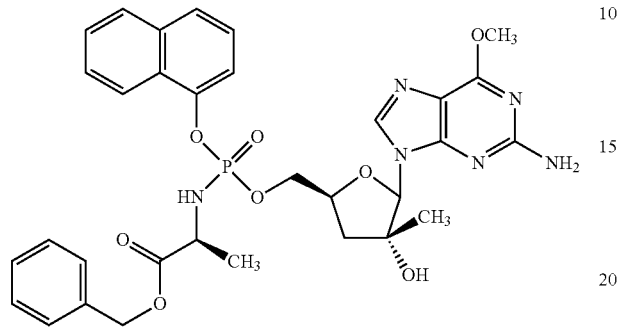

Using the general procedure for the synthesis of nucleoside 5'-phosphoramidates (Method A), to a solution of (3R,5S)-2-(2-amino-6-methoxy-9H-purin-9-yl)-5-(hydroxymethyl)-3-methyl-tetrahydrofuran-3-ol 100 mg (0.339 mmol) in 5 mL of THF, was added tert-BuMgCl 0.68 mL (0.68 mmol), followed by (2S)-benzyl 2-(chloro(naphthalen-1-yloxy)phosphorylamino)propanoate 273 mg (0.68 mmol), in 5 mL of THF. After work up and silica gel column chromatography, 131 mg of (2S)-benzyl 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate was obtained in a 58% yield, as an off-white solid. MS (ES+) m/e: 663.23 (MH+, 100%); Accurate mass: $C_{32}H_{36}N_6O_8P$ calculated: 663.2332. found 663.2341.

The following are the NMR results analyzing the synthesized compound:

$^1$H NMR (500 MHz, CD$_3$OD) δ 8.19-8.16 (m, 1H, H$_8$-naph), 7.99, 7.96 (2×s, 1H, H8), 7.84-7.81 (m, 1H, H$_5$-naph), 7.66, 7.64 (2×d, J=8.00 Hz, 1H, H$_4$-naph), 7.51-7.43 (m, 3H, H$_7$, H$_6$, H$_2$-naph), 7.36 (t, J=8.00 Hz, 1H, H$_3$-naph), 7.25-7.22 (m, 5H, Ph), 5.95 (s, 1H, H$_{1'}$), 5.06-4.98 (m, 2H, CH$_2$ ester), 4.67-4.59 (m, 1H, H$_{4'}$), 4.51-4.41 (m, 2H, H$_{5'}$), 4.14-4.07 (m, 1H, HαAla), 4.03, 4.01 (2×s, 3H, 6OCH$_3$), 2.30, 2.11 (2×t, J=12.00 Hz, 1H, H$_{3'a}$), 2.00, 1.93 (dd, J=5.00 Hz, J=12.00 Hz, 1H, H$_{3'b}$), 1.31 (d, J=7.50 Hz, 3H, CH$_3$, Ala), 0.99, 0.93 (2×s, 3H, 2'CH$_3$).

$^{13}$C NMR (126 MHz, CD$_3$OD) δ 174.85 (d, $^3J_{C-C-N-P}$=4.40 Hz, C=O ester), 174.58 (d, $^3J_{C-C-N-P}$=5.50 Hz, C=O ester), 162.72 (C6), 161.84, 161.80 (C2), 154.64, 154.59 (C4), 148.01, 147.96 (ipso Naph), 139.03, 138.73 (CH8), 137.13, 137.11 (ipso Ph), 136.25 (C10-napht), 129.56, 129.55, 129.28, 129.27, 129.20, 129.17, 128.88, 128.85 (CH-napht and Ph), 127.98, 127.92 (C9-naph), 127.87, 127.79, 127.60, 127.54, 126.55, 126.06, 126.01, 122.84, 122.76 (CH-napht and Ph), 116.42, 116.32 (2×d, $^3J_{C-C-O-P}$=4.40 Hz C2-naph), 115.62, 115.55 (C5), 94.89, 94.56 (C1'), 82.14, 82.09 (C2'), 80.11, 79.97 (2×d, $^3J_{C-C-O-P}$=8.50 Hz, C4'), 68.84 (d, $^2J_{C-O-P}$=7.50 Hz, C5'), 68.64 (d, $^2J_{C-O-P}$=5.00 Hz, C5'), 67.97, 67.95 (CH$_2$ ester), 54.33, 54.30 (6OCH$_3$), 51.87, 51.76 (Cα Ala), 41.21, 40.63 (C3'), 22.58 (2'C CH$_3$), 20.63, 20.39 (2×d, $^3J_{C-C-N-P}$=7.50 Hz, CH$_3$ Ala)

$^{31}$P NMR (202 MHz, CD$_3$OD) δ 4.45, 4.29

Example 96

The protide (2S)-((S)-1-phenylethyl) 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate was synthesized as follows

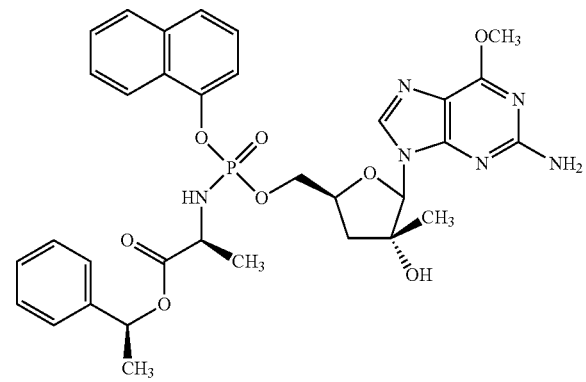 [SMILES: COc1nc(N)nc2c1ncn2C1O[C@H](COP(=O)(N[C@@H](C)C(=O)O[C@@H](C)c2ccccc2)Oc2cccc3ccccc23)C[C@@]1(C)O]

Using the general procedure for the synthesis of nucleoside 5'-phosphoramidates (Method A), to a solution of (3R,5S)-2-(2-amino-6-methoxy-9H-purin-9-yl)-5-(hydroxymethyl)-3-methyl-tetrahydrofuran-3-ol 93 mg (0.315 mmol) in 5 mL of THF was added tert-BuMgCl 0.63 mL (0.63 mmol) followed by (2S)-((S)-1-phenylethyl) 2-(chloro(naphthalen-1-yloxy)phosphorylamino)propanoate 282 mg (0.63 mmol) in 5 mL of THF. After work up and silica gel column chromatography, 40 mg of (2S)-((S)-1-phenylethyl) 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate was obtained in a 19% yield, as an off-white solid. MS (ES+) m/e: 677.25 (MH+, 100%); Accurate mass: $C_{33}H_{38}N_6O_8P$ calculated: 677.2489. found 677.2511.

The following are the NMR results analyzing the synthesized compound:

$^1$H NMR (500 MHz, CD$_3$OD) δ 8.20-8.18 (m, 1H, H$_8$-naph), 7.99, 7.97 (2×s, 1H, H8), 7.86-7.84 (m, 1H, H$_5$-naph), 7.69, 7.67 (2×d, J=8.00 Hz, 1H, H$_4$-naph), 7.53-7.47 (m, 3H, H$_7$, H$_6$, H$_2$-naph), 7.40, 7.36 (2×t, J=7.50 Hz, 1H, H$_3$-naph), 7.29-7.22 (m, 5H, Ph), 5.95 (s, 1H), 5.77, 5.72 (2×q, J=7.10 Hz, 1H, CH ester), 4.66-4.58 (m, 1H, H$_{4'}$), 4.56-4.38 (m, 2H, H$_{5'}$), 4.09-4.06 (m, 1H, Hα Ala), 4.05, 4.04 (2×s, 3H, 6OCH$_3$), 2.32, 2.12 (2×t, J=11.50 Hz, 1H, H$_{3'a}$), 1.99, 1.92 (dd, J=5.00 Hz, J=12.00 Hz, 1H, H$_{3'b}$), 1.41 (d, J=7.00 Hz, 3H, CH$_3$ ester), 1.28 (d, J=7.00 Hz, 3H, CH$_3$, Ala), 1.01, 0.95 (2×s, 3H, 2'CH$_3$)

$^{13}$C NMR (126 MHz, CD$_3$OD) δ 174.25 (d, $^3J_{C-C-N-P}$=4.40 Hz, C=O ester), 173.97 (d, $^3J_{C-C-N-P}$=5.50 Hz, C=O ester), 162.74 (C6), 161.85 (C2), 154.66, 154.63 (C4), 148.03, 147.97 (ipso Naph), 142.87, 142.84 (ipso Ph), 139.10, 138.75 (CH8), 136.28 (C10-napht), 129.57, 129.53, 128.96, 128.87, 128.84 (CH-napht and Ph), 127.97, 127.93 (C9-naph), 127.88, 127.77, 127.65, 127.50, 127.06, 127.02, 126.52, 126.01, 122.83, 122.76 (CH-napht and Ph), 116.35, 116.30

(2×d, $^3J_{C—C—O—P}$=5.50 Hz C2-naph), 115.58, 115.52 (C5), 94.90, 94.59 (C1'), 82.11, 82.05 (C2'), 80.11, 79.99 (2×d, $^3J_{C—C—O—P}$=8.50 Hz, C4'), 74.82, 74.75 (CH ester), 68.82, 68.65 (2×d, $^2J_{C—O—P}$=5.00 Hz, C5'), 54.26 (6OCH$_3$), 51.85, 51.75 (Cα Ala), 41.22, 40.73 (C3'), 22.6$\overline{3}$ (CH$_3$ ester), 22.52 (2'CCH$_3$), 20.47, 20.28 (2×d, $^3J_{C—C—N—P}$=7.50 Hz, $\underline{CH_3 \text{ Ala}}$)

$^{31}$P NMR (202 MHz, CD$_3$OD) δ 4.43, 4.30

Example 97

The protide (2S)-neopentyl 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate was synthesized as follows

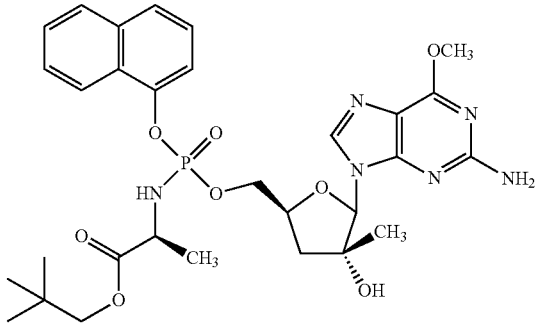 [SMILES: COc1nc(N)nc2c1ncn2C1O[C@H](COP(=O)(N[C@@H](C)C(=O)OCC(C)(C)C)Oc2cccc3ccccc23)C[C@@]1(C)O]

Using the general procedure for the synthesis of nucleoside 5'-phosphoramidates (Method B), to a solution of (3R,5S)-2-(2-amino-6-methoxy-9H-purin-9-yl)-5-(hydroxymethyl)-3-methyl-tetrahydrofuran-3-ol (100 mg) dissolved in 3 mL of THF was added tert-BuMgCl (0.68 mL) followed by (2S)-neopentyl 2-(chloro(naphthalen-1-yloxy)phosphorylamino)propanoate (260.2 mg) in THF (1.5 mL). After workup and silica gel column chromatography, 156 mg of protide was obtained (72% yield). HPLC t$_R$=22.94, 23.10 min (column: Varian Pursuit XRs 5, C$_{18}$, 150×4.6 mm; method: linear gradient of ACN (10% to 100%) in H$_2$O in 30 min).

The following are the NMR results analyzing the synthesized compound:

$^1$H NMR (500 MHz, CD$_3$OD) δ 8.22-8.15 (m, 1H), 7.99 and 7.97 (2s, 1H), 7.92-7.84 (m, 1H), 7.74-7.67 (m, 1H), 7.58-7.46 (m, 3H), 7.45-7.38 (m, 1H), 5.94 (s, 1H), 4.72-4.46 (m, 3H), 4.12-4.03 (m, 4H), 3.78, 3.74, 3.68, 3.63 (2 AB system, J$_{AB}$=10.5, 2H), 2.36 and 2.20 (2t, J=12.2, 1H), 2.01 and 1.96 (2 A-B system, J=4.3 and J=12.9, 1H), 1.37-1.32 (m, 3H), 1.02 and 0.96 (2s, 3H), 0.89 and 0.87 (6s, 9H)

$^{31}$P NMR (202 MHz, CD$_3$OD-d$_4$) δ 4.40, 4.33

Example 98

The protide (2S)-cyclohexyl 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate was synthesized as follows

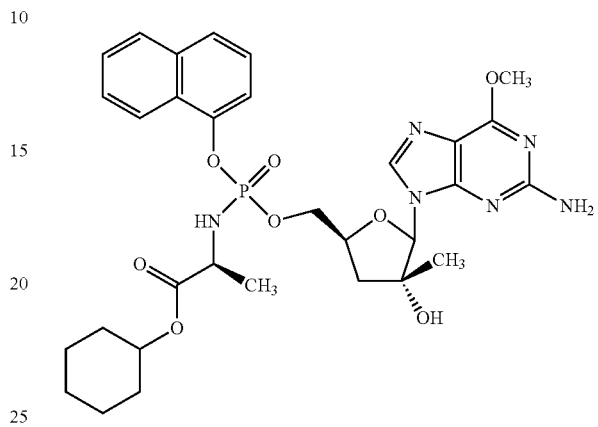

Using the general procedure for the synthesis of nucleoside 5'-phosphoramidates (Method A), to a solution of (3R,5S)-2-(2-amino-6-methoxy-9H-purin-9-yl)-5-(hydroxymethyl)-3-methyl-tetrahydrofuran-3-ol 100 mg (0.339 mmol) in 5 mL of THF was added tert-BuMgCl 0.68 mL (0.68 mmol), followed by (2S)-cyclohexyl 2-(chloro(naphthalen-1-yloxy)phosphorylamino)propanoate 268 mg (0.68 mmol) in 5 mL of THF. After work up and silica gel column chromatography, 131 mg of pure protide was obtained in a 52% yield, as an off-white solid. MS (ES+) m/e: 655.26 (MH$^+$, 100%); Accurate mass: C$_{31}$H$_{41}$N$_6$O$_8$P calculated: 655.2645. found 655.2640.

The following are the NMR results analyzing the synthesized compound:

$^1$H NMR (500 MHz, CD$_3$OD) δ 8.20-8.18 (m, 1H, H$_8$-naph), 7.99, 7.98 (2×s, 1H, H8), 7.88-7.83 (m, 1H, H$_5$-naph), 7.69, 7.67 (2×d, J=8.00 Hz, 1H, H$_4$-naph), 7.53-7.47 (m, 3H, H$_7$, H$_6$, H$_2$-naph), 7.41, 7.39 (2×t, J=8.00 Hz, 1H, H$_3$-naph), 5.95 (s, 1H, H$_1$·), 4.68-4.57 (m, 3H, H$_4$· and H$_5$·), 4.54-4.47 (m, 1H, CH ester), 4.04 (s, 3H, 6OCH$_3$), 4.03-4.00 (m, 1H, Hα Ala), 2.36, 2.17 (2×t, J=12.00 Hz, 1H, H$_{3'a}$), 1.98, 1.96 (dd, J=5.00 Hz, J=12.00 Hz, 1H, H$_{3'b}$), 1.71-1.63 (m, 4H, 2×CH$_2$ ester), 1.48-1.22 (m, 9H, 3×CH$_2$ ester and CH$_3$ Ala), 1.01, 0.95 (2×s, 3H, 2'CH$_3$)

$^{13}$C NMR (126 MHz, CD$_3$OD) δ 174.52 (d, $^3J_{C—C—N—P}$=4.40 Hz, C═O ester), 174.25 (d, $^3J_{C—C—N—P}$=5.50 Hz, C═O ester), 162.72 (C6), 161.84 (C2), 154.65, 154.60 (C4), 148.05, 148.00 (ipso Naph), 139.08, 138.78 (CH8), 136.30, 136.28 (C10-napht), 128.87, 128.83 (CH-napht), 127.98, 127.91 (C9-naph), 127.77, 127.55, 127.49, 126.53, 125.98, 122.82, 122.77 (CH-naph), 116.27 (C2-naph), 115.59, 115.50 (C5), 94.94, 94.60 (C1'), 82.11, 82.09 (C2'), 80.18, 80.02 (2×d, $^3J_{C—C—O—P}$=8.50 Hz, C4'), 74.92 (CH ester), 68.88, 68.72 (2×d, $^2J_{C—O—P}$=5.00 Hz, C5'), 54.27, 54.24 (6OCH$_3$), 51.89, 51.81 (Cα Ala), 41.24, 40.74 (C3'), 32.3$\overline{8}$, 32.34, 32.32 (2×CH$_2$-2 and 6 ester), 26.36 (2×CH$_2$-3 and 4 ester), 24.57 (CH$_2$-5 ester), 22.51 (2'C CH$_3$), 20.77 (d, $^3J_{C—C—N—P}$=6.30 Hz, CH$_3$ Ala), 20.54 ($\overline{d}$, $^3J_{C—C—N—P}$=7.50 Hz, CH$_3$ Ala)

$^{31}$P NMR (202 MHz, CD$_3$O$\overline{D}$) δ 4.39

Example 99

The protide benzyl (2S)-benzyl 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)-3-methylbutanoate was synthesized as follows

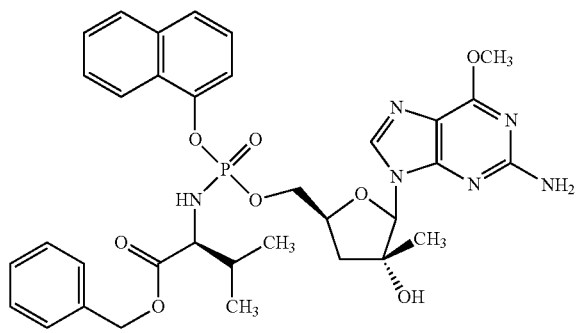 [SMILES: COc1nc(N)nc2c1ncn2C1O[C@H](COP(=O)(N[C@H](C(=O)OCc2ccccc2)C(C)C)Oc2cccc3ccccc23)C[C@@]1(C)O]

Using the general procedure for the synthesis of nucleoside 5'-phosphoramidates (Method A), to a solution of (3R,5S)-2-(2-amino-6-methoxy-9H-purin-9-yl)-5-(hydroxymethyl)-3-methyl-tetrahydrofuran-3-ol 150 mg (0.508 mmol) and NMI 0.20 mL (2.54 mmol), in 5 mL of THF was added (2S)-benzyl 2-(chloro(naphthalen-1-yloxy)phosphorylamino)-3-methylbutanoate 658 mg (1.52 mmol) in 5 mL of THF. After work up and silica gel column chromatography, 30 mg of benzyl (2S)-benzyl 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)-3-methylbutanoate was obtained in a 9% yield, as an off-white solid.

The following are the NMR results analyzing the synthesized compound:

$^1$H NMR (500 MHz, CD$_3$OD) δ 8.19-8.16 (m, 2H, H$_8$-naph and H8), 7.86, 7.83 (2×d, J=7.50 Hz, 1H, H$_5$-naph), 7.68, 7.66 (2×d, J=8.50 Hz, 1H, H$_4$-naph), 7.52-7.45 (m, 3H, H$_7$, H$_6$, H$_2$-naph), 7.37, 7.36 (2×t, J=8.00 Hz, 1H, H$_3$-naph), 7.28-7.24 (m, 5H, Ph), 5.95, 5.94 (s, 1H, H$_{1'}$), 5.06, 4.98 (2×d, J=12.00 Hz, 2H, CH$_2$ ester), 4.69-4.62 (m, 1H, H$_{4'}$), 4.58-4.42 (m, 2H, H$_{5'}$), 4.06, 4.05 (2×s, 3H, 6OCH$_3$), 3.82, 3.77 (2×dd, J=6.00 Hz, J=10.00 Hz, 1H, Hα Val), 2.38-2.33 (m, 1H, H$_{3'a}$), 2.15-2.11 (m, 1H, H$_{3'b}$), 2.07-1.92 (m, 1H, CHβ Val), 1.02, 0.96 (2×s, 3H, 2'CH$_3$), 0.85-0.80 (m, 6H, 2×CH$_3$, Val)

$^{13}$C NMR (126 MHz, CD$_3$OD) δ 174.11, 173.78 (C=O ester), 162.17 (C6), 162.11, 162.08 (C2), 153.98 (C4), 148.01, (ipso Naph), 147.95, 146.50 (ipso Ph), 138.80, 138.45 (CH8), 136.28, 136.24 (C10-napht), 130.79, 129.51, 129.45, 129.43, 129.31, 129.16, 128.86, 128.80 (CH-napht and Ph), 127.90 (d, $^3J_{C-C-O-P}$=6.30 Hz, C9-naph), 127.81 (d, $^3J_{C-C-O-P}$=8.80 Hz, C9-naph), 127.75, 127.51, 126.52, 126.47, 126.03, 125.97, 122.83, 122.78 (CH-napht and Ph), 116.43, 116.24 (2×d, $^3J_{C-C-O-P}$=4.40 Hz, C2-naph), 113.71, 113.41 (C5), 95.27, 94.93 (C1'), 82.06, 82.04 (C2'), 80.35, 80.23 (2×d, $^3J_{C-C-O-P}$=8.50 Hz, C4'), 68.97, 68.67 (2×d, $^2J_{C-O-P}$=7.50 Hz, C5'), 67.84, 67.77 (CH$_2$ ester), 62.11 (6OCH$_3$), 54.58, 54.51 (Cα Val), 41.14, 40.59 (C3'), 33.27, 33.04 (2×d, $^3J_{C-C-N-P}$=8.8 Hz, Cβ Val), 22.50, 22.32 (2'CCH$_3$), 19.51, 19.46, 18.41, 18.19 (2×CH$_3$ Val)

$^{31}$P NMR (202 MHz, CD$_3$OD) δ 5.22, 5.13

Further to the above Examples, representative compounds, prepared according to the examples were tested for potency in an HCV replicon assay (Genotype 1b) for activity against the virus (EC$_{50}$) and toxicity to the cells (CC$_{50}$). These results are set forth below.

Huh7 Replicon Cell Lines and Cell Culture Conditions: A luciferase-reporter genotype 1b subgenomic replicon cell line, and a genotype 1a full-length replicon cell line were obtained from Apath, LLC, Brooklyn, N.Y.: All cell lines were passaged twice a week by splitting 4 or 6 fold. Cells were maintained in DMEM-high glucose medium (HyClone, Logan, Utah) supplemented with 9% FBS (HyClone), 2 mM glutamine (Invitrogen, Carlsbad, Calif.), 100 U/ml PenStrep (Invitrogen). Media also contained 0.25 mg/ml of the antibiotic G-418 to maintain stable expression of the replicon (Invitrogen). Incubation was performed at 37° C. in 5% CO$_2$ atmosphere. Replicon cell lines were used until they accumulated 15-to-18 passages, after which cells were restarted from the frozen stock. Seeding cell counts were routinely determined using an automatic Cedex HiRes cell counter (Flownomics Analytical Instruments, Madison, Wis.) or manually using INCYTO C-Chip™ Disposable Hemacytometers (Fisher Scientific, Pittsburg, Pa.).

The anti-HCV assays were done accordingly:

Luciferase Genotype 1b Replicon Potency Assay. Replicon cells were seeded into white 96-well plates (Nunc/VWR) at a density of 2×10$^4$ cells/well in medium without G-418. A Stacker Multidrop Liquid Dispenser (MTX Lab Systems, Vienna, Va.) was employed to ensure uniform and fast cell seeding into multiple plates. 18-24 h after cell plating, inhibitors were added and cells were incubated for additional 24, 48, or 72 h (as indicated). Compounds were tested in triplicates and quadruplicates at 3× or 4× serial dilutions over a range of 0.0001-to-10 μM concentrations. HCV replication was monitored by *Renilla* luciferase reporter activity assay using *Renilla* luciferase reporter (Promega, Madison, Wis.) and a Veritas Luminometer (Turner Biosystems, Sunnyvale, Calif.). 50% and 90% inhibitory concentration (IC$_{50}$ and IC$_{90}$) values were calculated as the concentration of compound that results correspondingly in 50% and 90% decreases in the reporter expression as compared to untreated cells. The values were determined by non-linear regression (four-parameter sigmoidal curve fitting) analysis.

The cell cytotoxicity assay data was obtained as described below:

Cytotoxicity Assay. Cells were seeded into 96-well plates at a density of 2×10$^4$ cells per well. 24 h after cell plating, 11 serial 2× compound dilutions, starting with 100 μM, were applied to the testing plates (3 repeats per compound dilution). Each testing plate was run with a "no-compound" control. Incubation with compounds was continued at 37° C. in a CO$_2$ incubator for 72 h. To determine cell viability, the Cell-Titer-Glo® assay (Promega, Madison, Wis.) was performed according to the manufacturer's protocol. The compound concentration resulting in 50% luminescent signal was reported as the CC$_{50}$ concentration.

The results of the assay in terms of IC$_{50}$ (μM) and CC$_{50}$ (μM) are given in Table 1 below:

The results of the assay in terms of IC$_{50}$ (μM) and CC$_{50}$ (μM) are given in Table 1 below:

| Structure | Example # | IC$_{50}$ μM | CC$_{50}$ μM |
|---|---|---|---|
| (structure) | 2 | 3.1 | >100 |
| (structure) | 13 | 0.026 | 14 |
| (structure) | 14 | 0.04 | 15 |
| (structure) | 15 | 0.032 | 12 |

-continued

| Structure | Example # | IC$_{50}$ μM | CC$_{50}$ μM |
|---|---|---|---|
| 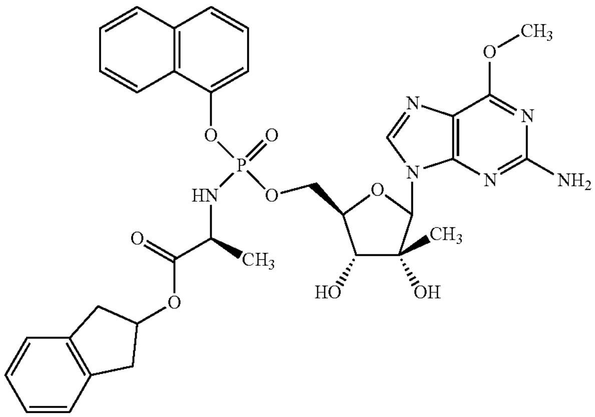 [SMILES: COc1nc(N)nc2c1ncn2C1O[C@H](COP(=O)(N[C@@H](C)C(=O)OC2Cc3ccccc3C2)Oc2cccc3ccccc23)[C@@H](O)[C@@]1(C)O] | 16 | 0.027 | 11 |
| 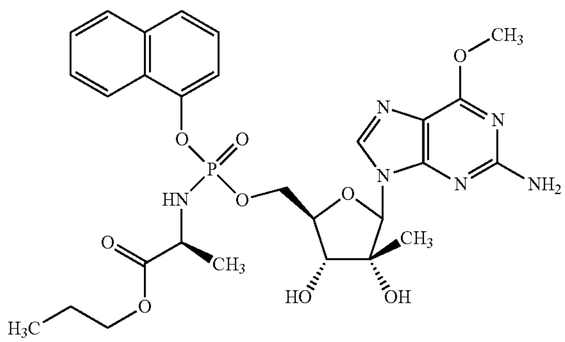 [SMILES: CCCOC(=O)[C@H](C)NP(=O)(OC[C@H]1OC(n2cnc3c(OC)nc(N)nc32)[C@](C)(O)[C@@H]1O)Oc1cccc2ccccc12] | 17 | 0.029 | 12 |
| 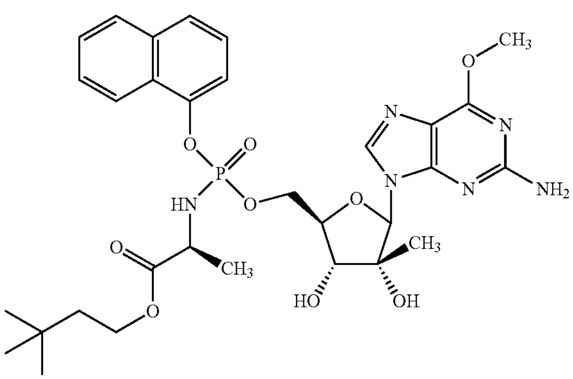 [SMILES: COc1nc(N)nc2c1ncn2C1O[C@H](COP(=O)(N[C@@H](C)C(=O)OCCC(C)(C)C)Oc2cccc3ccccc23)[C@@H](O)[C@@]1(C)O] | 18 | 0.013 | 7.6 |
| 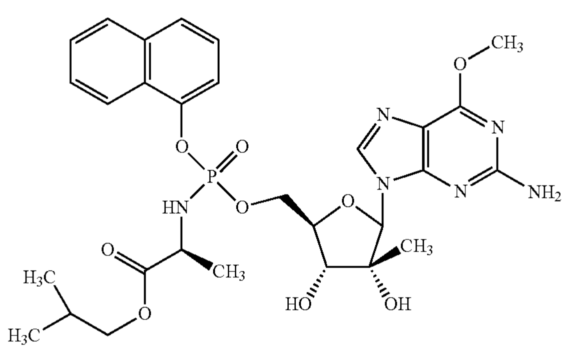 [SMILES: COc1nc(N)nc2c1ncn2C1O[C@H](COP(=O)(N[C@@H](C)C(=O)OCC(C)C)Oc2cccc3ccccc23)[C@@H](O)[C@@]1(C)O] | 19 | 0.037 | 14 |

-continued

| Structure | Example # | IC$_{50}$ μM | CC$_{50}$ μM |
|---|---|---|---|
| 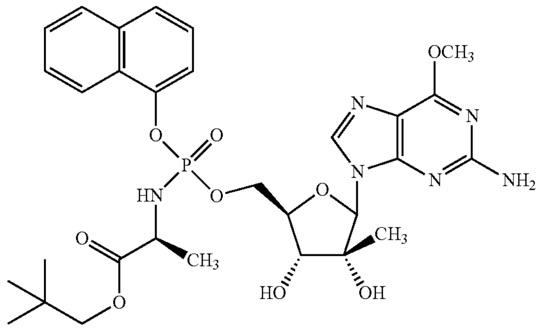 [SMILES: COc1nc(N)nc2c1ncn2C1O[C@H](COP(=O)(N[C@@H](C)C(=O)OCC(C)(C)C)Oc2cccc3ccccc23)[C@@H](O)[C@@]1(C)O] | 20 | 0.0010 | 7 |
| (S)-P | 21 | 0.043 | 13 |
| (R)-P | 22 | 0.019 | 6 |
| 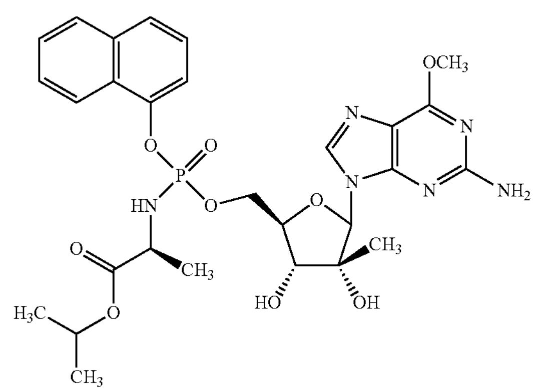 [SMILES: COc1nc(N)nc2c1ncn2C1O[C@H](COP(=O)(N[C@@H](C)C(=O)OC(C)C)Oc2cccc3ccccc23)[C@@H](O)[C@@]1(C)O] | 23 | 0.43 | 100 |

-continued
| Structure | Example # | IC$_{50}$ μM | CC$_{50}$ μM |
|---|---|---|---|
| 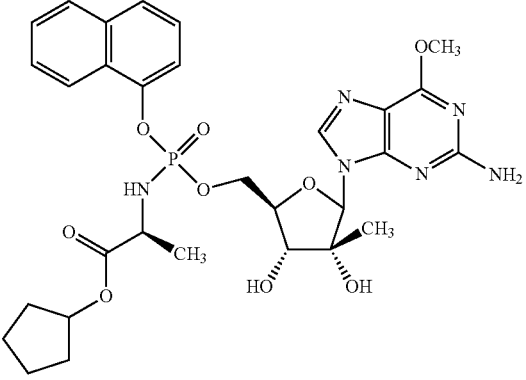 [SMILES: COc1nc(N)nc2c1ncn2C1O[C@H](COP(=O)(N[C@@H](C)C(=O)OC2CCCC2)Oc2cccc3ccccc23)[C@@H](O)[C@@]1(C)O] | 24 | 0.02 | 9 |
| 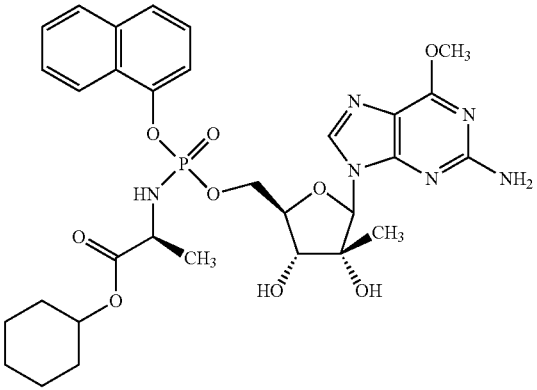 [SMILES: COc1nc(N)nc2c1ncn2C1O[C@H](COP(=O)(N[C@@H](C)C(=O)OC2CCCCC2)Oc2cccc3ccccc23)[C@@H](O)[C@@]1(C)O] | 25 | 0.014 | 6 |
| 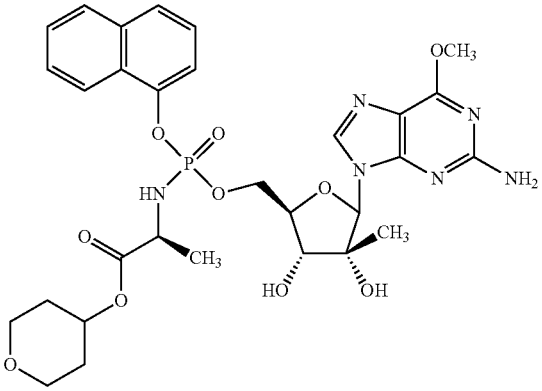 [SMILES: COc1nc(N)nc2c1ncn2C1O[C@H](COP(=O)(N[C@@H](C)C(=O)OC2CCOCC2)Oc2cccc3ccccc23)[C@@H](O)[C@@]1(C)O] | 26 | 0.08 | 130 |
| 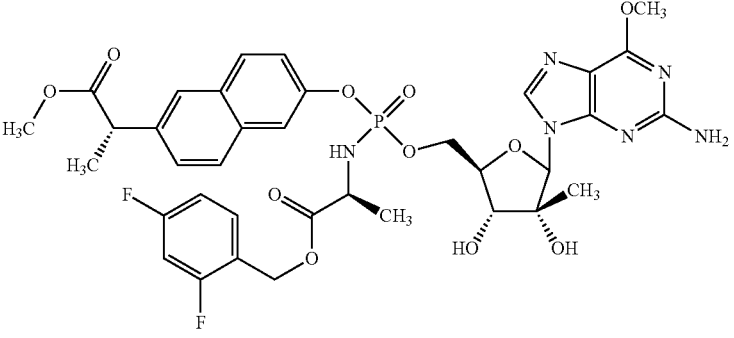 [SMILES: COC(=O)[C@@H](C)c1ccc2cc(OP(=O)(N[C@@H](C)C(=O)OCc3ccc(F)cc3F)OC[C@H]3OC(n4cnc5c(OC)nc(N)nc54)[C@](C)(O)[C@@H]3O)ccc2c1] | 27 | 0.055 | 28 |

-continued

| Structure | Example # | IC$_{50}$ μM | CC$_{50}$ μM |
|---|---|---|---|
| 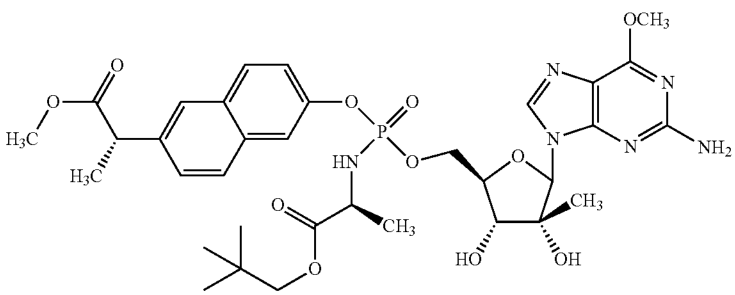 [SMILES: COC(=O)[C@@H](C)c1ccc2cc(OP(=O)(N[C@@H](C)C(=O)OCC(C)(C)C)OC[C@H]3OC(n4cnc5c(OC)nc(N)nc54)[C@](C)(O)[C@@H]3O)ccc2c1] | 28 | 0.023 | 19 |
| 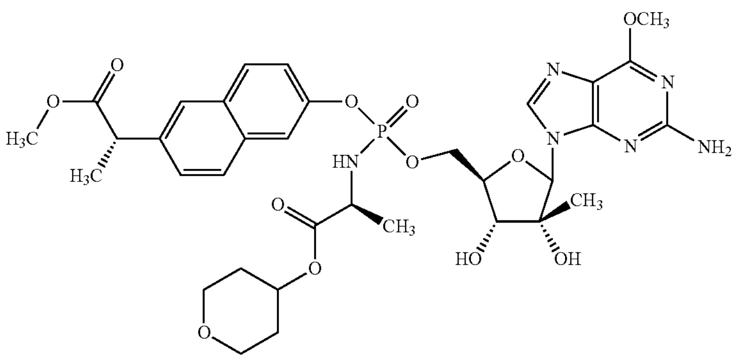 [SMILES: COC(=O)[C@@H](C)c1ccc2cc(OP(=O)(N[C@@H](C)C(=O)OC3CCOCC3)OC[C@H]3OC(n4cnc5c(OC)nc(N)nc54)[C@](C)(O)[C@@H]3O)ccc2c1] | 29 | 0.11 | >100 |
| 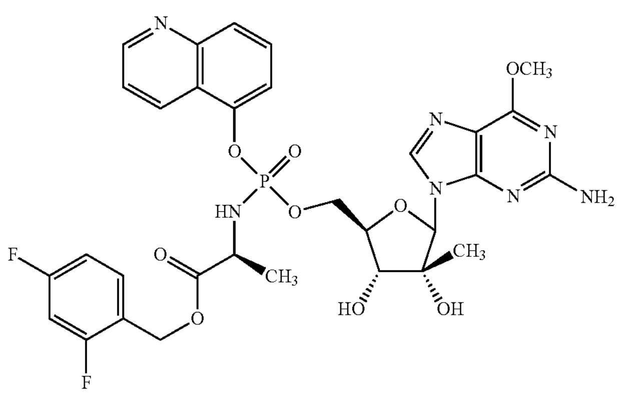 [SMILES: COc1nc(N)nc2c1ncn2C1O[C@H](COP(=O)(N[C@@H](C)C(=O)OCc2ccc(F)cc2F)Oc2cccc3ncccc23)[C@@H](O)[C@@]1(C)O] | 30 | 0.13 | 110 |
| 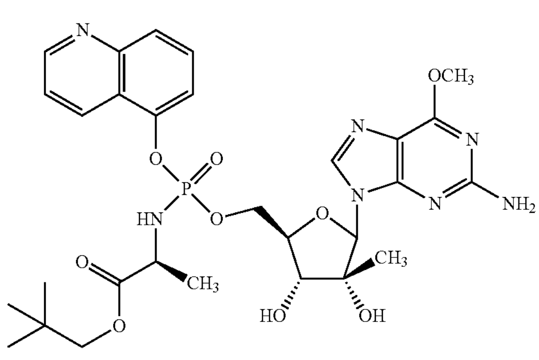 [SMILES: COc1nc(N)nc2c1ncn2C1O[C@H](COP(=O)(N[C@@H](C)C(=O)OCC(C)(C)C)Oc2cccc3ncccc23)[C@@H](O)[C@@]1(C)O] | 31 | 0.19 | >100 |

-continued
| Structure | Example # | IC$_{50}$ μM | CC$_{50}$ μM |
|---|---|---|---|
| 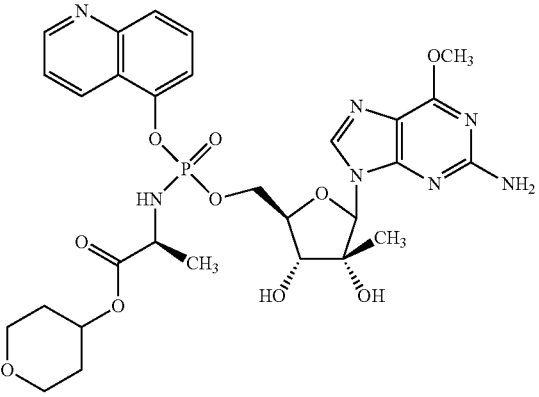 [SMILES: COc1nc(N)nc2c1ncn2C1O[C@H](COP(=O)(N[C@@H](C)C(=O)OC2CCOCC2)Oc2cccc3ncccc23)[C@@H](O)[C@@]1(C)O] | 32 | 1.2 | >100 |
| 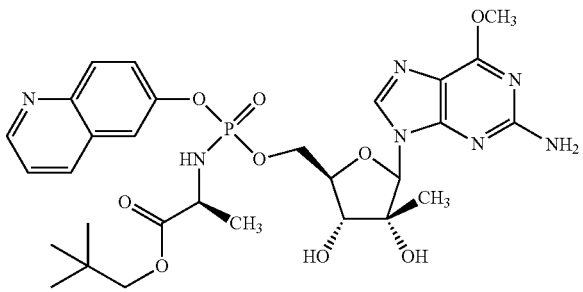 [SMILES: COc1nc(N)nc2c1ncn2C1O[C@H](COP(=O)(N[C@@H](C)C(=O)OCC(C)(C)C)Oc2ccc3ncccc3c2)[C@@H](O)[C@@]1(C)O] | 33 | 0.26 | >100 |
| 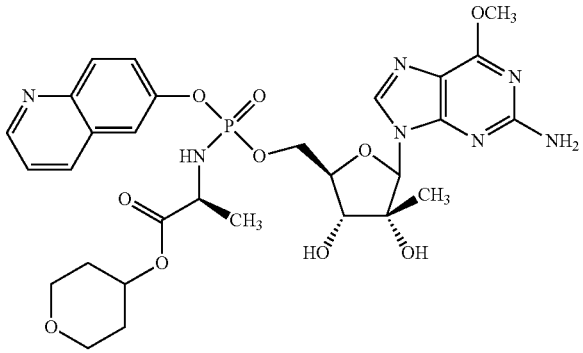 [SMILES: COc1nc(N)nc2c1ncn2C1O[C@H](COP(=O)(N[C@@H](C)C(=O)OC2CCOCC2)Oc2ccc3ncccc3c2)[C@@H](O)[C@@]1(C)O] | 34 | 1.1 | >100 |
| 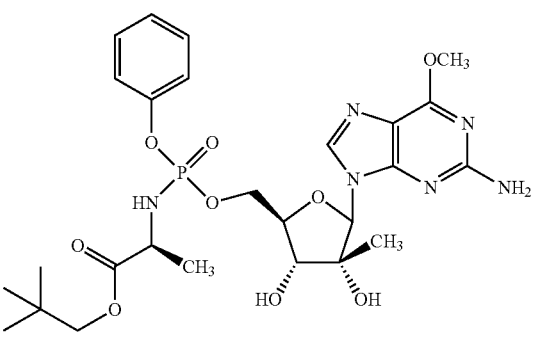 [SMILES: COc1nc(N)nc2c1ncn2C1O[C@H](COP(=O)(N[C@@H](C)C(=O)OCC(C)(C)C)Oc2ccccc2)[C@@H](O)[C@@]1(C)O] | 35 | 0.049 | 38 |

-continued

| Structure | Example # | IC$_{50}$ μM | CC$_{50}$ μM |
|---|---|---|---|
| 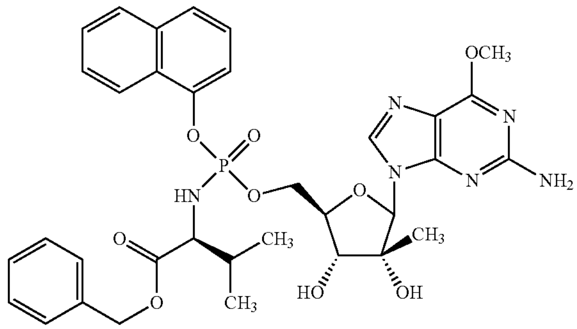 [SMILES: COc1nc(N)nc2c1ncn2C1O[C@H](COP(=O)(N[C@H](C(=O)OCc2ccccc2)C(C)C)Oc2cccc3ccccc23)[C@@H](O)[C@@]1(C)O] | 36 | 0.09 | 34 |
| 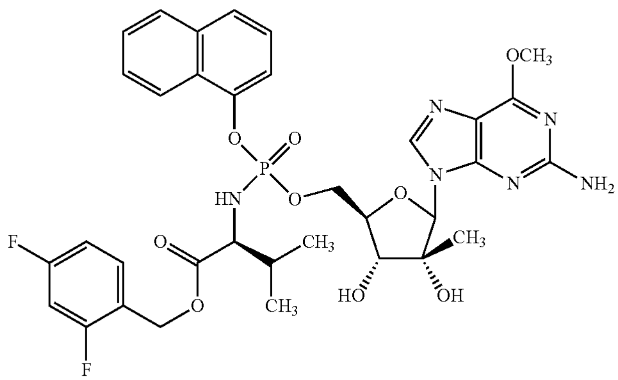 [SMILES: COc1nc(N)nc2c1ncn2C1O[C@H](COP(=O)(N[C@H](C(=O)OCc2ccc(F)cc2F)C(C)C)Oc2cccc3ccccc23)[C@@H](O)[C@@]1(C)O] | 37 | 0.043 | 16 |
| 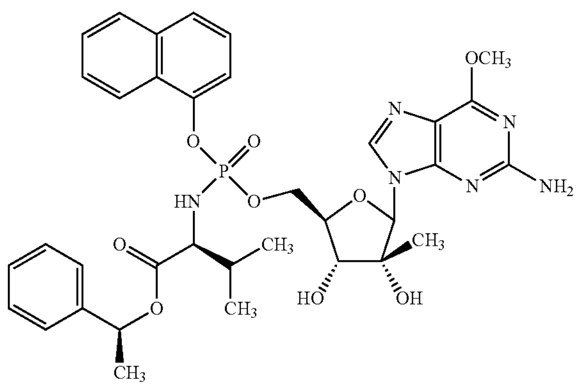 [SMILES: COc1nc(N)nc2c1ncn2C1O[C@H](COP(=O)(N[C@H](C(=O)O[C@@H](C)c2ccccc2)C(C)C)Oc2cccc3ccccc23)[C@@H](O)[C@@]1(C)O] | 38 | 0.94 | 29 |
| 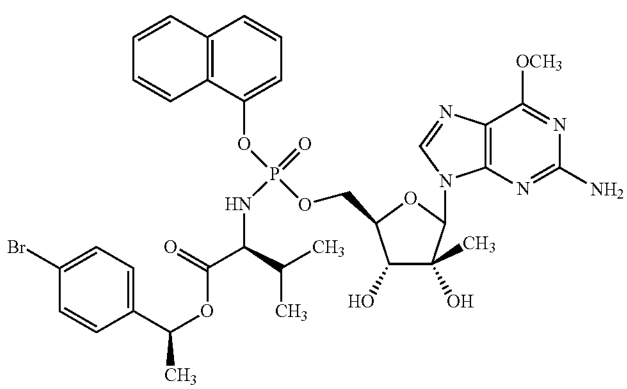 [SMILES: COc1nc(N)nc2c1ncn2C1O[C@H](COP(=O)(N[C@H](C(=O)O[C@@H](C)c2ccc(Br)cc2)C(C)C)Oc2cccc3ccccc23)[C@@H](O)[C@@]1(C)O] | 39 | 2.2 | 0.9 |

-continued

| Structure | Example # | IC$_{50}$ μM | CC$_{50}$ μM |
|---|---|---|---|
| 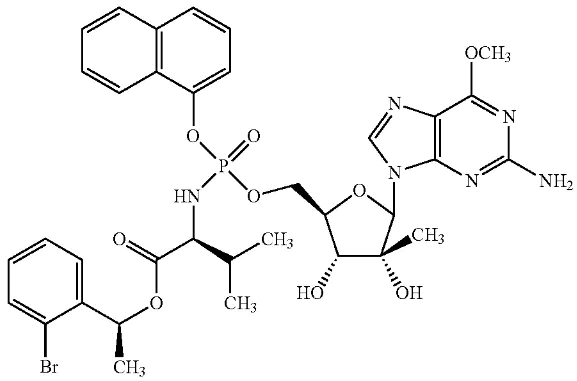 [SMILES: COc1nc(N)nc2c1ncn2C1O[C@H](COP(=O)(N[C@H](C(=O)O[C@@H](C)c2ccccc2Br)C(C)C)Oc2cccc3ccccc23)[C@@H](O)[C@@]1(C)O] | 40 | 2.9 | 44 |
| 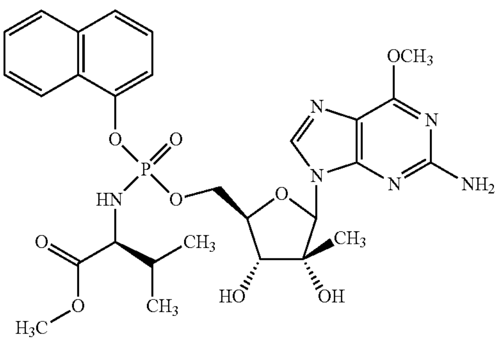 [SMILES: COC(=O)[C@@H](NP(=O)(OC[C@H]1OC(n2cnc3c(OC)nc(N)nc32)[C@](C)(O)[C@@H]1O)Oc1cccc2ccccc12)C(C)C] | 41 | 0.38 | 22 |
| 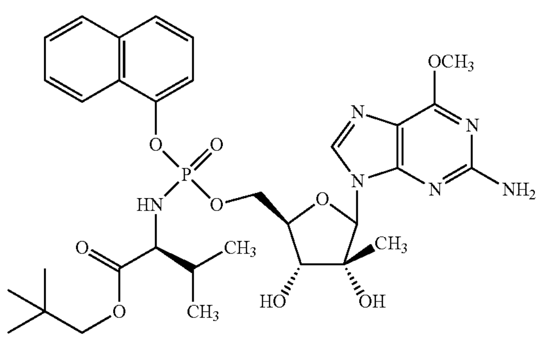 [SMILES: COc1nc(N)nc2c1ncn2C1O[C@H](COP(=O)(N[C@H](C(=O)OCC(C)(C)C)C(C)C)Oc2cccc3ccccc23)[C@@H](O)[C@@]1(C)O] | 42 | 0.21 | 30 |
| 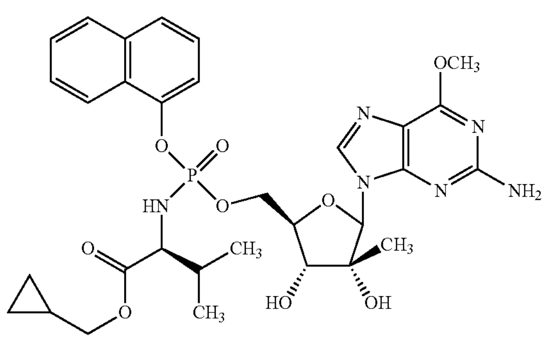 [SMILES: COc1nc(N)nc2c1ncn2C1O[C@H](COP(=O)(N[C@H](C(=O)OCC2CC2)C(C)C)Oc2cccc3ccccc23)[C@@H](O)[C@@]1(C)O] | 43 | 0.18 | 6 |

-continued

| Structure | Example # | IC₅₀ μM | CC₅₀ μM |
|---|---|---|---|
| (structure) | 44 | 0.39 | 64 |
| (structure) | 45 | 0.33 | 56 |
| (structure) | 46 | 0.42 | 24 |
| (structure) | 47 | 0.18 | >100 |

-continued

| Structure | Example # | IC$_{50}$ μM | CC$_{50}$ μM |
|---|---|---|---|
| 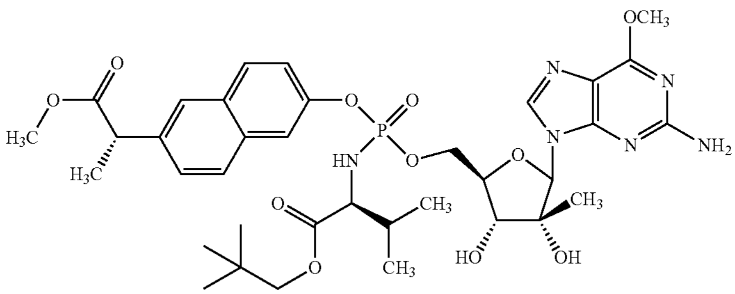 [SMILES: COC(=O)[C@@H](C)c1ccc2cc(OP(=O)(N[C@H](C(=O)OCC(C)(C)C)C(C)C)OC[C@H]3OC(n4cnc5c(OC)nc(N)nc54)[C@](C)(O)[C@@H]3O)ccc2c1] | 48 | 0.21 | 29 |
| 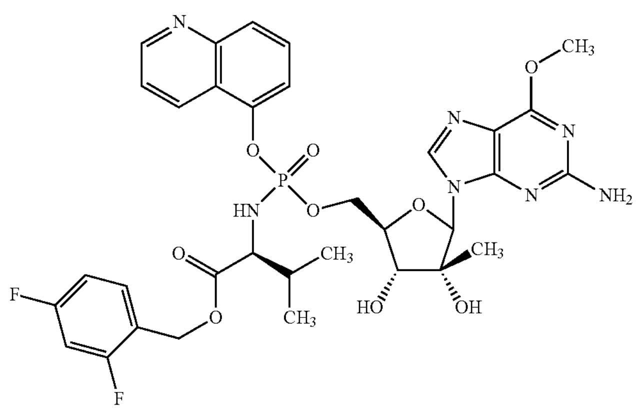 [SMILES: COc1nc(N)nc2c1ncn2C1O[C@H](COP(=O)(N[C@H](C(=O)OCc2ccc(F)cc2F)C(C)C)Oc2cccc3ncccc23)[C@@H](O)[C@@]1(C)O] | 49 | 0.17 | >100 |
| 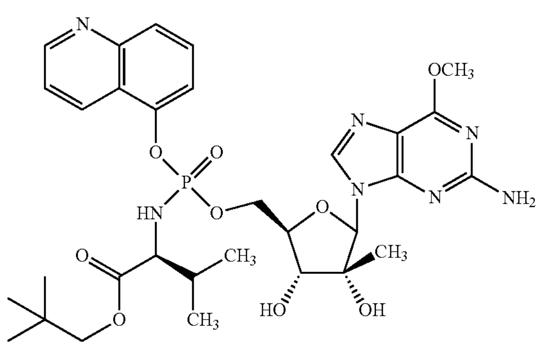 [SMILES: COc1nc(N)nc2c1ncn2C1O[C@H](COP(=O)(N[C@H](C(=O)OCC(C)(C)C)C(C)C)Oc2cccc3ncccc23)[C@@H](O)[C@@]1(C)O] | 50 | 0.55 | >100 |
| 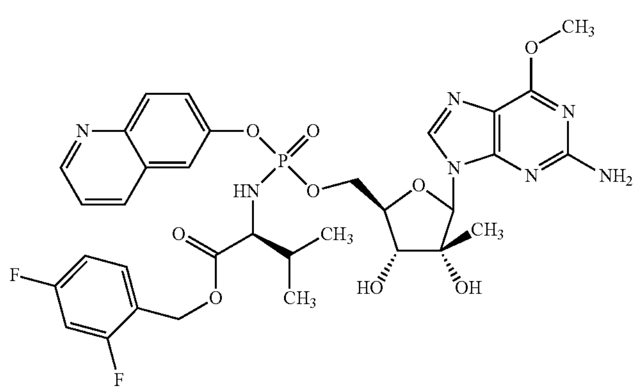 [SMILES: COc1nc(N)nc2c1ncn2C1O[C@H](COP(=O)(N[C@H](C(=O)OCc2ccc(F)cc2F)C(C)C)Oc2ccc3ncccc3c2)[C@@H](O)[C@@]1(C)O] | 51 | 0.11 | >100 |

-continued

| Structure | Example # | IC$_{50}$ μM | CC$_{50}$ μM |
|---|---|---|---|
| 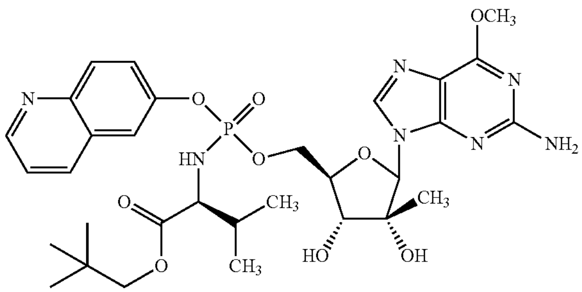 [SMILES: COc1nc(N)nc2c1ncn2C1O[C@H](COP(=O)(N[C@H](C(=O)OCC(C)(C)C)C(C)C)Oc2ccc3ncccc3c2)[C@@H](O)[C@@]1(C)O] | 52 | 0.19 | >100 |
| 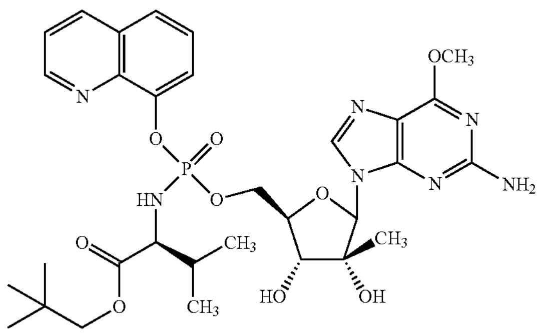 | 53 | 0.88 | >100 |
| 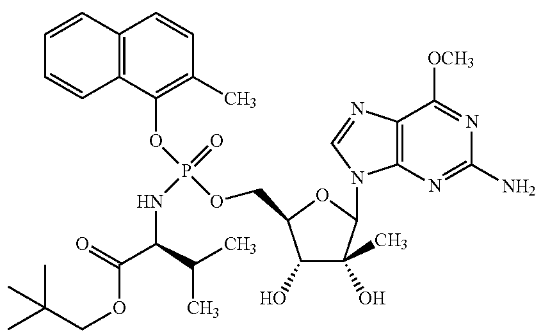 [SMILES: COc1nc(N)nc2c1ncn2C1O[C@H](COP(=O)(N[C@H](C(=O)OCC(C)(C)C)C(C)C)Oc2c(C)ccc3ccccc23)[C@@H](O)[C@@]1(C)O] | 54 | 1.5 | 23 |
| 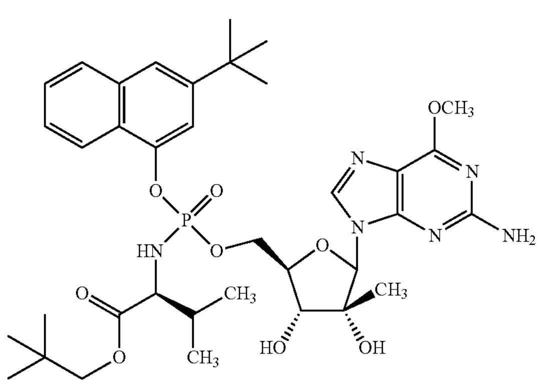 [SMILES: COc1nc(N)nc2c1ncn2C1O[C@H](COP(=O)(N[C@H](C(=O)OCC(C)(C)C)C(C)C)Oc2cc(C(C)(C)C)cc3ccccc23)[C@@H](O)[C@@]1(C)O] | 55 | 2.1 | 13 |

-continued

| Structure | Example # | IC₅₀ μM | CC₅₀ μM |
|---|---|---|---|
| 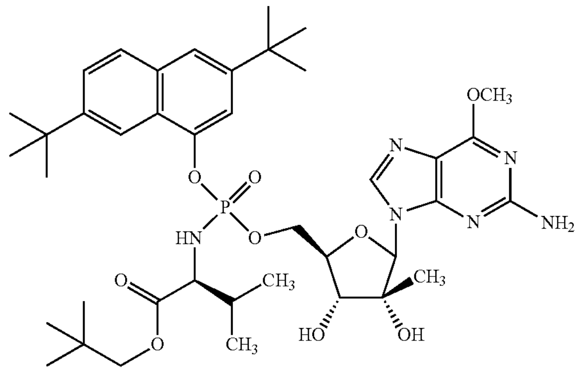 [SMILES: COc1nc(N)nc2c1ncn2C1O[C@H](COP(=O)(N[C@H](C(=O)OCC(C)(C)C)C(C)C)Oc2cc(C(C)(C)C)cc3ccc(C(C)(C)C)cc23)[C@@H](O)[C@@]1(C)O] | 56 | 2.1 | 13 |
| 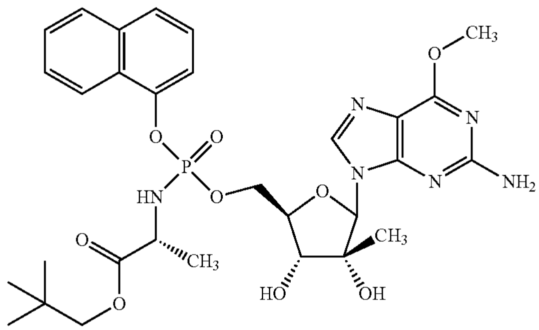 [SMILES: COc1nc(N)nc2c1ncn2C1O[C@H](COP(=O)(N[C@H](C)C(=O)OCC(C)(C)C)Oc2cccc3ccccc23)[C@@H](O)[C@@]1(C)O] | 57 | 0.24 | 51 |
| 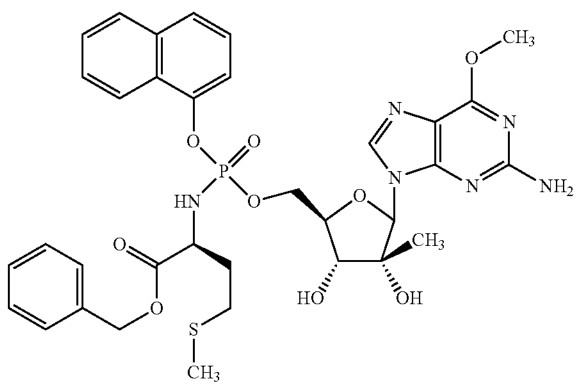 [SMILES: COc1nc(N)nc2c1ncn2C1O[C@H](COP(=O)(N[C@@H](CCSC)C(=O)OCc2ccccc2)Oc2cccc3ccccc23)[C@@H](O)[C@@]1(C)O] | 58 | 0.22 | NA |
| 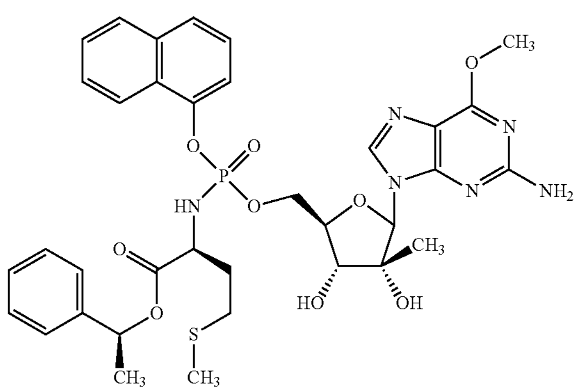 [SMILES: COc1nc(N)nc2c1ncn2C1O[C@H](COP(=O)(N[C@@H](CCSC)C(=O)O[C@@H](C)c2ccccc2)Oc2cccc3ccccc23)[C@@H](O)[C@@]1(C)O] | 59 | 0.32 | 30 |

-continued

| Structure | Example # | IC$_{50}$ μM | CC$_{50}$ μM |
|---|---|---|---|
| 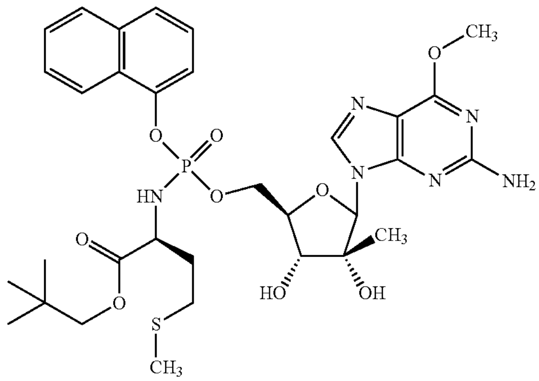 [SMILES: COc1nc(N)nc2c1ncn2C1O[C@H](COP(=O)(N[C@@H](CCSC)C(=O)OCC(C)(C)C)Oc2cccc3ccccc23)[C@@H](O)[C@@]1(C)O] | 60 | 0.060 | 28 |
| 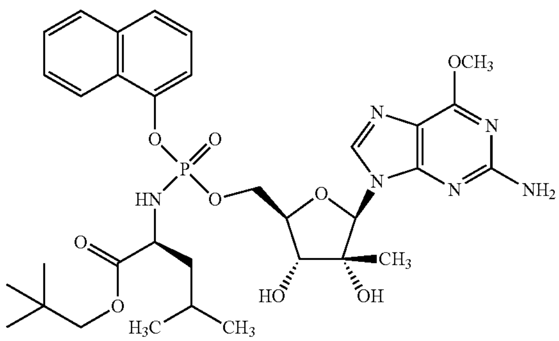 [SMILES: COc1nc(N)nc2c1ncn2[C@@H]1O[C@H](COP(=O)(N[C@@H](CC(C)C)C(=O)OCC(C)(C)C)Oc2cccc3ccccc23)[C@@H](O)[C@@]1(C)O] | 61 | 0.071 | 14 |
| 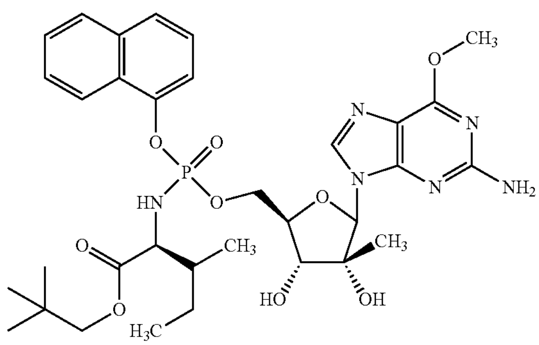 [SMILES: CCC(C)[C@H](NP(=O)(OC[C@H]1OC(n2cnc3c(OC)nc(N)nc32)[C@](C)(O)[C@@H]1O)Oc1cccc2ccccc12)C(=O)OCC(C)(C)C] | 62 | 0.86 | 18 |
| 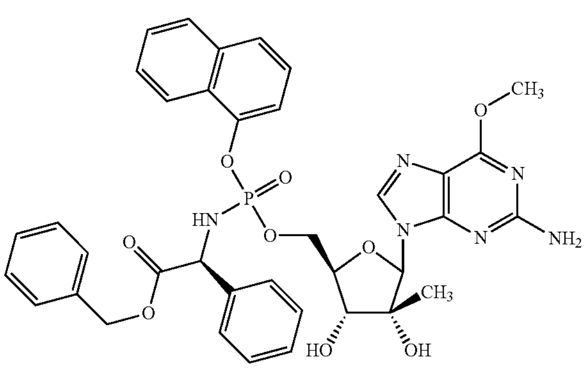 [SMILES: COc1nc(N)nc2c1ncn2C1O[C@H](COP(=O)(N[C@H](C(=O)OCc2ccccc2)c2ccccc2)Oc2cccc3ccccc23)[C@@H](O)[C@@]1(C)O] | 63 | 0.028 | 50 |

-continued
| Structure | Example # | IC$_{50}$ μM | CC$_{50}$ μM |
|---|---|---|---|
| 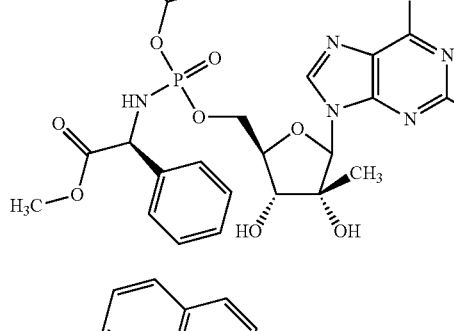 | 64 | 0.49 | >100 |
| 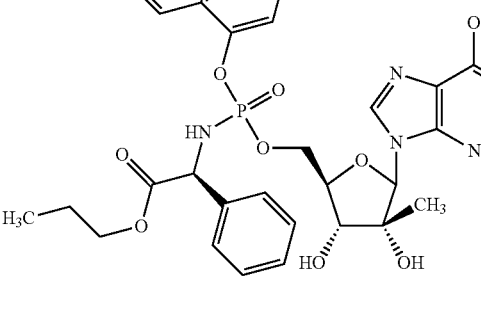 | 65 | 0.086 | NA |
| 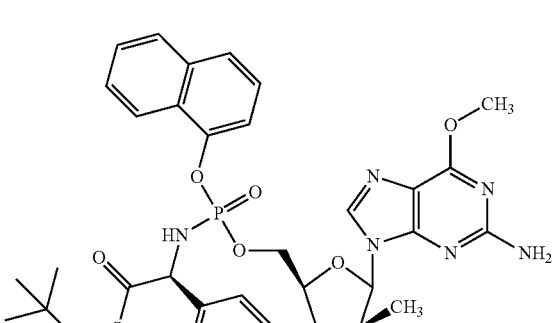 | 66 | 0.032 | 19 |
| 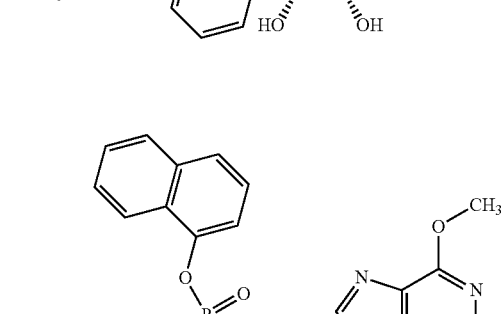 | 67 | 0.054 | 22 |

-continued

| Structure | Example # | IC$_{50}$ μM | CC$_{50}$ μM |
|---|---|---|---|
| | 68 | 1.3 | 50 |
| | 68 | 2.7 | NA |
| 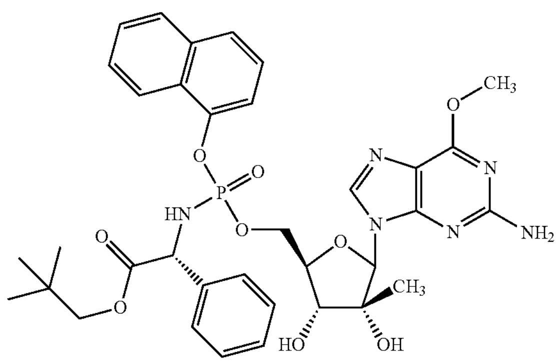 [SMILES: COc1nc(N)nc2c1ncn2C1O[C@H](COP(=O)(N[C@@H](C(=O)OCC(C)(C)C)c2ccccc2)Oc2cccc3ccccc23)[C@@H](O)[C@@]1(C)O] | 70 | 0.077 | 38 |
| 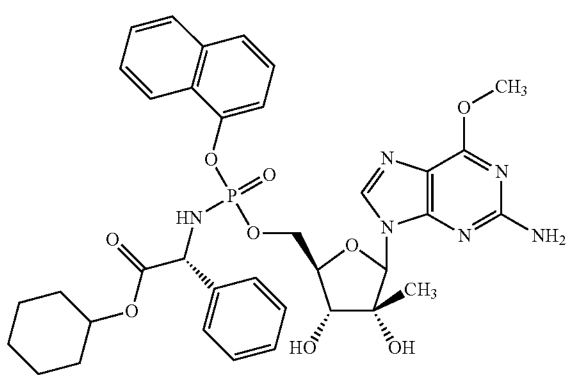 [SMILES: COc1nc(N)nc2c1ncn2C1O[C@H](COP(=O)(N[C@@H](C(=O)OC2CCCCC2)c2ccccc2)Oc2cccc3ccccc23)[C@@H](O)[C@@]1(C)O] | 71 | 2.5 | 26 |

-continued

| Structure | Example # | IC$_{50}$ μM | CC$_{50}$ μM |
|---|---|---|---|
| 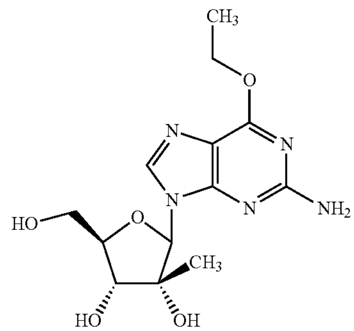 [SMILES: CCOc1nc(N)nc2c1ncn2C1O[C@H](CO)[C@@H](O)[C@@]1(C)O] | 72 | 11 | >100 |
| 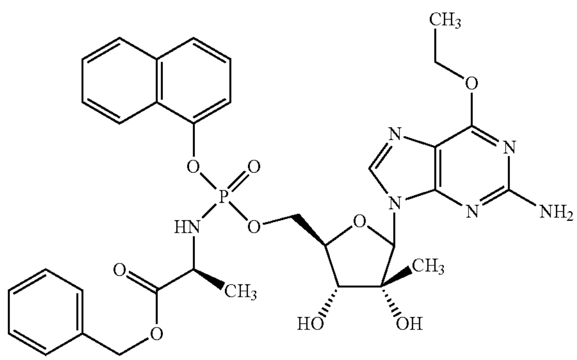 [SMILES: CCOc1nc(N)nc2c1ncn2C1O[C@H](COP(=O)(N[C@@H](C)C(=O)OCc2ccccc2)Oc2cccc3ccccc23)[C@@H](O)[C@@]1(C)O] | 73 | 0.037 | 11 |
| 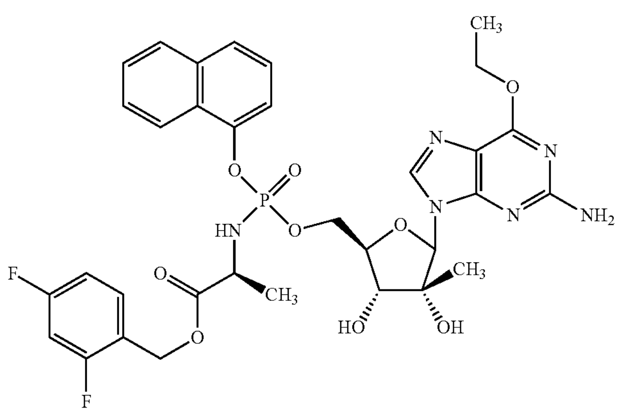 [SMILES: CCOc1nc(N)nc2c1ncn2C1O[C@H](COP(=O)(N[C@@H](C)C(=O)OCc2ccc(F)cc2F)Oc2cccc3ccccc23)[C@@H](O)[C@@]1(C)O] | 74 | 0.034 | 17 |
| 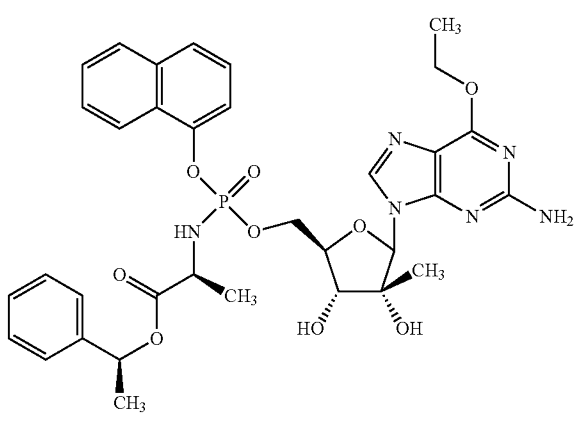 [SMILES: CCOc1nc(N)nc2c1ncn2C1O[C@H](COP(=O)(N[C@@H](C)C(=O)O[C@@H](C)c2ccccc2)Oc2cccc3ccccc23)[C@@H](O)[C@@]1(C)O] | 75 | 0.063 | 12 |

-continued

| Structure | Example # | IC$_{50}$ μM | CC$_{50}$ μM |
|---|---|---|---|
| (structure) | 76 | 0.010 | 10 |
| (structure) | 77 | 0.11 | 40 |
| (structure) | 78 | 0.059 | 47 |
| (structure) | 79 | 0.22 | 24 |

-continued

| Structure | Example # | IC$_{50}$ μM | CC$_{50}$ μM |
|---|---|---|---|
| (structure) | 80 | 13 | >100 |
| (structure) | 81 | 0.033 | 48 |
| (structure) | 82 | 0.11 | 54 |
| (structure) | 83 | 0.36 | >100 |

-continued

| Structure | Example # | IC₅₀ μM | CC₅₀ μM |
|---|---|---|---|
| 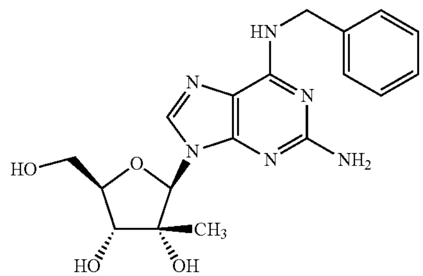 [SMILES: C[C@@]1(O)[C@H](O)[C@@H](CO)O[C@H]1n1cnc2c(NCc3ccccc3)nc(N)nc21] | 84 | 27 | >100 |
| 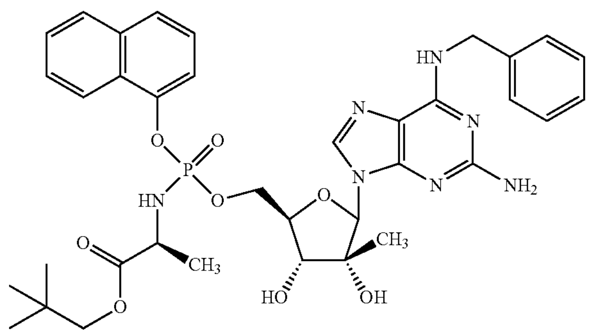 [SMILES: C[C@H](NP(=O)(OC[C@H]1OC(n2cnc3c(NCc4ccccc4)nc(N)nc32)[C@](C)(O)[C@@H]1O)Oc1cccc2ccccc12)C(=O)OCC(C)(C)C] | 85 | 0.58 | 15 |
| 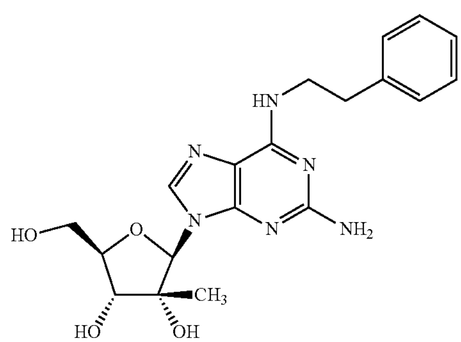 [SMILES: C[C@@]1(O)[C@H](O)[C@@H](CO)O[C@H]1n1cnc2c(NCCc3ccccc3)nc(N)nc21] | 86 | 23.6 | NA |
| 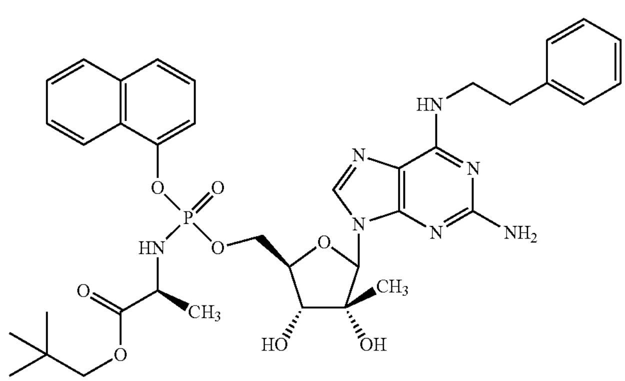 [SMILES: C[C@H](NP(=O)(OC[C@H]1OC(n2cnc3c(NCCc4ccccc4)nc(N)nc32)[C@](C)(O)[C@@H]1O)Oc1cccc2ccccc12)C(=O)OCC(C)(C)C] | 87 | 0.27 | 42 |
| 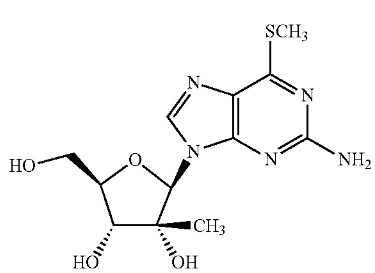 [SMILES: CSc1nc(N)nc2c1ncn2[C@@H]1O[C@H](CO)[C@@H](O)[C@@]1(C)O] | 88 | 11 | 150 |

-continued

| Structure | Example # | IC$_{50}$ μM | CC$_{50}$ μM |
|---|---|---|---|
| 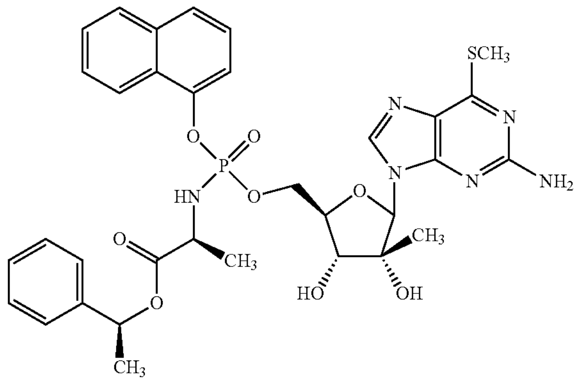 [SMILES: CSc1nc(N)nc2c1ncn2C1O[C@H](COP(=O)(N[C@@H](C)C(=O)O[C@@H](C)c2ccccc2)Oc2cccc3ccccc23)[C@@H](O)[C@@]1(C)O] | 89 | 0.14 | 27 |
| 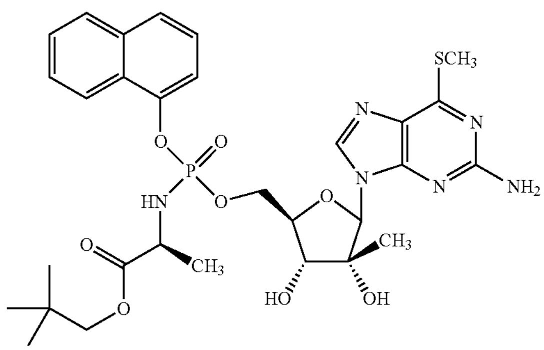 [SMILES: CSc1nc(N)nc2c1ncn2C1O[C@H](COP(=O)(N[C@@H](C)C(=O)OCC(C)(C)C)Oc2cccc3ccccc23)[C@@H](O)[C@@]1(C)O] | 90 | 0.033 | 41 |
| 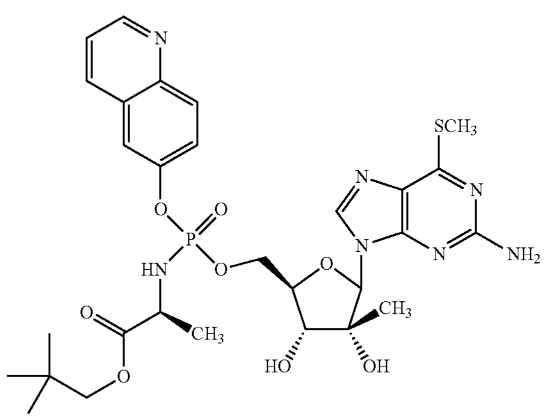 [SMILES: CSc1nc(N)nc2c1ncn2C1O[C@H](COP(=O)(N[C@@H](C)C(=O)OCC(C)(C)C)Oc2ccc3ncccc3c2)[C@@H](O)[C@@]1(C)O] | 91 | 0.26 | >100 |
| 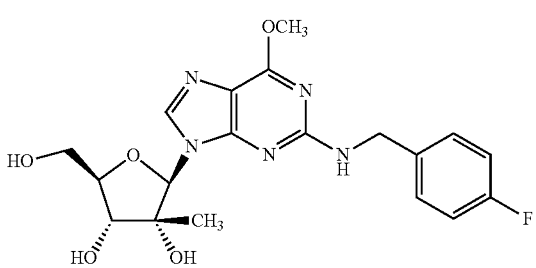 [SMILES: COc1nc(NCc2ccc(F)cc2)nc2c1ncn2[C@@H]1O[C@H](CO)[C@@H](O)[C@@]1(C)O] | 92 | >40 | >100 |

-continued

| Structure | Example # | IC$_{50}$ μM | CC$_{50}$ μM |
| --- | --- | --- | --- |
| 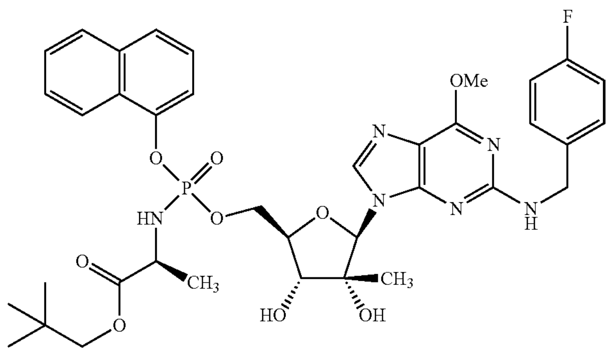 [SMILES: COc1nc(NCc2ccc(F)cc2)nc2c1ncn2[C@@H]1O[C@H](COP(=O)(N[C@@H](C)C(=O)OCC(C)(C)C)Oc2cccc3ccccc23)[C@@H](O)[C@@]1(C)O] | 93 | 7.2 | 17 |
| 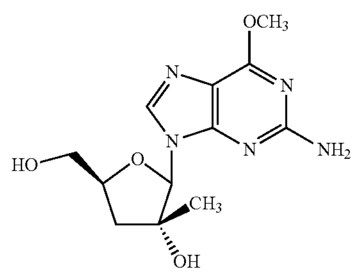 [SMILES: COc1nc(N)nc2c1ncn2C1O[C@H](CO)C[C@@]1(C)O] | 94 | >100 | >100 |
| 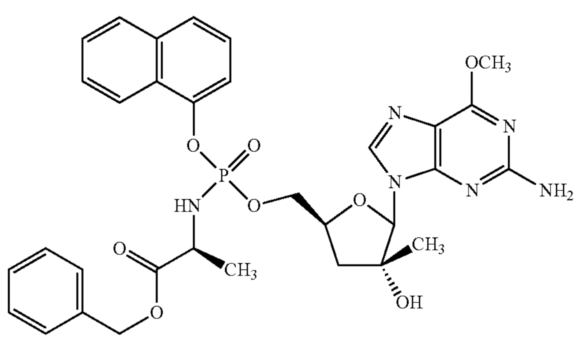 [SMILES: COc1nc(N)nc2c1ncn2C1O[C@H](COP(=O)(N[C@@H](C)C(=O)OCc2ccccc2)Oc2cccc3ccccc23)C[C@@]1(C)O] | 95 | 0.9 | 70 |
| 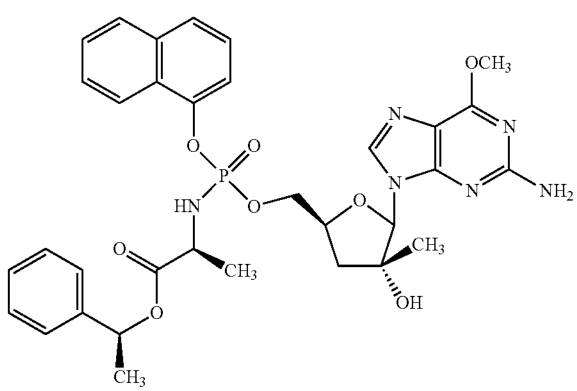 [SMILES: COc1nc(N)nc2c1ncn2C1O[C@H](COP(=O)(N[C@@H](C)C(=O)O[C@@H](C)c2ccccc2)Oc2cccc3ccccc23)C[C@@]1(C)O] | 96 | >10 | 20 |

| Structure | Example # | IC$_{50}$ µM | CC$_{50}$ µM |
|---|---|---|---|
| 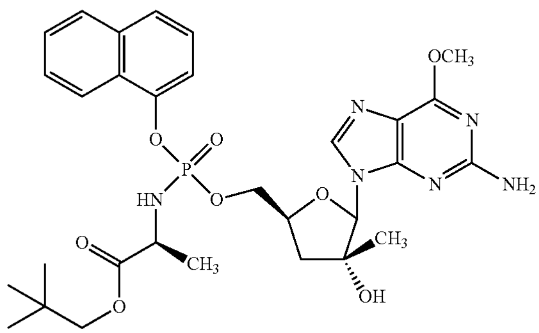 [SMILES: COc1nc(N)nc2c1ncn2C1O[C@H](COP(=O)(N[C@@H](C)C(=O)OCC(C)(C)C)Oc2cccc3ccccc23)C[C@@]1(C)O] | 97 | >10 | 44 |
| 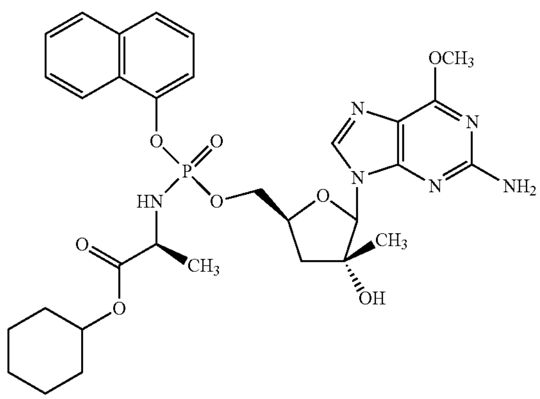 [SMILES: COc1nc(N)nc2c1ncn2C1O[C@H](COP(=O)(N[C@@H](C)C(=O)OC2CCCCC2)Oc2cccc3ccccc23)C[C@@]1(C)O] | 98 | >10 | 20 |
| 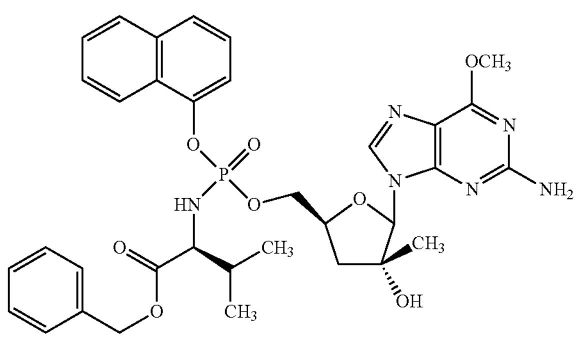 [SMILES: COc1nc(N)nc2c1ncn2C1O[C@H](COP(=O)(N[C@H](C(=O)OCc2ccccc2)C(C)C)Oc2cccc3ccccc23)C[C@@]1(C)O] | 99 | >10 | 22 |

Activity against other viruses. A representative compound, Example 20, Compound F, was tested against a panel of other RNA and DNA viruses. Compound F was synthesized as described in the Experimental section. Experimental conditions for growing the cells and viruses are listed below. Unless otherwise indicated, cells and viruses were obtained from the American Type Culture Collection (ATCC, Rockville, Md.).

HeLa cells (cervical epithelial, human, *Homo sapiens*) were used in cytoprotection assays with Adenovirus Type 1, and Yellow Fever Virus strain 17D. They were grown in Dulbecco's Modified Eagle's Medium (DMEM) supplemented with 5% fetal bovine serum (FBS), 2.0 mM L-Glutamine, 100 units/ml Penicillin 100 µg/ml Streptomycin, and 0.1 mM non-essential amino acids.

MDBK cells (Kidney, cow, Bos 249nocul) were used in cytoprotection assays with Bovine Viral Diarrhea Virus (BVDV) strain NADL and were grown in DMEM supplemented with 10% fetal horse serum (FHS), 2.0 mM L-Glutamine, 100 units/ml Penicillin, 100 µg/ml Streptomycin, and 0.1 mM non-essential amino acids.

MDCK cells (Kidney, dog, *Canis familiaris*) were used in cytoprotection assays with Influenza A strain Hong Kong and Influenza B strain Lee. They were grown in Eagle's Minimum Essential Medium with Earle's BSS (EMEM) supplemented with 10% FBS, 0.1 mM non-essential amino acids, 1.0 mM sodium pyruvate, 2.0 mM L-Glutamine, 100 units/ml Penicillin and 100 µg/ml Streptomycin.

MRC-5 cells ((ATCC CCL-171) embryonal lung fibroblast, diploid, male, human) were used in plaque reduction assays with HCMV Strain AD169 (ATCC VR-538) and in cytoprotection assays with Rhinovirus strain 1B. They were grown in EMEM supplemented with 10% FBS, 0.1 mM non-essential amino acids, 1.0 mM sodium pyruvate, 2.0 mM L-Glutamine, 100 units/ml Penicillin and 100 µg/ml Streptomycin.

MT-4 cells ((Catalog #120) Human T-cell Leukemia) were obtained from the NIH AIDS Reference Reagent Program and were used in cytoprotection assays with HIV-1 Strain IIIB (Southern Research). They were grown in RPMI-1640 medium supplemented with 10% FBS.

Vero cells (Kidney, African green monkey, *Cercopithecus aethiops*) were used in cytoprotection assays with Coxsackie virus strain B4, HSV-1 strain HF, Poliovirus strain Chat, RSV strain Long and West Nile virus strain NY-99. They were grown in DMEM supplemented with 10% FBS, 2.0 mM L-Glutamine, 100 units/ml Penicillin and 100 μg/ml Streptomycin.

Vero E6 cells ((ATCC CRL-1586) Kidney, African green monkey, *Cercopithecus aethiops*, clone) were used in plaque reduction assays with Vaccinia Strain Western Reserve and in cytoprotection assays with Dengue Virus Type 2 strain New Guinea. They were grown in EMEM supplemented with 10% FBS, 2.0 mM L-Glutamine, 100 units/ml Penicillin and 100 μg/ml Streptomycin.

General Cytoprotection Assays: Virus and cells were mixed in the presence of test compound and incubated for 7 days (5 days for HSV-1 and WNV; 10 days for Yellow Fever). The virus was pre-titered such that control wells exhibited 85 to 95% loss of cell viability due to virus replication at 6-7 days (5 days for HSV-1 and WNV; 7-10 days for Yellow Fever) post-infection. Antiviral effect or cytoprotection was observed when compounds prevented virus replication. Each assay plate contained cell control wells (cells only), virus control wells (cells plus virus), compound toxicity control wells (cells plus compound only), compound colorimetric control wells (compound only), as well as experimental wells (compound plus cells plus virus). Cytoprotection and compound cytotoxicity were assessed by MTS (CellTiter®96 Reagent, Promega, Madison Wis.) dye reduction. The plates were read spectrophotometrically at 490/650 nm with a Molecular Devices Vmax or SpectraMax Plus plate reader. The percent reduction in viral cytopathic effect (CPE) was determined and reported as follows: $IC_{50}$ (concentration inhibiting virus replication by 50%), $TC_{50}$ (concentration resulting in 50% cell death) and a calculated TI (therapeutic index $TC_{50}/IC_{50}$). Samples were evaluated for antiviral efficacy with triplicate measurements using 6 concentrations at half-log dilutions and duplicate measurements to determine cellular cytotoxicity. Each assay included an antiviral positive control compound appropriate for the virus in question as listed below: ribavirin (RBV) for Adenovirus, Dengue virus, Influenza A & B, and RSV; interferon alpha (IFN-α) for BVDV, Yellow Fever, and WNV; enviroxime (ENV) for Coxsackie virus, Poliovirus, and Rhinovirus; acyclovir (ACV) for HSV.

Cytoprotection Assay for HIV: MT-4 cells were sub-cultured one day prior to testing. Cells were plated in 96 well cell culture plates at a seeding density of $6 \times 10^5$ cells/ml ($3 \times 10^4$ cells/well). The HIV-1 IIIB virus was pre-titered such that control wells exhibited 85 to 95% loss of cell viability due to virus replication at 5 days post-infection. Virus and cells were mixed in the presence of serial dilutions of test compound and incubated for 5 days at 37° C., 5% $CO_2$. Each assay plate contained cell control wells (cells only), virus control wells (cells plus virus), compound toxicity control wells (cells plus compound only) as well as experimental wells (compound plus cells plus virus). Cytoprotection and compound cytotoxicity were assessed by XTT assay (Cat#11-465-015-001, Roche Diagnostics). The plates were read spectrophotometrically at 450/650 nm with a Molecular Devices SpectraMax M2 plate reader. The percent reduction in viral CPE was determined and reported as $IC_{50}$, $CC_{50}$ and a calculated TI. Samples were evaluated for antiviral efficacy and cytotoxicity with triplicate measurements using 9 concentrations at 2-fold dilutions. Each assay included Raltegravir (MK0518) as an antiviral positive control compound.

HCMV Plaque Reduction Assay: MRC-5 cells were seeded at 75,000 cells/well in 24 well plates. The plates were incubated overnight at 37° C. and 5% $CO_2$. The following day, media was aspirated and approximately 100 plaque forming units (pfu) of HCMV AD169 was added to 21 wells of each plate in a volume of 200 μL of assay medium (MRC-5 growth medium containing 2% FBS rather than 10% FBS). The remaining three wells of each plate served as cellular control wells and received 200 μL of assay medium without virus. The virus was allowed to adsorb onto the cells for 1 hr at 37° C. and 5% $CO_2$. Compounds were prepared by diluting them in assay medium containing 0.5% Methylcellulose. After the incubation period, 1 mL of each drug dilution was added to triplicate wells of a plate (without aspirating the virus inoculums). Assay medium (without drug) containing 0.5% Methylcellulose was added to the three cell control wells and to three virus control wells on each plate. The plates were incubated for 7-10 days to allow for plaque formation. Cultures were examined microscopically and compound precipitation and toxicity were noted. The media was then aspirated from the wells and the cells were fixed and stained using 20% Methanol containing Crystal Violet. Plaques were enumerated by microscopic inspection and the data was plotted as percent of virus control. To evaluate cytotoxicity, MRC-5 cells were seeded at 2,500 cells per well in 96 well plates using MRC-5 growth medium. The plates were incubated overnight at 37° C. and 5% $CO_2$. The following day, compounds were prepared in assay medium. Growth medium was removed from the plates and replaced with the prepared test compounds. Each dilution of compound was tested in triplicate. Each toxicity plate contained the necessary cell control and compound color controls. After a six day incubation period, cell viability was determined using CellTiter 96 Aqueous One Solution (Promega Corporation). The solution was added to the wells of the 96 well plate in a volume resulting in a final 10% concentration (volume:volume) in each well. Plates were incubated for an additional 4 hours at 37° C. Adhesive plate sealers were used in place of the lids, the sealed plates were inverted several times to mix the soluble formazan product and the plate was read spectrophotometrically at 490 and 650 nm with a Molecular Devices Vmax plate reader. The minimum inhibitory drug concentration that reduced plaque formation by 50% ($IC_{50}$) and the minimum drug concentration that inhibited cell growth by 50% ($TC_{50}$) were calculated. A therapeutic (selectivity) index (TI) for each active compound was determined by dividing the $TC_{50}$ by the $IC_{50}$.

Vaccinia Virus Plaque Reduction Assay: Vero E6 cells were seeded at 200,000 cells/well in 12 well plates using Vero E6 growth medium. The plates were incubated overnight at 37° C. and 5% $CO_2$. The following day, media was decanted and approximately 150 plaque forming units (pfu) of vaccinia virus (diluted in assay media of DMEM+2% fetal bovine serum (FBS)+2% L-glutamine) was added to 10 wells of each plate in a volume of 100 μL per well. The remaining two wells of each plate served as cellular control wells and received 200 μL of assay media without virus. Compounds were prepared by diluting them in assay media and dispensing 100 μL to each respective test well containing vaccinia virus. Each dilution of compound was run in duplicate test wells. The plates were gently rocked to mix the compound and virus. The virus/compound mixture was allowed to adsorb onto the cells for 1 hr at 37° C. and 5% $CO_2$, with gentle rocking every 10 to 15 minutes. Overlay media of DMEM+2% FBS+2% L-glutamine+0.5% methylcellulose was prepared during this incubation. Appropriate dilutions of compound were mixed with overlay media in separate tubes (one for each compound dilution). This ensured that the concentration of the compound in the overlay was the same as that in each of the test wells of the plate. After the incubation period, 1 mL of each drug dilution/overlay media mixture was added to duplicate wells of the plate (without aspirating the virus/compound inoculums). Assay media (without drug) containing 0.5% Methylcellulose was added to the two cell control wells and to the two virus control wells on each plate. The plates were incubated for approximately 72 hours to allow for plaque formation. Cultures were examined microscopically and compound precipitation and toxicity were noted. The media was then decanted from the wells and the cells were fixed and stained using a 0.1% Crystal Violet solution in 20% Methanol. Plaques were counted by visual inspection using a light box and the data was plotted as percent of virus control. For determination of cytotoxicity, Vero E6 cells were seeded at 10,000 cells per well in 96 well plates using Vero E6 growth medium. The plates were incubated overnight at 37° C. and 5% $CO_2$. The following day, compounds were prepared in assay medium. Growth medium was removed from the plates and replaced with the prepared test compounds. Each dilution of compound was tested in triplicate. Each toxicity plate contained the necessary cell control and compound color controls. After a 72-hour incubation period, cell viability was determined using CellTiter 96 Aqueous One Solution (Promega Corporation). This solution contains MTS-tetrazolium which was converted by viable cells into an intensely colored formazan product. The solution was added to the wells of the 96 well plate in a volume resulting in a final 10% concentration (volume:volume) in each well. Plates were incubated for an additional 4 hours at 37° C. Adhesive plate sealers were used in place of the lids, the sealed plates were inverted several times to mix the soluble formazan product and the plate was read spectrophotometrically at 490 and 650 nm with a Molecular Devices Vmax plate reader. The minimum inhibitory drug concentration that reduced plaque formation by 50% ($IC_{50}$) and the minimum drug concentration that inhibited cell growth by 50% ($TC_{50}$) were calculated. A therapeutic (selectivity) index (TI) was determined by dividing the $TC_{50}$ by the $IC_{50}$.

Below is shown the Structure of Compound F (Example 20)

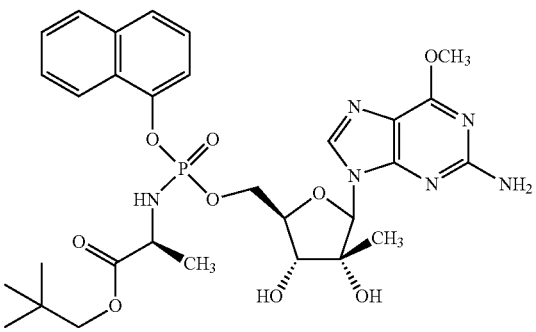 [SMILES: COc1nc(N)nc2c1ncn2C1O[C@H](COP(=O)(N[C@@H](C)C(=O)OCC(C)(C)C)Oc2cccc3ccccc23)[C@@H](O)[C@@]1(C)O]

The conversion of representative protides or nucleoside 5'-phosphoramidates to the putative active species 2'-C-methyl guanosine triphosphate was examined in primary human hepatocytes. A comparison was made between $O^6$-methylated 2'-C-methylguanosine 5'-phosphoramidates and 2'-C-methylguanosine 5'-phosphoramidates in terms of production of 2'-C-methyl guanosine triphosphate in these cells Human Primary Hepatocyte Cell Assay: Hepatocyte assay were done using cryopreserved inducible hepatocytes. Cryopreserved hepatocytes isolated from human (male donors) were obtained from Xenotech and thawed according to protocol. Briefly, cells were thawed in a 37° C. water bath and placed in a biological safety cabinet. Cells were isolated according to protocol using the vendor's Hepatocyte Isolation Kit (Xenotech). Subsequent viability and cell counts were determined by trypan blue exclusion method using a Cedex Automated Cell Counter or hemacytometer. Cells were resuspended in Hepatocyte Culture Media (Xenotech) and transferred to collagen-coated 12-well plates at $1 \times 10^6$ viable cells/well. The plates were placed in a 37° C., 5% $CO_2$ incubator for 3-6 hours to allow for cell attachment. Plates were then removed, refed with a matrigel overlay at 0.25-

TABLE 2

Activity of Compound F Against Other RNA and DNA Viruses

| Virus Type | Family | Species | Strain | $EC_{50}$ (μM) | Cell Line | $CC_{50}$ (μM) |
|---|---|---|---|---|---|---|
| Type IV ((+) ssRNA) | Flaviviridae | Dengue Virus Type 2 | New Guinea | 1.810 | Vero E6 | >10 |
| | | Yellow Fever | 17D | 0.418 | HeLa | >10 |
| | | BVDV | NADL | 0.748 | MDBK | >10 |
| | | West Nile Virus | NY-99 | 1.690 | Vero | >10 |
| | Picornaviridae | Poliovirus I | Chat | 4.710 | Vero | >10 |
| | | Coxsackie | B4 | >10 | Vero | >10 |
| | | Rhino | 1B | >10 | MRC-5 | 3.08 |
| Type V ((−) ssRNA) | Paramyxoviridae | RSV | Long | >10 | Vero | >10 |
| | Orthomyxoviridae | Influenza A | Hong Kong | >10 | MDCK | >10 |
| | | Influenza B | Lee | >10 | MDCK | >10 |
| Type I (dsDNA) | Herpesviridae | HSV-1 | HF | >10 | Vero | >10 |
| | | HCMV | AD169 | ND* | MRC-5 | 1.57 |
| | Poxviridae | Vaccinia | Western Reserve | 4.520 | Vero E6 | >10 |
| | Adenoviridae | Adenovirus | Type I | >10 | HeLa | >10 |
| Type VI (ssRNA-RT) | Retroviridae | HIV-1 | IIIB | >10 | MT-4 | 11 |

*ND = Not determined; a reduction in plaque formation paralleled the reduction in cell viability observed in this assay.

mg/mL matrigel (Matrigel matrix, phenol-red free, BD Biosciences) and placed back in incubator for 48 hours. Compounds were prepared in fresh Hepatocyte Culture Media for final concentration of 2 μM or 10 μM and added to wells. The plates were gently swirled and placed back in incubator. At time points indicated, plates were removed and supernatants were transferred to microtubes and centrifuged at high speed to remove precipitate and stored at −20° C. until time of LC-LC/MS analysis. Cells were scraped into 1 mL 70% cold methanol and vortexed. Cells were then placed at −20° C. overnight to facilitate extraction of metabolites. The following day, cells were pelleted by centrifugation at 4° C., 15 minutes at 10,000 rpm and cell extract was removed for LC-LC/MS analysis for 2'C-Methylguanosine triphosphate quantification.

Compounds E (Example 2), F (Example 20), C (Example 42) and H (Example 38) used in this study were synthesized as described in the experimental section. Compound D was purchased from CarboSynth Ltd. Compounds A, B and G used in this study where synthesized using procedures described in McGuigan et al. PCT/GB07/004,480 filed Nov. 23, 2007 published May 29, 2008 as WO2008062206.

Figure 3:
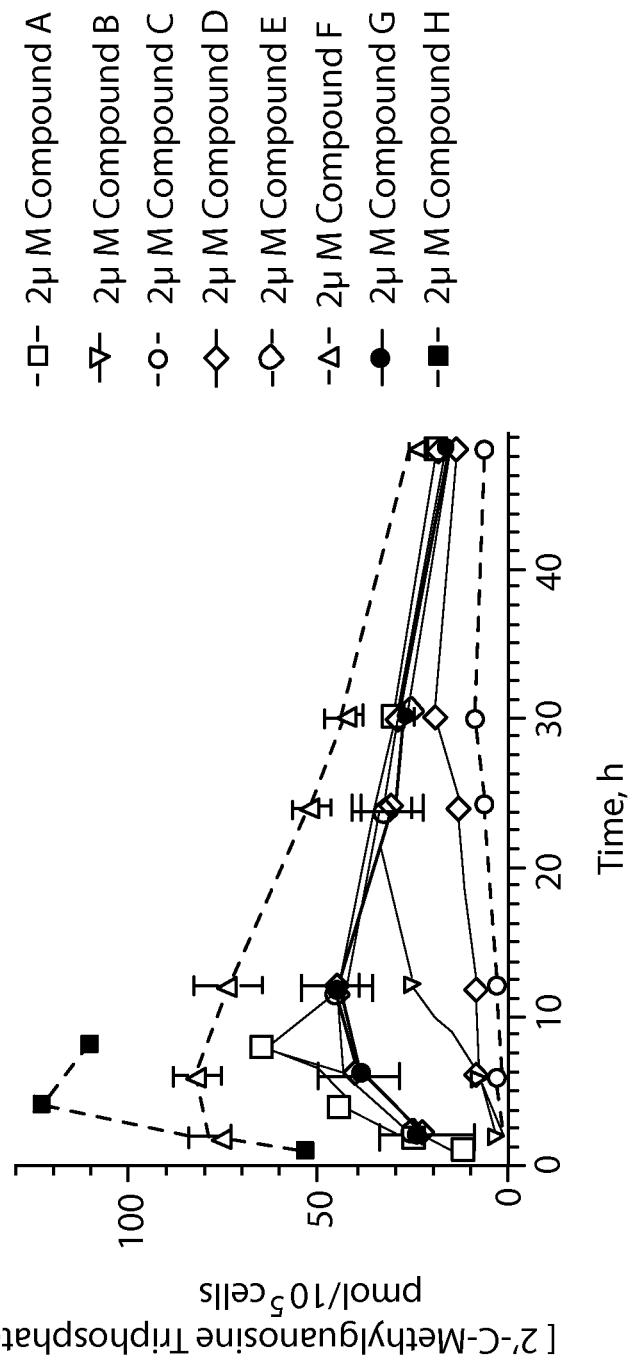
FIG. 3 is a graph showing the conversion of compounds A-H to 2'C-methylguanosine triphosphate in a human primary hepatocyte study.

The Conversion of Compounds A-H to 2'-C-Methylguanosine Triphosphate in Human Primary Hepatocyte Study is shown in FIG. 3.

Compounds A-H as used in the Primary Human Hepatocyte Study are shown below:

Compound D
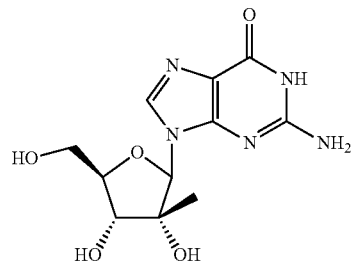

Compound E
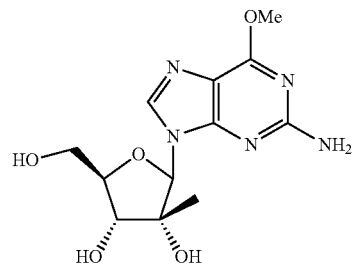

Compound A
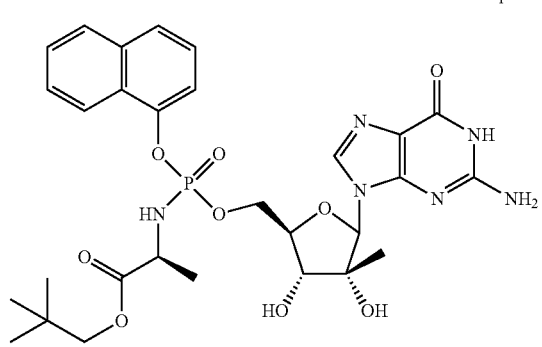

Compound F
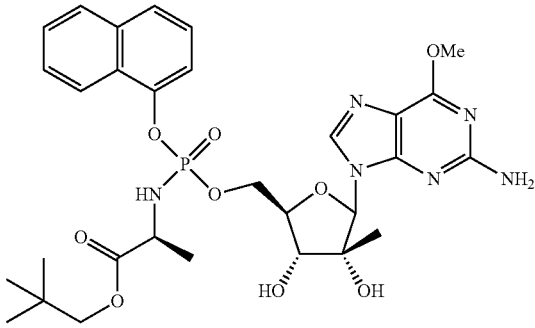

Compound B
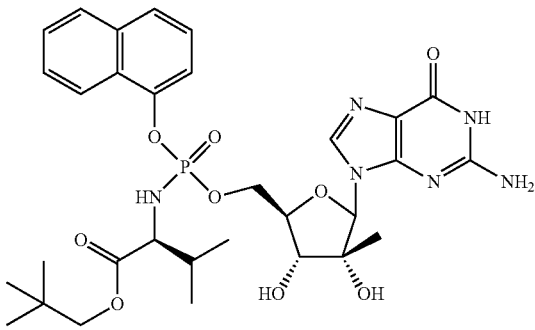

Compound C
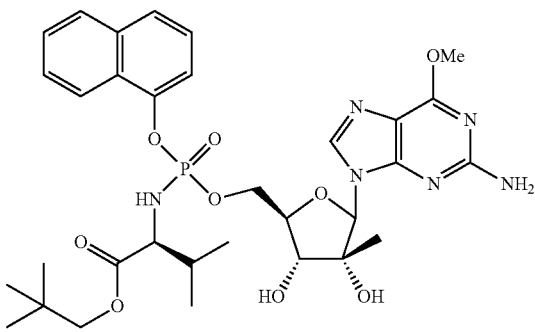

Compound G
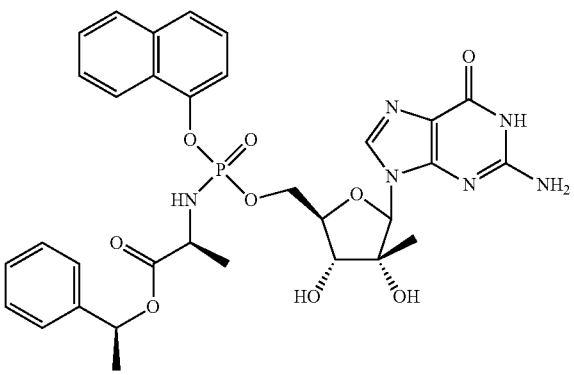

-continued

Compound H

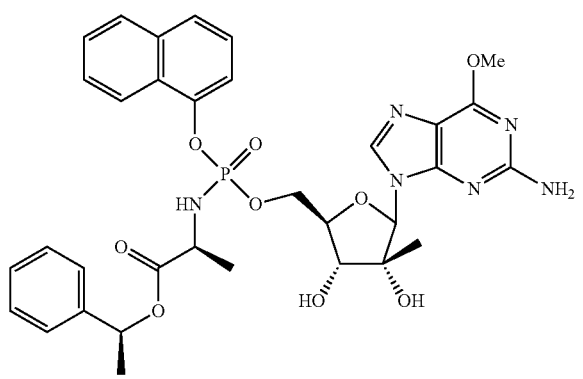

Selected nucleoside 5'-phosphoramidates were examined for stability in human, cynomolgous monkey, rat and mouse plasma at 37° C. at both 30 min and 90 min time points. Compounds C (Example 42), F (Example 20), I (Example 13), J (Example 47), K (Example 36) and L (Example 54) used in this study were synthesized as described in the Examples above. Compounds A, and B, were where synthesized using procedures described in McGuigan et al. PCT/GB07/004,480 filed Nov. 23, 2007 published May 29, 2008 as WO2008062206, incorporated herein by reference.

Protide Stability in Normal Plasma: Plasma samples were prepared for analysis as follows. 50 µl of each test sample were distributed a 96-well V-bottom plate. 200 µl of acetonitrile containing 10 ng/ml of an internal standard was added to each plasma sample. The precipitated samples were centrifuged at 2500 rpm, 4° C. for 20 minutes in a Sorvall RT6000S centrifuge (Thermo Scientific, Waltham Mass.) and 100 µl of supernatant from each sample was transferred into a 96 deep well plate followed by the addition of 100 µl $H_2O$ to each sample. Samples were covered, mixed well by vortexing and maintained at 2-8° C. before and during analysis. 15 µl of each test sample was analyzed for protide concentrations by liquid chromatography coupled to tandem mass spectrometry (LC-MS/MS). Liquid chromatography was performed with an Agilent 1100 Series HPLC system equipped with a Synergi 4 µm Polar-RP, 30×2.0 mm column (Phenomenex, Torrance, Calif.). The HPLC system was coupled to an API 4000 triple quadrupole mass spectrometer (Applied Biosystems, Framingham, Mass.). Mass spectrometry was performed in positive ion mode and data was analyzed using Analyst® v1.4.2 software (Applied Biosystems, Framingham, Mass.). Data was presented as the percentage of compound recovered as compared to the 0 time point control.

TABLE 3

Plasma stability of Protides in Multiple Species at 37° C.

| | Normal Plasma | | | | | | | |
|---|---|---|---|---|---|---|---|---|
| | Human | | Cynomolgous | | Rat | | Mouse | |
| Compound | % Compound Remaining Compared to %100 Acetonitrile Control | | | | | | | |
| | 30 min | 1.5 h | 30 min | 1.5 h | 30 min | 1.5 h | 30 min | 1.5 h |
| A | 83.2 | 80.8 | 98.5 | 102.4 | 0 | 0 | 0 | 0 |
| I | 97.2 | 85.4 | 89.1 | 77.0 | NT | NT | <3.9 | NT |
| F | 94.0 | 101.5 | 97.0 | 94.0 | 0 | 0 | 0 | 0 |
| B | 74.7 | 78.1 | 84.5 | 84.9 | 66.7 | 42.0 | 68.3 | 32.3 |
| C | 88.5 | 82.5 | 87.0 | 82.5 | 50.0 | 37.0 | 66.5 | 45.5 |
| J | 105.1 | 129.5 | 112.5 | 118.5 | 71.3 | 57.3 | 74.3 | 67.4 |
| K | 70.3 | 74.1 | 93.7 | 96 | 16.9 | 1.4 | 0.4 | 0 |
| L | 80.4 | 93.5 | 119.3 | 124.2 | 60.6 | 58.4 | 60.7 | 45.7 |

The Compounds used in the Plasma Stability Studies are shown below:

Compound A

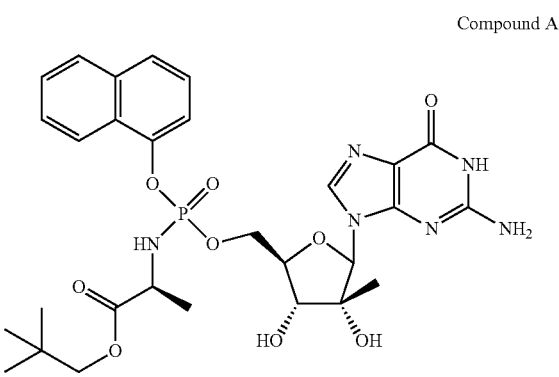

Compound I

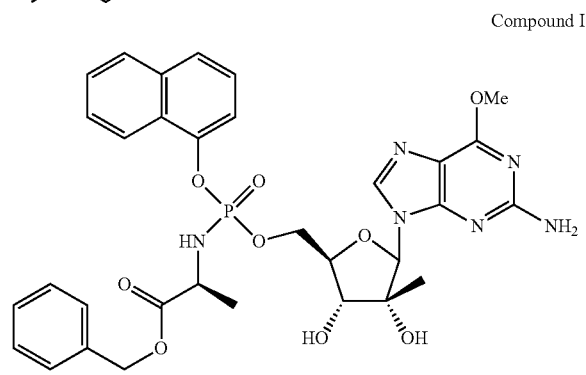

Compound F

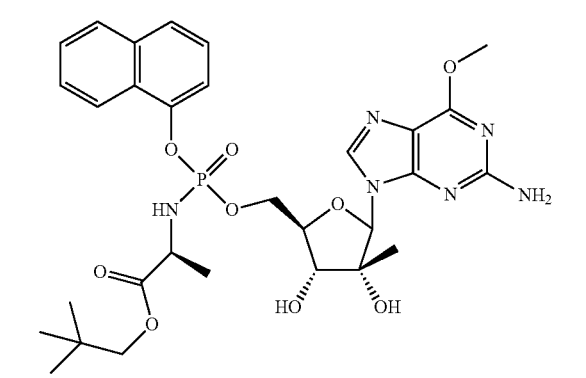

Compound B

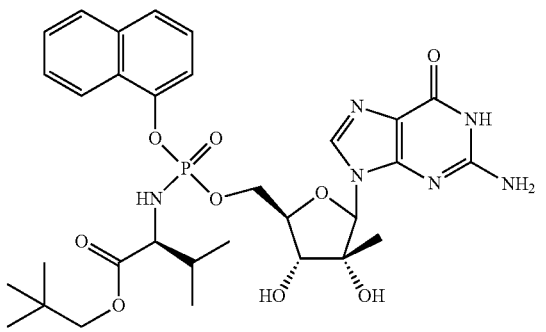

Compound C

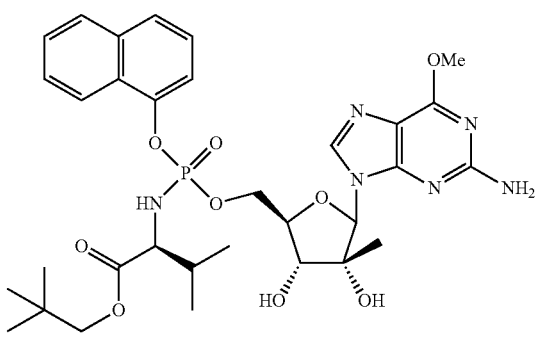

Compound J

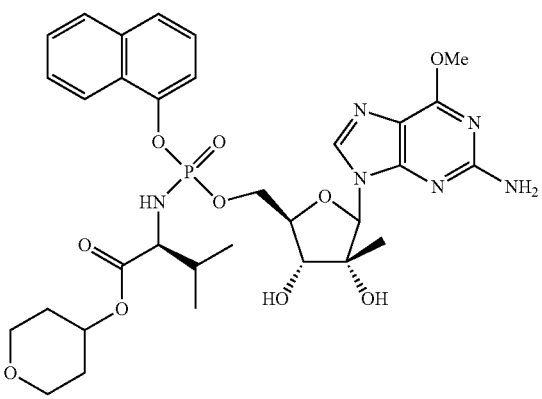

Compound K

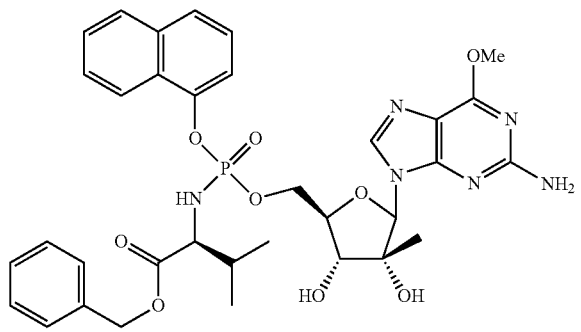

Compound L

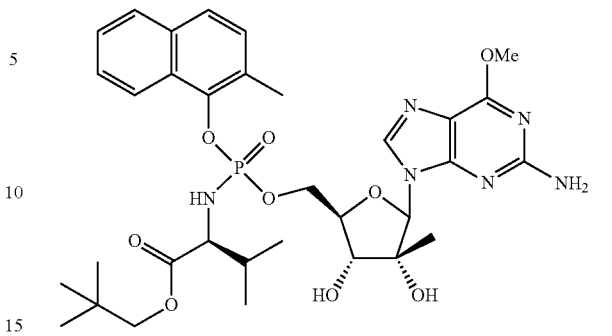

Selected compounds were examined in mouse PK experiments to determine the levels of 2'-C-methyl guanosine 5'-triphosphate in the liver. 2'-C-Methyl guanosine 5'-triphosphate was purchased from TriLink Biotechnologies, San Diego, Calif. 92121, and used to generate standard curves for determining liver concentrations. Compounds C (Example 42). F (Example 20), K (Example 36), E (Example 2) and H (Example 38) used in this study were synthesized as described in the Experimental section. Compounds A, G, M and N were synthesized using procedures described in McGuigan et al. PCT/GB07/004,480 filed Nov. 23, 2007 published May 29, 2008 as WO2008062206.

Mouse PK Analysis: Compounds were formulated in 5% Dimethylacetamide (DMA), 20% Solutol HS15, 20% Polyethylene glycol 400 (PEG), in 50 mM sodium acetate, pH=4. Formulations were prepared just prior to dosing. 20-30 gram, female ICR mice (Taconic Farms) were dosed by oral gavage. The volumes delivered were based on each animal's body weight at the time of administration to achieve the desired mg/kg target dose. Blood was collected from the retro-orbital sinus in tubes containing EDTA while under isoflurane gas anesthesia. Plasma was separated from blood samples within 30 minutes of sampling by centrifugation for 10 minutes at ~1500 RCF in a microcentrifuge. Plasma samples were stored frozen at −80° C. until analysis. Animals were sacrificed by cervical dislocation following loss of consciousness under $CO_2/O_2$ inhalation. Livers were harvested, cut into small sections and divided into 3 tubes per mouse. Tissue weights will be recorded and the samples were flash frozen in an ethanol/dry ice bath and stored at −80° C.

For quantitation of 2'-C-Methyl-D-Guanosine 5'-Triphosphate in rodent liver samples, tissues were homogenized in 3 equivalents of methanol (i.e. 3 mL of methanol to 1 gram of tissue) using 1 mm silicon carbide sharp particles (Biospec) in a bead mill (ThermoSavant FastPrep 120) at an agitating speed of 6 for 2 cycles of 30 seconds at 4° C. The homogenates were centrifuged for 30 minutes at 15,000 rpm at 4° C. using a microcentrifuge. The supernatants were collected and 200 μl of the supernatant from each sample was dried under nitrogen. The dried extracts were reconstituted with 50 μl of 10 mM dimethylhexylamine and 3 mM ammonium formate in water. A calibration curve was prepared in liver matrix from control animals using known quantities of 2'-C-Methyl-D-Guanosine 5'-Triphosphate. Samples of normal liver were homogenized as described above. The homogenates were centrifuged for 30 minutes at 15,000 rpm at 4° C. using a microcentrifuge. Serial dilutions of the triphosphate standard were prepared from the standard stock solution (1 mg/mL in 10 mM dimethylhexylamine and 3 mM ammonium formate in water pH 9; stored at −20° C.) using the recovered supernatant as diluent. The supernatants containing standard dilutions were dried under nitrogen. The dried standard samples were reconstituted with 50 μl of 10 mM dimethylhexylamine and 3 mM ammonium formate in water. Triphosphate levels were quantitated using LC-MS/MS analysis. The reconstituted samples were separated on a Waters' XTerra MS C18 2.1×50 mm 3.5 μm column (Waters, Milford, Mass.) at a flow rate of 300 μl per minute, 100 injection volume. A gradient elution was performed with the following buffers: A=10 mM dimethylhexylamine and 3 mM ammonium formate in water pH 9 and B=20 mM dimethylhexylamine and 6 mM ammonium formate in acetonitrile (at time 0, % B=0, at 7 minutes % B=100%, at 9 minutes % B=100%, at 9.5 minutes % B=0%, at 13 minutes 0% B=0%). MS/MS analysis was performed using a Sciex API 4000 triple quadrupole instrument was set to detect the m/z transition of 535.94/438.00 (negative ion mode).

In the Table shown below, mice were po dosed at 50 mg·kg in 5% DMA, 20% Solutol HS15, 20% PEG 400, 55% 50 mM Sodium acetate, pH 4.0

TABLE 4

2'-C-Methylguanosine Triphosphate Levels in Mouse Livers After 50 mg/kg PO Dose

| Compound | $C_{max}$ ng/g | Multiple Above IC$_{90}$ at $C_{max}$ | $T_{max}$ hours | $T_{1/2}$ hours | AUC$_{0-6}$ h·ng/g | AUC$_{0-24}$ h·ng/g |
|---|---|---|---|---|---|---|
| Compound A | 370.0 | 3.6 | 6.0 | — | 1584 | — |
| Compound M | 512.0 | 5.0 | 4.0 | — | 1937 | — |
| Compound G | 1950.0 | 19.1 | 4.0 | — | 6977 | — |
| Compound N | 275.7 | 2.7 | 4.0 | 10.2 | 815 | 3857 |
| Compound E | 2563.3 | 25.1 | 6.0 | 7.1 | 8748 | 30618 |
| Compound H | 3130.0 | 30.7 | 4.0 | 4.3 | 14380 | 26837 |
| Compound C | 311.3 | 3.1 | 4.0 | — | 1540 | — |
| Compound F | 8953.3 | 87.8 | 1.0 | 3.6 | 31940 | 59353 |
| Compound K | 1209.7 | 11.9 | 4.0 | 2.0 | 5055 | 6356 |

The Compounds used in the Mouse Liver PK Studies are shown below:

Compound A

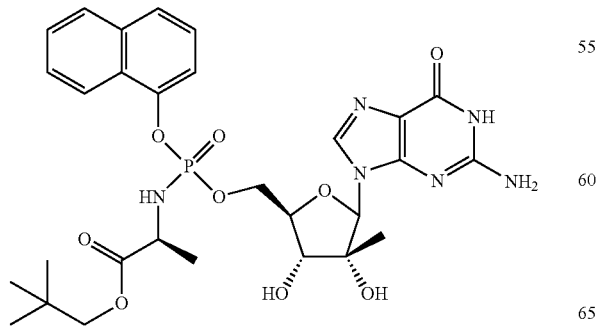

Compound M

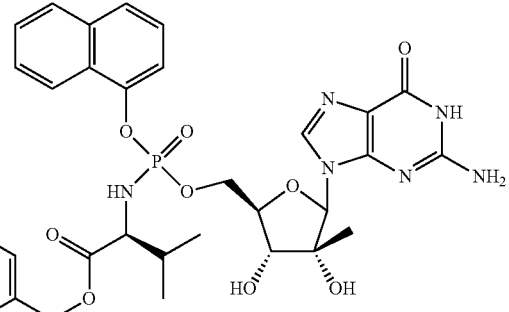

Compound G

Compound N

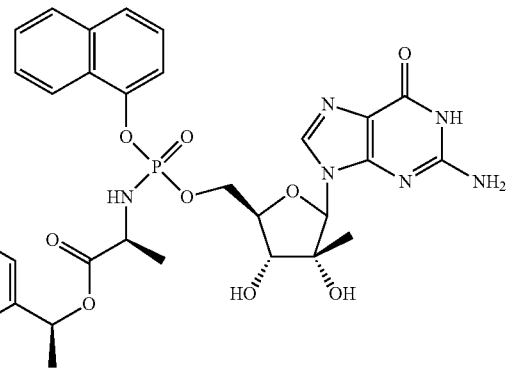

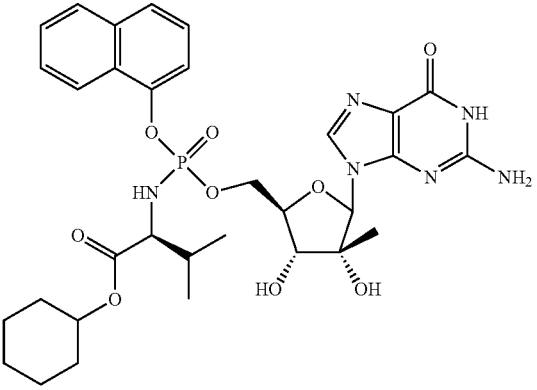

Compound E

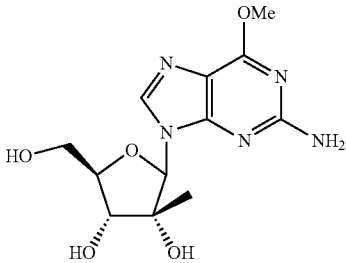

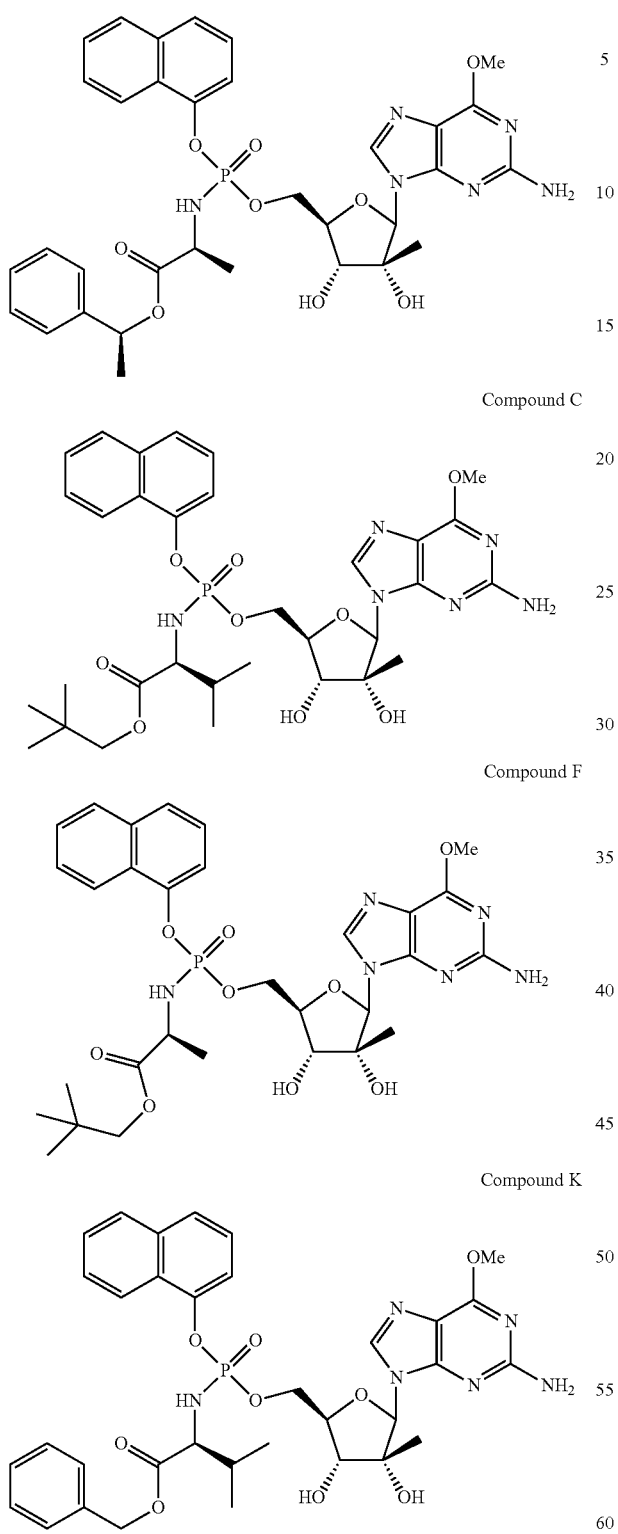

Compound H

Compound C

Compound F

Compound K

While the invention has been described with reference to particularly preferred embodiments and examples, those skilled in the art recognize that various modifications may be made to the invention without departing from the spirit and scope thereof.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

In the foregoing sections, a number of abbreviations and acronyms were used, and the full description of these are provided as follows:

| | |
|---|---|
| ACN | acetonitrile |
| AIBN | azobisisobutryonitrile |
| anhy | anhydrous |
| Bn | benzyl (phenylmethyl) |
| Boc | benzyloxycarbonyl |
| BSA | benzenesulfonic acid |
| Bu | butyl |
| n-BuOH | n-butanol |
| t-BuOH | tert-butanol |
| t-BuOK | potassium-tert-butoxide |
| tert-BuMgCl | tert-butylmagnesium chloride |
| $CDCl_3$ | deuterochloroform |
| $CD_3OD$ | methanol-$d_4$ |
| CI-MS | chemical ionization mass spectrometry |
| $^{13}C$ NMR | carbon-13 nuclear magnetic resonance spectroscopy |
| conc | concentrated |
| d | doublet (NMR) |
| dd | doublet of doublets (NMR) |
| ddd | double doublet of doublets (NMR) |
| DBU | diaza(1,3)bicyclo[5.4.0]undecane |
| DCC | dicyclohexylcarbodiimide |
| DCM | dichloromethane |
| DMAP | 4-dimethylaminopyridine |
| DMF | N,N-dimethylformamide |
| DMSO | dimethyl sulfoxide |
| dt | doublet of triplets (NMR) |
| EDCI | 1-(3-dimethylamnopropy1)-3-ethylcarbodiimide hydrochloride |
| ee | enantiomeric excess |
| El-MS | electron impact mass spectrometry |
| equiv | equivalent(s) |
| ESI | electrospray ionization |
| ES-MS | electrospray mass spectrometry |
| $Et_2O$ | ethyl ether |
| EtOAc | ethyl acetate |
| EtOH | ethanol |
| g | gram(s) |
| GC-MS | gas chromatography-mass spectrometry |
| h | hour |
| HCV | hepatitis C virus |
| $^1H$ NMR | proton nuclear magnetic resonance spectroscopy |
| HPLC | high performance liquid chromatography |
| HRMS | high resolution mass spectrometry |
| IMPDH | inosine 5'monophosphate dehydroxgenase |
| J | NMR coupling constant |
| LC/MS | liquid chromatography-mass spectrometry |
| LG | leaving group |
| LHMDS | Lithium hexamethyldisilazide |
| m | multiplet (NMR) |
| MDI | methylenediphenyldisocyanate |
| Me | methyl |
| MeOH | methanol |
| mg | milligram |
| MHz | megahertz |
| mL | milliliter |
| mmol | millimole |
| mp | melting point |
| MTBE | methyl t-butyl ether |
| NaOMe | sodium methoxide |
| NMI | N-methylimidazole |
| NMO | N-methylmorpholine-N-oxide |
| NMR | nuclear magnetic resonance |
| $^{31}P$ NMR | phosphorous-31 nuclear magnetic resonance spectroscopy |
| ppm | part per million |
| q | quartet (NMR) |
| PTSA | p-toluenesulfonic acid |
| RBV | ribavirin |
| Red-Al® | sodium bis(2-methoxyethoxy)aluminumhydride |

| | |
|---|---|
| $R_f$ | retention factor (TLC) |
| rt | room temperature |
| s | singlet (NMR) |
| t | triplet (NMR) |
| TBAF | tetra-n-butylammonium fluoride |
| TBPPS | tetra-n-butylphosphonium persulfate |
| TEA | triethylamine |
| TFA | trifluoroacetic acid |
| THF | tetrahydrofuran |
| TMS | tetramethylsilane |
| TMSOTf | trimethylsilyl trifluoromethanesulfonate |
| $t_R$ | retention time |
| TLC | thin layer chromatography |
| UV | ultraviolet |
| VCD | Vibrational Circular Dichroism |

What is claimed is:

1. A compound of formula (I) below having the structure:

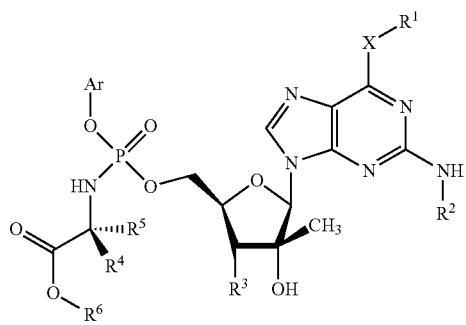

(I)

wherein Ar is selected from
naphthyl,

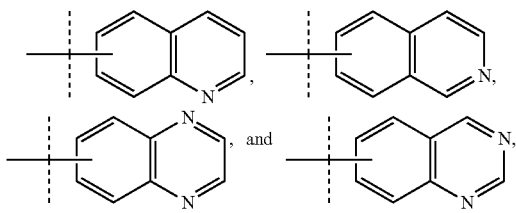

any of which are optionally substituted with
$C_1$-$C_6$alkyl,
$C_1$-$C_6$alkoxy,
di($C_1$-$C_6$)alkylamino or
$C_1$-$C_6$alkylcarboxy($C_1$-$C_6$)alkyl-;
X is selected from S, NH and O;
$R^1$ is selected from
$C_1$-$C_6$ alkyl,
benzyl,
substituted benzyl; and
aryl($C_0$-$C_6$)alkyl- wherein the aryl is optionally substituted by
halo,
$C_1$-$C_6$alkoxy, and
$C_1$-$C_6$alkyl;
$R^2$ is selected from
hydrogen,
phenyl,
aryl, and
aryl($C_0$-$C_6$)alkyl- wherein the aryl is optionally substituted by
halo,
$C_1$-$C_6$alkoxy, and
$C_1$-$C_6$alkyl;
$R^3$ is selected from H and OH;
$R^4$ and $R^5$ are independently selected from
hydrogen,
$C_1$-$C_6$alkyl optionally substituted with alkylthio,
benzyl optionally substituted with one or more
halo,
$C_1$-$C_6$alkyl, or
$C_1$-$C_6$alkoxy,
phenyl optionally substituted with one or more
halo,
$C_1$-$C_6$alkyl, or
$C_1$-$C_6$alkoxy;
$R^6$ is selected from
$C_1$-$C_{10}$alkyl,
$C_3$-$C_8$cycloalkyl,
$C_3$-$C_8$cycloalkyl-alkyl-,
phenyl($C_1$-$C_6$)alkyl- optionally substituted with
$C_1$-$C_6$alkyl,
$C_1$-$C_6$alkoxy, and
halo,
indanyl and
heterocycloalkyl;
and pharmaceutically acceptable salts thereof.

2. The compound of claim 1 wherein the compound is in the form of a polymorph.

3. A pharmaceutical composition comprising the compound of claim 1 and a pharmaceutically acceptable carrier, excipient or diluent.

4. The pharmaceutical composition of claim 3, wherein the pharmaceutically acceptable carrier is pure sterile water, phosphate buffered saline or an aqueous glucose solution.

5. The compound of claim 1 wherein Ar is selected from: naphthyl,

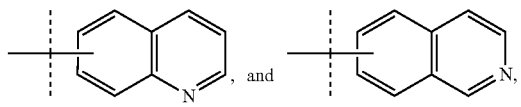

any of which are optionally substituted with
$C_1$-$C_6$alkyl,
$C_1$-$C_6$alkoxy,
di($C_1$-$C_6$)alkylamino; or
$C_1$-$C_6$alkylcarboxy($C_1$-$C_6$)alkyl-.

6. The compound of claim 1 wherein X is O.
7. The compound of claim 1 wherein R1 is C1-C6 alkyl.
8. The compound of claim 1 wherein R2 is hydrogen.
9. The compound of claim 1 wherein R3 is OH.
10. The compound of claim 1 wherein $R^4$ and $R^5$ are independently selected from
hydrogen,
$C_1$-$C_6$alkyl optionally substituted with alkylthio, and
phenyl optionally substituted with one or more
halo,
$C_1$-$C_6$alkyl, or
$C_1$-$C_6$alkoxy.

11. The compound of claim 1 wherein $R^4$ is selected from
$C_1$-$C_6$alkyl optionally substituted with alkylthio, and
phenyl optionally substituted with one or more
halo,
$C_1$-$C_6$alkyl, or $C_1$-$C_6$alkoxy; and
$R^5$ is hydrogen.

12. The compound of claim 1 wherein $R^6$ is selected from $C_1$-$C_{10}$alkyl,
phenyl($C_1$-$C_6$)alkyl- optionally substituted with halo.

13. A compound selected from the group consisting of the following formulas:

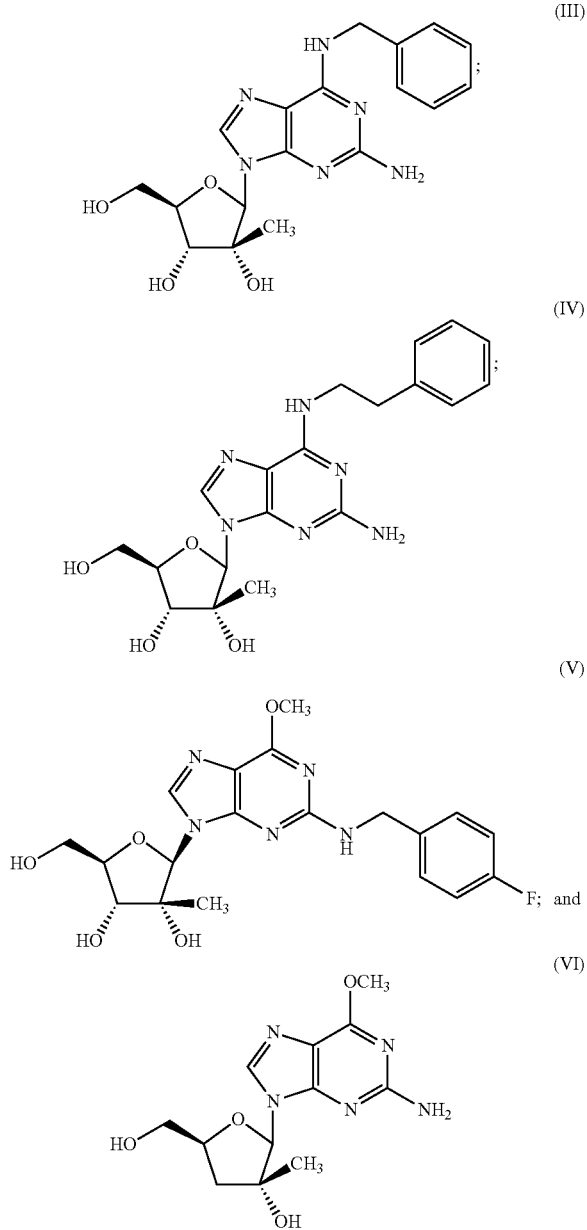

and pharmaceutically acceptable salts thereof.

14. A method for treating a viral infection in a mammal mediated at least in part by a virus in the Flaviviridae family of viruses comprising administering to a mammal in need thereof an effective amount of the compound of claim 1.

15. The method according to claim 14, wherein said virus is hepatitis C virus.

16. A method for treating a viral infection in a mammal mediated at least in part by a virus in the Flaviviridae family of viruses comprising administering to a mammal in need thereof an effective amount of the pharmaceutical composition of claim 3.

17. The method according to claim 16, wherein said virus is hepatitis C virus.

18. A method for treating a hepatitis C viral infection in a mammal comprising administering to a mammal in need thereof an effective amount of the compound of claim 1.

19. The method according to claim 18 wherein the compound is administered in combination with a therapeutically effective amount of one or more agents active against hepatitis C virus.

20. The method of claim 19 wherein said agent active against hepatitis C virus is interferon-alpha or pegylated interferon-alpha alone or in combination with ribavirin or levovirin.

21. The method of claim 19 wherein said agent active against hepatitis C virus is selected from the group consisting of ribavirin, levovirin, viramidine, thymosin alpha-1, an inhibitor of HCV NS3 serine protease, interferon-α, pegylated interferon-α (peginterferon-α), and combinations thereof.

22. The method of claim 21 wherein interferon-α is selected from the group consisting of recombinant interferon-α2a, interferon-α2b, a consensus interferon, and a purified interferon-α product.

23. The method of claim 19 wherein said agent active against hepatitis C virus is an agent that inhibits a material selected from the group consisting of HCV proteases, HCV polymerase, HCV helicase, HCV NS4B protein, HCV entry, HCV assembly, HCV egress, HCV NS5A protein, and inosine 5'-monophosphate dehydrogenase.

24. The method of claim 19 wherein said agent active against hepatitis C virus is a nucleoside analog for the treatment of an HCV infection.

25. The method of claim 19 wherein said agent active against hepatitis C virus is selected from the group consisting of Omega IFN, BILN-2061, Roferon A, Pegasys, Pegasys/Ribaravin, CellCept, Wellferon, Albuferon-α, Levovirin, IDN-6556, IP-501, Actimmune, Infergen A, ISIS 14803, JTK-003, Pegasys/Ceplene, Ceplene, Civacir, Intron A/Zadaxin, Levovirin, Viramidine, Heptazyme, Intron A, PEG-Intron, Rebetron, Ribavirin, PEG-Intron/Ribavirin, Zadazim, Rebif, IFN-β/EMZ701, T67, VX-497, VX-950/LY-5703 10, Omniferon, XTL-002, SCH 503034, isatoribine and its prodrugs ANA971 and ANA975, R1479, Valopicitabine, NIM811, and Actilon.

26. A method for treating a hepatitis C viral infection in a mammal comprising administering to a mammal in need thereof an effective amount of the pharmaceutical composition of claim 3.

27. The method according to claim 26 wherein the composition is administered in combination with a therapeutically effective amount of one or more agents active against hepatitis C virus.

28. A method for treating a viral infection in a mammal mediated at least in part by a virus in the Flaviviridae family of viruses comprising administering to a mammal in need thereof an effective amount of the compound of claim 13.

29. The method according to claim 28, wherein said virus is hepatitis C virus.

30. A method for treating a hepatitis C viral infection in a mammal comprising administering to a mammal in need thereof an effective amount of the compound of claim 13.

31. A pharmaceutical composition comprising the compound of claim 13 and a pharmaceutically acceptable carrier, excipient or diluent.

32. A method for treating a hepatitis C viral infection in a mammal comprising administering to a mammal in need thereof an effective amount of the composition of claim 31.

33. The compound according to claim 1 wherein the compound includes different diastereomers around phosphorous in formula I.

34. The compound according to claim 33 wherein the compound includes a mixture of two phosphorous diastereomers in any proportion from 1:99 to 99:1.

35. A method of separating the phosphorous diastereomers of the compound of claim 34 comprising conducting a chiral chromatographic step performed on a chiral resin.

36. The compound according to claim 1 wherein the compound has a specific formula selected from the group consisting of the following:

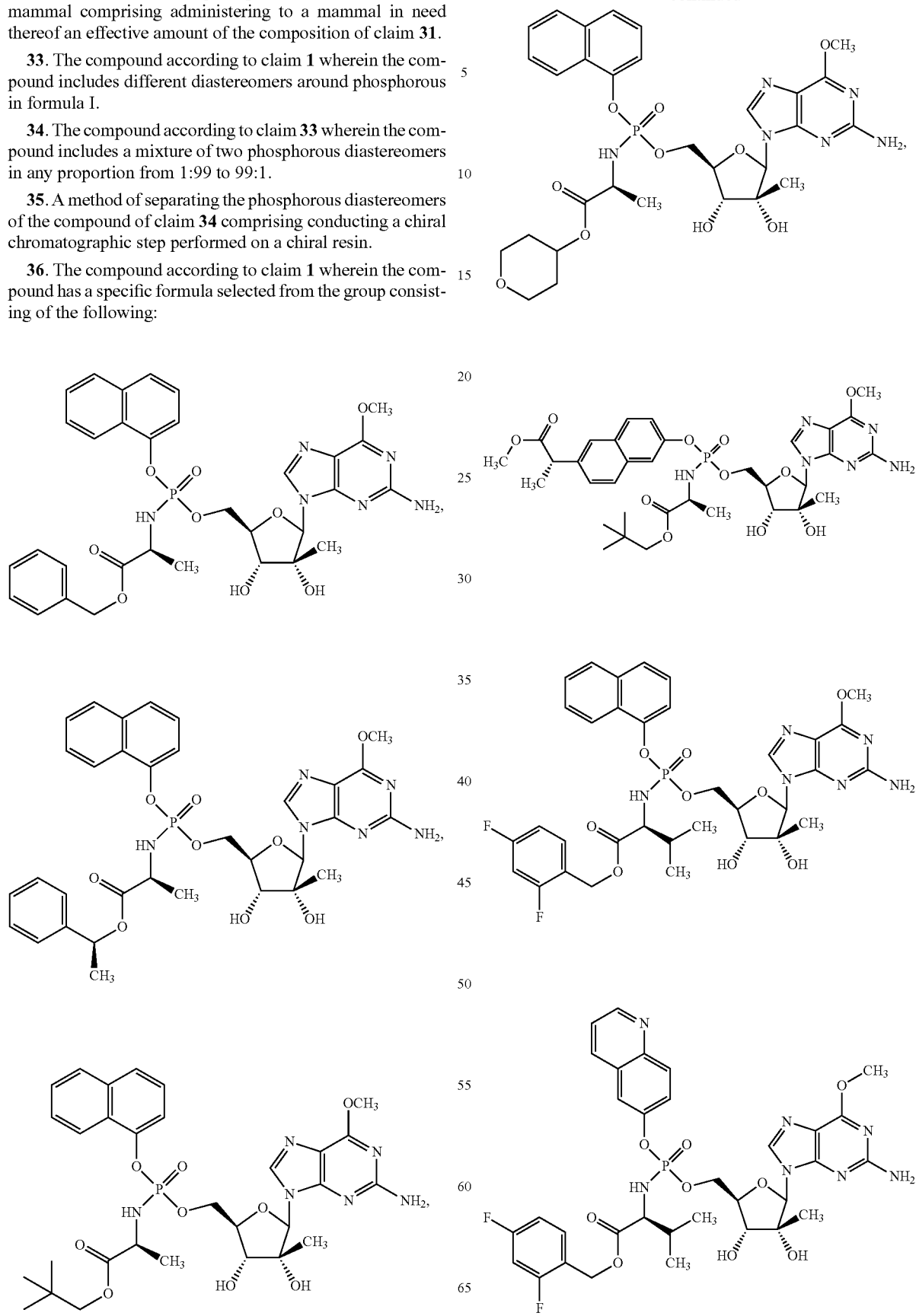

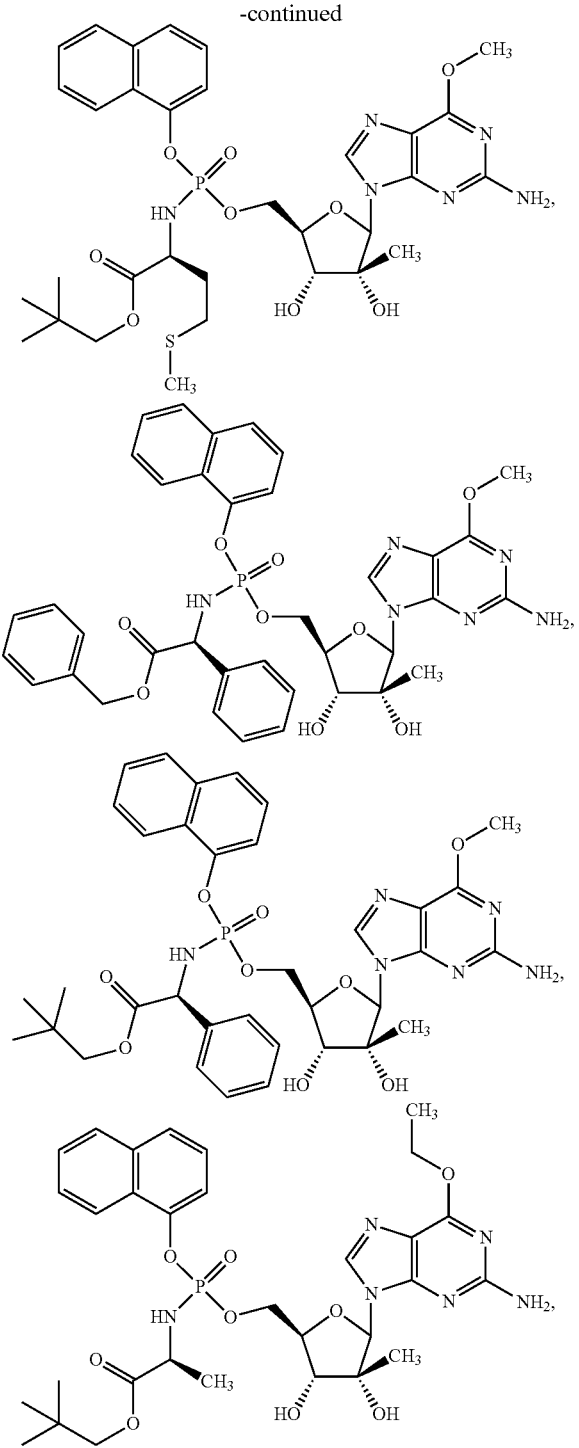

and phosphorus diastereomers thereof.

37. The compound according to claim 1 wherein the compound is selected from the group consisting of the following:

Benzyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)propanoate;

1(S)-Phenylethyl 2(S)-(((((2R,3R,4R,5R)-5-(2-amino-6-methoxy-9H-purin-9-yl) -3,4-dihydroxy-4-methyltetrahydrofuran-2-yl)methoxy(naphthalene-1-yloxy) phosphorylamino)propanoate;

2,2-Dimethylpropyl 2(S)-(((((2R,3R,4R,5R)-5-(2-amino-6-methoxy-9H-purin-9-yl) -3,4-dihydroxy-4-methyltetrahydrofuran-2-yl)methoxy(naphthalene-1-yloxy) phosphorylamino)propanoate;

(2S)-Tetrahydro-2H-pyran-4-yl 2-((((2R,3R,4R)-5-(2-amino-6-methoxy-9H-purin -9-yl)-3,4-dihydroxy-4-methyltetrahydrofuran-2-yl)methoxy)(naphthalen-1-yloxy)phosphorylamino)propanoate;

(2S)-Methyl 2-(6-((((2R, 3R,4R)-5-(2-amino-6-methoxy-9H-purin-9-yl)-3,4-dihydroxy-4-methyltetrahydrofuran-2-yl(methoxy)((S)- 1 -(neopentyloxy)- 1 -oxopropan-2-ylamino)phosphoryloxy)naphthalen-2-yl) propanoate;

2,4-Difluorobenzyl 2(S)-(((((2R,3R,4R,5R)-5-(2-amino-6-methoxy-9H-purin-9-yl) -3,4-dihydroxy-4-methyltetrahydrofuran-2-yl)methoxy(naphthalene-1-yloxy) phosphorylamino)-3 -methylbutanoate;

(2S)-2,4-Difluorobenzyl 2-((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)-3-methylbutanoate;

(2S)-Neopentyl 2-(((((2R,-3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-4-(methylthio)butanoate;

(2S)-Benzyl 2-(((((2R,-3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-Neopentyl 2-(((((2R,-3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

2,2-Dimethylpropyl 2(S)-(((((2R,3R,4R,5R)- 5-(2-amino-6-ethoxy-9H-purin-9-yl) -3,4-dihydroxy-4-methyltetrahydrofuran-2-yl)methoxy(naphthalene-1-yloxy) phosphorylamino)propanoate;

1(S)-Phenylethyl 2(S)-(((((2R,3R,4R,5R)-5-(2-amino-6-methoxy-9H-purin-9-yl) -3,4-dihydroxy-4-methyltetrahydrofuran-2-yl)methoxy(naphthalene-1-yloxy) phosphorylamino)propanoate;

2,2-Dimethylpropyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate;

Benzyl 2(S)-(((((2R,-3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)propanoate;

(2S)-2,4-Difluorobenzyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy) phosphorylamino)propanoate;

1(S)-Phenylethyl 2(S)-(((((2R,-3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate;

(2S)-2,3-Dihydro-1H-inden-2-yl 2-((((2R,-3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

(2S)-Propyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino) propanoate;

(2S)-3,3-Dimethylbutyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy) phosphorylamino)propanoate;

(2S)-Isobutyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

2,2-Dimethylpropyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate;

(S)-P 2,2-Dimethylpropyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)propanoate;

(R)-P 2,2-Dimethylpropyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)propanoate;

(2S)-Isopropyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

(2S)-Cyclopentyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

(2S)-Cyclohexyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

(2S)-Tetrahydro-2H-pyran-4-yl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)propanoate;

(2S)-2,4-difluorobenzyl 2-((((2R,3R,4R)-5-(2-amino-6-methoxy-9H-purin-9-yl-3,4-dihydroxy-4-methyltetrahydrofuran-2-yl)methoxy)(6-((S)-1-methoxy-1-oxopropan-2-yl)naphthalen-2-yloxy)phosphorylamino)propanoate;

(2S)-methyl 2-(6-((((2R, 3R,4R)-5-(2-amino-6-methoxy-9H-purin-9-yl)-3,4-dihydroxy-4-methyltetrahydrofuran-2-yl)methoxy)((,S)-1-(neopentyloxy)-1-oxopropan-2-ylamino)phosphoryloxy)naphthalen-2-yl)propanoate;

(2S)-methyl2-(6-((((2R, 3R,4R)-5-(2-amino-6-methoxy-9H-purin-9-yl)-3,4-dihydroxy-4-methyltetrahydrofuran-2-yl)methoxy)((S)-1-oxo-1-(tetrahydro-2H-pyran-4-yloxy)propan-2-ylamino)phosphoryloxy) naphthalen-2-yl)propanoate;

(2S)-2,4-difluorobenzyl 2-((((2R, 3R,4R)-5-(2-amino-6-methoxy-9H-purin-9-yl)-3,4-dihydroxy-4-methyltetrahydrofuran-2-yemethoxy)(quinolin-5-yloxy)phosphorylamino)propanoate;

(2S)-neopentyl 2-((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)propanoate, (2S)-tetrahydro-2H-pyran-4-yl 2-((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)propanoate;

(2S)-neopentyl 2-((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)propanoate;

(2S)-tetrahydro-2H-pyran-4-yl 2-((((2R,3R,4R)-5-(2-amino-6-methoxy-9H-purin-9-yl)-3,4-dihydroxy-4-methyltetrahydrofuran-2-yl(methoxy)(quinolin-6-yloxy)phosphorylamino)propanoate;

(2S)-neopentyl 2-((((2R,3R,4R)-5-(2-amino-6-methoxy-9H-purin-9-yl)-3,4-dihydroxy-4-methyltetrahydrofuran-2-yl)methoxy)(phenoxy)phosphorylamino)propanoate;

(2S)-Neopentyl 2-(((2R,3R,4R)-5-(2-amino-6-methoxy-9H-purin-9-yl)-3,4-dihydroxy-4-methyltetrahydrofuran-2-yl)methoxy)(6-((S)-1-methoxy-1-oxopropan-2-yl)naphthalen-2-yloxy)phosphorylamino)-3-methylbutanoate;

(2S)-2,4-Difluorobenzyl 2-(((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)-3-methylbutanoate;

(2S)-Neopentyl 2-(((((2R,3R,4R)-5-(2-amino-6-methoxy-9H-purin-9-yl)-3,4-dihydroxy-4-methyltetrahydrofuran-2-yl)methoxy)(quinolin-5-yloxy)phosphorylamino)-3-methylbutanoate;

(2S)-2,4-Difluorobenzyl 2-(((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)-3-methylbutanoate;

(2S)-Neopentyl 2-(((((2R,3R,4R)-5-(2-amino-6-methoxy-9H-purin-9-yl)-3,4-dihydroxy-4-methyltetrahydrofuran-2-yl)methoxy)(quinolin-6-yloxy)phosphorylamino)-3-methylbutanoate;

(2S)-Neopentyl 2-(((((2R,3R,4R)-5-(2-amino-6-methoxy-9H-purin-9-yl)-3 ,4-dihydroxy-4-methyltetrahydrofuran-2-yl)methoxy)(quinolin-8-yloxy)phosphorylamino)-3-methylbutanoate;

(2S)-Neopentyl 2-(((((2R,3R,4R))-5-(2-amino-6-methoxy-9H-purin-9-yl)-3,4-dihydroxy-4-methyltetrahydrofuran-2-yl)methoxy)(2-methylnaphthalen-1-yloxy) phosphorylamino)-3-methylbutanoate;

(2S)-Neopentyl 2-((((((2R,3R,4R)-5-(2-amino-6-methoxy-9H-purin-9-yl)-3,4-dihydroxy-4-methyltetrahydrofuran-2-yl)methoxy)(3-tert-butylnaphthalen--yloxy)phosphorylamino)-3-methylbutanoate;

(2S)-Neopentyl 2-((((((2R,3R,4R)-5-(2-amino-6-methoxy-9H-purin-9-yl)-3,4-dihydroxy-4-methyltetrahydrofuran-2-yl)methoxy)(3,7-di-tert-butylnaphthalen-1-yloxy)phosphorylamino)-3-methylbutanoate;

Benzyl 2(S)-(((((2R,3R,4R, 5R)-5-(2-amino-6-methoxy-9H-purin-9-yl)-3,4-dihydroxy-4-methyltetrahydrofuran-2-yl)methoxy(naphthalene-1-yloxy)phosphorylamino)-3-methylbutanoate;

2,4-Difluorobenzyl 2(S)-(((((2R,3R,4R,5R)-5-(2-amino-6-methoxy-9H-purin-9-yl)-3,4-dihydroxy-4-methyltetrahydrofuran-2-yl)methoxy(naphthalene-1-yloxy) phosphorylamino)-3 -methylbutanoate;

(2)-((S)-1-Phenylethyl) 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy) phosphorylamino)-3-methylbutanoate;

(2S)-((S)-1-(4-BromophenyDethyl) 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-((S)-1-(2-Bromophenyl)ethyl) 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-Methyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-Neopentyl 2-((((2R,-3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-Cyclopropylmethyl 2-((((2R,-3R,4R)-5-(2-amino-6-methoxy-9H-purin-9-yl)-3,4-dihydroxy-4-methyltetrahydrofuran-2-yl)methoxy)(naphthalen-1-yloxy) phosphorylamino)-3-methylbutanoate;

(2S)-Cyclobutyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate;

Cyclopentyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)-3-methylbutanoate;

Cyclohexyl 2(S)-((((2R,3R,4R,5R)-5-(2-amino-6-methoxy-9H-purin-9-yl)-3,4-dihydroxy-4-methyltetrahydrofuran-2-yl)methoxy(naphthalene-1-yloxy)phosphorylamino)-3-methylbutanoate;

(2S)-Tetrahydro-2H-pyran-4-yl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-benzyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-methyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-propyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-neopentyl 2-(((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-cyclohexyl 2-((((2R,3R,4R)-5-(2-amino-6-methoxy-9H-purin-9-yl)-3,4-dihydroxy-4-methyltetrahydrofuran-2-yl)methoxy)(naphthalen-1-yloxy)phosphorylamino)-2-phenylacetate;

(2S)-benzyl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino) propanoate;

(2S)-2,4-difluorobenzyl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate;

(2S)-((S)-1-phenylethyl) 2-((((2R, 3R,4R)-5-(2-amino-6-ethoxy-9H-purin-9-yl)-3,4-dihydroxy-4-methyltetrahydrofuran-2-yl)methoxy)(naphthalen-1-yloxy) phosphorylamino)propanoate;

2,2-dimethylpropyl 2(S)-((((2R,3R,4R,5R)-5-(2-amino-6-ethoxy-9H-purin-9-yl)-3,4-dihydroxy-4-methyltetrahydrofuran-2-yl)methoxy(naphthalene-1-yloxy) phosphorylamino)propanoate;

(2S)-isopropyl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate;

(2S)-tetrahydro-2H-pyran-4-yl 2-((((2R,3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)propanoate;

(2S)-neopentyl 2-((((2R, 3R,4R)-5-(2-amino-6-ethoxy-9H-purin-9-yl)-3,4-dihydroxy-4-methyltetrahydrofuran-2-yl)methoxy)(naphthalen-1-yloxy)phosphorylamino)-3-methylbutanoate;

(2S)-neopentyl 2-((((2R,3R,4R)-5-(2-amino-6-(methylamino)-9H-purin-9-yl)-3,4-dihydroxy-4-methyltetrahydrofuran-2-yl)methoxy)(naphthalen-1-yloxy) phosphorylamino)propanoate;

(2S)-((S)-1-phenylethyl) 2-((((2R,3R,4R)-5-(2-amino-6-(methylamino)-9H-purin-9-yl)-3,4-dihydroxy-4-methyltetrahydrofuran-2-yl)methoxy)(naphthalen-1-yloxy) phosphorylamino)propanoate;

(2S)-neopentyl 2-4((((2R,3R,4R,5R)-5-(2-amino-6-(methylamino)-9H-purin-9-yl)-3,4-dihydroxy-4-methyltetrahydrofuran-2-yl)methoxy)(quinolin-6-yloxy)phosphorylamino)propanoate;

2,2-Dimethylpropyl 2(S)-((((2R,3R,4R,5R)-5-(2-amino-6-benzylamino-9H-purin-9-yl)-3,4-dihydroxy-4-methyltetrahydrofuran-2-yl)methoxy(naphthalene-1-yloxy) phosphorylamino)propionate;

(2S)-neopentyl 2-((((2R,3R,4R)-5-(2-amino-6-(phenethylamino)-9H-purin-9-yl)-3,4-dihydroxy-4-methyltetrahydrofuran-2-yl)methoxy)(naphthalen-1-yloxy) phosphorylamino)propanoate;

(2S)-((S)-1-phenylethyl) 2-((((2R,3R,4R)-5-(2-amino-6-(methylthio)-9H-purin-9-yl)-3,4-dihydroxy-4-methyltetrahydrofuran-2-yl)methoxy)(naphthalen-1-yloxy) phosphorylamino)propanoate;

(2S)-neopentyl 2-((((2R,3R,4R)-5-(2-amino-6-(methylthio)-9H-purin-9-yl)-3,4-dihydroxy-4-methyltetrahydrofuran-2-yl)methoxy)(naphthalen-1-yloxy) phosphorylamino)propanoate;

(2S)-neopentyl 2-((((2R,3R,4R,5R)-5-(2-amino-6-(methylthio)-9H-purin-9-yl)-3,4-dihydroxy-4-methyltetrahydrofuran-2-yl)methoxy)(quinolin-6-yloxy)phosphorylamino)propanoate;

(2S)-benzyl 2-((((2S,4R)-5-(2-amino-6-methoxy-9H-purin-9-yl)-4-hydroxy-4-methyltetrahydrofuran-2-yemethoxy)(naphthalen-1-yloxy)phosphorylamino) propanoate;

(2S)-((S)-1-phenylethyl) 2-(((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate;

(2S)-neopentyl 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate;

(2S)-cyclohexyl 2-((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)propanoate;

benzyl (2S)-benzyl 2-(((((2S,4R)-5-(2-amino-6-methoxy-9H-purin-9-yl)-4-hydroxy-4-methyltetrahydrofuran-2-yl)methoxy)(naphthalen-1-yloxy)phosphorylamino)-3-methylbutanoate;

(2S)-neopentyl 2-((((2R,3R,4R,5R)-5-(2-(4-fluorobenzylamino)-6-methoxy-9H-purin-9-yl)-3,4-dihydroxy-4-methyltetrahydrofuran-2-yl)methoxy) (naphthalen-1-yloxy)phosphorylamino)propanoate;

and phosphorus diastereomers thereof.

38. A pharmaceutical composition comprising a liquid oral formulation of a compound according to claim 1.

39. The composition according to claim 38 wherein the formulation comprises DMA/PEG 400/Solutol HS 15/sodium acetate pH 4.0 and Capmul/Tween 80; SEDDS-4; MLM; SE-21.

40. A compound selected from the group consisting of the following:
- (3R,4R,5R)-2-(2-amino-6-ethoxy-9H-purin-9-yl)-5-(hydroxymethyl)-3-methyltetrahydrofuran-3,4-diol;
- (3R,4R,5R)-2-(2-amino-6-(benzylamino)-9H-purin-9-yl)-5-(hydroxymethyl)-3-methyltetrahydrofuran-3,4-diol;
- (3R,4R,5R)-2-(2-amino-6-(phenethylamino)-9H-purin-9-yl)-5-(hydroxymethyl)-3-methyltetrahydrofuran-3,4-diol;
- (2R,3R,4R, 5R)-2-(2-(4-fluorobenzylamino)-6-methoxy-9H-purin-9-yl)-5-(hydroxymethyl)-3-methyltetrahydrofuran-3,4-diol; and
- (3R,5S)-2-(2-amino-6-methoxy-9H-purin-9-yl)-5-(hydroxymethyl)-3-methyl-tetrahydrofuran-3-ol.

41. A compound of formula (XL) below having the structure:

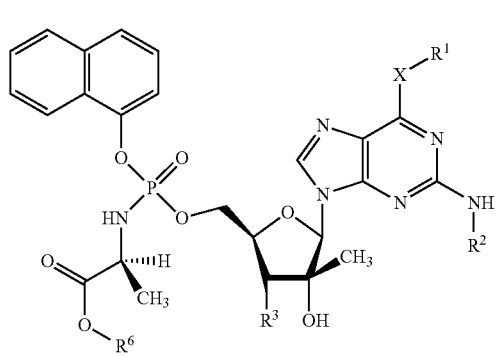

(XL)

wherein X,
is selected from S, NH and O;
$R^1$ is selected from
- $C_1$-$C_6$ alkyl,
- benzyl,
- substituted benzyl; and
- aryl($C_0$-$C_6$)alkyl- wherein the aryl is optionally substituted by
  - halo,
  - $C_1$-$C_6$alkoxy, and
  - $C_1$-$C_6$alkyl;

$R^2$ is selected from
- hydrogen,
- phenyl,
- aryl, and
- aryl($C_0$-$C_6$)alkyl- wherein the aryl is optionally substituted by
  - halo,
  - $C_1$-$C_6$alkoxy, and
  - $C_1$-$C_6$alkyl;

$R^3$ is selected from H and OH;
$R^4$ and $R^5$ are independently selected from
- hydrogen,
- $C_1$-$C_6$alkyl optionally substituted with alkylthio,
- benzyl optionally substituted with one or more
  - halo,
  - $C_1$-$C_6$alkyl, or
  - $C_1$-$C_6$alkoxy,
- phenyl optionally substituted with one or more
  - halo,
  - $C_1$-$C_6$alkyl, or
  - $C_1$-$C_6$alkoxy; and $R^6$ is selected from
- $C_1$-$C_{10}$alkyl,
- $C_3$-$C_8$cycloalkyl,
- $C_3$-$C_8$cycloalkyl-alkyl-,
- phenyl($C_1$-$C_6$)alkyl- optionally substituted with
  - $C_1$-$C_6$alkyl,
  - $C_1$-$C_6$alkoxy, and
  - halo,
- indanyl and
- heterocycloalkyl;

and pharmaceutically acceptable salts thereof.

42. The compound of claim 41 wherein
$R^6$ is selected from
- benzyl,
- (S)-1-(2-bromo)benzyl,
- 2,4-difluorobenzyl,
- (S)-1-phenylethyl,
- (S)-1-(4-bromophenyl)ethyl,
- (S)-1-(2-bromophenyl)ethyl,
- 2,3-dihydro-1H-inden-2-yl,
- methyl,
- n-propyl,
- 3,3-dimethyl butyl,
- 2-methylpropyl,
- 2,2-dimethylpropyl,
- isopropyl,
- cyclopropylmethyl,
- cyclobutyl,
- cyclopentyl,
- cyclohexyl, and
- tetrahydropyran-4-yl.

43. A compound of formula (XLI) below having the structure:

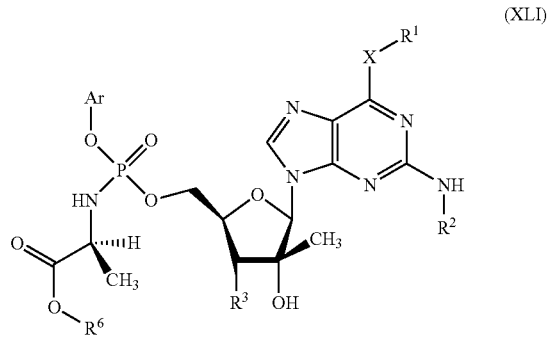

(XLI)

wherein
Ar is selected from
- naphthyl,

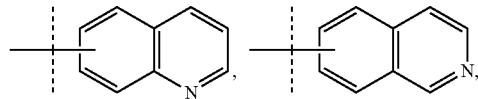

-continued

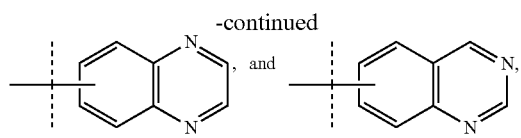

any of which are optionally substituted with
C$_1$-C$_6$alkyl,
C$_1$-C$_6$alkoxy,
di(C$_1$-C$_6$)alkylamino or
C$_1$-C$_6$alkylcarboxy(C$_1$-C$_6$)alkyl-;
X is selected from S, NH and O;
R$^1$ is selected from
C$_1$-C$_6$ alkyl,
benzyl,
substituted benzyl; and
aryl(C$_O$-C$_6$)alkyl- wherein the aryl is optionally substituted by
halo,
C$_1$-C$_6$alkoxy, and
C$_1$-C$_6$alkyl;
R$^2$ is selected from
hydrogen,
phenyl,
aryl, and
aryl(C$_0$-C$_6$)alkyl- wherein the aryl is optionally substituted by
halo,
C$_1$-C$_6$alkoxy, and
C$_1$-C$_6$alkyl;
R$^3$ is selected from H and OH;
R$^6$ is selected from
C$_1$-C$_{10}$alkyl,
C$_3$-C$_8$cycloalkyl,
C$_3$-C$_8$cycloalkyl-alkyl-,
phenyl(C$_1$-C$_6$)alkyl- optionally substituted with
C$_1$-C$_6$alkyl,
C$_1$-C$_6$alkoxy, and
halo,
indanyl and
heterocycloalkyl;
and pharmaceutically acceptable salts thereof.

44. The compound of claim 43 wherein
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl,
2-naphthyl,
quinolin-5-yl,
quinolin-6-yl, and
quinolin-8 yl.

45. The compound of claim 43 wherein
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl, and
quinolin 8-yl; and
R$^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl,
2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl.

46. The compound of claim 43 wherein X=O, R$^1$=Me, R$^2$=H, and R$^3$=OH.

47. A compound of formula (XLII) below having the structure:

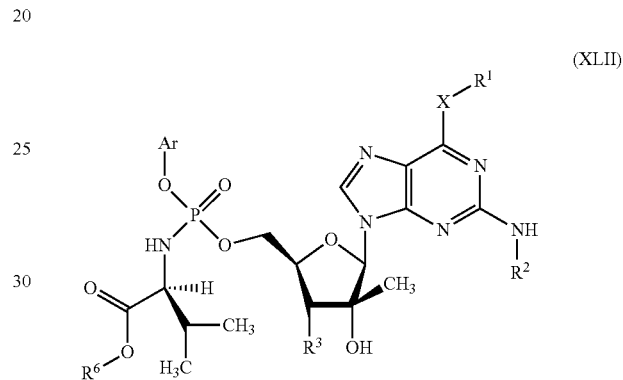

(XLII)

wherein
Ar is selected from
naphthyl,

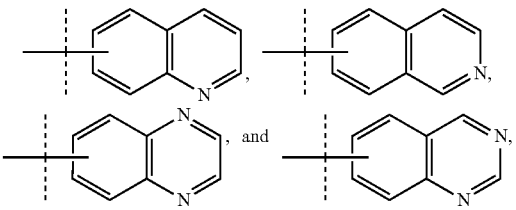

any of which are optionally substituted with
C$_1$-C$_6$alkyl,
C$_1$-C$_6$alkoxy,
di(C$_1$-C$_6$)alkylamino or
C$_1$-C$_6$alkylcarboxy(C$_1$-C$_6$)alkyl-;
X is selected from S, NH and O;
R$^1$ is selected from
C$_1$-C$_6$ alkyl,
benzyl,
substituted benzyl; and
aryl(C$_0$-C$_6$)alkyl- wherein the aryl is optionally substituted by
halo,
C$_1$-C$_6$alkoxy, and
C$_1$-C$_6$alkyl;
R$^2$ is selected from
hydrogen,
phenyl, aryl, and
aryl($C_0$-$C_6$)alkyl- wherein the aryl is optionally substituted by
   halo,
   $C_1$-$C_6$alkoxy, and
   $C_1$-$C_6$alkyl;
$R^3$ is selected from H and OH; and
$R^6$ is selected from
   $C_1$-$C_{10}$alkyl,
   $C_3$-$C_8$cycloalkyl,
   $C_3$-$C_8$cycloalkyl-alkyl-,
   phenyl($C_1$-$C_6$)alkyl- optionally substituted with
      $C_1$-$C_6$alkyl,
      $C_1$-$C_6$alkoxy, and
      halo,
   indanyl and
   heterocycloalkyl;
and pharmaceutically acceptable salts thereof.

48. The compound of claim 47 wherein
Ar is selected from
   (S)-2-(3-methoxybut-3-oxo-2-yl)naphthalen-6-yl,
   2-methylnaphthalen-1-yl,
   3-tert-butylnaphthalen-1-yl,
   3,7-di-tert-butylnaphthalen-1-yl,
   1-naphthyl, 2-naphthyl,
   quinolin-5-yl, quinolin-6-yl, and
   quinolin 8 yl; and
$R^6$ is selected from
   benzyl,
   (S)-1-(2-bromo)benzyl,
   2,4-difluorobenzyl,
   (S)-1-phenylethyl,
   (S)-1-(4-bromophenyl)ethyl,
   (S)-1-(2-bromophenyl)ethyl, 2,3-dihydro-1H-inden-2-yl,
   methyl,
   n-propyl,
   3,3-dimethyl butyl,
   2-methylpropyl,
   2,2-dimethylpropyl,
   isopropyl,
   cyclopropylmethyl,
   cyclobutyl,
   cyclopentyl,
   cyclohexyl, and
   tetrahydropyran-4-yl.

49. The compound of claim 47 wherein
Ar is 1-naphthyl.

50. The compound of claim 47 wherein
Ar is 1-naphthyl; and
   $R^6$ is selected from
      benzyl,
      (S)-1-(2-bromo)benzyl,
      2,4-difluorobenzyl,
      (S)-1-phenylethyl,
      (S)-1-(4-bromophenyl)ethyl,
      (S)-1-(2-bromophenyl)ethyl, 2,3-dihydro-1H-inden-2-yl,
      methyl,
      n-propyl,
      3,3-dimethyl butyl,
      2-methylpropyl,
      2,2-dimethylpropyl,
      isopropyl,
      cyclopropylmethyl,
      cyclobutyl,
      cyclopentyl,
      cyclohexyl, and
      tetrahydropyran-4-yl.

51. The compound of claim 47 wherein X=O, $R^1$=Me, $R^2$=H, and $R^3$=OH.

52. A compound of formula (XLIII) below having the structure:

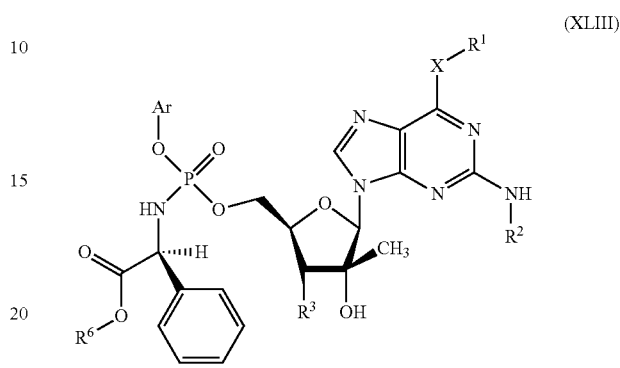

(XLIII)

wherein
Ar is selected from
   naphthyl,

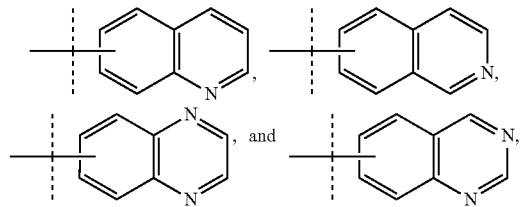

any of which are optionally substituted with
   $C_1$-$C_6$alkoxy,
   di($C_1$-$C_6$)alkylamino or
   $C_1$-$C_6$alkylcarboxy($C_1$-$C_6$)alkyl-;
X is selected from S, NH and O;
$R^1$ is selected from
   $C_1$-$C_6$ alkyl,
   benzyl,
   substituted benzyl; and
   aryl($C_0$-$C_6$)alkyl- wherein the aryl is optionally substituted by
      halo,
      $C_1$-$C_6$alkoxy, and
      $C_1$-$C_6$alkyl;
$R^2$ is selected from
   hydrogen,
   phenyl,
   aryl, and
   aryl($C_0$-$C_6$)alkyl- wherein the aryl is optionally substituted by
      halo,
      $C_1$-$C_6$alkoxy, and
      $C_1$-$C_6$alkyl;
$R^3$ is selected from H and OH; and
$R^6$ is selected from
   $C_1$-$C_{10}$alkyl,
   $C_3$-$C_8$cycloalkyl,
   $C_3$-$C_8$cycloalkyl-alkyl-, phenyl(C$_1$-C$_6$)alkyl- optionally substituted with
C$_1$-C$_6$alkyl,
C$_1$-C$_6$alkoxy, and
halo,
indanyl and
heterocycloalkyl;
and pharmaceutically acceptable salts thereof.

53. The compound of claim 52 wherein
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl, and
quinolin 8 yl; and
R$^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl.

54. The compound of claim 52 wherein
wherein Ar is 1-naphthyl.

55. The compound of claim 52 wherein
wherein Ar is 1-naphthyl; and
R$^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl.

56. The compound of claim 52 wherein X=O, R$^1$=Me, R$^2$=H, and R$^3$=OH.

57. The compound of claim 1 wherein X=O.

58. The compound of claim 57 wherein
R$^4$ and R$^5$ are independently selected from
hydrogen,
methyl,
isopropyl,
2-thiomethylethyl,
2-methylpropyl,
1-methylpropyl, and
phenyl.

59. The compound of claim 57 wherein
R$^1$ is ethyl.

60. The compound of claim 57 wherein
R$^1$ is ethyl;
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl, and
quinolin 8yl;
R$^4$ and R$^5$ are independently selected from
methyl,
isopropyl,
2-thiomethylethyl,
2-methylpropyl,
1-methylpropyl, and
phenyl; and
R$^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl.

61. The compound of claim 57 wherein R$^2$=H, and R$^3$=OH.

62. The compound of claim 1 wherein X=NH.

63. The compound of claim 62 wherein
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl, and
quinolin-8-yl;
R$^4$ and R$^5$ are independently selected from
hydrogen,
methyl,
isopropyl,
2-thiomethylethyl,
2-methylpropyl,
1-methylpropyl, and
phenyl; and
R$^6$ is selected from
benzyl,
(S)-1-(2-bromo)benzyl,
2,4-difluorobenzyl,
(S)-1-phenylethyl,
(S)-1-(4-bromophenyl)ethyl, (S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl.

64. The compound of claim 62 wherein $R^2$=H, and $R^3$=OH.

65. The compound of claim 1 wherein X=S.

66. The compound of claim 65 wherein
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl, and
quinolin-8-yl,
$R^4$ and $R^5$ are independently selected from
hydrogen,
methyl,
isopropyl,
2-thiomethylethyl,
2-methylpropyl,
1-methylpropyl, and
phenyl; and
$R^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl.

67. The compound of claim 65 wherein $R^1$=Me, $R^2$=H, and $R^3$=OH.

68. The compound of claim 1 wherein $R^3$ is H.

69. The compound of claim 68 wherein
X is O.

70. The compound of claim 68 wherein
Ar is selected from
(S)-2-(3-rnethoxybut-3-oxo-2-yl)naphthalen-6-yl,
2-methylnaphthalen-1-yl,
3-tert-butylnaphthalen-1-yl,
3,7-di-tent-butylnaphthalen-1-yl,
1-naphthyl, 2-naphthyl,
quinolin-5-yl, quinolin-6-yl, and
quinolin-8-yl
$R^1$ is methyl;

$R^4$ and $R^5$ are independently selected from
hydrogen,
methyl,
isopropyl,
2-thiomethylethyl,
2-methylpropyl,
1-methylpropyl, and
phenyl; and
$R^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl.

71. The compound of claim 68 wherein
Ar is selected from
(S)-2-(3-methoxybut-3-oxo-2-yl)naphthalen-6-yl,
2-methylnaphthalen-1-yl,
3-tent-butylnaphthalen-1-yl,
3,7-di-tert-butylnaphthalen-1-yl,
1-naphthyl, 2-naphthyl,
quinolin-5-yl, quinolin-6-yl, and
quinolin-8-yl;
X is O;
$R^4$ and $R^5$ are independently selected from
hydrogen,
methyl,
isopropyl,
2-thiomethylethyl,
2-methylpropyl,
1-methylpropyl, and
phenyl; and
$R^6$ is selected from
benzyl,
(S)-1-(2-bromo) benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl.

72. The compound of claim 68 wherein
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl, and
quinolin-8yl
X is O;
$R^1$ is methyl;
$R^4$ and $R^5$ are independently selected from
hydrogen,
methyl,
isopropyl,
2-thiomethylethyl,
2-methylpropyl,
1-methylpropyl, and
phenyl; and
$R^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl.
73. The compound of claim 68 wherein $R^2$=H.
74. The compound of claim 1
wherein X=O and wherein $R^2$ is other than H.
75. The compound of claim 74 wherein
Ar is selected from
(S)-2-(3-methoxybut-3-oxo-2-yl)naphthalen-6-yl,
2-methylnaphthalen-1-yl,
3-tert-butylnaphthalen-1-yl,
3,7-di-tert-butylnaphthalen-1-yl,
1-naphthyl, 2-naphthyl,
quinolin-5-yl, quinolin-6-yl, and
quinolin-8-yl,
$R^1$ is methyl;
$R^2$ is other than H;
$R^4$ and $R^5$ are independently selected from
hydrogen,
methyl,
isopropyl,
2-thiomethylethyl,
2-methylpropyl,
1-methylpropyl, and
phenyl; and
$R^6$ is selected from
benzyl,
(S)-1-(2-bromo)benzyl,
2,4-difluorobenzyl,
(S)-1-phenylethyl,
(S)-1-(4-bromophenyl)ethyl,
(S)-1-(2-bromophenyl)ethyl, 2,3-dihydro-1H-inden-2-yl,
methyl,
n-propyl,
3,3-dimethyl butyl,
2-methylpropyl,
2,2-dimethylpropyl,
isopropyl,
cyclopropylmethyl,
cyclobutyl,
cyclopentyl,
cyclohexyl, and
tetrahydropyran-4-yl.
76. The compound of claim 74 wherein $R^3$=OH.
77. The method of claim 35 wherein the chiral resin is selected from the group consisting of CHIRALPAK® IA™, CHIRALPAK® IA-3, CHIRALPAK® AD-H, CHIRALPAK® AD, CHIRALPAK® AD-3, CHIRALPAK® AD-3R, CHIRALPAK® AS-H, CHIRALPAK® AS, CHIRALPAK® AY-H, CHIRALPAK® AY, CHIRALPAK® AZ-H, CHIRALPAK® AZ, CHIRALPAK® IB™, CHIRALCEL® OD-H, CHIRALCEL® OD, CHIRALCEL® OD-3, CHIRALCEL® OD-3R, CHIRALCEL® OD-I, CHIRALPAK® IC™, CHIRALPAK® IC-3, CHIRALCEL® OC-H, CHIRALCEL® OC, CHIRALCEL® OA, CHIRALCEL® OB-H, CHIRALCEL® OB, CHIRALCEL® OG, CHIRALCEL® OJ-H, CHIRALCEL® OJ, CHIRALCEL® OF, CHIRALCEL® OK, CHIRALCEL® OZ-H, and CHIRALCEL® OZ.
78. A compound of formula (I) below having the structure:

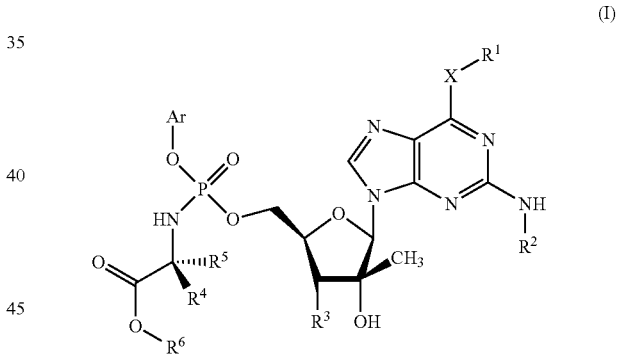

wherein Ar is selected from
phenyl,
naphthyl,

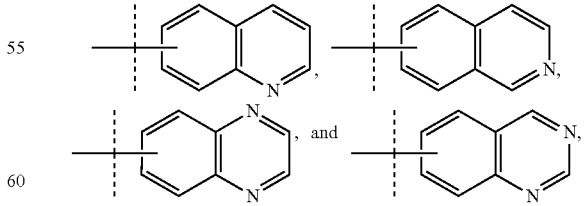

any of which are optionally substituted with
$C_1$-$C_6$alkyl,
$C_1$-$C_6$alkoxy,
di($C_1$-$C_6$)alkylamino or
$C_1$-$C_6$alkylcarboxy($C_1$-$C_6$)alkyl-;

X is selected from S, NH and O;
R$^1$ is selected from
  C$_1$-C$_6$ alkyl,
  benzyl,
  substituted benzyl; and
  aryl(C$_0$-C$_6$)alkyl- wherein the aryl is optionally substituted by
    halo,
    C$_1$-C$_6$alkoxy, and
    C$_1$-C$_6$alkyl;
R$^2$ is selected from
  hydrogen,
  phenyl,
  aryl, and
  aryl(C$_0$-C$_6$)alkyl- wherein the aryl is optionally substituted by
    halo,
    C$_1$-C$_6$alkoxy, and
    C$_1$-C$_6$alkyl;
R$^3$ is selected from H and OH;
R$^4$ and $^5$ are independently selected from
  hydrogen,
  C$_1$-C$_6$alkyl optionally substituted with alkylthio,
  benzyl optionally substituted with one or more
    halo,
    C$_1$-C$_6$alkyl, or
    C$_1$-C$_6$alkoxy,
  phenyl optionally substituted with one or more
    halo,
    C$_1$-C$_6$alkyl, or
    C$_1$-C$_6$alkoxy;
R$^6$ is selected from
  C$_1$-C$_{10}$alkyl,
  C$_3$-C$_8$cycloalkyl,
  C$_3$-C$_8$cycloalkyl-alkyl-,
  phenyl(C$_1$-C$_6$)alkyl- optionally substituted with
    C$_1$-C$_6$alkyl,
    C$_1$-C$_6$alkoxy, and
    halo,
  indanyl and
  heterocycloalkyl;
and pharmaceutically acceptable salts thereof,
wherein n the compound is in the form of a polymorph.

* * * * *